US009919036B2

(12) United States Patent
Sahin et al.

(10) Patent No.: US 9,919,036 B2
(45) Date of Patent: *Mar. 20, 2018

(54) IDENTIFICATION OF TUMOR-ASSOCIATED ANTIGENS FOR DIAGNOSIS AND THERAPY

(71) Applicants: GANYMED PHARMACEUTICALS AG, Mainz (DE); JOHANNES GUTENBERG-UNIVERSITAT MAINZ, Mainz (DE)

(72) Inventors: Ugur Sahin, Mainz (DE); Ozlem Tureci, Mainz (DE); Michael Koslowski, Mainz (DE); Dirk Usener, Wiesbaden (DE)

(73) Assignees: GANYMED PHARMACEUTICALS AG, Mainz (DE); JOHANNES GUTENBERG-UNIVERSITAT MAINZ, Mainz (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/606,729

(22) Filed: Jan. 27, 2015

(65) Prior Publication Data

US 2015/0197576 A1 Jul. 16, 2015

Related U.S. Application Data

(60) Division of application No. 13/086,176, filed on Apr. 13, 2011, now Pat. No. 8,975,375, which is a continuation of application No. 12/066,399, filed as application No. PCT/EP2006/008695 on Sep. 6, 2006, now abandoned.

(30) Foreign Application Priority Data

Sep. 12, 2005 (EP) .................................... 05019786

(51) Int. Cl.
| A61K 39/00 | (2006.01) |
| C07K 14/47 | (2006.01) |
| C07K 16/28 | (2006.01) |
| C07K 16/30 | (2006.01) |
| C12Q 1/68 | (2018.01) |
| G01N 33/574 | (2006.01) |
| A61K 45/06 | (2006.01) |

(52) U.S. Cl.
CPC .......... *A61K 39/0011* (2013.01); *A61K 45/06* (2013.01); *C07K 14/4748* (2013.01); *C07K 16/2803* (2013.01); *C07K 16/30* (2013.01); *C12Q 1/6886* (2013.01); *G01N 33/574* (2013.01); *A61K 2039/5256* (2013.01); *A61K 2039/54* (2013.01); *A61K 2039/57* (2013.01); *A61K 2039/572* (2013.01); *C07K 2317/34* (2013.01); *C12Q 2600/158* (2013.01)

(58) Field of Classification Search
None
See application file for complete search history.

(56) References Cited

U.S. PATENT DOCUMENTS

| 4,439,196 A | 3/1984 | Higuchi |
| 4,447,224 A | 5/1984 | DeCant et al. |
| 4,447,233 A | 5/1984 | Mayfield |
| 4,474,893 A | 10/1984 | Reading |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,790,824 A | 12/1988 | Morrow et al. |
| 4,881,175 A | 11/1989 | Ladner |
| 4,941,880 A | 7/1990 | Burns |
| 4,946,778 A | 8/1990 | Ladner et al. |
| 4,954,617 A | 9/1990 | Fanger et al. |
| 5,013,653 A | 5/1991 | Huston et al. |
| 5,064,413 A | 11/1991 | McKinnon et al. |
| 5,091,513 A | 2/1992 | Huston et al. |
| 5,132,405 A | 7/1992 | Huston et al. |
| 5,258,498 A | 11/1993 | Huston et al. |
| 5,260,203 A | 11/1993 | Ladner et al. |
| 5,312,335 A | 5/1994 | McKinnon et al. |
| 5,374,548 A | 12/1994 | Caras |
| 5,383,851 A | 1/1995 | McKinnon et al. |
| 5,399,163 A | 3/1995 | Peterson et al. |
| 5,399,331 A | 3/1995 | Loughrey et al. |
| 5,416,016 A | 5/1995 | Low et al. |
| 5,455,030 A | 10/1995 | Ladner et al. |
| 5,476,786 A | 12/1995 | Huston |
| 5,482,858 A | 1/1996 | Huston et al. |

(Continued)

FOREIGN PATENT DOCUMENTS

| CN | 1663603 | 9/2005 |
| EP | 0338841 | 10/1989 |

(Continued)

OTHER PUBLICATIONS

Ranade, J. Clin. Pharmacol., 29:685-694 (1989).
Rice et al., Trends Genet., 16:276-277 (2000).
Riechmann et al., Nature, 332:323-327 (1998).
Rossi et al., Am. J. Clin. Pathol., 124:295-302 (2005).
Scheurle et al., Cancer Res., 60:4037-4043 (2000).
Sherr, Cancer Res., 60:3689-3695 (2000).
Sherr, Cell, 73:1059-1065 (1993).
Shields et al., J. Biol. Chem., 277:26733-26740 (2002).
Slamon et al., Science, 244:707-712 (1989).
Spieker-Polet et al., Proc. Natl. Acad. Sci. USA, 92:9348-9352 (1995).
Strejan et al., J. Neuroimmunol., 7:27-41 (1984).
Sutherland et al., J. Mammary Gland Biol. Neoplasia, 9:95-104 (2004).
Thorpe et al., Immunol. Rev., 62:119-158 (1982).

(Continued)

*Primary Examiner* — Lei Yao
(74) *Attorney, Agent, or Firm* — McAndrews, Held & Malloy, Ltd.

(57) ABSTRACT

The invention relates to genetic products the expression of which is associated with cancer diseases. The invention also relates to the therapy and diagnosis of diseases in which the genetic products are expressed or aberrantly expressed, in particular cancer diseases.

21 Claims, 46 Drawing Sheets

(56) References Cited

U.S. PATENT DOCUMENTS

Figure 1:
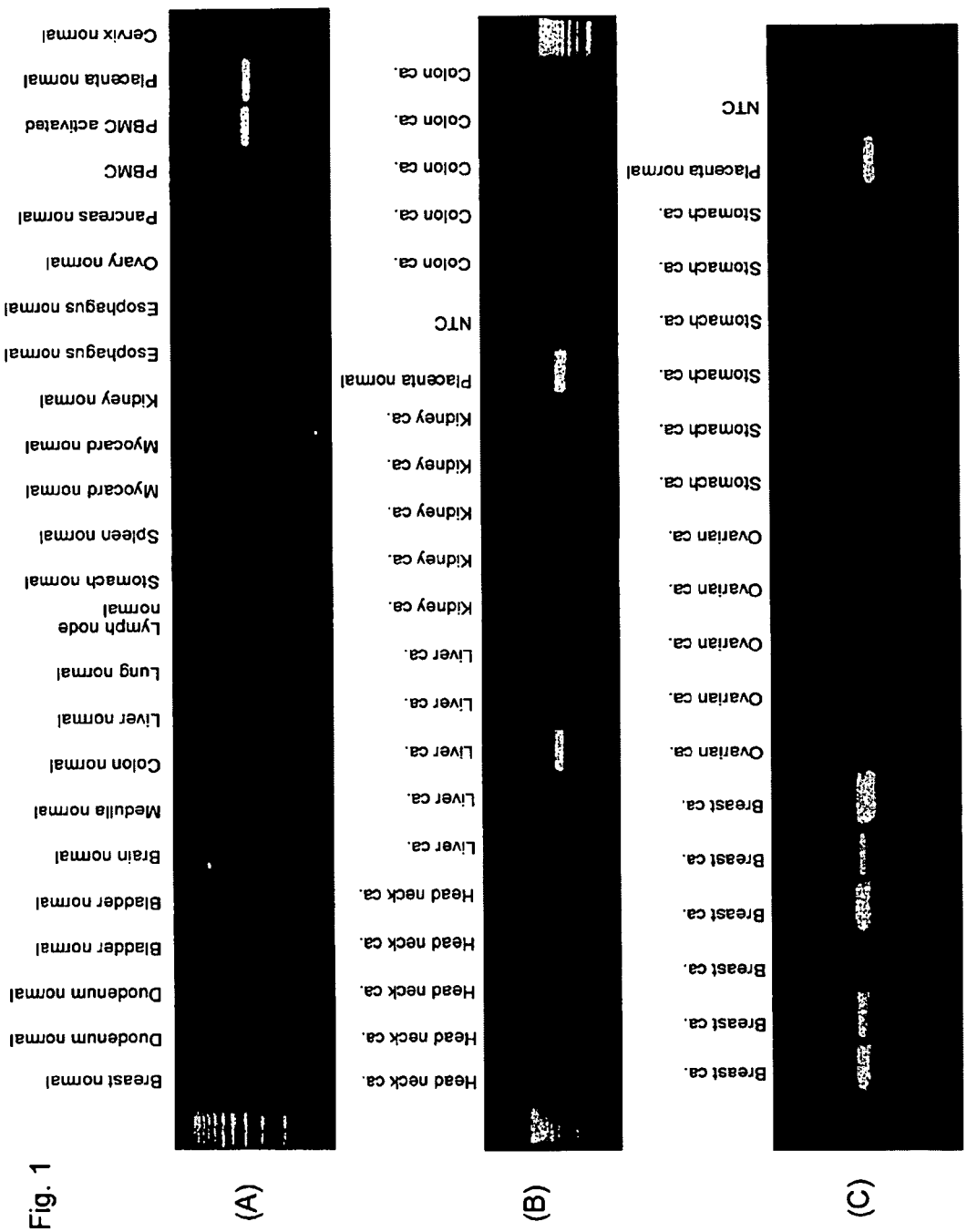

| | | | |
|---|---|---|---|
| 5,624,821 | A | 4/1997 | Winter et al. |
| 5,648,260 | A | 7/1997 | Winter et al. |
| 5,744,585 | A | 4/1998 | Medenica et al. |
| 6,121,022 | A | 9/2000 | Presta et al. |
| 6,194,551 | B1 | 2/2001 | Idusogie et al. |
| 6,277,375 | B1 | 8/2001 | Ward |
| 6,812,339 | B1 | 11/2004 | Venter et al. |
| 8,354,104 | B2 | 1/2013 | Sahin et al. |
| 8,946,388 | B2 | 2/2015 | Sahin et al. |
| 8,961,980 | B2 | 2/2015 | Sahin et al. |
| 9,216,218 | B2 | 12/2015 | Sahin et al. |
| 9,475,867 | B2 | 10/2016 | Sahin et al. |
| 2002/0065394 | A1 | 5/2002 | Jacobs et al. |
| 2002/0177547 | A1 | 11/2002 | Molling et al. |
| 2002/0192748 | A1 | 12/2002 | Rastelli et al. |
| 2003/0017534 | A1 | 1/2003 | Buelow et al. |
| 2003/0118592 | A1 | 6/2003 | Ledbetter et al. |
| 2003/0133939 | A1 | 7/2003 | Ledbetter et al. |
| 2004/0043387 | A1 | 3/2004 | Liu et al. |
| 2004/0203037 | A1 | 10/2004 | Lo et al. |
| 2005/0255114 | A1 | 11/2005 | Labat et al. |
| 2011/0223182 | A1 | 9/2011 | Sahin et al. |
| 2011/0300144 | A1 | 12/2011 | Sahin et al. |
| 2011/0318264 | A1 | 12/2011 | Sahin et al. |
| 2017/0058044 | A1 | 3/2017 | Sahin et al. |

FOREIGN PATENT DOCUMENTS

| | | | |
|---|---|---|---|
| EP | 1762575 | A | 3/2007 |
| EP | 1970384 | A1 | 9/2008 |
| EP | 2166021 | A1 | 3/2010 |
| JP | 2389675 | B2 | 1/2014 |
| MX | 2009009816 | A | 11/2009 |
| WO | 87/04462 | | 7/1987 |
| WO | 88/00052 | | 1/1988 |
| WO | 89/01036 | | 2/1989 |
| WO | 94/10332 | | 5/1994 |
| WO | 99/45962 | | 9/1999 |
| WO | 00/32769 | | 6/2000 |
| WO | 02/43478 | | 6/2002 |
| WO | 03/016475 | A2 | 2/2003 |
| WO | 20031075014 | A2 | 9/2003 |
| WO | WO2003075014 | * | 9/2003 |
| WO | 03/102159 | A2 | 12/2003 |
| WO | 04/35607 | | 4/2004 |
| WO | 20041065629 | A1 | 8/2004 |
| WO | 2008/110379 | A2 | 9/2008 |
| WO | 20101031551 | A2 | 3/2010 |

OTHER PUBLICATIONS

Umezawa et al., Biochem. Biophys. Res. Commun., 153:1038-1044 (1988).
Verma et al., J. Immunol. Methods, 216:165-181 (1998).
Ward et al., Nature, 341:544-546 (1989).
Yang et al., Proc. Natl. Acad. Sci. USA, 100(12):6934-6939 (2003).
Roguska et al., Current Protocols in Pharmacology 2005 (Abstract).
Scallon et al., J Immunother 2006, 29:351-364.
Weiner et al., Lancet 2009, 373(9668):1033-1040.
Lacroix et al., Relevance of breast cancer cell lines as models for breast tumours: an update, Breast Cancer Research and Treatment 83:249-289 (2004).
"Human protein Q9H2U9, SEQ ID No. 9901", Jan. 29, 2004 (Jan. 29, 2004), retrieved from EBI accession No. GSP: ADE63955, Database accession No. ADE63955.
"Novel human nucleic acid NOV22c", Mar. 25, 2004 (Mar. 25, 2004), retrieved from EBI accession No. GSN:ADH41740, Database accession No. ADH41740, sequence.
Database Geneseq [Online], May 20, 2004 (May 20, 2004), "Human ADAM7 (GP-83) beta form cDNA.", retrieved from EBI accession No. GSN:ADJ92368, Database accession No. ADJ92368, sequence.
*Homo sapiens* a disintegrin and metalloproteinase 7 (ADAM7) mRNA, compldete cds. [online]. Jan. 2, 2001 uploaded. NCBI Entrez Nucleotide, Accession No. AF215824 (GI:12004291) [Retrieved on Jun. 5, 2014]. Retrieved from the Internet: URL:http://www.ncbi.nlm.nih.gov/nuccore/12004291.
Proceedings of the Japanese Cancer Association, (2002), 61st, p. 390 (1840).
Ernst et al., "Decrease and Gain of Gene Expression Are Equally Discriminatory Markers for Prostate Carcinoma", Amer. Journ. Pathology, vol. 160, No. 6, Jun. 2002 (+ SEQ ID No. 5).
Yan et al., "Oosp1 Encodes a Novel Mouse Oocyte-Secreted Protein" genesis 31:105-110 (2001).
Lu et al., "Selection of Potential Markers for Epithelial Ovarian Cancer with Gene Expression Arrays and Recursive Descent Partition Analysis", Vo. 10, pp. 3291-3300, May 15, 2004.
Lin Y C et al: "Cloning and characterization of a complementary DNA encoding a human epididymis-associated disintegrin and metalloprotease 7 protein.", Biology of Reproduction Sep. 2001, vol. 65, No. 3, pp. 944-950.
Bendig M. M., Methods: A Companion to Methods in Enzymology, 1995; 8:83-93.
Colman, Research in Immunology, vol. 145, p. 33-36, 1994.
Rudikoff, Proceedings of the National Academy of Sciences, U.S.A., vol. 79, p. 1979-1983, 1982.
Paul, Fundamental Immunology, Third Edition, p. 292-295, 1993.
Harris, Biotechnology, vol. 11, p. 1293-1297, 1993.
Sominskaya, Medical Microbiology and Immunology, vol. 181, p. 215-226, 1992.
Int'l Search Report and Written Opinion for PCT/EP2011/001198, dated May 12, 2011.
IPRP and Written Opinion of PCT/EP2011/001198 dated Sep. 25, 2012.
Binz et al., Nat. Biotechnol., 23(10):1257-1268 (2005).
Bird et al., Science, 242:423-426 (1988).
Molecular Cloning: A Laboratory Manual, J. Sambrook et al., Editors, 2nd Edition, Cold Spring Harbor Laboratory Press, Cold Spring Harbor, New York (1989).
Smith et al., Ads App. Math., 2:482 (1981).
Pearson et al., Proc. Natl. Acad. Sci. USA, 85:2444 (1988).
Neddleman et al., J. Mol. Biol., 48:443 (1970) 48.
Morton et al., Critical Reviews in Immunology, 16:423-440 (1996).
Weintraub, B. Principles of Radioimmunoassays, Seventh Training Course on Radioligand Assay Techniques, The Endocrine Society, Mar. 1986.
Arnon et al., "Monoclonal Antibodies for Immunotargeting of Drugs in Cancer Therapy", in Monoclonal Antibodies and Cancer Therapy, Resifeld et al. (eds.), pp. 243-256 (Alan R. Liss, Inc. 1985).
Robinson et al. (eds.), pp. 623-653 (Marcel Dekker, Inc. 1987).
"Analysis, Results, and Future Prospective of the Therapeutic Use of Radiolabeled Antibody in Cancer Therapy", in Monoclonal Antibodies for Cancer Detection and Therapy, Baldwin et al. (eds.), pp. 303-316 (Academic Press 1985).
Briscoe et al., Am. J. Physiol., 1233:134 (1995).
Hofmann, K and Stoffel, W., Biol. Chem Hoppe-Seyler 374, 166 (1993).
IPRP and Written Opinion of PCT/EP2009/006704 dated Mar. 31, 2011.
Dr. Rainer Wessel, "Neue, hoch tumorspezifische Antikörper and ihre Targets" [online] Nov. 22, 2007 (Nov. 22, 2007), pp. 1-30, XP002527064 Würzburg Retrieved from the Internet: URL :http://www.bayern-innovativ.de.ib.site/documents/media/8b861e13-3717-d967-ed57-03d37f988a16.pdf/Wessel.pdf.
Pinchera et al. (eds.), pp. 475-506 (1985).
Final Office Action, U.S. Appl. No. 13/086,176, dated Sep. 25, 2012.
RCE, U.S. Appl. No. 13/086,176, dated Jan. 9, 2013.
Examiner sequence search result (Chen) in U.S. Appl. No. 12/066,399, dated Oct. 14, 2010.
Examiner sequence search result (Jacobs) in U.S. Appl. No. 12/066,399, dated Oct. 14, 2010.
Examiner sequence search result (Daviet) in U.S. Appl. No. 12/066,399, dated Oct. 14, 2010.

(56) References Cited

OTHER PUBLICATIONS

Pardoll, M., Cancer Vaccines, Nature Medicine, May 1998, pp. 525-531, vol. 4., No. 5, Nature Publishing Group, New York, NY, US.
Sahin, U. et al.,Serological Identification of Human Tumor Antigens, Current Opinion in Immunology, Oct. 1997, pp. 709-716, vol. 9, No. 5, Current Biology Ltd.
Bruggen Van Der, P. et al., A Gene Encoding an Antigen Recognized by Cytolytic T Lymphocytes on a Human Melanoma, Science, Dec. 13, 1991, pp. 1643-1647, vol. 254, American Association for the Advancement of Science, US.
Nakata Yuji et al., Nucleic Acid Modulation of Gene Expression: Approaches for Nucleic Acid Therapeutics Against Cancer, Critical Reviews in Eukaryotic Gene Expression, 2005, pp. 163-182, vol. 15, No. 2.
Otsuki, T. et al. DNA Res., 2005, pp. 117-126, vol. 12, No. 2.
EMBL Database, Database accession No. AK075086, Sep. 7, 2002, webpage printout.
IPRP for PCT/EP2006/008695, dated Mar. 27, 2008.
Int'l and Written Opinion for PCT/EP2006/008695, dated Jun. 13, 2007.
Restriction Requirement, U.S. Appl. No. 12/066,399, dated Apr. 28, 2010.
Non-Final Office Action, U.S. Appl. No. 12/066,399, dated Oct. 14, 2010.
Freshney (Culture of Animals Cells, A Manual of Basic Technique, Alan R. Liss, Inc., 1983 New York, p. 4).
Dermer (Bio/Technology, 1994, 12:320).
Gura (Science, 1997, 278:1041-1042).
Jain (Sci. Am., 1994, 271:58-65).
Fant et al., Mol Reprod Dev. 63:430-6, 2002.
Seals et al., Genes Dev. 17(1) :7-30, 2003.
Adachi et al., Mol Reprod Dev. 64:414-21, 2003.
Beauchemin et al., Exp Cell Res. 252(2) :243-9, 1999.
Salahshor et al, BMC Cancer. 5:66, 2005.
Cheng et al., J Biol. Chem. 260:15834-9, 1985.
Boehm et al., J Immunol. 161(12):6715-23, 1998.
Guenzi et al., EMBO J. 20(20) :5568-77, 2001.
Arunachalam et al. Proc. Natl Acad Sci U S A. 97(2):745-50, 2000.
Bera et al., Biochem Biophys Res Commun. 312(4):1209-15, 2003.
Int'l Search Report and Written Opinion for PCT/EP2009/006704, dated Aug. 2, 2010, 24 pages.
Evans et al., Serum-free hybridoma culture: ethical, scientific and safety considerations, Trends in Biotechnology, Vo. 24 No. 3, (105-108) Mar. 2006.
Schultze-Mosgau et al., (1975) Fetal placental antigens in the serum of tumor patients; Zentralblatt far Gynakologie 97 (9):563-567.
Chang et al., (1977) Preliminary characterization of isoimmunogenic placental antigens in the rabbit; Tissue Antigens 10(1):16-26.
Cancer Immunity, 2007, vol. 7, p. 18.
Aschheim Kathy et al: "Focus on antibody engineering and manufacture", Nature Biotechnology, vol. 23, No. 9, Sep. 1, 2005 (Sep. 1, 2005), pp. vii-viii.
International Preliminary Report on Patentability dated Sep. 24, 2009 for International Application No. PCT/EP2008/002063.
Chen Jing et al: "[PLAC1/CP1 gene expression and autologous humoral immunity in gastric cancer patients]" Beijing Da Xue Xue Bao. Yi Xue Ban= Journal of Peking University. Health Sciences Apr. 18, 2006, vol. 38, No. 2, Apr. 18, 2006 (Apr. 18, 2006), pp. 124-127, XP009085470 ISSN: 1671-167X.
Cocchia M et al: "PLAC1, an Xq26 Gene with Placenta-Specific Expression" Genomics, Academic Press, San Diego, US, vol. 68, No. 3, Sep. 15, 2000 (Sep. 15, 2000), pp. 305-312, XP004437833 ISSN: 0888-7543.
Koslowski Michael et al: "A placenta-specific gene ectopically activated in many human cancers is essentially involved in malignant cell processes" Cancer Research, American Association for Cancer Research, Baltimore, MD, vol. 67, No. 19, Oct. 1, 2007 (Oct. 1, 2007), pp. 9528-9534, XP002471063 ISSN: 0008-5472.
Dong Xue-Yuan et al: "PLAC1 is a tumor-specific antigen capable of eliciting spontaneous antibody responses in human cancer patients" International Journal of Cancer, vol. 122, No. 9, May 2008 (May 2008), pp. 2038-2043, XP009102971 ISSN: 0020-7136.
Adams et al., Nat. Biotechnol., 23:1147-1157 (2005).
Berge et al., J. Pharm. Sci., 66:1-19 (1977).
Bloemen et al., FEBS Lett., 357:140-144 (1995).
Bork et al., FEBS Lett, 300:237-240 (1992).
Brekke et al., Nat. Rev. Drug Discov., 2:52-62 (2003).
Brennan et al., Science, 229:81-83 (1985).
Caldon et al., J. Cell Biochem., 97:261-274 (2006).
Cantley, Science, 296:1655-1657 (2002).
Carter, Nat. Rev. Cancer, 1:118-129 (2001).
Crone et al., Nat. Med., 8:459-465 (2002).
Cunningham-Rundles et al., J. Immunol. Methods, 152:177-190 (1992).
D'Amico et al., J. Biol. Chem., 275:32649-32657 (2000).
Diehl et al., Genes Dev., 12:3499-3511 (1998).
Fischer et al., Biol. Chem., 380:825-839 (1999).
Garnier et al., J. Mol. Biol., 120:97-120 (1978).
Glennie et al., J. Immunol., 139:2367-2375 (1987).
Graziano et al., J. Immunol., 155(10):4996-5002 (1995).
Holliger et al., Proc. Natl. Acad. Sci. USA, 90:6444-6448 (1993).
Houshmand et al., Curr. Opin. Cell Biol., 15:640-644 (2003).
Huston et al., Proc. Natl. Acad. Sci. USA, 85:5879-5883 (1988).
Jones et al., Biochemistry, 33:3038-3049 (1994).
Jones et al., Nature, 321:522-525 (1986).
Jovine et al., BMC Biochem, 7:11 (2006).
Karpovsky et al., J. Exp. Med., 160:1686-1701 (1984).
Kohler et al., Nature, 256:495-497 (1975).
Koslowski et al., Cancer Res., 62:6750-6755 (2002).
Koslowski et al., Cancer Res., 64:5988-5993 (2004).
Koslowski et al., Hum. Mol. Genet., 15:2392-2399 (2006).
Kozak, J. Biol. Chem., 266:19867-19870 (1991).
Kranz et al., Proc. Natl. Acad. Sci. USA, 78:5807-5811 (1981).
Landor, Ann. Allergy Asthma Immunol., 74:279-283 (1995).
Liu et al., Proc. Natl. Acad. Sci. USA, 82:8648-8652 (1985).
Luo et al., Cancer Cell, 4:257-262 (2003).
Monteiro et al., J. Immunol., 148:1764-1770 (1992).
Morgan, Annu. Rev. Cell Dev. Biol., 13:261-291 (1997).
Morrison, Science, 229:1202-1207 (1985).
Muise-Helmericks et al., J. Biol. Chem., 273:29864-29872 (1998).
Owais et al., Antimicrob. Agents Chemother., 39:180-184 (1995).
Paulus, Behring Ins. Mitt., (78):118-132 (1985).
Poljak, Structure, 2:1121-1123 (1994).
Pollock et al., J. Immunol. Methods, 231:147-157 (1999).
Queen et al., Proc. Natl. Acad. Sci. USA, 86:10029-10033 (1989).
Radu et al., Mol. Cell Biol., 23:6139-6149 (2003).
Documentation for Affymetrix Array 95C, 2 pages, 2014.
Hellstrom et al., "Antibodies for Drug Delivery", in Controlled Drug Delivery (2nd Ed.), 31 pages, 1987.
Thorpe, "Antibody Carriers of Cytotoxic Agents in Cancer Therapy: A Review", in Monoclonal Antibodies '84: Biological and Clinical Applications, pp. 475-506, 1985.
Babcook et al., "A novel strategy for generating monoclonal antibodies from single, isolated lymphocytes producing antibodies of defined specificities," Proc. Natl. Acad. Sci., vol. 93, pp. 7843-7848, 1996.
Panka et al. (Proceedings of the National Academy of Sciences USA, vol. 85, 1988).
Wall et al., Theriogenology, vol. 45, p. 57-68, 1996.
Houdebine et al., Journal of Biotechnology, vol. 34, p. 269-287, 1994.
Kappel et al., Current Opinions in Biotechnology, vol. 3, p. 548-553, 1992.
Komenaka et al., Clinics in Dermatology, 2004, vol. 22, pp. 251-265.
Evans et al., (Q.J. Med 1999: 92: 299-307).
Schiffman et al., The New England Journal of Medicine, vol. 353, No. 20, pp. 2101-2104, 2005.
Cuzick et al. (The Lancet, vol. 361, pp. 296-300, 2003).
Hernandez-Ledesma (Peptides vol. 30, pp. 426-430, 2009).

(56) References Cited

OTHER PUBLICATIONS

Baxevanis (Expert Opinion: Drug Discovery, vol. 3, No. 4, pp. 441-452, 2008).
Polyak et al., (Blood, vol. 99, No. 9, pp. 3256-3262, 2002).
Munodzana et al., (Infection and Immunity, vol. 66, No. 6, pp. 2619-2624, 1998).

* cited by examiner

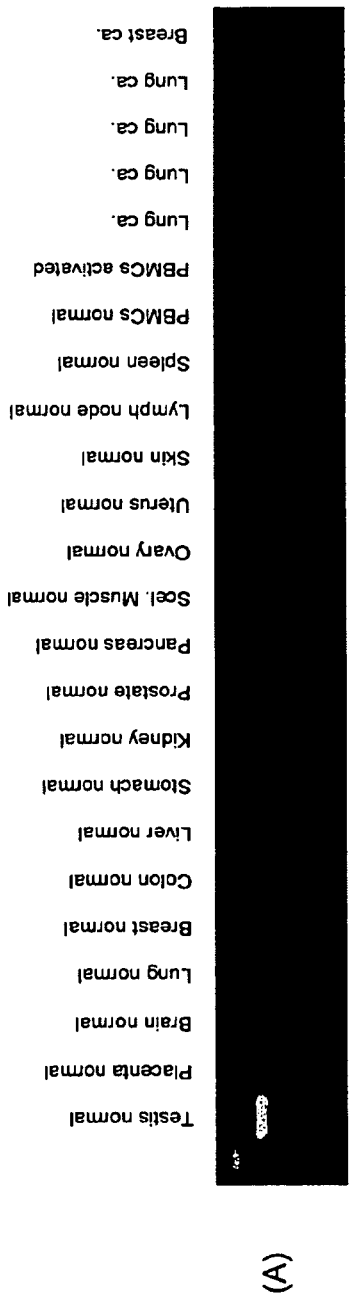
Fig. 3

FIG. 31A

| SeqID | Sequence |
|---|---|
| 1 | ATATATCAGACCATCAGAAGGATTTGTATAAAGAGTGACTCTCCTATGAAGGTAAAGGCCACCCCTCTTC<br>AGTTCCAGTGACTGAGATACATTTTTCCAATCCTGGGGGCAAATACAGACACAGCAAGTTCCTTCTTCCC<br>TTTGGAAATTTGGCAGCTGCCTTCACCAGTGAGCACAAAGCCACATTTCAAAGGAAACTGACAAATTATC<br>CCCAGCTGCCAGAAGAAGAAATCCTCACTGGACGGCTTCCTGTTTCCTGTGGTTCATTATCTGATTGGCT<br>GCAGGGATGAAAGTTTTTAAGTTCATAGGACTGATGATCCTCCTCACCTCTGCGTTTTCAGCCGGTTCAG<br>GACAAAGTCCAATGACTGTGCTGTGCTCCATAGACTGGTTCATGGTCACAGTGCACCCCTTCATGCTAAA<br>CAACGATGTGTGTGTACACTTTCATGAACTACACTTGGGCCTGGGTTGCCCCCCAAACCATGTTCAGCCA<br>CACGCCTACCAGTTCACCTACCGTGTTACTGAATGTGGCATCAGGGCCAAAGCTGTCTCTCAGGACATGG<br>TTATCTACAGCACTGAGATACACTACTCTTCTAAGGGCACGCCATCTAAGTTTGTGATCCCAGTGTCATG<br>TGCTGCCCCCCAAAAGTCCCCATGGCTCACCAAGCCCTGCTCCATGAGAGTAGCCAGCAAGAGCAGGGCC<br>ACAGCCCAGAAGGATGAGAAATGCTACGAGGTGTTCAGCTTGTCACAGTCCAGTCAAAGGCCCAACTGCG<br>ATTGTCCACCTTGTGTCTTCAGTGAAGAAGAGCATACCCAGGTCCCTTGTCACCAAGCAGGGGCTCAGGA<br>GGCTCAACCTCTGCAGCCATCTCACTTTCTTGATATTTCTGAGGATTGGTCTCTTCACACAGATGATATG<br>ATTGGGTCCATGTGATCCTCAGGTTTGGGGTCTCCTGAAGATGCTATTTCTAGAATTAGTATATAGTGTA<br>CAAATGTCTGACAAATAAGTGCTCTTGTGACCCTCATGTGAGCACTTTTGAGAAAGAGAAACCTATAGCA<br>ACTTCATGAATTAAGCCTTTTTCTATATTTTTATATTCATGTGTAAACAAAAAATAAAATAAAATTCTGA<br>TCGCAT |
| 2 | MKVFKFIGLMILLTSAFSAGSGQSPMTVLCSIDWFMVTVHPFMLNNDVCVHFHELHLGLGCPPNHVQPHA<br>YQFTYRVIECGIRAKAVSQDMVIYSTEIHYSSKGTPSKFVIPVSCAAPQKSFWLTKFCSMRVASKSRATA<br>QKDEKCYEVFSLSQSSQRPNCDCPPCVFSEEEHTQVPCHQAGAQEAQPLQPSHFLDISEDWSLHTDDMIG<br>SM |
| 3 | AAATTTGGCAGCTGCCTTCAC |
| 4 | TGATGCCACATTCAGTAACAC |
| 5 | ATCCCTGCAGTGGAAGTGAGGAGGAAGAAAGGTGAACTCCTTTTCTCAAGCACTTCTGCTCTCCTCTACCAGA<br>ATCACTCAGAATGCTTCCCGGGTGTATATTCTTGATGATTTTACTCATTCCTCAGGTTAAAGAAAAGTTCATC<br>CTTGGAGTAGAGGGTCAACAACTGGTTCGTCCTAAAAAGCTTCCTCTCGATACAGAAGCGAGATACTGGACACA<br>CCCATGATGATGACATACTGAAAACGTATGAAGAAGAATTGTTTGTATCAAATAAAACTAAATAGAAAAACCTT<br>AGTCCTTCATCTTCTAAGATCCAGGGAGTTCCTAGGCTCAAATTACAGTGAAACATTCTACTCCATGAAGGA<br>GAAGCGTTCACCAGGCATCCTCAGATCATGGATCATTGTTTTTACCAAGGATCCATAGTACACGAATATGATT<br>CAGCTGCCAGTATCAGTACGTGTAATGGTCTAAGGGGATTCTTCAGAATAAACGACCAAAGATACCTCATTGA<br>ACCAGTGAAATACTCAGATGAGGGAGAACATTTGGTGTTCAAATATAACCTGAGGGTGCCGTATGGTGCCAAT<br>TATTCCTGTACAGAGCTTAATTTTACCAGAAAACTGTTCCAGGGGATAATGAATCTGAAGAAGACTCCAAAA<br>TAAAAGGCATCCATGATGAAAAGTATGTTGAATTGTTCATTGTTGCTGATGATACTGTGTATCGCAGAAATGG<br>TCATCCTCACAATAAACTAAGGAACCGAATTTGGGGAATGGTCAATTTTCTCAACATGATTTATAAAACCTTA<br>AACATCCATGTGACGTTGGTTGGCATTGAAATATGGCACATGAACATAAAATAGAACTATATTCAAATATGA<br>AAACTACCTTATTGCGTTTTTCATTTTGGCAAGAAAAGATCCTTAAAACACGGAAGGATTTTGATCATGTTGT<br>ATTACTCAGTGGGAAGTGGCTCTACTCACATCTGCAAGGAATTTCTTATCCAGGGGGTATGTGCCTGCCCTAT<br>TATTCCACCAGTATCATTAAGGATCTTTTACCTGACACAAACATAATTGCAAACAGAATGGCACATCAACTGG<br>GGCATAACCTTGGGATGCAGCATGACGAGTTCCCATGCACCTGTCCTTCAGGAAAATGCGTGATGGACAGTGA<br>TGGAAGCATTCCTGCACTGAAATTCAGTAAATGCAGCCAAAACCAATACCACCAGTACTTGAAGGATTATAAG<br>CCAACATGCATGCTCAACATTCCATTTCCTTACAATTTTCATGATTTCCAATTTTGTGGAAACAAGAAGTTGG<br>ATGAGGGTGAAGAGTGTGACTGTGGCCCTGCTCAGGAGTGTACTAATCCTTGCTGTGATGCACACACATGTGT<br>ACTGAAGCCAGGATTTACTTGTGCAGAAGGAGAATGCTGTGAATCTTGTCAGATAAAAAAGCAGGGTCCATA<br>TGCAGACCGGCGAAAGATGAATGTGATTTTCCTGAGATGTGCACTGGCCACTCGCCTGCCCTGTCCTAAGGACC<br>AGTTCAGGGTCAATGGATTTCCTTGCAAGAACTCAGAAGGCTACTGTTTCATGGGGAAATGTCCAACTCGTGA<br>GGATCAGTGCTCTGAACTATTTGATGATGATGCAATAGAGAGTCATGATATCTGCTACAAGATGAATACAAAA<br>GGAAATAAATTTGGATACTGCAAAAACAAGGAAAACAGATTTCTTCCCTGTGAGGAGAAAGATGTCAGATGTG<br>GAAAGATCTACTGCACTGGAGGGGAGCTTTCCTCTCTCCTTGGAGAAGACAAGACTTATCACCTTAAGGATCC<br>CCAGAAGAATGCTACTGTCAAATGCAAAACTATTTTTTTATACCATGATTCTACAGACATTGGCCTGGTGGCG<br>TCAGGAACAAAATGTGGAGAGGGAATGGTGTGCAACAATGGTGAATGTCTAAACATGGAAAAGGTCTATATCT<br>CAACCAATTGCCCCTCTCAGTGCAATGAAAATCTGTGGATGCCACGGACTCCAGTGCCACTGTGAGGAAGG<br>ACAGGCACCTGTAGCCTGTGAAGAAACCTTACATGTTACCAATATCACCATCTTGGTTGTTGTGCTTGTCCTG<br>GTTATTGTCGGTATCGGAGTTCTTATACTATTAGTTCGTTACCGAAATGTATCAAGTTGAAGCAAGTTCAGA<br>GCCCACCTACAGAAACCCTGGGAGTGGAGAACAAAGGATACTTTGGTGATGAGCAGCAGATAAGGACTGAGCC<br>AATCCTGCCAGAAATTCATTTCCTAAATAAACCTGCAAGTAAAGATTCAAGAGGAATCGCAGATCCCAATCAA<br>AGTGCCAAGTGAGCTTGAAGTTGGATATCCAAAATGGCCGTGCAAGCTTAGCTGGGGATTCTGGATGCAACG<br>TCTTTACAACCTTACCTAGATATCTGCTACTCACATTTTTGGTAGTGTTTCAAACGTTCTTTATCCAGACAGA<br>CAATGTTTAAGAGAAACAACTTATTTCTGTTAATATTTACCGGTAGAATTCACACCCTCTATCATAAACATAT<br>CCTCCACAAAAAAAAAAAAAAAAAAA |

FIG. 31B

| | |
|---|---|
| 6 | MLPGCIFLMILLIPQVKEKFILGVEGQQLVRPKKLPLIQKRDTGHTHDDDILKTYEEELLYEIKLNRKTL VLHLLRSREFLGSNYSETFYSMKGEAFTRHPQIMDHCFYQGSIVHEYDSAASISTCNGLRGFFRINDQRY LIEPVKYSDEGEHLVFKYNLRVPYGANYSCTELNFTRKTVPGDNESEEDSKIKGIHDEKYVELFIVADDT VYRRNGHPHNKLRNRIWGMVNFVNMIYKTLNIHVTLVGIEIWTHEDKIELYSNIETTLLRFSFWQEKILK TRKDFDHVVLLSGKWLYSHVQGISYPGGMCLPYYSTSIIKDLLPDTNIIANRMAHQLGHNLGMQHDEFPC TCPSGKCVMDSDGSIPALKFSKCSQNQYHQYLKDYKPTCMLNIPFPYNFHDFQFCGNKKLDEGEECDCGP AQECTNPCCDAHTCVLKPGFTCAEGECCESCQIKKAGSICRPAKDECDFPEMCTGHSPACPKDQFRVNGF PCKNSEGYCFMGKCPTREDQCSELFDDDAIESHDICYKMNTKGNKFGYCKNKENRFLPCEEKDVRCGKIY CTGGELSSLLGEDKTYHLKDPQKNATVKCKTIFLYRDSTDIGLVASGTKCGEGMVCNNGECLNMEKVYIS TNCPSQCNENPVDGHGLQCHCEEGQAPVACEETLHVTNITILVVVLVLVIVGIGVLILLVRYRKCIKLKQ VQSPPTETLGVENKGYFGDEQQIRTEPILFEIHFLNKPASKDSRGIADPNQSAK |
| 7 | GTGCAGAAGGAGAATGCTGTG |
| 8 | TCCACATCTGACATCTTTCTC |
| 9 | AGAAGGAGGAAGGACAGCACAGCTGACAGCCGTGCTCAGACAGCTTCTGGATCCCAGGCTCATCTCCACA GAGGAGAACACACAGGCAGCAGAGACCATGGGGCCCCTCCCAGCCCCTTCCTGCACACAGCGCATCACCT GGAAGGGGCTCCTGCTCACAGCATCACTTTTAAACTTCTGGAACCCGCCCACCACTGCCGAAGTCACGAT TGAAGCCCAGCCACCCAAAGTTTCTGAGGGGAAGGATGTTCTTCTACTTGTCCACAATTTGCCCCAGAAT CTTCCTGGCTACTTCTGGTACAAAGGGGAAATGACGGACCTCTACCATTACATTATATCGTATATAGTTG ATGGTAAAATAATTATATATGGGCCTGCATACAGTGGAAGAGAAACAGTATATTCCAACGCATCCCTGCT GATCCAGAATGTCACCCGGAAGGATGCAGGAACCTACACCTTACACATCATAAAGCGAGGTGATGAGACT AGAGAAGAAATTCGACATTTCACCTTCACCTTATACTTGGAGACTCCCAAGCCCTACATCTCCAGCAGCA ACTTAAACCCCAGGGAGGCCATGGAGGCTGTGCGCTTAATCTGTGATCCTGAGACTCTGGACGCAAGCTA CCTATGGTGGATGAATGGTCAGAGCCTCCCTGTGACTCACAGGTTGCAGCTGTCCAAAACCAACAGGACC CTCTATCTATTTGGTGTCACAAAGTATATTGCAGGCCCTATGAATGTGAAATACGGAACCCAGTGAGTG CCAGTCGCAGTGACCCAGTCACCCTGAATCTCCTCCCGAAGCTGCCCATCCCCTACATCACCATCAACAA CTTAAACCCCAGGGAGAATAAGGATGTCTTAGCCTTCACCTGTGAACCTAAGAGTGAGAACTACACCTAC ATTTGGTGGCTAAACGGTCAGAGCCTCCCCGTCAGTCCCGGGGTAAAGCGACCCATTGAAAACAGGATAC TCATTCTACCCAGTGTCACGAGAAATGAAACAGGACCCTATCAATGTGAAATACAGGACCGATATGGTGG CCTCCGCAGTAACCCAGTCATCCTAAATGTCCTCTATGGTCCAGACCTCCCCAGAATTTACCCTTCATTC ACCTATTACCGTTCAGGAGAAAAACCTCGACTTGTTCACGGAATCTAACCCACCGGCAGAGTATT TTTGGACAATTAATGGGAAGTTTCAGCAATCAGGACAAAAGCTCTTTATCCCCAAATTACTAGAAATCA TAGCGGGCTCTATGCTTGCTCTGTTCATAACTCAGCCACTGGCAAGGAAATCTCCAAATCCATGACAGTC AAAGTCTCTGGTCCCTGCCATGGAGACCTGACAGAGTCTCAGTCATGACTGCAACAACTGAGACACTGAG AAAAAGAACAGGCTGATACCTTCATGAAATTCAAGACAAAGAAGAAAAAAACTCAATGTTATTGGACTAA ATAATCAAAAGGATAATGTTTTCATAATTTTTTATTGGAAAATGTGCTGATTCTTTGAATGTTTATTCT CCAGATTTATGAACTTTTTTTTCTTCAGCAATTGGTAAAGTATACTTTTATAAACAAAAATTGAAATATTT GCTTTTGCTGTCTATCTGAATGCCCCAGAATTGTGAAACTATTCATGAGTATTCATAGGTTTATGGTAAT AAAGTTATTTGCACATGTTCCAAAAAAAAAAAAAAAAAAAAAAAAAAAAAA |
| 10 | MGPLPAFSCTQRITWKGLLLTASLLNFWNFPTTAEVTIEAQPPKVSEGKDVLLLVHNLPQNLPGYFWYKG EMTDLYHYIISYIVDGKIIIYGPAYSGRETVYSNASLLIQNVTRKDAGTYTLHIIKRGDETREEIRHFTF TLYLETPKPYISSSNLNPREAMEAVRLICDPETLDASYLWWMNGQSLPVTHRLQLSKTNRTLYLFGVTKY IAGPYECEIRNPVSASRSDPVTLNLLPKLFIPYITINNLNPRENKDVLAFTCEPKSENYTYIWWLNGQSL PVSPGVKRPIENRILILPSVTRNETGPYQCEIQDRYGGLRSNPVILNVLYGPDLPRIYPSFTYYRSGENL DLSCFTESNPPAEYFWTINGKFQQSGQKLFIPQITRNHSGLYACSVHNSATGKEISKSMTVKVSGPCHGD LTESQS |
| 11 | CTCCTCYATGGTCCAGACCTC |
| 12 | GTTGCAGTCATGACTGAGACTC |

FIG. 31C

| | |
|---|---|
| 13 | ATGACAGTGACTCCACAGTATCTACCAGAATACAAGGGCAAGCATCCAAAATGTGACTCACTGGTGGTGT<br>TCCGCAATGTGTGCGTCTGTGTGTCCACCGCGACAGGCATCAGTACATTGGATCAGAGTGTCGCTTTCAG<br>TTGTAACGGACTTCATCACATCACAAATTGTACTCGTTCTCATCCTTTTAAGAAAGTTCAGACCCAGGAA<br>AATTTCCATAGTACCTTAATGAAAAGATAGAAATCAGTGGGACGTGTCTTTCCTTTCATCTCCTTTTCG<br>GCTTGGAAATCAGAATGAGAAGGATTGTTTTTGCTGGTGTTATCTTATTCCGCCTCTTAGGTGTTATCTT<br>ATTCCGCCTCTTAGGTGTTATCTTATTCGGCCGCTTAGGTGACCTGGGAACCTGCCAGACAAAACCTGGT<br>CAGTACTGGAAAGAAGAGGTCCACATTCAAGATGTTGGAGGTTTGATTTGCAGAGCATGCAATCTTTCAC<br>TGCCCTTCCATGGATGTCTTTTAGACCTGGGAACCTGCCAGGCAGAACCTGGTCAGTACTGTAAAGAAGA<br>GGTCCACATTCAAGGTGGCATTCAATGGTATTCAGTCAAAGGCTGCACAAAGAACACATCAGAGTGCTTC<br>AAGAGTACTCTCGTCAAGAGAATTCTGCAACTGCATGAACTTGTAACTACTCACTGCTGCAATCATTCTT<br>TGTGCAATTTCTGAGTCAGTGGCCCATATCTAAATGCTTGGCAGATCAATCAGTCTCGAAGCCTGACCT<br>CGCTATCACAAAATGATGGCTATTGTCAATTAGCCCACTTCAGAAACCTCAGACCCTTGTAGGTAGAAGG<br>AATTTGATCTGAAATTGACTTTGGTTTTCAATATTCCCAATATCTCCCCCACCACCTCCAACTCATCTG<br>AGAAATAGCCCTTTCAACACCATTTCTCTCCTCCTCCTCCTTCTGCTTAATTTACCTTCCTACCACAAGGC<br>TACAAAGAAGGAAAAATGTTAGTGATTCTCCAAGTCAAACTAGGCATGTCACCTCTAACTACTTTCATTT<br>CCCTCAATAATTCCATACTCCAAAATATGGTTACAAATGTTTCACAAGACAGCAAGTGACCTGAGAATAT<br>TCATTTGGTTTCCAAAGCAAACTGCCTTGCTCCTTTGGGGTGATTTATGGTATAGAAGAAACTGACTTAA<br>CATATACTATAGGGAAAAAATAAGCCATGAATCAGCAAGCCAGGCCTGCGGGAAAAGTATGAACCCAAAC<br>AGGAAAGGGCTGAGGCAGGTGGTAGGGCTGGCACTTATTTCTTCCATCTGCCTCAGAGTTTATCCAAATT<br>TTGAATTTTCCGTACCTTAACCATGCCTAAATGCTTTGGCTTGTTCAATTTTGGCAGATTAAGCAGTTCA<br>AGGTAAGCAGAGATAAGTTCCCAACCACAAGGAATTTAAAAGGAGTAGGAACGTACTTTGAACTACAT<br>TTCCCATTTTGCGATCATTACGTCTTCTATTACAATGCCCTACTTTGGCAGCATGAAGAGTACTGCATTA<br>ATTTAATTTAATITAAAATTTAATTTAAAACTGTCTTTCTCTGTATTTTCAGGAGTTTGAAAATTCAAAA<br>AATAAATAATAAATGTCAATAAAA |
| 14 | MTVTPQYLPEYKCKHPKCDSLVVFRNVCVCVSTATGISTLDQSVAFSCNGLHHITNCTRSHPFKKVQTQE<br>NFHSTLMKKIEISGICLSFHLLFGLEIRMRRIVFAGVILFRLLGVILFRLLGVILFGRLGDLGTCQTKPG<br>QYWKEEVHIQDVGGLICRACNLSLPFHGCLLDLGTCQAEPGQYCKEEVHIQGGIQWYSVKGCTKNTSECF<br>KSTLVKRILQLHELVTTHCCNHSLCNF |
| 15 | GACAAAACCTGGTCAGTACTG |
| 16 | CCCATTGAATGCCACCTTGAATG |
| 17 | ATCAGGTTCAACGCAGTGACTGCTCAGTAGAAGCCATGGCTCGCAGACACTGCTTCTCCTACTGGTTACT<br>GGTATGCTGGTTGGTGGTAACTGTGGCAGAAGGACAAGAAGAGGTATTTACGCTTCCTGGAGATTCACAA<br>AATAATGCGGACGCTACCGACTGCAGATCTTTACACTCACCCCTCCACCTGCCCCGAGGAGTCCGGTCA<br>CAAGGGCCCAGCCCATCACAAAGCACACCCAGGTGTCCCTTCCATTTTTTTCCACGAAGGCCCAGAATCCA<br>TTTTAGGTTTCCAAACAGACCTTTCGTCCCTTCAAGGTGTAACCACCGTTTTCCATTCCAGCCATTTTAT<br>TGGCCACACCGTTACCTTACTTATAGGTATTTCCCCAGAAGAAGACTCCAGAGAGGAAGCTCATCTGAGG<br>AAAGCTGAGAGGGAAGAGAAACCCAAACATACTGAAGCAAAAAAAGCCTATCCTTCAGAAAAAGCAAC<br>AAAAAGATTTCTGTTTTATCTTTCGAAACTAAAAACTATTGGATTTGAAGATTAAGTATCCTAAACATCAC<br>TGACTAGAAACTGTTCTCTTTGTCAGCAGTGAAGATATTGGATACTAGGTTATTGATGGTTGCAAAATTG<br>GACAATAACCACGTTATTTTTATCCTCAACCTCTTATGGTCACAGGATATTTATGCAAATAAAATCTTTA<br>AATGGGAAAAAAAAAAAAAAAAAAAAAAAAAAAAAAAAAAAAAAA |
| 18 | MARRHCFSYWLLVCWLVVTVAEGQEEVFTLPGDSQNNADATDCQIFTLTPFPAPRSPVTRAQPITKTPRC<br>PFHFFPRRPRIHFRFPNRPFVPSRCNHRFPFQPFYWPHRYLTYRYFPRRRLQRGSSSEES |
| 19 | TAACTGTGGCAGAAGGACAAG |
| 20 | AGATGAGCTTCCTCTCTGGAG |
| 21 | ACAGAAGCGCGCAGAGTCCCATCCTGCCACGCCACGAGGAGAGAAGAAGGAAAGATACAGTGTTAGGAAA<br>GAGACCTCCCTCGCCCCTACGCCCCGCGCCCTGCGCCTCGCTTCAGCCTCAGGACAGTCCTGCCGGGAC<br>GGTGAGCGCATTCAGCACCCTGGACAGCACCGCGGTTGCGCTGCCTCCAGGGCGGCCCCGGGCTGCTCCT<br>GCTCCGCAGAGCTACGCCCTCCCCCGGGTGCCCCGGACCCTGCACTTGCCGCCGCTTTCCTCGCGCTGC<br>TCTGGACCTTGCTAGCCGGCTCTGCACCTCCCAGAAGCCGTGGGCGCGCCGCTCAGCTGCTCCATCGCCT<br>CACTTTCCCAGGCTCGCGCCCGAAGCAGAGCCATGAGAACCCCAGGGTGCCTGGCGAGCCGCTAGCGCCA<br>TGGGCCCCGGCGAGGCGCTGCTGGCGGGTCTCCTGGTGATGGTACTGGCCGTGGCGCTGCTATCCAACGC<br>ACTGGTGCTGCTTTGTTGCGCCTACAGCGCTGAGCTCCGCACTCGAGCCTCAGGCGTCCTCCTGGTGAAT<br>CTGTCTCTGGGCCACCTGCTGCTGGCGGCGCTGGACATGCCCTTCACGCTGCTCGGTGTGATGCGCGGGC<br>GGACACCGTCGGCGCCCGGCGCATGCCAAGTCATTGGCTTCCTGGACACCTTCCTGGCGTCCAACGCGGC<br>GCTGAGCGTGGCGGCGCTGAGCGCAGACCAGTGGCTGGCAGTGGGCTTCCCACTGCGCTACGCCGGACGC<br>CTGCGACCGCGCTATGCCGGCCTGCTGCTGGGCTGTGCCTGGGGACAGTCGCTGGCCTTCTCAGGCGCTG<br>CACTTGGCTGCTCGTGGCTTGGCTACAGCAGCGCCTTCGCGTCCTGTTCGCTGCGCCTGCCGCCCGAGCC<br>TGAGCGTCCGCGCTTCGCAGCCTTCACCGCCACGCTCCATGCCGTGGGCTTCGTGCTGCCGCTGGCGGTG<br>CTCTGCCTCACCTCGCTCCAGGTGCACCGGGTGGCACGCAGACACTGCCAGCGCATGGACACCGTCACCA |

FIG. 31D

| | |
|---|---|
| | TGAAGGCGCTCGCGCTGCTCGCCGACCTGCACCCCAGTGTGCGGCAGCGCTGCCTCATCCAGCAGAAGCG |
| | GCGCCGCCACCGCGCCACCAGGAAGATTGGCATTGCTATTGCGACCTTCCTCATCTGCTTTGCCCCGTAT |
| | GTCATGACCAGGCTGGCGGAGCTCGTGCCCTTCGTCACCGTGAACGCCCAGTGGGGCATCCTCAGCAAGT |
| | GCCTGACCTACAGCAAGGCGGTGGCCGACCCGTTCACGTACTCTCTGCTCCGCCGGCCGTTCCGCCAAGT |
| | CCTGGCCGGCATGGTGCACCGGCTGCTGAAGAGAACCCCGCGCCCAGCATCCACCCATGACAGCTCTCTG |
| | GATGTGGCCGGCATGGTGCACCAGCTGCTGAAGAGAACCCCGCGCCCAGCGTCCACCCACAACGGCTCTG |
| | TGGACACAGAGAATGATTCCTGCCTGCAGCAGACACACTGAGGGCCTGGCAGGGCTCATCCGCCCCCACCT |
| | TCTAAGAAGCCCTGTGGAAAGGGCACTGGCCCTGCCACAGAGATGCCACTGGGGACCCCCAGACACCAGT |
| | GGCTTGACTTTGAGCTAAGGCTGAAGTACAGGAGGAGGAGGAGGAGAGGGCCGGATGTGGGTGTGGACAG |
| | CAGTAGTCGCGGAGGAGAGCTCGGGGCTGGGCTGCCTGGCTGCTGGGTGGCCCCGGGACAGTGGCTTTTC |
| | CTCTCTGAACCTTAGCTTCCTCACCCTTGTTCTGGGGTCATCGCGATGCTTCGAGACAGTGGGTAGGGAA |
| | GTGCCCGTGTGGCATATGGTACTCGTGGGCGTGCTATAAGTGACTGCTGTTCATGTGGGTGAGGTGGTC |
| | ACTCTTGCTCAGGGTCTGTTGTGCAGCCCAGATGGACACCTGTTTCTCCAAAAAAAAAAAAAAAAAA |
| 22 | MGPGEALLAGLLVMVLAVALLSNALVLLCCAYSAELRTRASGVLLVNLSLGHLLLAALDMPFTLLGVMRG |
| | RTPSAPGACQVIGFLDTFLASNAALSVAALSADQWLAVGFPLRYAGRLRPRYAGLLLGCAWGQSLAFSGA |
| | ALGCSWLGYSSAFASCSLRLPPEPERPRFAAFTATLHAVGFVLPLAVLCLTSLQVHRVARRHCQRMDTVT |
| | MKALALLADLHPSVRQRCLIQQKRRRHRATRKIGIAIATFLICFAPYVMTRLAELVPFVTVNAQWGILSK |
| | CLTYSKAVADPFIYSLLRRPFRQVLAGMVHRLLKRTPRPASTHDSSLDVAGMVHQLLKRTPRPASTHNGS |
| | VDTENDSCLQQTH |
| 23 | CCGTATGTCATGACCAGGCTG |
| 24 | AAGTCAAGCCCACTGGTGTCTG |
| 25 | AGCACAGAAGGAGGAAGGACAGCACAGCTGACAGCCGTACTCAGGAAGCTTCTGGATCCTAGGCTTATCT |
| | CCACAGAGGAGAACACACAAGCAGCAGAGACCATGGGGCCCCTCTCAGCCCCTCCCTGCACACAGCGCAT |
| | CACCTGGAAGGGGGTCCTGCTCACAGCATCACTTTTAAACTTCTGGAATCCGCCCACAACTGCCCAAGTC |
| | ACGATTGAAGCCCAGCCACCCAAAGTTTCTGAGGGGAAGGATGTTCTTCTACTTGTCCACAATTTGCCCC |
| | AGAATCTTGCTGGCTACATTTGGTACAAAGGGCAAATGACATACCTCTACATTACATCATATGT |
| | AGTAGACGGTCAAAGAATTATATATGGGCCTGCATACAGTGGAAGAGAAAGAGTATATTCCAATGCATCC |
| | CTGCTGATCCAGAATGTCACGCAGGAGGATGCAGGATCCTACACCTTACACATCATAAAGCGACGCGATG |
| | GGACTGAGGAGTAACTGGACATTTCACCTTCACCTTACACCTGGAGACTCCCAAGCCCTCCATCTCCAG |
| | CAGCAACTTAAATCCCAGGGAGGCCATGGAGGCTGTGATCTTAACCTGTGATCCTGCGACTCCAGCCGCA |
| | AGCTACCAGTGGTGGATGAATGGTCAGAGCCTCCCTATGACTCACAGGTTGCAGCTGTCCAAAACCAACA |
| | GGACCCTCTTTATATTTGGTGTCACAAAGTATATTGCAGGACCCTATGAATGTGAAATACGGAACCCAGT |
| | GAGTGCCAGCCGCAGTGACCCAGTCACCCTGAATCTCCTCCCAAAGCTGTCCAAGCCCTACATCACAATC |
| | AACAACTTAAACCCCAGAGAGAATAAGGATGTCTTAACCTTCACCTGTGAACCTAAGAGTAAGAACTACA |
| | CCTACATTTGGTGGCTAAATGGTCAGAGCCTCCCTGTCAGTCCCAGGGTAAAGCGACCCATTGAAAACAG |
| | GATCCTCATTCTACCCAATGTCACGAGAAATGAAACACGCACCTTATCAATGTGAAATACGGGACCGATAT |
| | GGTGGCATCCGTCAGTGACCCAGTCACCCTGAATGTCCTCTATGGTCCAGACCTCCCCAGCATTTACCCTT |
| | CATTCACCTATTACCGTTCAGGAGAAAACCTCTACTTGTCCTGCTTCGCCGAGTCTAACCCACGGGCACA |
| | ATATTCTTGGACAATTAATGGGAAGTTTCAGCTATCAGGACAAAAGCTCTCTATCCCCAAATAACTACA |
| | AAGCATAGTGGCTCTATGCTTGCTCTGTTCGTAACTCAGCCACTGGCAAGGAAAGCTCCAAATCCATCA |
| | CAGTCAAAGTCTCTGACTGGATATTACCCTGAATTCTACTAGTTCCTCCAATTCCATTTCTCCCATGGA |
| | ATCACGAAGAGCAAGACCCACTCTGTTCCAGAAGCCCTATAAGCTGGAGGTGGACAACTCGATGTAAATT |
| | TCATGGGAAAACCCTTGTACCTGACATGTGAGCCACTCAGAACTCACCAAAATGTTCGACACCATAACAA |
| | CAGCTACTCAAACTGTAAACCAGGATAACAAGTTGATGACTTCACACTGTGGACAGTTTTTCCAAAGATG |
| | TCAGAACAAGACTCCCCATCATGATAAGGCTCCCACCCCTCTTAACCGTCCTTGCTCATGCCTGCCTCTT |
| | TCACTTGGCAGGATAATGCAGTCATTAGAATTTCACATGTAGTAGCTTCTGAGGGTAACAACAGAGTGTC |
| | AGATATGTCATCTCAACCTCAAACTTTTACGTAACATCTCAGGGCAAATGTGGCTCTCTCCATCTTGCAT |
| | ACAGGGGCTCCCAATAGAAATGAACACAGATATTGCCTGTGTGTTTGCAGAGAAGATGGTTTCTATAAA |
| | GAGTAGGAAAGCTGAAATTATAGTAGAGTCTCCTTTAAATGCACATTGTGTGGATGGCTCTCACCATTTC |
| | CTAAGAGATACAGTGTAAAACGTGACAGTAATACTGATTCTAGCAGAATAAAACATGTACCACATTTGCT |
| | AAAAAAAAAAAAAAAAAAAAAAAAAAAAA |
| 26 | MGPLSAPPCTQRITWKGVLLTASLLNFWNPPTTAQVTIEAQPPKVSEGKDVLLLVHNLPQNLAGYIWYKG |
| | QMTYLYHYITSYVVDGQRIIYGPAYSGRERVYSNASLLIQNVTQEDAGSYTLHIIKRRDGTGGVTGHFTF |
| | TLHLETPKPSISSSNLNPREAMEAVILTCDPATPAASYQWWMNGQSLPMTHRLQLSKTNRTLFIEGVTKY |
| | IAGPYECEIRNPVSASRSDPVTLNLLPKLSKPYITINNLNPRENKDVLTFTCEPKSKNYTYIWWLNGQSL |
| | PVSPRVKRPIENRILILPNVTRNETGPYQCEIRDRYGGIRSDPVTLNVLYGPDLPSIYPSFTYYRSGENL |
| | YLSCFAESNPRAQYSWTINGKFQLSGQKLSIPQITTKHSGLYACSVRNSATGKESSKSITVKVSDWILP |
| 27 | GTTGTTACCCTCAGAAGCTAC |

FIG. 31E

| | |
|---|---|
| 28 | AGCACAGAAGGAGGAAGGACAGCACAGCTGACAGCCGTACTCAGGAAGCTTCTGGATCCTAGGCTTATCT<br>CCACAGAGGAGAACACACAAGCAGCAGAGACCATGGGGCCCCTCTCAGCCCCTCCCTGCACACAGCGCAT<br>CACCTGGAAGGGGGTCCTGCTCACAGCATCACTTTTAAACTTCTGGAATCCGCCCACAACTGCCCAAGTC<br>ACGATTGAAGCCCAGCCACCCAAAGTTTCTGAGGGGAAGGATGTTCTTCTACTTGTCCACAATTTGCCCC<br>AGAATCTTGCTGGCTACATTTGGTACAAAGGGCAAATGACATACCTCTACCATTACATTACATCATATGT<br>AGTAGACGGTCAAAGAATTATATATGGGCCTGCATACAGTGGAAGAGAAAGAGTATATTCCAATGCATCC<br>CTGCTGATCCAGAATGTCACGCAGGAGGATGCAGGATCCTACACCTTACACATCATAAAGCGACGCGATG<br>GGACTGGAGGAGTAACTGGACATTTCACCTTCACCTTACACCTGGAGACTCCCAAGCCCTCCATCTCCAG<br>CAGCAACTTAAATCCCAGGGAGGCCATGGAGGCTGTGATCTTAACCTGTGATCCTGCGACTCCAGCCGCA<br>AGCTACCAGTGGTGGATGAATGGTCAGAGCCTCCCTATGACTCACAGGTTGCAGCTGTCCAAAACCAACA<br>GGACCCTCTTTATATTTGGTGTCACAAAGTATATTGCAGGACCCTATGAATGTGAAATACGGAACCCAGT<br>GAGTGCCAGCCGCAGTGACCCAGTCACCCTGAATCTCCTCCATGGTCCAGACCTCCCCAGCATTTACCCT<br>TCATTCACCTATTACCGTTCAGGAGAAAACCTCTACTTGTCCTGCTTCGCCGAGTCTAACCCACGGGCAC<br>AATATTCTTGACAATTAATGGGAAGTTTCAGCTATCAGGACAAAAGCTCTCTATCCCCAAATAACTAC<br>AAAGCATAGTGGGCTCTATGCTTGCTCTGTTCGTAACTCAGCCACTGGCAAGGAAAGCTCCAAATCCATC<br>ACAGTCAAAGTCTCTGACTGGATATTACCCTGAATTCTACTAGTTCCTCCAATTCCATTTTCTCCCATGG<br>AATCACGAAGCAAGACCCACTCTGTTCCAGAAGCCCTATAAGCTGGAGGTGGACAACTCGATGTAAAT<br>TTCATGGGAAAACCCTTGTACCTGACATCTGAGCCACTCAGAACTCACCAAAATGTTCGACACCATAACA<br>ACAGCTACTCAAACTGTAAACCAGGATAACAAGTTGATGACTTCACACTGTGGACAGTTTTTCCAAAGAT<br>GTCAGAACAAGACTCCCCATCATGATAAGGCTCCCACCCCTCTTAACCGTCCTTGCTCATGCCTGCCTCT<br>TTCACTTGGCAGGATAATGCAGTCATTAGAATTTCACATGTAGTAGCTTCTGAGGGTAACAACAGAGTGT<br>CAGATATGTCATCTCAACCTCAAACTTTTACGTAACATCTCAGGGGAAATGTGGCTCTCTCCATCTTGCA<br>TACAGGGCTCCCAATAGAAATGAACACAGAGATATTGCCTGTGTGTTTGCAGAGAAGATGGTTTCTATAA<br>AGAGTAGGAAAGCTGAAATTATAGTAGAGTCTCCTTTAAATGCACATTGTGTGGATGGCTCTCACCATTT<br>CCTAAGAGATACAGTGTAAAACGTGACAGTAATACTGATTCTAGCAGAATAAAACATGTACCACATTTGC<br>TAAAAAAAAAAAAAAAAAAAAAAAAAAAA |
| 29 | MGPLSAPPCTQRITWKGVLLTASLLNFWNPPTTAQVTIEAQPPKVSEGKDVLLLVHNLPQNLAGYIWYKG<br>QMTYLYHYITSYVVDGQRIIYGPAYSGRERVYSNASLLIQNVTQEDAGSYTLHIIKRRDGTGGVTGHFTF<br>TLHLETPKPSISSSNLNPREAMEAVILTCDPATPAASYQWWMNGQSLPMTHRLQLSKTNRTLFIFGVTKY<br>IAGPYECEIRNPVSASRSDPVTLNLLHGPDLPSIYPSFTYYRSGENLYLSCFAESNPRAQYSWTINGKFQ<br>LSGQKLSIPQIITKHSGLYACSVRNSATGKESSKSITVKVSDWILP |
| 30 | ATTCGGGCCTAGGCTCATCTCCACAGAGGAGAACACGCAGGGAGCAGAGACCATGGGGCCCCTCTCAGCC<br>CCTCCCTGCACACAGCATATAACCTGGAAAGGGCTCCTGCTCACAGCATCACTTTTAAACTTCTGGAACC<br>CGCCCACCACAGCCCAAGTCACGATTGAAGCCCAGCCACCCAAAAGTTTCTGAGGGGAAGGATGTTCTTCT<br>ACTTGTCCACAATTTGCCCCAGAATCTTACTGGCTACATCTGGTACAAAGGACAAATCAGGGACCTCTAC<br>CATTATGTTACATCATATGTAGTAGACGGTCAAATAATTAAATATGGGCCTGCATACAGTGGACGAGAAA<br>CAGTATATTCCAATGCATCCCTGCTGATCCAGAATGTCACCCAGGAAGACACAGGATCCTACACTTTACA<br>CATCATAAAGCGAGGTGATGGGACTGGAGGAGTAACTGGACGTTTCACCTTCACCTTATACCTGGAGACT<br>CCCAAACCCTCCATCTCCAGCAGCAATTTCAACCCCAGGGAGGCCACGGAGGCTGTGATCTTAACCTGTG<br>ATCCTGAGACTCCAGATGCAAGCTACCTGTGGTGGATGAATGGTCAGAGCCTCCCTATGACTCACAGCTT<br>GCAGCTGTCTGAAACCAACAGGACCCTCTACCTATTTGGTGTCACAAACTATACTGCAGGACCCTATGAA<br>TGTGAAATACGGAACCCAGTGAGTGCCAGCCGCAGTGACCCAGTCACCCTGAATCTCCTCCCGAAGCTGC<br>CCAAGCCCTACATCACCATCAATAACTTAAACCCCAGGGAGAATAAGGATGTCTCAACCTTCACCTGTGA<br>ACCTAAGAGTGAGAACTACACCTACATTTGGTGGCTAAATGGTCAGAGCCTCCCGGTCAGTCCCAGGGTA<br>AAGCGACGCATTGAAAACAGGATCCTCATTCTACCCAGTGTCACGAGAAATGAAACAGGACCCTATCAAT<br>GTGAAATACGGGACCGATATGGTGGCATCCGCAGTGACCCAGTCACCCTGAATGTCCTCTATGGTCCAGA<br>CCTCCCCAGAATTTACCCTTCGTTCACCTATTACCATTCAGGACAAAACCTCTACTTGTCCTGCTTTGCG<br>GACTCTAACCCACCGGCACAGTATTCTTGGACAATTAATGGGAAGTTTCAGCTATCAGGACAAAAGCTTT<br>CTATCCCCCAGATTACTACAAAGCATAGCGGGCTCTATGCTTGCTCTGTTCGTAACTCAGCCACTGGCAA<br>GGAAAGCTCCAAATCCGTGACAGTCCAGAGTCTCTGACTGGACATTACCCTGAATTCTACTAGTTCCTCCA<br>ATTCCATCTTCTCCCATGGAACCTCAAAGAGCAAGACCCACTCTGTTCCAGAAGCCCTATAAGTCAGAGT<br>TGGACAACTCAATGTAAATTTCATGGGAAAATCCTTGTACCTGATGTCTGAGCCACTCAGAACTCACCAA<br>AATGTTCAACACCATAACAACAGCTGCTCAAACTGTAAACAAGGAAAACAAGTTGATGACTTCACACTGT<br>GGACAGTTTTTCCCAAGATGTCAGAATAAGACTCCCCATCATGATGAGGCTCTCACCCCTCTTAGCTGTC<br>CTTGCTTGTGCCTGCCTCTTTCACTTGGCAGGATAATGCAGTCATTAGAATTTCACATGTAGTATAGGAG<br>CTTCTGAGGGTAACAACAGAGTGTCAGATATGTCATCTCAACCTCAAACTTTTACATAACATCTCAGGAG<br>GAAATGTGGCTCTCTCCATCTTGCATACAGGGCTCCCAATAGAAATGAACACAGAGATATTGCCTGTGTG<br>TTTGCAGAGAAGATGGTTTCTATAAAGAGTAGGAAAGCTGAAATTATAGTAGAGTCCCCTTTAAATGCAC<br>ATTGTGTGGATGGCTCTCACCATTTCCTAAGAGATACATTGTAAAACGTGACAGTAAGACTGATTCTAGC<br>AGAATAAAACATGTACTACATTTGCTAAA |

FIG. 31F

| | |
|---|---|
| 31 | MGPLSAPPCTQHITWKGLLLTASLLNFWNPPTTAQVTIEAQPPPKVSEGKDVLLLVHNLPQNLTGYIWYKG QIRDLYHYVTSYVVDGQIIKYGPAYSGRETVYSNASLLIQNVTQEDTGSYTLHIIKRGDGTGGVTGRFTF TLYLETPKPSISSSNFNPREATEAVILTCDPETPDASYLWWMNGQSLPMTHSLQLSETNRTLYLFGVTNY TAGPYECEIRNPVSASRSDPVTLNLLPKLPKPYITINNLNPRENKDVSTFTCEPKSENYTYIWWLNGQSL PVSPRVKRRIENRILILPSVTRNETGPYQCEIRDRYGGIRSDPVTLNVLYGPDLPRIYPSFTYYHSGQNL YLSCFADSNPPAQYSWTINGKFQLSGQKLSIPQITTKHSGLYACSVRNSATGKESSKSVTVRVSDWTLP |
| 32 | TACCCTCAGAAGCTCCTATAC |
| 33 | cgtgagcgcttcgagatgttccg |
| 34 | cctaaccagctgcccaactgtag |
| 35 | ACAGAAGTGCTACAAGCCAGTGCTCGTGAACTAAGGAGAAAAAGAACAGACAAGGGAACAGCCTGGACAT GGCATCAGAGATCCACATGACAGGCCCAATGTGCCTCATTGAGAACACTAATGGGCGACTGATGGCGAAT CCAGAAGCTCTGAAGATCCTTTCTGCCATTACACAGCCTATGGTGGTGGTGGCAATTGTGGGCCTCTACC GCACAGGCAAATCCTACCTGATGAACAAGCTGGCTGGAAAGAAAAAGGGCTTCTCTCTGGGCTCCACGGT GCAGTCTCACACTAAAGGAATCTGGATGTGGTGTGTGCCCCACCCCAAGAAGCCAGGCCACATCCTAGTT CTGCTGGACACCGAGGGTCTGGGAGATGTAGAGAAGGGTGACAACCAGAATGACTCCTGGATCTTCGCCC TGGCCGTCCTCCTGAGCAGCACCTTCGTGTACAATAGCATAGGAACCATCAACCAGCAGGCTATGGACCA ACTGTACTATGTGACAGAGCTGACACATAGAATCCGATCAAAATCCTCACCTGATGAGAATGAGAATGAG GTTGAGGATTCAGCTGACTTTGTGAGCTTCTTCCCAGACTTTGTGTGGACACTGAGAGATTTCTCCCTGG ACTTGGAAGCAGATGGACAACCCCTCACACCAGATGGTACCTGACATACTCCCTGAAGCTGAAGAAAGG TACCAGTCAAAAGATGAAACTTTTAACCTGCCCAGACTCTGTATCCGGAAATTCTTCCCAAAGAAAAAA TGCTTTGTCTTTCATCGGCCCGTTCACCGCAGGAAGCTTGCCCAGCTCGAGAAACTACAAGATGAAGAGC TGGACCCCGAATTGTGCAACAAGTAGCAGACTTCTGTTCCTACATCTTTAGTAATTCCAAAACTAAAAC TCTTTCAGGAGGCATCCAGGTCAACGGGCCTCGTCTAGAGAGCCTGGTGCTGACCTACGTCAATGCCATC AGCAGTGGGGATCTGCCGTGCATGGAGAACGCAGTCCTGGCCTTGGCCCAGATAGAGAACTCAGCTGCAG TGCAAAAGCTATTGCCCACTATGAACAGCAGATGGGCCAGAAGGTGCAGCTGCCCACAGAAAGCCTCCA GGAGCTGCTGGACCTGCACAGGGACAGTGAGAGAGAGGCCATTGAAGTCTTCATCAGGAGTTCCTTCAAA GATGTGGACCATCTATTTCAAAAGGAGTTAGCGGCCCAGCTAGAAAAAAGCGGGATGACTTTTGTAAAC AGAATCAGGAAGCATCATCAGATCGTTGCTCAGGTTTACTTCAGGTCATTTTCAGTCCTCTAGAAGAAGA AGTGAAGGCGGGAATTTATTCGAAACCAGGGGCTATCGTCTCTTTGTTCAGAAGCTACAAGACCTGAAG AAAAAGTACTATGAGGAACCGAGGAAGGGGATACAGGCTGAAGAGATTCTGCAGACATACTTGAAATCCA AGGAGTCTATGACTGATGCAATTCTCCAGACAGACCAGACTCTCACAGAAAAAGAAAAGGAGATTGAAGT GGAACGTGTGAAAGCTGAGTCTGCACAGGCTTCAGCAAAAATGTTGCAGGAAATGCAAAGAAAGAATGAG CAGATGATGGAACAGAAGGAGAGGAGTTATCAGGAACACTTGAAACAACTGACTGAGAAGATGGAGAACG ACAGGGTCCAGTTGCTGAAAGAGCAAGAGAGGACCCTCGCTCTTAAACTTCAGGAACAGGAGCAACTACT AAAAGAGGGATTTCAAAAAGAAAGCAGAATAATGAAAAATGAGATACAGGATCTCCAGACGAAAATGAGA CGACGAAAGGCATGTACCATAAGCTAAAGACCCAGAGCCTTCCTGTCACCCCTAACCAAGGCATAATTGAA ACAATTTTAGAATTTGGAACAAGCGTCACTACATTTGATAATAATTAGATCTTGCATCATAACACCAAAA GTTTATAAAGGCATGTGGTACAATGATCAAAATCATGTTTTTCTTAAAAAAAAAAAAAGACTGTAAAT TGTGCAACAAAGATGCATTTACCTCTGTATCAACTCAGGAAATCTCATAAGCTGGTACCACTCAGGAGAA GTTTATTCTTCCAGATGACCAGCAGTAGACAAATGGATACTGAGCAGAGTCTTAGGTAAAAGTCTTGGGA AATATTTGGGCATTGGTCTGGCCAAGTCTACAATGTCCCAATATCAAGGACAACCACCCTAGCTTCTTAG TGAAGACAATGTACAGTTATCCATTAGATCAAGACTACACGGTCTATGAGCAATAATGTGATTTCTGGAC ATTGCCCATGTATAATCCTCACTGATGATTTCAAGCTAAAGCAAACCAACCACCTTATACAGAGATCTAGAATC TCTTTATGTTCTCCAGAGGAAGGTGGAAGAAACCATGGGCAGGAGTAGGAATTGACTGATAAACAATTGG GCTAATGAAGAAACTTCTCTTATTGTTCAGTTCATCCAGATTATAACTTCAATGGGACACTTTAGACCA TTAGACAATTGACACTGGATTAAACAAATTCACATAATGCCAAATACACAATGTATTTATAGCAACGTAT AATTTGCAAAGATGGACTTTAAAAGATGCTGTGTAACTAAACTGAAATAATTCAATTACTTATTATTTAG AATGTTAAAGCTTATGATAGTCTTTTCTAATTCTTAACACTCATACTTGAAATCTTTCCGAGTTTCCCCA GAAGAGAATATGGGATTTTTTTGACATTTTTGACCCATTTAATAATGCTCTTGTGTTTACCTAGTATAT GTAGACTTTGTCTTATGTGTCAAAAGTCCTAGGAAAGTGGTTGATGTTTCTTATAGCAATTAAAAATTAT TTTTGAACTGA |
| 36 | MASEIHMTGPMCLIENTKGRLMANPEALKILSAITQPMVVAIVGLYRTGKSYLMNKLAGKKKGFSLGST VQSHTKGIWMWCVPHPKKPGHILVLLDTEGLGDVEKGDNQNDSWIFALAVLLSSTFVYNSIGTINQQAMD QLYYVTELTHRIRSKSSPDENENEVEDSADFVSFFPDFVWTLRDFSLDLEADGQPLTPDEYLTYSLKLKK GTSQKDETFNLPRLCIRKFFPKKKCFVFDRPVHRRKLAQLEKLQDEELDPEFVQQVADFCSYIFSNSKTK TLSGGIQVNGPRLESLVLTYVNAISSGDLPCMENAVLALAQIENSAAVQKAIAHYEQQMGQKVQLPTESL QELLDLHRDSEREAIEVFIRSSFKDVDHLFQKELAAQLEKKRDDFCKQNQEASSDRCSGLLQVIFSPLEE EVKAGIYSKPGGYRLFVQKLQDLKKKYYEEPRKGIQAEEILQTYLKSKESMTDAILQTDQTLTEKEKEIE VERVKAESAQASARMLQEMQRKNEQMMEQKERSYQEHLKQLTEKMENDRVQLLKEQERTLALKLQEQEQL LKEGFQKESRIMKNEIQDLQTKMRRRKACTIS |
| 37 | AGGAGATTGAAGTGGAAC |
| 38 | TTGCTCCTGTTCCTGA |

FIG. 31G

| | |
|---|---|
| 39 | CTCCAGGCTGTGGAACCTTTGTTCTTTCACTCTTTGCAATAAATCTTGCTGCTGCTCACTCTTTGGGTCC<br>ACACTGCCTTTATGAGCTGTAACACTCACTGGGAATGTCTGCAGCTTCACTCCTGAAGCCAGCCAGACCA<br>CGAACCCACCAGCAGGAACAAACAACTCCAGACGCGCAGCCTTAAGAGCTGTAACACTCACCGCGAAGGT<br>CTGCAGCTTCACTCCTGAGCCAGCCAGACCACGAACCCACCAGAAGGAAGAAACTCCAAACACATCCGAA<br>CATCAGAAGGAGCAAACTCCTGACACGCCACCTTTAAGAACCGTGACACTCAACGCTAGGGTCCGCGGCT<br>TCATTCTTGAAGTCAGTGAGACCAAGAACCCACCAATTCCGGACACGCTAATTGTTGTAGATCATCACTT<br>CAAGGTGCCCATATCTTTCTAGTGGAAAAATTATTCTGGCCTCCGCTGCATACAAATCAGGCAACCAGAA<br>TTCTACATATATAAGGCAAAGTAACATCCTAGACATGGCTTTAGAGATCCACATGTCAGACCCCATGTGC<br>CTCATCGAGAACTTTAATGAGCAGCTGAAGGTTAATCAGGAAGCTTTGGAGATCCTGTCTGCCATTACGC<br>AACCTGTAGTTGTGGTAGCGATTGTGGGCCTCTATCGCACTGGCAAATCCTACCTGATGAACAAGCTGGC<br>TGGGAAGAACAAGGGCTTCTCTGTTGCATCTACGGTGCAGTCTCACACCAAGGGAATTTGGATATGGTGT<br>GTGCCTCATCCCAACTGGCCAAATCACACATTAGTTCTGCTTGACACCGAGGGCCTGGGAGATGTAGAGA<br>AGGCTGACAACAAGAATGATATCCAGATCTTTGCACTGGCACTCTTACTGAGCAGCACCTTTGTGTACAA<br>TACTGTGAACAAAATTGATCAGGGTGCTATCGACCTACTGCACAATGTGACAGAACTGACAGATCTGCTC<br>AAGGCAAGAAACTCACCCGACCTTGACAGGGTTGAAGATCCTGCTGACTCTGCGAGCTTCTTCCCAGACT<br>TAGTGTGGACTCTGAGAGATTTCTGCTTAGGCCTGGAAATAGATGGGCAACTTGTCACACCAGATGAATA<br>CCTGGAGAATTCCCTAAGGCCAAAGCAAGGTAGTGATCAAAGAGTTCAAAATTTCAATTTGCCCCGTCTG<br>TGTATACAGAAGTTCTTTCCAAAAAAGAAATGCTTTATCTTTGACTTACCTGCTCACCAAAAAAAGCTTG<br>CCCAACTTGAAACACTGCCTGATGATGAGCTAGAGCCTGAATTTGTGCAACAAGTGACAGAATTCTGTTC<br>CTACATCTTTAGCCATTCTATGACCAAGACTCTTCCAGGTGGCATCATGGTCAATGGATCTCGTCTAAAG<br>AACCTGGTGCTGACCTATGTCAATGCCATCAGCAGTGGGGATCTGCCTTGCATAGAGAATGCAGTCCTGG<br>CCTTGGCTCAGAGAGAGAACTCAGCTGCAGTGCAAAAGGCCATTGCCCACTATGACCAGCAAATGGGCCA<br>GAAAGTGCAGCTGCCCATGGAAACCCTCCAGGGAGCTGCTGGACCTGCACAGGACCAGTGAGAGGGAGGCC<br>ATTGAAGTCTTCATGAAAAACTCTTTCAAGGATGTAGACCAAAGTTTCCAGAAAGAATTGGAGACTCTAC<br>TAGATGCAAAACAGAATGACATTTGTAAACGGAACCTGGAAGCATCCTCGGATTATTGCTCGGCTTTACT<br>TAAGGATATTTTTGGTCCTCTAGAAGAAGCAGTGAACCAGGGCAATTTATTCTAAGCCAGGAGCCCATAAT<br>CTCTTCATTCAGAAAACAGAAGAACTGAAGGCAAAGTACTATCGGGAGCCTCGGAAAGGAATACAGGCTG<br>AAGAAGTTCTGCAGAAATATTTAAAGTCCAAGGAGTCTGTGAGTCATGCAATATTACAGACTGACCAGGC<br>TCTCACAGAGACCGAAAAAAAGAAGAAAGCTGAAGCTGAAGCAAGTGAAAAGCTGAAAAGGCTGAAGCGCAA<br>AGGTTGGCGGCGATTCAAAGGCAGAACGAGCAAATGATGCAGGAGAGGGAGAGACTCCATCAGGAACAAG<br>TGAGACAAATGGAGATAGCCAAACAAAATTGGCTGGCAGAGCAACAGAAAATGCAGGAACAACAGATGCA<br>GGAACAGGCTGCACAGCTCAGCACAACATTCCAAGCTCAAAATAGAAGCCTTCTCAGTGAGCTCCAGCAC<br>GCCCAGAGGACTGTTAATAACGATGATCCATGTGTTTTACTCTAAAGTGCTAAATATGGGAGTTTCCTTT<br>TTTTACTCTTTGTCACTGATGACACAACAGAAAAGAAACTGTAGACCTTGGGACAATCAACATTTAAATA |
| 40 | MALEIHMSDPMCLIENFNEQLKVNQEALEILSAITQPVVVAIVGLYRTGKSYLMNKLAGKNKGFSVAST<br>VQSHTKGIWIWCVPHPNWPNHTLVLLDTEGLGDVEKADNKNDIQIFALALLLSSTFVYNTVNKIDQGAID<br>LLHNVTELTDLLKARNSPDLDRVEDPADSASFFPDLVWTLRDFCLGLEIDGQLVTPDEYLENSLRPKQGS<br>DQRVQNFNLPRLCIQKFFPKKKCFIFDLPAHQKKLAQLETLPDDELEPEFVQQVTEFCSYIFSHSMTKTL<br>PGGIMVNGSRLKNLVLTYVNAISSGDLPCIENAVLALAQRENSAAVQKAIAHYDQQMGQKVQLPMETLQE<br>LLDLHRTSEREAIEVFMKNSFKDVDQSFQKELETLLDAKQNDICKRNLEASSDYCSALLKDIFGPLEEAV<br>KQGIYSKPGGHNLFIQKTEELKAKYYREPRKGIQAEEVLQKYLKSKESVSHAILQTDQALTETEKKKEA<br>QVKAEAEKAEAQRLAAIQRQNEQMMQERERLHQEQVRQMEIAKQNWLAEQQKMQEQQMQEQAAQLSTTFQ<br>AQNRSLLSELQHAQRTVNNDDPCVLL |
| 41 | GGACCGCCGCCTGGTTAAAGGCGCTTATTTCCCAGGCAGCCGCTGCAGTCGCCACACCTTTGCCCCTGCT<br>GCGATGACCCTGTCGCCACTTCTGCTGTTCCTGCCACCGCTGCTGCTGCTGGACGTCCCCACGGCGG<br>CGGTGCAGGCGTCCCCTCTGCAAGCGTTAGACTTCCTTTGGGAATGGGCCACCAGTTAACTACAAGACAGG<br>CAATCTATACCTCCGGGGCCCCTGAAGAAGTCCAATGCACCGCTTGTCAATGTGACCCTCTACTATGAA<br>GCACTGTGCGGTGGCTGCCGAGCCTTCCTGATCCGGGAGCTCTTCCCAACATGGCTGTTGGTCATGGAGA<br>TCCTCAATGTCACGCTGGTGCCCTACGGAAACGCACAGGAACAAAATGTCAGTGGCAGGTGGGAGTTCAA<br>GTGCCAGCATGGAGAAGAGGAGTGCAAATTCAACAAGTGGAGGCCTGCGTGTTGGATGAACTTGACATG<br>GAGCTAGCCTTCCTGACCATTGTCTGCATGGAAGAGTTTGAGGACATGGAGAGAAGTCTGCCACTATGCC<br>TGCAGCTCTACCCCCAGGGCTGTCGCCAGACACTATCATGGAGTGTGCAATGGGGACCGCGGCATGCA<br>GCTCATGCACGCCAACGCCCAGCGGACAGATGCTCTCCAGCCACCACACGAGTATGTGCCCTGGGTCACC<br>GTCAATGGGAAACCCTTGGAAGATCAGACCCAGCTCCTTACCCTTGTCTGCCAGTTGTACCAGGGCAAGA<br>AGCCGGATGTCTGCCCTTCCTCAACCAGCTCCCTCGGAGTGTTTGCTTCAAGTGATGGCCGGTGAGCTG<br>CGGAGAGCTCATGGAAGGCGAGTGGGAACCCGGCTGCCTGCCTTTTTTTCTGATCCAGACCCTCGGCACC<br>TGCTACTTACCAACTGGAAAATTTTATGCATCCCATGAAGCCCAGATACACAAAATTCCACCCCATGATC<br>AAGAATCCTGCTCCACTAAGAATGGTGCTAAAGTAAAACTAGTTTAATAAGCAAAAAAAAAAAAAAAAAA<br>A |

FIG. 31H

| | |
|---|---|
| 42 | MTLSPLLLFLPPLLLLLDVPTAAVQASPLQALDFFGNGPPVNYKTGNLYLRGPLKKSNAPLVNVTLYYEA LCGGCRAFLIRELFPTWLLVMEILNVTLVPYGNAQEQNVSGRWEFKCQHGEEECKFNKVEACVLDELDME LAFLTIVCMEEFEDMERSLPLCLQLYAPGLSPDTIMECAMGDRGMQLMHANAQRTDALQPPHEYVPWVTV NGKPLEDQTQLLTLVCQLYQGKKPDVCPSSTSSLRSVCFK |
| 43 | CTACAAGACAGGCAATC |
| 44 | TTCATCCAACACGCAGG |
| 45 | GGTTGCTAAGGAGTGGGTGCCTCAGAATCAGGCTGCAATGGGCATTGTCTGTGCACAATGTTCCTTTATT CTGCTGCTGTCCATAATAAGGGCTCGTCCACCTCCCTTCCTCTTCTGCCCATTGAGCAGTCAAAGAACTG AAAGTCCTTATAAGCCTGTGCACCTGGGCCTGGGCCCTACAGATAAGGTAGCTGCTATTGCTATGGCCCG CATCATTGACCTGGTGCCCTGGGACGATGGCTCCACACATGTGTATGCCTCCCCGGCCATCCTGCTTCCC ATGGAGCGGCAGCGCAACCAGCTGGCGGGCGTGAAGCAGCAGCTCTACCACCCAGCCCTGCCCACCCTGC GCCACATGGACAGGGACACCGTCAAGGCCTGCCTTCCTGATGAGCACTGCCAGTCCACCACCTACTGCCG CAAAGATGAATTTGACAACGCCCATTTTACACTCCTTGGGGTCCCCAACAAACCCTGCAGTGTTTGGAC ATCACCGCCACAGGCCAGAAGCTTCGCAACAGGTACCACGAGGGAAAGCTGGCGCCCATCGCGCCAGGCA TCAACCGAGTGGACTGGCCCTGCTTCACCCGCGCCCATCGAGGACTGGTCCCACTTCGTGTCCTCCGCCGG GGAGTTCAAGCTGCCTTGCCTGAGGAAGCGAGCGGAGGGTCTCAGCGGCTACGCGGTGCGGTACTTGAAG CCCGACGTGACCCAGACCTGGCGGTACTGCCTCAACCAGAACCCCAGCCTGGACCGCTACGGACAGAAGC CCCTGCCTTTCGACTCCCTGAACACTTTCCGAAGCTTCGGCTCCAGCTACAGTCGTGTCAACTACCTGAC CCCCTGGCATTAATCTCTGGAAAGGAGGCTGACTC |
| 46 | MGIVCAQCSFILLLSIIRARPPPFLFCPLSSQRTESPYKPVHLGLGPTDKVAAIAMARIIDLVPWDDGST HVYASPAILLPMERQRNQLAGVKQQLYHPALPTLRHMDRDTVKACLPDEHCQSTTYCRKDEFDNAHFTLL GVPNKPLQCLDITATGQKLRNRYHEGKLAPIAPGINRVDWPCFTRAIEDWSHFVSSAGEFKLPCLRKRAE GLSGYAVRYLKPDVTQTWRYCLNQNPSLDRYGQKPLPFDSLNTFRSFGSSYSRVNYLTPWH |
| 47 | TCCACCACCTACTGCCGCAAAG |
| 48 | ACCCTCCGCTCGCTTCCTCA |
| 49 | GGTTGCTAAGGAGTGGGTGCCTCAGAATCAGGCTGCAATGGGCATTGTCTGTGCACAATGTTCCTTTATT CTGCTGCTGTCCATAATAAGGGCTCGTCCACCTCCCTTCCTCTTCTGCCCATTGAGCAGTCAAAGAACTG AAAGTCCTTATAAGCCTGTGCACCTGGGCCTGGGCCCTACAGATAAGGTAGCTGCTATTGCTATGGCCCG CATCATTGACCTGGTGCCCTGGGACGATGGCTCCACACATGTGTATGCCTCCCCGGCCATCCTGCTTCCC ATGGAGCGGCAGCGCAACCAGCTGGCGGGCGTGAAGCAGCAGCTCTACCACCCAGCCCTGCCCACCCTGC GCCACATGGACAGGGACACCGTCAAGGCCTGCCTTCCTGATGAGCACTGCCAGTCCACCACCTACTGCCG CAAAGATGAATTTGACAACGCCCATTTTACACTCCTTGGGGTCCCCAACAAACCCTGCAGTGTTTGGAC ATCACCGCCACAGGCCAGAAGCTTCGCAACAGGTACCACGAGGGAAAGCTGGCGCCCATCGCGCCAGGCA TCAACCGAGTGGACTGGCCCTGCTTCACGCGCGCCATCGAGGACTGGTCCCACTTCGTGTCCTCCGGCCGG GGAGTTCAAGCTGCCTTGCCTGAGGAAGCCAGCGGAGGGTCTCAGCGGCTACGCGGTGCGGTACTTGAAG CCCGACGTGACCCAGACCTGGCGGCAGGAAGCCCTGTGTGGGGCGTGGGCAGGGCGTCCGTGCTCCCCCG ACTCACCGCGCCCCTATCCCTGCTGCCCGCCTCAGTACTGCCTCAACCAGAACCCCAGCCTGGACCGCTA CGGACAGAAGCCCCTGCCTTTCGACTCCCTGAACACTTTCCGAAGCTTCGGCTCCAGCTACAGTCGTGTC AACTACCTGACCCCCTGGCATTAATCTCTGGAAAGGAGGCTGACTC |
| 50 | MGIVCAQCSFILLLSIIRARPPPFLFCPLSSQRTESPYKPVHLGLGPTDKVAAIAMARIIDLVPWDDGST HVYASPAILLPMERQRNQLAGVKQQLYHPALPTLRHMDRDTVKACLPDEHCQSTTYCRKDEFDNAHFTLL GVPNKPLQCLDITATGQKLRNRYHEGKLAPIAPGINRVDWPCFTRAIEDWSHFVSSAGEFKLPCLRKRAE GLSGYAVRYLKPDVTQTWRQEALCGAWAGRPCSPDSPRPYPCCPPQYCLNQNPSLDRYGQKPLPFDSLNT FRSFGSSYSRVNYLTPWH |
| 51 | CSKDSRGIADPNQSAK |
| 52 | CEEDSKIKGIHDE |
| 53 | CKLRNRIWGMVN |
| 54 | RYRKCIKLKQVQSPPTETLGVENKGYFGDEQQIRTEPILPEIHFLNKPASKDSRGIADPNQSAK |
| 55 | MLPGCIFLMILLIPQVKEKFILGVEGQQLVRPKKLPLIQKRDTGHTHDDDILKTYEEELLYEIK LNRKTLVLHLLRSREFLGSNYSETFYSMKGEAFTRHPQIMDHCFYQGSIVHEYDSAASISTCNG LRGFFRINDQRYLIEPVKYSDEGEHLVFKYNLRVPYGANYSCTELNFTRKTVPGDNESEEDSKI KGIHDEKYVELFIVADDTVYRRNGHPHNKLRNRIWGMVNFVNMIYKTLNIHVTLVGIEIWTHED KIELYSNIETTLLRFSFWQEKILKTRKDFDHVVLLSGKWLYSHVQGISYPGGMCLPYYSTSIIK DLLPDTNIIANRMAHQLGHNLGMQHDEFPCTCPSGKCVMDSDGSIPALKFSKCSQNQYHQYLKD YKPTCMLNIPFPYNFHDFQFCGNKKLDEGEECDCGPAQECTNPCCDAHTCVLKPGFTCAEGECC ESCQIKKAGSICRPAKDECDFPEMCTGHSPACPKDQFRVNGFPCKNSEGYCFMGKCPTREDQCS ELFDDDAIESHDICYKMNTKGNKFGYCKNKENRFLPCEEKDVRCGKIYCTGGELSSLLGEDKTY HLKDPQKNATVKCKTIFLYHDSTDIGLVASGTKCGEGMVCNNGECLNMEKVYISTNCPSQCNEN PVDGHGLQCHCEEGQAPVACEETLHVT |

FIG. 31I

| 56 | ISTNCPSQCNENPVDGHGLQCHCEEGQAPVACEETLHVT |
|---|---|
| 57 | ISTNCPSQCNENPVDGHGLQCHCEEGQAPVACEETLHVTNITILVVVLVLVIVGIGVLILLV |
| 58 | APQKSPWLTKPC |
| 59 | CPLQPSHFLDISED |
| 60 | CIYSTEIHYSSK |
| 61 | GCAGCCTCACTGTCCTGTCTTGAACATCCTCCACCAAAGTGTGAACACAGGTGGCATGGGCTTC<br>GTAACGAATAAGAGCGCCTTCAAAGCAGGAGATTCCCTGTACCTGCGAAGGGCCTTCGTGAACA<br>ACCTTGGAGGAGGAAAGGGAGAACCAGGATTCAGATCCAAAGCATCCAGAAGGCTTTAGACATCCA<br>GATCAGGCAGATTGATAGAGAAAAAGCAGCCCTGAAGGATTTTTGGTAAAGCTTCACAAGACA<br>ACTGGCTATTTTCCTCAAAAGCCATTGTGGTGACTGATGCTGTGCCACCATAGGGGACGAGTTC<br>ATCTGAAACATCCAATACAGACAGAACACACCTGGGTCTCCTTCTGTATCTCTCTGTGACCCAA<br>GAAAGCACTAGAAGTGGCTACTGGCACAAGCCCAAAAAGAAAAAAAAGGACTACATAATTGAGG<br>ACACAAATGGACTGCCTCTAAAATAATAAACAAAACCTCCTACAAAAGAGAG |
| 62 | atgcggctgatgggccccctgagcctgagagtagggatgaccctggaagcggcgctagtg<br>ctgatccgcaggtccccgcgctcccgccagagccgcgaccccggcttgtgccacccagctt<br>cggggcctgcaggagcgctgcttctctgagcctgagtctgggaccctctttgcagtgt<br>ggctgtgggggcgctggtcccatcacggccttttcataaagcacatggtgccaactgtt<br>agtgatctaccatcctggaggatgatagccctcttctaacagctccactaggcagtgcc<br>ccagtagggactctgtgtaggcgcctcacccacatttccttccacactgccctagca<br>gaggttctccatgacggcgctgcccctgcagcaaacttctgcctggacatccaggaaccg<br>ccccagtggtcagctgccgcgctgttgctaggcaacagcgtgcgagctcagatcagcgtg<br>gggtggaggagaagtggagtttggaagttcagggcgcaggggcacaggcccacgactgc<br>agcgggatggaccactactgcatcctggccgcatcggggaggcgccacggcatcgtc<br>ttcaaggccaagcacgtggagccgagggtgggctggcagtgtctgccttctatcctgcag<br>actgcgagatagttgccctcaagaaggtggccctaaggcggttggaggacggcttccct<br>aaccaggccctgcgcgagattaaggctctgcaggagatggaggacaatcagtatgtggta<br>caactgaaggctgtcttcccacacggtggaggctttgtgctggcctttgagttcatgctg<br>tcggatctggccgacgtggtgcgcgcatgcccagagccgcctaggcacaggtcaag<br>agctacctgcagatctgctcaaggtgtcgccttctgccatgccaacaacattgtacat<br>cgggacctgaaacctgccaacctgctcatcagcgcctcaggccagctcaagatagcggac<br>tttggcctggctcgagtcttttcccccagacggcagccgcctctacacacaccaggtggcc<br>accaggtggtaccgagccccgagctcctgtatggtgcccgccagtatgaccagggcgtc<br>gatctgtggtctgtcggctgcatcatggggagctgttgaatgggtcccccttttcccg<br>ggcaagaacgatattgaacagctttgctatgtgcttcgcatcttgggcaccccaaaccct<br>caagtctggccggagctcactgagctgccggactacaacaagatctcctttaaggagcag<br>gtgcccatgccctggaggaggtgctgcctgacgtctctcccaggcattggatctgctg<br>ggtcaattccttctctaccctcctcaccagcgcatcgcagcttccaagctgtgggagccc<br>caggagagaggcaaggccgactttggggtcaagcaaagcttcctggtggagggcaggttt<br>aagcatgagatgtttgaggaggtgttcgctgaagagagaaatgctccctgcctgccat<br>ccatctgagctgccgattcctcagcgtctaggggacctgcccaaggccatccaggg<br>cccccccacatccatgacttccacgtggaccggcctcttgaggagtcgctgttgaaccca<br>gagctgattcggccccttcatcctggagggccccttgcgagggttggtctcgaggcagaggt<br>catgttcccagccaagagtatgagaacatccagtcgagcagaggagattcatggcctgtg<br>ctcgtttcactgacctgcatgttctggaaggagccaggacagcagctaccccgcaagct<br>gcccagaagccccggatggcccctcagccagctgaaaccaccgtccactggaagatggc<br>tacttggaggcctctggaggggagggggttgttcacgaaggccttcgcaggtacaggga<br>atctcctgctttgaaggcgctcttattcgttacgaagccatgccacctgtgttcacact<br>ttggtggagatgttcaagacaggacacatctactggccctcctaaagcctttgcctgg<br>ctgctcctgcaagagcatgcacaaagcacagcctccactgccttgcctgggaacactttg<br>gctccccagcacagccaatgctcaactcaacaggacaaagctgcaggccagtcccaaa<br>ccgccagggtgtgagaatatagctcaggagtattga |
| 63 | MRLMGPLSLRVGMTLEAALVLIRRSPRSRQSRDPACATQLRGLQGALLLSLSLGPSLQCGCGGAG<br>PITAFFIKHMVPTVSGSTILEDDSPLLTAPLGSAPVGTLCRRPHPTFPFHTALAEVLHEGAAPAAN<br>FCLDIQEFPQWSAAALLLGNSVRAQISVCWRRSCVWKFRGTCAQAHDCSCMDQYCILCRIGECAHC<br>IVFKAKHVEPRVGWQCLPSILQTGEIVALKKVALRRLEDGFPNQALREIKALQEMEDNQYVVQLKA<br>VFPHGGGFVLAFEFMLSDLAEVVRHAQRPLAQAQVKSYLQMLLKGVAFCHANNIVHRDLKPANLLI<br>SASGQLKIADFGLARVFSPDGSRLYTHQVATRWYRAPELLYGARQYDQGVDLWSVGCIMGELLNGS<br>PLFPGKNDIEQLCYVLRILGTPNPQVWPELTELPDYNKISFKEQVPMPLEEVLPDVSPQALDLLGQ<br>FLLYPPHQRIAASKLWEPQERGKADFGVKQSFLVEGRFKHEMFEEVFAEERNAPLPAHPSELPIPQ<br>RLGGPAPKAHPGPPHIHDFHVDRPLEESLLNPELIRPFILEGPCEGWSRGRGHVPSQEYENIQSSR<br>GDSWPV |

FIG. 31J

| | |
|---|---|
| | LVSLTCMFWKEPGQQPTFQAAQKPRMAPQPAETTVHWEDGYLEASGGEGVVHEGPSQVQG<br>ISCFEGALIRYEAHATCVHTLVEDVQDRTHLLAPPKAFAWLLLQEHAQSTASTALPGNTL<br>APPAQPMLNSTGQSCRPSPKPPGCENIAQEY |
| 64 | TCAGACCGACAGTCAGGCAGAAGCAGGGCCCCCGGTCTGTCTAGGCTTCAGGATGCCTAA<br>GAAGCTCTCGGTGGGCAGCCAGTGCTCCAGAACCAGGGGGTTGTTGTGGGCAGGTCTCTG<br>GGGAGGCCTGAGGGGCCACACGGTGTCCTGGGTGTGGGGTCTGCATCTACATACGACTCA<br>TAGGCACCTGCCATTGGGGCGATTTGTGATGCTTTAGGGAAACAGGGGTCTGCCCCTTGGAT<br>GGGCTGGCCTACAGTCAGGGGCCTTCCTTGTCTGTCTTACTTTCCCCGCTCTGCCAGAGT<br>GAACCCAAGGATGCCGCCAGCCTCACCCCAGTGGGTGGCAGTTACGCCGGCATGGAACTC<br>AGACTCACCGGCACGCATGACTTCCAACCGTCCACACATCTTTGCACCCACAGTATCTGC<br>TTCAGAGAATGTATTCTAAATAATAAAAATCATAA |
| 65 | CCCACTTTGCTGGATGAAGCTCTGTGAAC<br>TCTTCCTGGTTCTTAGTACTGCCTAATTCATGAATCCTTCTTTGCTCAAATGAACTCAAA<br>GTTAATTTAAAGTTTTTATTCTAACATGAGACTCTTTCTCCCATGAGACTTTGCATGAGG<br>GAGAACAGTCGCTAATTAACAGCCAGTTCTTGAAATCACGCAGTCCTGAAATCCAGCTGA<br>TGCTGCTCAGCAGAGAAGCAGATGTTTGGAGGTTAAAACAAAGTCACAAGTCTGACCCAC<br>ACTCAAAGGGAGAAGATTATGCAAGAGCAAAAGCACGAGATGGAAACCATGGGCCATCT<br>TATAGTCTGTCTGCCGGAGAAAGATGAACACAAATCCTCGTGCAGAAAAGTGTGACACTA<br>AAAGAACCAACCTGATACTACTATCCTTAGAAAAGCCTGCATACAAGGTTGGCTGTCATC<br>TGGGAATGTAGGTGATCAAGAGTTCTCTCCACTGACATAAACTTTGTTTAAATAATAAGG<br>ATGACTCATTGTGACTAGACTATGCAAATAATGGGATGTGTGTTAAACATCTCCTTTCCT<br>TCTGGGAGTCTGGAATTTTGGTGTATGCTAAACAGTGGGTGCCTGCAAGACCAGCCTCAA<br>ATAAAAACCCTGGGCACTGAGTCTCTAAAAAGACTCCCAGTAGGCAATATTTCACACGTG<br>TTCTCACAAACTTACTGCTGGAGGAATTATGCACGCCTTGCATGACTCTATTGGAAA |
| 66 | GCACGAGAGATGTTAT<br>AATAATTTTCAAAAGAAGGTAAAATCATGACTCATATGGATATAAAAATGAACACCTTGT<br>TATGGATTGAACTGTGTGCCCCTAAAAGATATGTTGAAGCCTGAACTCCCAGTACCTGAG<br>AATGTGACCATGTTTGGAAATAGTGTCTTTGCAGGTTTAATCAAGTTAAGATGAGGTCAT<br>TAGATGGGACCTAATTTAATATGGCTGATGCCCTTATAAGAAGAGGGAATTTTGGACACA<br>GACATACAAGGAGGACGCCATGTGAAGACACAGTTGGAAAAGCAGGGAAGAGATGGCCTT<br>GTGTATAAGGAGGCAGAGACTGGAGTTATGCTGCCACAAGCCAAGGAACAACTGGGGCTA<br>CCTGAGCTGGAAGAGGCGAGGAAGGATTCTCCCCTAGAGGGTTCTGAGGGAGCGTGGACC<br>TGCCAACAACTTGGTTTCAGATTTCTAGTCTCCAGAACTATGCAGTAATAAATTTCTGTT<br>GTTTTAAGCCACCCAGTTTGTGGCACTTTGTTACGTCAGCCCTGTGAAACAAACAAACAA<br>ACAAACAAAAACAAGTTAAATATTTTATTTAACTCATAATATGGAAATAGGTGAGGTGT<br>TACAACCAATTCAAAAAAGAAGTGAAAAATAAGCCCAAATGTATATAGAGTAAAGGAATG<br>TTGAAATGAATGTGCAAATGGAAGCAAAACTAGATTCTCCTACAATGGGACAGAAAAGTC<br>AATTGAACCTCTACTGGACAGAACATAATTTGCATGTGTATAGAAA |
| 67 | GCACCAGGTTTCTGGTAAGGGGCAATTTTGTGTTTGCCTGTTCTTTGGGAATATCACCTG<br>GAGATAGATGGATTCCCAGACCCACCCAAATCTAGGTTTTAGACCAAAAAAGAATGTTTTA<br>TTATTAGAATTCAGTATATCTCAGGTCCTCTTTCATTACTACAACACAAAATAAATCTGG<br>GGGCCAGGAACGGTGGCTCACACCTGTAATCCCAGAGTGCTAGGATTACAAGCAACAAGC<br>ATGAGCTACCACGCTCGGCCTATGCATCTCAGTCTTAAATTTTCTTCTAGGTGGATTTAG<br>GGGTTTGTGCTCGTGGCCCTAAAAATGAACATGAGAAAGGCAGGGAGTACCTGCTTAGTT<br>GCAATAGGCCTTGTTTAGGCTAAAAATAAGCTCGATACCTGTATTTTATATACTGTAAAG<br>AGCATTAACCATAACCTGCCTGCAACAGCCTCTGTAGGTAGAAACAATTATGGAGGTGTC<br>AAGTAAGAATAAAGAGCTGATAACATCAAAAAAAAAAAAAAAAA |
| 68 | APQKSPWLTKP |
| 69 | PLQPSHFLDISED |
| 70 | r(CCAUGAGAGUAGCCAGCAA)dTdT |
| 71 | r(UUGCUGGCUACUCUCAUGG)dAdG |
| 72 | r(GGUUCAGGACAAAGUCCAA)dTdT |
| 73 | r(UUGGACUUUGUCCUGAACC)dGdG |

SEQUENCE LISTING

<160> NUMBER OF SEQ ID NOS: 73

<210> SEQ ID NO 1
<211> LENGTH: 1126
<212> TYPE: DNA
<213> ORGANISM: Homo sapiens

<400> SEQUENCE: 1

```
atatatcaga ccatcagaag gatttgtata aagagtgact ctcctatgaa ggtaaaggcc      60
acccctcttc agttccagtg actgagatac atttttccaa tcctgggggc aaatacagac     120
acagcaagtt ccttcttccc tttggaaatt tggcagctgc cttcaccagt gagcacaaag     180
ccacatttca aaggaaactg acaaattatc cccagctgcc agaagaagaa atcctcactg     240
gacggcttcc tgtttcctgt ggttcattat ctgattggct gcagggatga aagtttttaa     300
gttcatagga ctgatgatcc tcctcacctc tgcgttttca gccggttcag gacaaagtcc     360
aatgactgtg ctgtgctcca tagactggtt catggtcaca gtgcacccct tcatgctaaa     420
caacgatgtg tgtgtacact ttcatgaact acacttgggc ctgggttgcc ccccaaacca     480
tgttcagcca cacgcctacc agttcaccta ccgtgttact gaatgtggca tcagggccaa     540
agctgtctct caggacatgg ttatctacag cactgagata cactactctt ctaagggcac     600
gccatctaag tttgtgatcc cagtgtcatg tgctgccccc caaaagtccc catggctcac     660
caagccctgc tccatgagag tagccagcaa gagcagggcc acagcccaga aggatgagaa     720
atgctacgag gtgttcagct tgtcacagtc cagtcaaagg cccaactgcg attgtccacc     780
ttgtgtcttc agtgaagaag agcataccca ggtcccttgt caccaagcag gggctcagga     840
ggctcaacct ctgcagccat ctcactttct tgatatttct gaggattggt ctcttcacac     900
agatgatatg attgggtcca tgtgatcctc aggtttgggg tctcctgaag atgctatttc     960
tagaattagt atatagtgta caaatgtctg acaaataagt gctcttgtga ccctcatgtg    1020
agcactttg agaaagagaa acctatagca acttcatgaa ttaagccttt ttctatattt    1080
ttatattcat gtgtaaacaa aaaataaaat aaaattctga tcgcat                  1126
```

<210> SEQ ID NO 2
<211> LENGTH: 212
<212> TYPE: PRT

<213> ORGANISM: Homo sapiens

<400> SEQUENCE: 2

Met Lys Val Phe Lys Phe Ile Gly Leu Met Ile Leu Leu Thr Ser Ala
1               5                   10                  15

Phe Ser Ala Gly Ser Gly Gln Ser Pro Met Thr Val Leu Cys Ser Ile
            20                  25                  30

Asp Trp Phe Met Val Thr Val His Pro Phe Met Leu Asn Asn Asp Val
        35                  40                  45

Cys Val His Phe His Glu Leu His Leu Gly Leu Gly Cys Pro Pro Asn
50                  55                  60

His Val Gln Pro His Ala Tyr Gln Phe Thr Tyr Arg Val Thr Glu Cys
65                  70                  75                  80

Gly Ile Arg Ala Lys Ala Val Ser Gln Asp Met Val Ile Tyr Ser Thr
                85                  90                  95

Glu Ile His Tyr Ser Ser Lys Gly Thr Pro Ser Lys Phe Val Ile Pro
            100                 105                 110

Val Ser Cys Ala Ala Pro Gln Lys Ser Pro Trp Leu Thr Lys Pro Cys
        115                 120                 125

Ser Met Arg Val Ala Ser Lys Ser Arg Ala Thr Ala Gln Lys Asp Glu
130                 135                 140

Lys Cys Tyr Glu Val Phe Ser Leu Ser Gln Ser Ser Gln Arg Pro Asn
145                 150                 155                 160

Cys Asp Cys Pro Pro Cys Val Phe Ser Glu Glu His Thr Gln Val
                165                 170                 175

Pro Cys His Gln Ala Gly Ala Gln Glu Ala Gln Pro Leu Gln Pro Ser
            180                 185                 190

His Phe Leu Asp Ile Ser Glu Asp Trp Ser Leu His Thr Asp Asp Met
        195                 200                 205

Ile Gly Ser Met
    210

<210> SEQ ID NO 3
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 3
aaatttggca gctgccttca c                                             21

<210> SEQ ID NO 4
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 4
tgatgccaca ttcagtaaca c                                             21

<210> SEQ ID NO 5
<211> LENGTH: 2582
<212> TYPE: DNA
<213> ORGANISM: Homo sapiens

<400> SEQUENCE: 5

```
atccctgcag tggaagtgag gaggaagaaa ggtgaactcc ttttctcaag cacttctgct      60
ctcctctacc agaatcactc agaatgcttc ccgggtgtat attcttgatg attttactca     120
ttcctcaggt taaagaaaag ttcatccttg gagtagaggg tcaacaactg gttcgtccta     180
aaaagcttcc tctgatacag aagcgagata ctggacacac ccatgatgat gacatactga     240
aaacgtatga agaagaattg ttgtatgaaa taaaactaaa tagaaaaacc ttagtccttc     300
atcttctaag atccagggag ttcctaggct caaattacag tgaaacattc tactccatga     360
aaggagaagc gttcaccagg catcctcaga tcatggatca ttgttttttac caaggatcca     420 tagtacacga atatgattca gctgccagta tcagtacgtg taatggtcta agggattct     480 tcagaataaa cgaccaaaga tacctcattg aaccagtgaa atactcagat gagggagaac     540
atttggtgtt caaatataac ctgagggtgc cgtatggtgc caattattcc tgtacagagc     600
ttaattttac cagaaaaact gttccagggg ataatgaatc tgaagaagac tccaaaataa     660
aaggcatcca tgatgaaaag tatgttgaat tgttcattgt tgctgatgat actgtgtatc     720
gcagaaatgg tcatcctcac aataaactaa ggaaccgaat ttggggaatg gtcaattttg     780
tcaacatgat ttataaaacc ttaaacatcc atgtgacgtt ggttggcatt gaaatatgga     840
cacatgaaga taaaatagaa ctatattcaa atatagaaac taccttattg cgttttttcat     900 tttggcaaga aaagatcctt aaaacacgga aggattttga tcatgttgta ttactcagtg     960
ggaagtggct ctactcacat gtgcaaggaa tttcttatcc aggggggtatg tgcctgccct    1020 attattccac cagtatcatt aaggatcttt tacctgacac aaacataatt gcaaacagaa    1080
tggcacatca actggggcat aaccttggga tgcagcatga cgagttccca tgcacctgtc    1140
cttcaggaaa atgcgtgatg gacagtgatg gaagcattcc tgcactgaaa ttcagtaaat    1200
gcagccaaaa ccaataccac cagtacttga aggattataa gccaacatgc atgctcaaca    1260
ttccatttcc ttacaatttt catgatttcc aattttgtgg aaacaagaag ttggatgagg    1320
gtgaagagtg tgactgtggc cctgctcagg agtgtactaa tccttgctgt gatgcacaca    1380
catgtgtact gaagccagga tttacttgtg cagaaggaga atgctgtgaa tcttgtcaga    1440
taaaaaaagc agggtccata tgcagaccgg cgaaagatga atgtgatttt cctgagatgt    1500
gcactggcca ctcgcctgcc tgtcctaagg accagttcag ggtcaatgga tttccttgca    1560
agaactcaga aggctactgt ttcatgggga atgtccaac tcgtgaggat cagtgctctg    1620
aactatttga tgatgatgca atagagagtc atgatatctg ctacaagatg aatacaaaag    1680
gaaataaatt tggatactgc aaaaacaagg aaaacagatt tcttccctgt gaggagaaag    1740
atgtcagatg tggaaagatc tactgcactg gaggggagct ttcctctctc cttggagaag    1800
acaagactta tcaccttaag gatccccaga agaatgctac tgtcaaatgc aaaactattt    1860 ttttataccaa tgattctaca gacattggcc tggtggcgtc aggaacaaaa tgtggagagg    1920
gaatggtgtg caacaatggt gaatgtctaa acatggaaaa ggtctatatc tcaaccaatt    1980
gcccctctca gtgcaatgaa atcctgtgg atggccacgg actccagtgc cactgtgagg    2040
aaggacaggc acctgtagcc tgtgaagaaa ccttacatgt taccaatatc accatcttgg    2100
ttgttgtgct tgtcctggtt attgtcggta tcggagttct tatactatta gttcgttacc    2160
gaaaatgtat caagttgaag caagttcaga gcccacctac agaaaccctg ggagtggaga    2220
acaaaggata ctttggtgat gagcagcaga taaggactga gccaatcctg ccagaaattc    2280
atttcctaaa taaacctgca agtaaagatt caagaggaat cgcagatccc aatcaaagtg    2340
```

-continued

```
ccaagtgagc ttgaagttgg atatccaaaa tggccgtgca agcttaggct ggggattctg    2400
gatgcaacgt ctttacaacc ttacctagat atctgctact cacattttg gtagtgtttc    2460 aaacgttctt tatccagaca gacaatgttt aagagaaaca acttatttct gttaatattt    2520
accggtagaa ttcacaccct ctatcataaa catatgctgc agaaaaaaaa aaaaaaaaaa    2580
aa                                                                    2582
```

<210> SEQ ID NO 6
<211> LENGTH: 754
<212> TYPE: PRT
<213> ORGANISM: Homo sapiens

<400> SEQUENCE: 6

```
Met Leu Pro Gly Cys Ile Phe Leu Met Ile Leu Ile Pro Gln Val
1               5                   10                  15

Lys Glu Lys Phe Ile Leu Gly Val Glu Gly Gln Gln Leu Val Arg Pro
                20                  25                  30

Lys Lys Leu Pro Leu Ile Gln Lys Arg Asp Thr Gly His Thr His Asp
                35                  40                  45

Asp Asp Ile Leu Lys Thr Tyr Glu Glu Glu Leu Leu Tyr Glu Ile Lys
50                  55                  60

Leu Asn Arg Lys Thr Leu Val Leu His Leu Leu Arg Ser Arg Glu Phe
65                  70                  75                  80

Leu Gly Ser Asn Tyr Ser Glu Thr Phe Tyr Ser Met Lys Gly Glu Ala
                85                  90                  95

Phe Thr Arg His Pro Gln Ile Met Asp His Cys Phe Tyr Gln Gly Ser
                100                 105                 110

Ile Val His Glu Tyr Asp Ser Ala Ala Ser Ile Ser Thr Cys Asn Gly
                115                 120                 125

Leu Arg Gly Phe Phe Arg Ile Asn Asp Gln Arg Tyr Leu Ile Glu Pro
130                 135                 140

Val Lys Tyr Ser Asp Glu Gly Glu His Leu Val Phe Lys Tyr Asn Leu
145                 150                 155                 160

Arg Val Pro Tyr Gly Ala Asn Tyr Ser Cys Thr Glu Leu Asn Phe Thr
                165                 170                 175

Arg Lys Thr Val Pro Gly Asp Asn Glu Ser Glu Glu Asp Ser Lys Ile
                180                 185                 190

Lys Gly Ile His Asp Glu Lys Tyr Val Glu Leu Phe Ile Val Ala Asp
                195                 200                 205

Asp Thr Val Tyr Arg Arg Asn Gly His Pro His Asn Lys Leu Arg Asn
210                 215                 220

Arg Ile Trp Gly Met Val Asn Phe Val Asn Met Ile Tyr Lys Thr Leu
225                 230                 235                 240

Asn Ile His Val Thr Leu Val Gly Ile Glu Ile Trp Thr His Glu Asp
                245                 250                 255

Lys Ile Glu Leu Tyr Ser Asn Ile Glu Thr Thr Leu Leu Arg Phe Ser
                260                 265                 270

Phe Trp Gln Glu Lys Ile Leu Lys Thr Arg Lys Asp Phe Asp His Val
                275                 280                 285

Val Leu Leu Ser Gly Lys Trp Leu Tyr Ser His Val Gln Gly Ile Ser
                290                 295                 300

Tyr Pro Gly Gly Met Cys Leu Pro Tyr Tyr Ser Thr Ser Ile Ile Lys
305                 310                 315                 320

Asp Leu Leu Pro Asp Thr Asn Ile Ile Ala Asn Arg Met Ala His Gln
```

-continued

```
               325                 330                 335
Leu Gly His Asn Leu Gly Met Gln His Asp Glu Phe Pro Cys Thr Cys
            340                 345                 350
Pro Ser Gly Lys Cys Val Met Asp Ser Asp Gly Ser Ile Pro Ala Leu
            355                 360                 365
Lys Phe Ser Lys Cys Ser Gln Asn Gln Tyr His Gln Tyr Leu Lys Asp
        370                 375                 380
Tyr Lys Pro Thr Cys Met Leu Asn Ile Pro Phe Pro Tyr Asn Phe His
385                 390                 395                 400
Asp Phe Gln Phe Cys Gly Asn Lys Lys Leu Asp Glu Gly Glu Glu Cys
                405                 410                 415
Asp Cys Gly Pro Ala Gln Glu Cys Thr Asn Pro Cys Cys Asp Ala His
            420                 425                 430
Thr Cys Val Leu Lys Pro Gly Phe Thr Cys Ala Glu Gly Glu Cys Cys
            435                 440                 445
Glu Ser Cys Gln Ile Lys Lys Ala Gly Ser Ile Cys Arg Pro Ala Lys
        450                 455                 460
Asp Glu Cys Asp Phe Pro Glu Met Cys Thr Gly His Ser Pro Ala Cys
465                 470                 475                 480
Pro Lys Asp Gln Phe Arg Val Asn Gly Phe Pro Cys Lys Asn Ser Glu
                485                 490                 495
Gly Tyr Cys Phe Met Gly Lys Cys Pro Thr Arg Glu Asp Gln Cys Ser
            500                 505                 510
Glu Leu Phe Asp Asp Asp Ala Ile Glu Ser His Asp Ile Cys Tyr Lys
            515                 520                 525
Met Asn Thr Lys Gly Asn Lys Phe Gly Tyr Cys Lys Asn Lys Glu Asn
        530                 535                 540
Arg Phe Leu Pro Cys Glu Glu Lys Asp Val Arg Cys Gly Lys Ile Tyr
545                 550                 555                 560
Cys Thr Gly Gly Glu Leu Ser Ser Leu Gly Glu Asp Lys Thr Tyr
                565                 570                 575
His Leu Lys Asp Pro Gln Lys Asn Ala Thr Val Lys Cys Lys Thr Ile
            580                 585                 590
Phe Leu Tyr His Asp Ser Thr Asp Ile Gly Leu Val Ala Ser Gly Thr
        595                 600                 605
Lys Cys Gly Glu Gly Met Val Cys Asn Asn Gly Glu Cys Leu Asn Met
            610                 615                 620
Glu Lys Val Tyr Ile Ser Thr Asn Cys Pro Ser Gln Cys Asn Glu Asn
625                 630                 635                 640
Pro Val Asp Gly His Gly Leu Gln Cys His Cys Glu Glu Gly Gln Ala
                645                 650                 655
Pro Val Ala Cys Glu Glu Thr Leu His Val Thr Asn Ile Thr Ile Leu
            660                 665                 670
Val Val Val Leu Val Leu Val Ile Val Gly Ile Gly Val Leu Ile Leu
            675                 680                 685
Leu Val Arg Tyr Arg Lys Cys Ile Lys Leu Lys Gln Val Gln Ser Pro
        690                 695                 700
Pro Thr Glu Thr Leu Gly Val Glu Asn Lys Gly Tyr Phe Gly Asp Glu
705                 710                 715                 720
Gln Gln Ile Arg Thr Glu Pro Ile Leu Pro Glu Ile His Phe Leu Asn
                725                 730                 735
Lys Pro Ala Ser Lys Asp Ser Arg Gly Ile Ala Asp Pro Asn Gln Ser
            740                 745                 750
```

Ala Lys

<210> SEQ ID NO 7
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 7
gtgcagaagg agaatgctgt g                                         21

<210> SEQ ID NO 8
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 8
tccacatctg acatctttct c                                         21

<210> SEQ ID NO 9
<211> LENGTH: 1731
<212> TYPE: DNA
<213> ORGANISM: Homo sapiens

<400> SEQUENCE: 9
agaaggagga aggacagcac agctgacagc cgtgctcaga cagcttctgg atcccaggct     60
catctccaca gaggagaaca cacaggcagc agagaccatg gggcccctcc cagccccttc    120
ctgcacacag cgcatcacct ggaaggggct cctgctcaca gcatcacttt taaacttctg    180
gaacccgccc accactgccg aagtcacgat tgaagcccag ccaccaaag tttctgaggg     240 gaaggatgtt cttctacttg tccacaattt gccccagaat cttcctggct acttctggta    300
caaaggggaa atgacggacc tctaccatta cattatatcg tatatagttg atggtaaaat    360
aattatatat gggcctgcat acagtggaag agaaacagta tattccaacg catccctgct    420
gatccagaat gtcacccgga aggatgcagg aacctacacc ttacacatca taaagcgagg    480
tgatgagact agaagaaaa ttcgacattt caccttcacc ttatacttgg agactcccaa     540
gccctacatc tccagcagca acttaaaccc cagggaggcc atggaggctg tgcgcttaat    600
ctgtgatcct gagactctgg acgcaagcta cctatggtgg atgaatggtc agagcctccc    660
tgtgactcac aggttgcagc tgtccaaaac caacaggacc ctctatctat tggtgtcac    720 aaagtatatt gcaggaccct atgaatgtga aatacggaac ccagtgagtg ccagtcgcag    780
tgacccagtc accctgaatc tcctcccgaa gctgcccatc ccctacatca ccatcaacaa    840
cttaaacccc agggagaata aggatgtctt agccttcacc tgtgaaccta gagtgagaa     900 ctacacctac atttggtggc taacggtca gagcctcccc gtcagtcccg ggtaaagcg      960 acccattgaa aacaggatac tcattctacc cagtgtcacg agaaatgaaa caggaccta    1020 tcaatgtgaa atacaggacc gatatggtgg cctccgcagt aacccagtca tcctaaatgt   1080
cctctatggt ccagacctcc ccagaattta cccttcattc acctattacc gttcaggaga   1140
aaacctcgac ttgtcctgct tcacggaatc taacccaccg gcagagtatt tttggacaat   1200
taatgggaag tttcagcaat caggacaaaa gctctttatc ccccaaatta ctagaaatca   1260

```
tagcgggctc tatgcttgct ctgttcataa ctcagccact ggcaaggaaa tctccaaatc    1320
catgacagtc aaagtctctg gtccctgcca tggagacctg acagagtctc agtcatgact    1380
gcaacaactg agacactgag aaaaagaaca ggctgatacc ttcatgaaat tcaagacaaa    1440
gaagaaaaaa actcaatgtt attggactaa ataatcaaaa ggataatgtt ttcataattt    1500
tttattggaa aatgtgctga ttcttttgaat gtttttattct ccagatttat gaactttttt    1560
tcttcagcaa ttggtaaagt atactttat aaacaaaaat tgaaatattt gcttttgctg    1620
tctatctgaa tgccccagaa ttgtgaaact attcatgagt attcataggt ttatggtaat    1680 aaagttatt gcacatgttc caaaaaaaaa aaaaaaaaa aaaaaaaaa a                1731
```

<210> SEQ ID NO 10
<211> LENGTH: 426
<212> TYPE: PRT
<213> ORGANISM: Homo sapiens

<400> SEQUENCE: 10

```
Met Gly Pro Leu Pro Ala Pro Ser Cys Thr Gln Arg Ile Thr Trp Lys
1               5                   10                  15

Gly Leu Leu Leu Thr Ala Ser Leu Leu Asn Phe Trp Asn Pro Pro Thr
            20                  25                  30

Thr Ala Glu Val Thr Ile Glu Ala Gln Pro Pro Lys Val Ser Glu Gly
        35                  40                  45

Lys Asp Val Leu Leu Leu Val His Asn Leu Pro Gln Asn Leu Pro Gly
    50                  55                  60

Tyr Phe Trp Tyr Lys Gly Glu Met Thr Asp Leu Tyr His Tyr Ile Ile
65                  70                  75                  80

Ser Tyr Ile Val Asp Gly Lys Ile Ile Ile Tyr Gly Pro Ala Tyr Ser
                85                  90                  95

Gly Arg Glu Thr Val Tyr Ser Asn Ala Ser Leu Leu Ile Gln Asn Val
            100                 105                 110

Thr Arg Lys Asp Ala Gly Thr Tyr Thr Leu His Ile Ile Lys Arg Gly
        115                 120                 125

Asp Glu Thr Arg Glu Glu Ile Arg His Phe Thr Phe Thr Leu Tyr Leu
    130                 135                 140

Glu Thr Pro Lys Pro Tyr Ile Ser Ser Ser Asn Leu Asn Pro Arg Glu
145                 150                 155                 160

Ala Met Glu Ala Val Arg Leu Ile Cys Asp Pro Glu Thr Leu Asp Ala
                165                 170                 175

Ser Tyr Leu Trp Trp Met Asn Gly Gln Ser Leu Pro Val Thr His Arg
            180                 185                 190

Leu Gln Leu Ser Lys Thr Asn Arg Thr Leu Tyr Leu Phe Gly Val Thr
        195                 200                 205

Lys Tyr Ile Ala Gly Pro Tyr Glu Cys Glu Ile Arg Asn Pro Val Ser
    210                 215                 220

Ala Ser Arg Ser Asp Pro Val Thr Leu Asn Leu Leu Pro Lys Leu Pro
225                 230                 235                 240

Ile Pro Tyr Ile Thr Ile Asn Asn Leu Asn Pro Arg Glu Asn Lys Asp
                245                 250                 255

Val Leu Ala Phe Thr Cys Glu Pro Lys Ser Glu Asn Tyr Thr Tyr Ile
            260                 265                 270

Trp Trp Leu Asn Gly Gln Ser Leu Pro Val Ser Pro Gly Val Lys Arg
        275                 280                 285

Pro Ile Glu Asn Arg Ile Leu Ile Leu Pro Ser Val Thr Arg Asn Glu
```

```
              290                 295                 300
Thr Gly Pro Tyr Gln Cys Glu Ile Gln Asp Arg Tyr Gly Gly Leu Arg
305                 310                 315                 320

Ser Asn Pro Val Ile Leu Asn Val Leu Tyr Gly Pro Asp Leu Pro Arg
            325                 330                 335

Ile Tyr Pro Ser Phe Thr Tyr Tyr Arg Ser Gly Glu Asn Leu Asp Leu
            340                 345                 350

Ser Cys Phe Thr Glu Ser Asn Pro Pro Ala Glu Tyr Phe Trp Thr Ile
            355                 360                 365

Asn Gly Lys Phe Gln Gln Ser Gly Gln Lys Leu Phe Ile Pro Gln Ile
            370                 375                 380

Thr Arg Asn His Ser Gly Leu Tyr Ala Cys Ser Val His Asn Ser Ala
385                 390                 395                 400

Thr Gly Lys Glu Ile Ser Lys Ser Met Thr Val Lys Val Ser Gly Pro
                405                 410                 415

Cys His Gly Asp Leu Thr Glu Ser Gln Ser
                420                 425
```

<210> SEQ ID NO 11
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 11
ctcctcyatg gtccagacct c                                               21

<210> SEQ ID NO 12
<211> LENGTH: 22
<212> TYPE: DNA
<213> ORGANISM: Artificial Sequence
<220> FEATURE:
<223> OTHER INFORMATION: Description of artificial sequence:
      Oligonucleotide

<400> SEQUENCE: 12
gttgcagtca tgactgagac tc                                              22

<210> SEQ ID NO 13
<211> LENGTH: 1634
<212> TYPE: DNA
<213> ORGANISM: Homo sapiens

<400> SEQUENCE: 13
atgacagtga ctccacagta tctaccagaa tacaagggca agcatccaaa atgtgactca      60
ctggtggtgt tccgcaatgt gtgcgtctgt gtgtccaccg cgacaggcat cagtacattg     120
gatcagagtg tcgctttcag ttgtaacgga cttcatcaca tcacaaaattg tactcgttct     180 catccttta agaaagttca gacccaggaa aatttccata gtaccttaat gaaaaagata     240
gaaatcagtg ggacgtgtct ttcctttcat ctcctttcg gcttggaaat cagaatgaga     300
aggattgttt tgctggtgt tatcttattc cgcctcttag gtgttatctt attccgcctc     360
ttaggtgtta tcttattcgg ccgcttaggt gacctgggaa cctgccagac aaaacctggt     420
cagtactgga agaagaggt ccacattcaa gatgttggag gtttgatttg cagagcatgc     480
aatctttcac tgcccttcca tggatgtctt ttagacctgg gaacctgcca ggcagaacct     540
ggtcagtact gtaaagaaga ggtccacatt caaggtggca ttcaatggta ttcagtcaaa     600
```

-continued

```
ggctgcacaa agaacacatc agagtgcttc aagagtactc tcgtcaagag aattctgcaa    660
ctgcatgaac ttgtaactac tcactgctgc aatcattctt tgtgcaattt ctgagtcagt    720
ggcccatatc taaaatgctt ggcagatcaa tcagtctcga agcctgacct ggctatcaca    780
aaatgatggc tattgtcaat tagcccactt cagaaacctc agaccttgt aggtagaagg     840 aattttgatc tgaaattgac tttggttttc aatattccca atatctcccc caccacctcc    900
aactcatctg agaaatagcc ctttcaacac catttctctc ctctcctcct tctgcttaat    960
ttaccttcct accacaaggc tacaagaag gaaaaatgtt agtgattctc caagtcaaac    1020
taggcatgtc acctctaact actttcattt ccctcaataa ttccatactc caaaatatgg   1080
ttacaaatgt tcacaagac agcaagtgac ctgagaatat tcatttggtt tccaaagcaa    1140
actgccttgc tcctttgggg tgatttatgg tatagaagaa actgacttaa catatactat   1200
agggaaaaaa taagccatga atcagcaagc caggcctgcg ggaaaagtat gaacccaaac   1260
aggaaagggc tgaggcaggt ggtagggctg gcacttattt cttccatctg cctcagagtt   1320
tatccaaatt ttgaattttc cgtaccttaa ccatgcctaa atgctttggc ttgttcaatt   1380
ttggcagatt aagcagttca aggtaagcag agaagtaagt tcccaaccac aaggaattta   1440
aaaggagtag gaacgtactt tgaactacat ttcccatttt gcgatcatta cgtcttctat   1500
tacaatgccc tactttggca gcatgaagag tactgcatta atttaattta atttaaaatt   1560
taatttaaaa ctgtctttct ctgtattttc aggagtttga aaattcaaaa aataaataat   1620
aaatgtcaat aaaa                                                      1634

<210> SEQ ID NO 14
<211> LENGTH: 237
<212> TYPE: PRT
<213> ORGANISM: Homo sapiens

<400> SEQUENCE: 14

Met Thr Val Thr Pro Gln Tyr Leu Pro Glu Tyr Lys Gly Lys His Pro
1               5                   10                  15

Lys Cys Asp Ser Leu Val Val Phe Arg Asn Val Cys Val Cys Val Ser
            20                  25                  30

Thr Ala Thr Gly Ile Ser Thr Leu Asp Gln Ser Val Ala Phe Ser Cys
        35                  40                  45

Asn Gly Leu His His Ile Thr Asn Cys Thr Arg Ser His Pro Phe Lys
    50                  55                  60

Lys Val Gln Thr Gln Glu Asn Phe His Ser Thr Leu Met Lys Lys Ile
65                  70                  75                  80

Glu Ile Ser Gly Thr Cys Leu Ser Phe His Leu Leu Phe Gly Leu Glu
                85                  90                  95

Ile Arg Met Arg Arg Ile Val Phe Ala Gly Val Ile Leu Phe Arg Leu
            100                 105                 110

Leu Gly Val Ile Leu Phe Arg Leu Leu Gly Val Ile Leu Phe Gly Arg
        115                 120                 125

Leu Gly Asp Leu Gly Thr Cys Gln Thr Lys Pro Gly Gln Tyr Trp Lys
    130                 135                 140

Glu Glu Val His Ile Gln Asp Val Gly Gly Leu Ile Cys Arg Ala Cys
145                 150                 155                 160

Asn Leu Ser Leu Pro Phe His Gly Cys Leu Leu Asp Leu Gly Thr Cys
                165                 170                 175

Gln Ala Glu Pro Gly Gln Tyr Cys Lys Glu Glu Val His Ile Gln Gly
```

```
            180                 185                 190
Gly Ile Gln Trp Tyr Ser Val Lys Gly Cys Thr Lys Asn Thr Ser Glu
        195                 200                 205

Cys Phe Lys Ser Thr Leu Val Lys Arg Ile Leu Gln Leu His Glu Leu
        210                 215                 220

Val Thr Thr His Cys Cys Asn His Ser Leu Cys Asn Phe
225                 230                 235
```

```
<210> SEQ ID NO 15
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 15
gacaaaacct ggtcagtact g                                          21

<210> SEQ ID NO 16
<211> LENGTH: 23
<212> TYPE: DNA
<213> ORGANISM: Artificial Sequence
<220> FEATURE:
<223> OTHER INFORMATION: Description of artificial sequence:
      Oligonucleotide

<400> SEQUENCE: 16
cccattgaat gccaccttga atg                                        23

<210> SEQ ID NO 17
<211> LENGTH: 744
<212> TYPE: DNA
<213> ORGANISM: Homo sapiens

<400> SEQUENCE: 17
atcaggttca acgcagtgac tgctcagtag aagccatggc tcgcagacac tgcttctcct    60
actggttact ggtatgctgg ttggtggtaa ctgtggcaga aggacaagaa gaggtattta   120
cgcttcctgg agattcacaa aataatgcgg acgctaccga ctgccagatc tttacactca   180
cccctccacc tgccccgagg agtccggtca caagggccca gcccatcaca aagacaccca   240
ggtgtccctt ccatttttt ccacgaaggc ccagaatcca tttttaggttt ccaaacagac   300 ctttcgtccc ttcaaggtgt aaccaccgtt ttccattcca gccatttttat tggccacacc   360 gttaccttac ttataggtat ttccccagaa gaagactcca gagaggaagc tcatctgagg   420
aaagctgaga gggaagagaa acccaaacat actgaagcaa aaaaagcct atccttcaga    480 aaaaagcaac aaaaagattt ctgttttatc tttcgaaact aaaactattg gatttgaaga   540
ttaagtatcc taaacatcac tgactagaaa ctgttctctt tgtcagcagt gaagatattg   600
gatcataggt tattgatggt tgcaaaattg gacaataacc acgttatttt tatcctcaac   660
ctcttatggt cacaggatat ttatgcaaat aaaatcttta aatgggaaaa aaaaaaaaaa   720
aaaaaaaaaa aaaaaaaaaa aaaa                                         744

<210> SEQ ID NO 18
<211> LENGTH: 130
<212> TYPE: PRT
<213> ORGANISM: Homo sapiens

<400> SEQUENCE: 18
```

Met Ala Arg Arg His Cys Phe Ser Tyr Trp Leu Leu Val Cys Trp Leu
1               5                   10                  15

Val Val Thr Val Ala Glu Gly Gln Glu Val Phe Thr Leu Pro Gly
            20                  25                  30

Asp Ser Gln Asn Asn Ala Asp Ala Thr Asp Cys Gln Ile Phe Thr Leu
            35                  40                  45

Thr Pro Pro Ala Pro Arg Ser Pro Val Thr Arg Ala Gln Pro Ile
50                  55                  60

Thr Lys Thr Pro Arg Cys Pro Phe His Phe Pro Arg Pro Arg
65                  70                  75                  80

Ile His Phe Arg Phe Pro Asn Arg Pro Phe Val Pro Ser Arg Cys Asn
                85                  90                  95

His Arg Phe Pro Phe Gln Pro Phe Tyr Trp Pro His Arg Tyr Leu Thr
                100                 105                 110

Tyr Arg Tyr Phe Pro Arg Arg Arg Leu Gln Arg Gly Ser Ser Ser Glu
                115                 120                 125

Glu Ser
    130

<210> SEQ ID NO 19
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 19
taactgtggc agaaggacaa g                                          21

<210> SEQ ID NO 20
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 20
agatgagctt cctctctgga g                                          21

<210> SEQ ID NO 21
<211> LENGTH: 1955
<212> TYPE: DNA
<213> ORGANISM: Homo sapiens

<400> SEQUENCE: 21
acagaagcgc gcagagtccc atcctgccac gccacgagga gagaagaagg aaagatacag    60
tgttaggaaa gagacctccc tcgcccctac gccccgcgcc cctgcgcctc gcttcagcct   120
caggacagtc ctgccgggac ggtgagcgca ttcagcaccc tggacagcac cgcggttgcg   180
ctgcctccag gcggccccg ggctgctcct gctccgcaga gctacgccct ccccccgggt    240
gccccggacc ctgcacttgc cgccgctttc ctcgcgctgc tctggacctt gctagccggc   300
tctgcacctc ccagaagccg tgggcgcgcc gtcagctgc tccatcgcct cactttccca    360
ggctcgcgcc cgaagcagag ccatgagaac cccagggtgc ctggcgagcc gctagcgcca   420
tgggccccgg cgaggcgctg ctggcgggtc tcctggtgat ggtactggcc gtggcgctgc   480
tatccaacgc actggtgctg ctttgttgcg cctacagcgc tgagctccgc actcgagcct   540

```
caggcgtcct cctggtgaat ctgtctctgg gccacctgct gctggcggcg ctggacatgc   600
ccttcacgct gctcggtgtg atgcgcgggc ggacaccgtc ggcgcccggc gcatgccaag   660
tcattggctt cctggacacc ttcctggcgt ccaacgcggc gctgagcgtg cggcgctga   720 gcgcagacca gtggctggca gtgggcttcc cactgcgcta cgccggacgc ctgcgaccgc   780
gctatgccgg cctgctgctg ggctgtgcct ggggacagtc gctggccttc tcaggcgctg   840
cacttggctg ctcgtggctt ggctacagca gcgccttcgc gtcctgttcg ctgcgcctgc   900
cgcccgagcc tgagcgtccg cgcttcgcag ccttcaccgc cacgctccat gccgtgggct   960
tcgtgctgcc gctggcggtg ctctgcctca cctcgctcca ggtgcaccgg gtggcacgca  1020
gacactgcca gcgcatggac accgtcacca tgaaggcgct cgcgctgctc gccgacctgc  1080
accccagtgt gcggcagcgc tgcctcatcc agcagaagcg gcgccgccac cgcgccacca  1140
ggaagattgg cattgctatt gcgaccttcc tcatctgctt tgcccccgtat gtcatgacca  1200 ggctggcgga gtcgtgcccc ttcgtcaccg tgaacgccca gtgggcatc ctcagcaagt  1260 gcctgaccta cagcaaggcg gtggccgacc cgttcacgta ctctctgctc cgccggccgt  1320
tccgccaagt cctggccggc atggtgcacc ggctgctgaa gagaaccccg cgcccagcat  1380
ccacccatga cagctctctg gatgtggccg gcatggtgca ccagctgctg aagagaaccc  1440
cgcgcccagc gtccacccac aacggctctg tggacacaga gaatgattcc tgcctgcagc  1500
agacacactg agggcctggc agggctcatc gcccccacct tctaagaagc cctgtggaaa  1560
gggcactggc cctgccacag agatgccact ggggaccccc agacaccagt ggcttgactt  1620
tgagctaagg ctgaagtaca ggaggaggag gaggagaggg ccggatgtgg gtgtggacag  1680
cagtagtggc ggaggagagc tcggggctgg gctgcctggc tgctgggtgg ccccgggaca  1740
gtggcttttc ctctctgaac cttagcttcc tcacccttgt tctggggtca tggcgatgct  1800
tcgagacagt gggtagggaa gtgccctgtg tggcatatgg tactcgtggg cgtgctataa  1860
gtgactgctg ttcatgtggg tgaggtggtc actcttgctc agggtctgtt gtgcagccca  1920
gatggacacc tgtttctcca aaaaaaaaaa aaaaa                             1955
```

<210> SEQ ID NO 22
<211> LENGTH: 363
<212> TYPE: PRT
<213> ORGANISM: Homo sapiens

<400> SEQUENCE: 22

```
Met Gly Pro Gly Glu Ala Leu Leu Ala Gly Leu Leu Val Met Val Leu
1               5                   10                  15

Ala Val Ala Leu Leu Ser Asn Ala Leu Val Leu Cys Cys Ala Tyr
                20                  25                  30

Ser Ala Glu Leu Arg Thr Arg Ala Ser Gly Val Leu Leu Val Asn Leu
            35                  40                  45

Ser Leu Gly His Leu Leu Ala Ala Leu Asp Met Pro Phe Thr Leu
        50                  55                  60

Leu Gly Val Met Arg Gly Arg Thr Pro Ser Ala Pro Gly Ala Cys Gln
65                  70                  75                  80

Val Ile Gly Phe Leu Asp Thr Phe Leu Ala Ser Asn Ala Ala Leu Ser
                85                  90                  95

Val Ala Ala Leu Ser Ala Asp Gln Trp Leu Val Gly Phe Pro Leu
            100                 105                 110

Arg Tyr Ala Gly Arg Leu Arg Pro Arg Tyr Ala Gly Leu Leu Leu Gly
        115                 120                 125
```

-continued

Cys Ala Trp Gly Gln Ser Leu Ala Phe Ser Gly Ala Ala Leu Gly Cys
            130                 135                 140

Ser Trp Leu Gly Tyr Ser Ser Ala Phe Ala Ser Cys Ser Leu Arg Leu
145                 150                 155                 160

Pro Pro Glu Pro Glu Arg Pro Arg Phe Ala Ala Phe Thr Ala Thr Leu
                165                 170                 175

His Ala Val Gly Phe Val Leu Pro Leu Ala Val Leu Cys Leu Thr Ser
            180                 185                 190

Leu Gln Val His Arg Val Ala Arg Arg His Cys Gln Arg Met Asp Thr
        195                 200                 205

Val Thr Met Lys Ala Leu Ala Leu Leu Ala Asp Leu His Pro Ser Val
    210                 215                 220

Arg Gln Arg Cys Leu Ile Gln Gln Lys Arg Arg His Arg Ala Thr
225                 230                 235                 240

Arg Lys Ile Gly Ile Ala Ile Ala Thr Phe Leu Ile Cys Phe Ala Pro
                245                 250                 255

Tyr Val Met Thr Arg Leu Ala Glu Leu Val Pro Phe Val Thr Val Asn
                260                 265                 270

Ala Gln Trp Gly Ile Leu Ser Lys Cys Leu Thr Tyr Ser Lys Ala Val
            275                 280                 285

Ala Asp Pro Phe Thr Tyr Ser Leu Leu Arg Arg Pro Phe Arg Gln Val
290                 295                 300

Leu Ala Gly Met Val His Arg Leu Leu Lys Arg Thr Pro Arg Pro Ala
305                 310                 315                 320

Ser Thr His Asp Ser Ser Leu Asp Val Ala Gly Met Val His Gln Leu
                325                 330                 335

Leu Lys Arg Thr Pro Arg Pro Ala Ser Thr His Asn Gly Ser Val Asp
            340                 345                 350

Thr Glu Asn Asp Ser Cys Leu Gln Gln Thr His
                355                 360

<210> SEQ ID NO 23
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 23
ccgtatgtca tgaccaggct g                                              21

<210> SEQ ID NO 24
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 24
aagtcaagcc actggtgtct g                                              21

<210> SEQ ID NO 25
<211> LENGTH: 2059
<212> TYPE: DNA
<213> ORGANISM: Homo sapiens

<400> SEQUENCE: 25

```
agcacagaag gaggaaggac agcacagctg acagccgtac tcaggaagct tctggatcct      60
aggcttatct ccacagagga gaacacacaa gcagcagaga ccatgggggcc cctctcagcc    120
cctccctgca cacagcgcat cacctggaag ggggtcctgc tcacagcatc acttttaaac    180
ttctggaatc cgcccacaac tgcccaagtc acgattgaag cccagccacc caaagtttct    240
gaggggaagg atgttcttct acttgtccac aatttgcccc agaatcttgc tggctacatt    300
tggtacaaag gcaaatgac  atacctctac cattacatta catcatatgt agtagacggt    360
caaagaatta tatatgggcc tgcatacagt ggaagagaaa gagtatattc caatgcatcc    420
ctgctgatcc agaatgtcac gcaggaggat gcaggatcct acaccttaca catcataaag    480
cgacgcgatg ggactggagg agtaactgga catttcacct tcaccttaca cctggagact    540
cccaagccct ccatctccag cagcaactta atcccaggg  aggccatgga ggctgtgatc    600
ttaacctgtg atcctgcgac tccagccgca agctaccagt ggtggatgaa tggtcagagc    660
ctccctatga ctcacaggtt gcagctgtcc aaaaccaaca ggaccctctt tatatttggt    720
gtcacaaagt atattgcagg accctatgaa tgtgaaatac ggaacccagt gagtgccagc    780
cgcagtgacc cagtcaccct gaatctcctc ccaaagctgt ccaagcccta catcacaatc    840
aacaacttaa  ccccagaga  gaataaggat gtcttaacct tcacctgtga acctaagagt    900
aagaactaca cctacatttg gtggctaaat ggtcagagcc tccctgtcag tcccagggta    960
aagcgaccca ttgaaaacag gatcctcatt ctacccaatg tcacgagaaa tgaaacagga   1020
ccttatcaat gtgaaatacg ggaccgtat  ggtggcatcc gcagtgaccc agtcaccctg   1080
aatgtcctct atggtccaga cctccccagc atttacccctt cattcaccta ttaccgttca   1140
ggagaaaacc tctacttgtc ctgcttcgcc gagtctaacc cacgggcaca atattcttgg   1200
acaattaatg ggaagtttca gctatcagga caaaagctct ctatccccca ataactaca    1260
aagcatagtg ggctctatgc ttgctctgtt cgtaactcag ccactggcaa ggaaagctcc   1320
aaatccatca cagtcaaagt ctctgactgg atattaccct gaattctact agttcctcca   1380
attccatttt ctcccatgga atcacgaaga gcaagaccca ctctgttcca gaagccctat   1440
aagctggagg tggacaactc gatgtaaatt tcatgggaaa acccttgtac ctgacatgtg   1500
agccactcag aactcaccaa aatgttcgac accataacaa cagctactca aactgtaaac   1560
caggataaca agttgatgac ttcacactgt ggacagtttt tccaaagatg tcagaacaag   1620
actccccatc atgataaggc tcccaccccct cttaaccgtc cttgctcatg cctgcctctt   1680
tcacttggca ggataatgca gtcattagaa tttcacatgt agtagcttct gagggtaaca   1740
acagagtgtc agatatgtca tctcaacctc aaacttttac gtaacatctc aggggaaatg   1800
tggctctctc catcttgcat acagggctcc caatagaaat gaacacagag atattgcctg   1860
tgtgtttgca gagaagatgg tttctataaa gagtaggaaa gctgaaatta tagtagagtc   1920
tcctttaaat gcacattgtg tggatggctc tcaccatttc ctaagagata cagtgtaaaa   1980
cgtgacagta atactgattc tagcagaata aaacatgtac cacatttgct aaaaaaaaaa   2040
aaaaaaaaaa aaaaaaaa                                                 2059
```

<210> SEQ ID NO 26
<211> LENGTH: 419
<212> TYPE: PRT
<213> ORGANISM: Homo sapiens

<400> SEQUENCE: 26

```
Met Gly Pro Leu Ser Ala Pro Pro Cys Thr Gln Arg Ile Thr Trp Lys
1               5                   10                  15

Gly Val Leu Leu Thr Ala Ser Leu Leu Asn Phe Trp Asn Pro Pro Thr
            20                  25                  30

Thr Ala Gln Val Thr Ile Glu Ala Gln Pro Pro Lys Val Ser Glu Gly
            35                  40                  45

Lys Asp Val Leu Leu Leu Val His Asn Leu Pro Gln Asn Leu Ala Gly
50                  55                  60

Tyr Ile Trp Tyr Lys Gly Gln Met Thr Tyr Leu Tyr His Tyr Ile Thr
65                  70                  75                  80

Ser Tyr Val Val Asp Gly Gln Arg Ile Ile Tyr Gly Pro Ala Tyr Ser
                85                  90                  95

Gly Arg Glu Arg Val Tyr Ser Asn Ala Ser Leu Leu Ile Gln Asn Val
            100                 105                 110

Thr Gln Glu Asp Ala Gly Ser Tyr Thr Leu His Ile Ile Lys Arg Arg
            115                 120                 125

Asp Gly Thr Gly Gly Val Thr Gly His Phe Thr Phe Thr Leu His Leu
            130                 135                 140

Glu Thr Pro Lys Pro Ser Ile Ser Ser Ser Asn Leu Asn Pro Arg Glu
145                 150                 155                 160

Ala Met Glu Ala Val Ile Leu Thr Cys Asp Pro Ala Thr Pro Ala Ala
                165                 170                 175

Ser Tyr Gln Trp Trp Met Asn Gly Gln Ser Leu Pro Met Thr His Arg
            180                 185                 190

Leu Gln Leu Ser Lys Thr Asn Arg Thr Leu Phe Ile Phe Gly Val Thr
            195                 200                 205

Lys Tyr Ile Ala Gly Pro Tyr Glu Cys Glu Ile Arg Asn Pro Val Ser
            210                 215                 220

Ala Ser Arg Ser Asp Pro Val Thr Leu Asn Leu Leu Pro Lys Leu Ser
225                 230                 235                 240

Lys Pro Tyr Ile Thr Ile Asn Asn Leu Asn Pro Arg Glu Asn Lys Asp
                245                 250                 255

Val Leu Thr Phe Thr Cys Glu Pro Lys Ser Lys Asn Tyr Thr Tyr Ile
            260                 265                 270

Trp Trp Leu Asn Gly Gln Ser Leu Pro Val Ser Pro Arg Val Lys Arg
            275                 280                 285

Pro Ile Glu Asn Arg Ile Leu Ile Leu Pro Asn Val Thr Arg Asn Glu
            290                 295                 300

Thr Gly Pro Tyr Gln Cys Glu Ile Arg Asp Arg Tyr Gly Gly Ile Arg
305                 310                 315                 320

Ser Asp Pro Val Thr Leu Asn Val Leu Tyr Gly Pro Asp Leu Pro Ser
                325                 330                 335

Ile Tyr Pro Ser Phe Thr Tyr Tyr Arg Ser Gly Glu Asn Leu Tyr Leu
            340                 345                 350

Ser Cys Phe Ala Glu Ser Asn Pro Arg Ala Gln Tyr Ser Trp Thr Ile
            355                 360                 365

Asn Gly Lys Phe Gln Leu Ser Gly Gln Lys Leu Ser Ile Pro Gln Ile
            370                 375                 380

Thr Thr Lys His Ser Gly Leu Tyr Ala Cys Ser Val Arg Asn Ser Ala
385                 390                 395                 400

Thr Gly Lys Glu Ser Ser Lys Ser Ile Thr Val Lys Val Ser Asp Trp
                405                 410                 415

Ile Leu Pro
```

<210> SEQ ID NO 27
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 27
gttgttaccc tcagaagcta c                                           21

<210> SEQ ID NO 28
<211> LENGTH: 1780
<212> TYPE: DNA
<213> ORGANISM: Homo sapiens

<400> SEQUENCE: 28

| | | | | | |
|---|---|---|---|---|---|
| agcacagaag | gaggaaggac | agcacagctg | acagccgtac | tcaggaagct | tctggatcct | 60 |
| aggcttatct | ccacagagga | gaacacacaa | gcagcagaga | ccatgggggcc | cctctcagcc | 120 |
| cctccctgca | cacagcgcat | cacctggaag | ggggtcctgc | tcacagcatc | actttttaaac | 180 |
| ttctggaatc | cgcccacaac | tgcccaagtc | acgattgaag | cccagccacc | caaagttttct | 240 |
| gaggggaagg | atgttcttct | acttgtccac | aatttgcccc | agaatcttgc | tggctacatt | 300 |
| tggtacaaag | gcaaatgac | atacctctac | cattacatta | tcatatatgt | agtagacggt | 360 |
| caaagaatta | tatatgggcc | tgcatacagt | ggaagagaaa | gagtatattc | caatgcatcc | 420 |
| ctgctgatcc | agaatgtcac | gcaggaggat | gcaggatcct | acaccttaca | catcataaag | 480 |
| cgacgcgatg | ggactggagg | agtaactgga | catttcacct | tcaccttaca | cctggagact | 540 |
| cccaagccct | ccatctccag | cagcaactta | aatcccaggg | aggccatgga | ggctgtgatc | 600 |
| ttaacctgtg | atcctgcgac | tccagccgca | agctaccagt | ggtggatgaa | tggtcagagc | 660 |
| ctccctatga | ctcacaggtt | gcagctgtcc | aaaaccaaca | ggaccctctt | tatatttggt | 720 |
| gtcacaaagt | atattgcagg | accctatgaa | tgtgaaatac | ggaacccagt | gagtgccagc | 780 |
| cgcagtgacc | cagtcaccct | gaatctcctc | catggtccag | acctccccag | catttaccct | 840 |
| tcattcacct | attaccgttc | aggagaaaac | ctctacttgt | cctgcttcgc | cgagtctaac | 900 |
| ccacgggcac | aatattcttg | gacaattaat | gggaagtttc | agctatcagg | acaaaagctc | 960 |
| tctatccccc | aaataactac | aaagcatagt | gggctctatg | cttgctctgt | tcgtaactca | 1020 |
| gccactggca | aggaaagctc | caaatccatc | acagtcaaag | tctctgactg | gatattaccc | 1080 |
| tgaattctac | tagttcctcc | aattccattt | tctcccatgg | aatcacgaag | agcaagaccc | 1140 |
| actctgttcc | agaagcccta | taagctggag | gtggacaact | cgatgtaaat | ttcatgggaa | 1200 |
| aacccttgta | cctgacatgt | gagccactca | gaactcacca | aaatgttcga | caccataaca | 1260 |
| acagctactc | aaactgtaaa | ccaggataac | aagttgatga | cttcacactg | tggacagttt | 1320 |
| ttccaaagat | gtcagaacaa | gactcccccat | catgataagg | ctcccacccc | tcttaaccgt | 1380 |
| ccttgctcat | gcctgcctct | ttcacttggc | aggataatgc | agtcattaga | atttcacatg | 1440 |
| tagtagcttc | tgagggtaac | aacagagtgt | cagatatgtc | atctcaacct | caaacttttta | 1500 |
| cgtaacatct | caggggaaat | gtggctctct | ccatcttgca | tacagggctc | ccaatagaaa | 1560 |
| tgaacacaga | gatattgcct | gtgtgtttgc | agagaagatg | gtttctataa | agagtaggaa | 1620 |
| agctgaaatt | atagtagagt | ctcctttaaa | tgcacattgt | gtggatggct | ctcaccattt | 1680 |
| cctaagagat | acagtgtaaa | acgtgacagt | aatactgatt | ctagcagaat | aaaacatgta | 1740 | ccacatttgc taaaaaaaaa aaaaaaaaaa aaaaaaaaa                               1780

<210> SEQ ID NO 29
<211> LENGTH: 326
<212> TYPE: PRT
<213> ORGANISM: Homo sapiens

<400> SEQUENCE: 29

Met Gly Pro Leu Ser Ala Pro Pro Cys Thr Gln Arg Ile Thr Trp Lys
1               5                   10                  15

Gly Val Leu Leu Thr Ala Ser Leu Leu Asn Phe Trp Asn Pro Pro Thr
            20                  25                  30

Thr Ala Gln Val Thr Ile Glu Ala Gln Pro Pro Lys Val Ser Glu Gly
        35                  40                  45

Lys Asp Val Leu Leu Leu Val His Asn Leu Pro Gln Asn Leu Ala Gly
    50                  55                  60

Tyr Ile Trp Tyr Lys Gly Gln Met Thr Tyr Leu Tyr His Tyr Ile Thr
65                  70                  75                  80

Ser Tyr Val Val Asp Gly Gln Arg Ile Ile Tyr Gly Pro Ala Tyr Ser
                85                  90                  95

Gly Arg Glu Arg Val Tyr Ser Asn Ala Ser Leu Leu Ile Gln Asn Val
            100                 105                 110

Thr Gln Glu Asp Ala Gly Ser Tyr Thr Leu His Ile Ile Lys Arg Arg
        115                 120                 125

Asp Gly Thr Gly Gly Val Thr Gly His Phe Thr Phe Thr Leu His Leu
    130                 135                 140

Glu Thr Pro Lys Pro Ser Ile Ser Ser Ser Asn Leu Asn Pro Arg Glu
145                 150                 155                 160

Ala Met Glu Ala Val Ile Leu Thr Cys Asp Pro Ala Thr Pro Ala Ala
                165                 170                 175

Ser Tyr Gln Trp Trp Met Asn Gly Gln Ser Leu Pro Met Thr His Arg
            180                 185                 190

Leu Gln Leu Ser Lys Thr Asn Arg Thr Leu Phe Ile Phe Gly Val Thr
        195                 200                 205

Lys Tyr Ile Ala Gly Pro Tyr Glu Cys Glu Ile Arg Asn Pro Val Ser
    210                 215                 220

Ala Ser Arg Ser Asp Pro Val Thr Leu Asn Leu Leu His Gly Pro Asp
225                 230                 235                 240

Leu Pro Ser Ile Tyr Pro Ser Phe Thr Tyr Tyr Arg Ser Gly Glu Asn
                245                 250                 255

Leu Tyr Leu Ser Cys Phe Ala Glu Ser Asn Pro Arg Ala Gln Tyr Ser
            260                 265                 270

Trp Thr Ile Asn Gly Lys Phe Gln Leu Ser Gly Gln Lys Leu Ser Ile
        275                 280                 285

Pro Gln Ile Thr Thr Lys His Ser Gly Leu Tyr Ala Cys Ser Val Arg
    290                 295                 300

Asn Ser Ala Thr Gly Lys Glu Ser Ser Lys Ser Ile Thr Val Lys Val
305                 310                 315                 320

Ser Asp Trp Ile Leu Pro
                325

<210> SEQ ID NO 30
<211> LENGTH: 1989
<212> TYPE: DNA
<213> ORGANISM: Homo sapiens

<400> SEQUENCE: 30

```
attcgggcct aggctcatct ccacagagga gaacacgcag ggagcagaga ccatggggcc      60
cctctcagcc cctccctgca cacagcatat aacctggaaa gggctcctgc tcacagcatc     120
acttttaaac ttctggaacc cgcccaccac agcccaagtc acgattgaag cccagccacc     180
aaaagtttct gaggggaagg atgttcttct acttgtccac aatttgcccc agaatcttac     240
tggctacatc tggtacaaag gacaaatcag ggacctctac cattatgtta catcatatgt     300
agtagacggt caaataatta aatatgggcc tgcatacagt ggacgagaaa cagtatattc     360
caatgcatcc ctgctgatcc agaatgtcac ccaggaagac acaggatcct acactttaca     420
catcataaag cgaggtgatg ggactggagg agtaactgga cgtttcaccct tcaccttata     480
cctggagact cccaaaccct ccatctccag cagcaatttc aaccccaggg aggccacgga     540
ggctgtgatc ttaacctgtg atcctgagac tccagatgca agctacctgt ggtggatgaa     600
tggtcagagc ctccctatga ctcacagctt gcagctgtct gaaaccaaca ggaccctcta     660
cctatttggt gtcacaaact atactgcagg accctatgaa tgtgaaatac ggaacccagt     720
gagtgccagc cgcagtgacc cagtcaccct gaatctcctc ccgaagctgc ccaagcccta     780
catcaccatc aataacttaa accccaggga gaataaggat gtctcaacct tcacctgtga     840
acctaagagt gagaactaca cctacatttg gtggctaaat ggtcagagcc tcccggtcag     900
tcccagggta agcgacgca ttgaaaacag gatcctcatt ctacccagtg tcacgagaaa     960
tgaaacagga ccctatcaat gtgaaatacg ggaccgatat ggtggcatcc gcagtgaccc    1020
agtcaccctg aatgtcctct atggtccaga cctccccaga atttacccctt cgttcaccta    1080
ttaccattca ggacaaaacc tctacttgtc ctgctttgcg gactctaacc caccggcaca    1140
gtattcttgg acaattaatg ggaagtttca gctatcagga caaaagcttt ctatccccca    1200
gattactaca aagcatagcg ggctctatgc ttgctctgtt cgtaactcag ccactggcaa    1260
ggaaagctcc aaatccgtga cagtcagagt ctctgactgg acattaccct gaattctact    1320
agttcctcca attccatctt ctcccatgga acctcaaaga gcaagaccca ctctgttcca    1380
gaagccctat aagtcagagt tggacaactc aatgtaaatt tcatgggaaa atccttgtac    1440
ctgatgtctg agccactcag aactcaccaa aatgttcaac accataacaa cagctgctca    1500
aactgtaaac aaggaaaaca agttgatgac ttcacactgt ggacagtttt tcccaagatg    1560
tcagaataag actccccatc atgatgaggc tctcacccct cttagctgtc cttgcttgtg    1620
cctgcctctt tcacttggca ggataatgca gtcattagaa tttcacatgt agtataggag    1680
cttctgaggg taacaacaga gtgtcagata tgtcatctca acctcaaact tttacataac    1740
atctcaggag gaaatgtggc tctctccatc ttgcatacag ggctcccaat agaaatgaac    1800
acagagatat tgcctgtgtg tttgcagaga agatggtttc tataaagagt aggaaagctg    1860
aaattatagt agagtcccct ttaaatgcac attgtgtgga tggctctcac catttcctaa    1920
gagatacatt gtaaaacgtg acagtaagac tgattctagc agaataaaac atgtactaca    1980
tttgctaaa                                                             1989
```

<210> SEQ ID NO 31
<211> LENGTH: 419
<212> TYPE: PRT
<213> ORGANISM: Homo sapiens

<400> SEQUENCE: 31

```
Met Gly Pro Leu Ser Ala Pro Pro Cys Thr Gln His Ile Thr Trp Lys
1               5                   10                  15

Gly Leu Leu Leu Thr Ala Ser Leu Leu Asn Phe Trp Asn Pro Pro Thr
            20                  25                  30

Thr Ala Gln Val Thr Ile Glu Ala Gln Pro Pro Lys Val Ser Glu Gly
            35                  40                  45

Lys Asp Val Leu Leu Leu Val His Asn Leu Pro Gln Asn Leu Thr Gly
50                  55                  60

Tyr Ile Trp Tyr Lys Gly Gln Ile Arg Asp Leu Tyr His Tyr Val Thr
65                  70                  75                  80

Ser Tyr Val Val Asp Gly Gln Ile Ile Lys Tyr Gly Pro Ala Tyr Ser
            85                  90                  95

Gly Arg Glu Thr Val Tyr Ser Asn Ala Ser Leu Leu Ile Gln Asn Val
            100                 105                 110

Thr Gln Glu Asp Thr Gly Ser Tyr Thr Leu His Ile Ile Lys Arg Gly
            115                 120                 125

Asp Gly Thr Gly Gly Val Thr Gly Arg Phe Thr Phe Thr Leu Tyr Leu
            130                 135                 140

Glu Thr Pro Lys Pro Ser Ile Ser Ser Ser Asn Phe Asn Pro Arg Glu
145                 150                 155                 160

Ala Thr Glu Ala Val Ile Leu Thr Cys Asp Pro Glu Thr Pro Asp Ala
            165                 170                 175

Ser Tyr Leu Trp Trp Met Asn Gly Gln Ser Leu Pro Met Thr His Ser
            180                 185                 190

Leu Gln Leu Ser Glu Thr Asn Arg Thr Leu Tyr Leu Phe Gly Val Thr
            195                 200                 205

Asn Tyr Thr Ala Gly Pro Tyr Glu Cys Glu Ile Arg Asn Pro Val Ser
            210                 215                 220

Ala Ser Arg Ser Asp Pro Val Thr Leu Asn Leu Leu Pro Lys Leu Pro
225                 230                 235                 240

Lys Pro Tyr Ile Thr Ile Asn Asn Leu Asn Pro Arg Glu Asn Lys Asp
            245                 250                 255

Val Ser Thr Phe Thr Cys Glu Pro Lys Ser Glu Asn Tyr Thr Tyr Ile
            260                 265                 270

Trp Trp Leu Asn Gly Gln Ser Leu Pro Val Ser Pro Arg Val Lys Arg
            275                 280                 285

Arg Ile Glu Asn Arg Ile Leu Ile Leu Pro Ser Val Thr Arg Asn Glu
            290                 295                 300

Thr Gly Pro Tyr Gln Cys Glu Ile Arg Asp Arg Tyr Gly Gly Ile Arg
305                 310                 315                 320

Ser Asp Pro Val Thr Leu Asn Val Leu Tyr Gly Pro Asp Leu Pro Arg
            325                 330                 335

Ile Tyr Pro Ser Phe Thr Tyr Tyr His Ser Gly Gln Asn Leu Tyr Leu
            340                 345                 350

Ser Cys Phe Ala Asp Ser Asn Pro Pro Ala Gln Tyr Ser Trp Thr Ile
            355                 360                 365

Asn Gly Lys Phe Gln Leu Ser Gly Gln Lys Leu Ser Ile Pro Gln Ile
            370                 375                 380

Thr Thr Lys His Ser Gly Leu Tyr Ala Cys Ser Val Arg Asn Ser Ala
385                 390                 395                 400

Thr Gly Lys Glu Ser Ser Lys Ser Val Thr Val Arg Val Ser Asp Trp
            405                 410                 415

Thr Leu Pro
```

<210> SEQ ID NO 32
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 32
taccctcaga agctcctata c                                            21

<210> SEQ ID NO 33
<211> LENGTH: 23
<212> TYPE: DNA
<213> ORGANISM: Artificial Sequence
<220> FEATURE:
<223> OTHER INFORMATION: Description of artificial sequence:
      Oligonucleotide

<400> SEQUENCE: 33
cgtgagcgct tcgagatgtt ccg                                          23

<210> SEQ ID NO 34
<211> LENGTH: 23
<212> TYPE: DNA
<213> ORGANISM: Artificial Sequence
<220> FEATURE:
<223> OTHER INFORMATION: Description of artificial sequence:
      Oligonucleotide

<400> SEQUENCE: 34
cctaaccagc tgcccaactg tag                                          23

<210> SEQ ID NO 35
<211> LENGTH: 2881
<212> TYPE: DNA
<213> ORGANISM: Homo sapiens

<400> SEQUENCE: 35
acagaagtgc tagaagccag tgctcgtgaa ctaaggagaa aaagaacaga caagggaaca      60
gcctggacat ggcatcagag atccacatga caggcccaat gtgcctcatt gagaacacta     120
atgggcgact gatggcgaat ccagaagctc tgaagatcct ttctgccatt acacagccta     180
tggtggtggt ggcaattgtg ggcctctacc gcacaggcaa atcctacctg atgaacaagc     240
tggctggaaa gaaaaagggc ttctctctgg gctccacggt gcagtctcac actaaaggaa     300
tctggatgtg gtgtgtgccc caccccaaga agccaggcca catcctagtt ctgctggaca     360
ccgagggtct gggagatgta gagaagggtg acaaccagaa tgactcctgg atcttcgccc     420
tggccgtcct cctgagcagc accttcgtgt acaatagcat aggaaccatc aaccagcagg     480
ctatggacca actgtactat gtgacagagc tgacacatag aatccgatca aaatcctcac     540
ctgatgagaa tgagaatgag gttgaggatt cagctgactt tgtgagcttc ttcccagact     600
ttgtgtggac actgagagat ttctcccctg acttggaagc agatggacaa cccctcacac     660
cagatgagta cctgacatac tccctgaagc tgaagaaagg taccagtcaa aaagatgaaa     720 ctttttaacct gcccagactc tgtatccgga aattcttccc aaagaaaaaa tgctttgtct     780
ttgatcggcc cgttcaccgc aggaagcttg cccagctcga gaaactacaa gatgaagagc     840 tggacccga atttgtgcaa caagtagcag acttctgttc ctacatcttt agtaattcca     900
aaactaaaac tctttcagga ggcatccagg tcaacgggcc tcgtctagag agcctggtgc     960

-continued

```
tgacctacgt caatgccatc agcagtgggg atctgccgtg catggagaac gcagtcctgg   1020
ccttggccca gatagagaac tcagctgcag tgcaaaaggc tattgcccac tatgaacagc   1080
agatgggcca gaaggtgcag ctgcccacag aaagcctcca ggagctgctg gacctgcaca   1140
gggacagtga gagagaggcc attgaagtct tcatcaggag ttccttcaaa gatgtggacc   1200

atctatttca aaaggagtta gcggcccagc tagaaaaaaa gcgggatgac ttttgtaaac   1260
agaatcagga agcatcatca gatcgttgct caggtttact tcaggtcatt ttcagtcctc   1320
tagaagaaga agtgaaggcg ggaatttatt cgaaaccagg gggctatcgt ctctttgttc   1380
agaagctaca agacctgaag aaaaagtact atgaggaacc gaggaagggg atacaggctg   1440
aagagattct gcagacatac ttgaaatcca aggagtctat gactgatgca attctccaga   1500
cagaccagac tctcacagaa aaagaaaagg agattgaagt ggaacgtgtg aaagctgagt   1560
ctgcacaggc ttcagcaaaa atgttgcagg aaatgcaaag aaagaatgag cagatgatgg   1620
aacagaagga gaggagttat caggaacact tgaaacaact gactgagaag atggagaacg   1680
acagggtcca gttgctgaaa gagcaagaga ggaccctcgc tcttaaactt caggaacagg   1740
agcaactact aaaagaggga tttcaaaaag aaagcagaat aatgaaaaat gagatacagg   1800
atctccagac gaaaatgaga cgacgaaagg catgtaccat aagctaaaga ccagagcctt   1860
cctgtcaccc ctaaccaagg cataattgaa acaattttag aatttggaac aagcgtcact   1920
acatttgata ataattagat cttgcatcat aacaccaaaa gtttataaag gcatgtggta   1980
caatgatcaa aatcatgttt tttcttaaaa aaaaaaaaaa gactgtaaat tgtgcaacaa   2040
agatgcattt acctctgtat caactcagga aatctcataa gctggtacca ctcaggagaa   2100
gtttattctt ccagatgacc agcagtagac aaatggatac tgagcagagt cttaggtaaa   2160
agtcttggga aatatttggg cattggtctg gccaagtcta caatgtccca atatcaagga   2220
caaccaccct agcttcttag tgaagacaat gtacagttat ccattagatc aagactacac   2280
ggtctatgag caataatgtg atttctggac attgcccatg tataatcctc actgatgatt   2340
tcaagctaaa gcaaaccacc ttatacagag atctagaatc tctttatgtt ctccagagga   2400
aggtggaaga aaccatgggc aggagtagga attgagtgat aaacaattgg gctaatgaag   2460
aaaacttctc ttattgttca gttcatccag attataactt caatgggaca ctttagacca   2520
ttagacaatt gacactggat taaacaaatt cacataatgc caaatacaca atgtatttat   2580
agcaacgtat aatttgcaaa gatggacttt aaaagatgct gtgtaactaa actgaaataa   2640
ttcaattact tattatttag aatgttaaag cttatgatag tcttttctaa ttcttaacac   2700
tcatacttga aatctttccg agtttcccca gaagagaata tgggattttt tttgacattt   2760
ttgacccatt taataatgct cttgtgttta cctagtatat gtagactttg tcttatgtgt   2820
caaaagtcct aggaaagtgg ttgatgtttc ttatagcaat taaaaattat ttttgaactg   2880
a                                                                   2881
```

<210> SEQ ID NO 36
<211> LENGTH: 592
<212> TYPE: PRT
<213> ORGANISM: Homo sapiens

<400> SEQUENCE: 36

```
Met Ala Ser Glu Ile His Met Thr Gly Pro Met Cys Leu Ile Glu Asn
1               5                   10                  15

Thr Asn Gly Arg Leu Met Ala Asn Pro Glu Ala Leu Lys Ile Leu Ser

```

```
             20                  25                  30
Ala Ile Thr Gln Pro Met Val Val Ala Ile Val Gly Leu Tyr Arg
             35                  40                  45
Thr Gly Lys Ser Tyr Leu Met Asn Lys Leu Ala Gly Lys Lys Gly
             50                  55                  60
Phe Ser Leu Gly Ser Thr Val Gln Ser His Thr Lys Gly Ile Trp Met
 65                  70                  75                  80
Trp Cys Val Pro His Pro Lys Lys Pro Gly His Ile Leu Val Leu Leu
                     85                  90                  95
Asp Thr Glu Gly Leu Gly Asp Val Glu Lys Gly Asp Asn Gln Asn Asp
                    100                 105                 110
Ser Trp Ile Phe Ala Leu Ala Val Leu Leu Ser Ser Thr Phe Val Tyr
                    115                 120                 125
Asn Ser Ile Gly Thr Ile Asn Gln Gln Ala Met Asp Gln Leu Tyr Tyr
                    130                 135                 140
Val Thr Glu Leu Thr His Arg Ile Arg Ser Lys Ser Ser Pro Asp Glu
145                 150                 155                 160
Asn Glu Asn Glu Val Glu Asp Ser Ala Asp Phe Val Ser Phe Phe Pro
                    165                 170                 175
Asp Phe Val Trp Thr Leu Arg Asp Phe Ser Leu Asp Leu Glu Ala Asp
                    180                 185                 190
Gly Gln Pro Leu Thr Pro Asp Glu Tyr Leu Thr Tyr Ser Leu Lys Leu
                    195                 200                 205
Lys Lys Gly Thr Ser Gln Lys Asp Glu Thr Phe Asn Leu Pro Arg Leu
                    210                 215                 220
Cys Ile Arg Lys Phe Phe Pro Lys Lys Cys Phe Val Phe Asp Arg
225                 230                 235                 240
Pro Val His Arg Arg Lys Leu Ala Gln Leu Glu Lys Leu Gln Asp Glu
                    245                 250                 255
Glu Leu Asp Pro Glu Phe Val Gln Gln Val Ala Asp Phe Cys Ser Tyr
                    260                 265                 270
Ile Phe Ser Asn Ser Lys Thr Lys Thr Leu Ser Gly Gly Ile Gln Val
                    275                 280                 285
Asn Gly Pro Arg Leu Glu Ser Leu Val Leu Thr Tyr Val Asn Ala Ile
                    290                 295                 300
Ser Ser Gly Asp Leu Pro Cys Met Glu Asn Ala Val Leu Ala Leu Ala
305                 310                 315                 320
Gln Ile Glu Asn Ser Ala Ala Val Gln Lys Ala Ile Ala His Tyr Glu
                    325                 330                 335
Gln Gln Met Gly Gln Lys Val Gln Leu Pro Thr Glu Ser Leu Gln Glu
                    340                 345                 350
Leu Leu Asp Leu His Arg Asp Ser Glu Arg Glu Ala Ile Glu Val Phe
                    355                 360                 365
Ile Arg Ser Ser Phe Lys Asp Val Asp His Leu Phe Gln Lys Glu Leu
                    370                 375                 380
Ala Ala Gln Leu Glu Lys Lys Arg Asp Asp Phe Cys Lys Gln Asn Gln
385                 390                 395                 400
Glu Ala Ser Ser Asp Arg Cys Ser Gly Leu Leu Gln Val Ile Phe Ser
                    405                 410                 415
Pro Leu Glu Glu Glu Val Lys Ala Gly Ile Tyr Ser Lys Pro Gly Gly
                    420                 425                 430
Tyr Arg Leu Phe Val Gln Lys Leu Gln Asp Leu Lys Lys Lys Tyr Tyr
                    435                 440                 445
```

```
Glu Pro Arg Lys Gly Ile Gln Ala Glu Glu Ile Leu Gln Thr Tyr
    450                 455                 460
Leu Lys Ser Lys Glu Ser Met Thr Asp Ala Ile Leu Gln Thr Asp Gln
465                 470                 475                 480
Thr Leu Thr Glu Lys Glu Lys Glu Ile Glu Val Glu Arg Val Lys Ala
                485                 490                 495
Glu Ser Ala Gln Ala Ser Ala Lys Met Leu Gln Glu Met Gln Arg Lys
                500                 505                 510
Asn Glu Gln Met Met Glu Gln Lys Glu Arg Ser Tyr Gln Glu His Leu
            515                 520                 525
Lys Gln Leu Thr Glu Lys Met Glu Asn Asp Arg Val Gln Leu Leu Lys
        530                 535                 540
Glu Gln Glu Arg Thr Leu Ala Leu Lys Leu Gln Glu Gln Glu Gln Leu
545                 550                 555                 560
Leu Lys Glu Gly Phe Gln Lys Glu Ser Arg Ile Met Lys Asn Glu Ile
                565                 570                 575
Gln Asp Leu Gln Thr Lys Met Arg Arg Arg Lys Ala Cys Thr Ile Ser
            580                 585                 590
```

```
<210> SEQ ID NO 37
<211> LENGTH: 18
<212> TYPE: DNA
<213> ORGANISM: Artificial Sequence
<220> FEATURE:
<223> OTHER INFORMATION: Description of artificial sequence:
      Oligonucleotide

<400> SEQUENCE: 37
aggagattga agtggaac                                                    18

<210> SEQ ID NO 38
<211> LENGTH: 16
<212> TYPE: DNA
<213> ORGANISM: Artificial Sequence
<220> FEATURE:
<223> OTHER INFORMATION: Description of artificial sequence:
      Oligonucleotide

<400> SEQUENCE: 38
ttgctcctgt tcctga                                                      16

<210> SEQ ID NO 39
<211> LENGTH: 2380
<212> TYPE: DNA
<213> ORGANISM: Homo sapiens

<400> SEQUENCE: 39
ctccaggctg tggaaccttt gttctttcac tctttgcaat aaatcttgct gctgctcact        60
ctttgggtcc acactgcctt tatgagctgt aacactcact gggaatgtct gcagcttcac       120
tcctgaagcc agcgagacca cgaacccacc aggaggaaca aacaactcca gacgcgcagc       180
cttaagagct gtaacactca ccgcgaaggt ctgcagcttc actcctgagc cagccagacc       240
acgaacccac cagaaggaag aaactccaaa cacatccgaa catcagaagg agcaaactcc       300
tgacacgcca cctttaagaa ccgtgacact caacgctagg gtccgcggct tcattcttga       360
agtcagtgag accaagaacc caccaattcc ggacacgcta attgttgtag atcatcactt       420
caaggtgccc atatctttct agtggaaaaa ttattctggc ctccgctgca tacaaatcag       480
gcaaccagaa ttctacatat ataaggcaaa gtaacatcct agacatggct ttagagatcc       540
```

```
acatgtcaga cccatgtgc ctcatcgaga actttaatga gcagctgaag gttaatcagg    600
aagctttgga gatcctgtct gccattacgc aacctgtagt tgtggtagcg attgtgggcc    660
tctatcgcac tggcaaatcc tacctgatga caagctggc tgggaagaac aagggcttct    720
ctgttgcatc tacggtgcag tctcacacca agggaatttg gatatggtgt gtgcctcatc    780
ccaactggcc aaatcacaca ttagttctgc ttgacaccga gggcctggga gatgtagaga    840
aggctgacaa caagaatgat atccagatct ttgcactggc actcttactg agcagcacct    900
ttgtgtacaa tactgtgaac aaaattgatc agggtgctat cgacctactg cacaatgtga    960
cagaactgac agatctgctc aaggcaagaa actcacccga ccttgacagg ttgaagatc    1020 ctgctgactc tgcgagcttc ttcccagact tagtgtggac tctgagagat ttctgcttag    1080
gcctggaaat agatgggcaa cttgtcacac cagatgaata cctggagaat tccctaaggc    1140
caaagcaagg tagtgatcaa agagttcaaa atttcaattt gccccgtctg tgtatacaga    1200 agttcttttcc aaaaagaaa tgctttatct ttgacttacc tgctcaccaa aaaaagcttg    1260
cccaacttga aacactgcct gatgatgagc tagagcctga atttgtgcaa caagtgacag    1320
aattctgttc ctacatctttt agccattcta tgaccaagac tcttccaggt ggcatcatgg    1380
tcaatggatc tcgtctaaag aacctggtgc tgacctatgt caatgccatc agcagtgggg    1440
atctgccttg catagagaat gcagtcctgg ccttggctca gagagagaac tcagctgcag    1500
tgcaaaaggc cattgcccac tatgaccagc aaatgggcca gaaagtgcag ctgcccatgg    1560
aaaccctcca gggagctgctg gacctgcaca ggaccagtga gagggaggcc attgaagtct    1620
tcatgaaaaa ctctttcaag gatgtagacc aaagtttcca gaaagaattg gagactctac    1680
tagatgcaaa acagaatgac atttgtaaac ggaacctgga agcatcctcg gattattgct    1740
cggctttact taaggatatt tttggtcctc tagaagaagc agtgaagcag ggaattttatt    1800 ctaagccagg aggccataat ctcttcattc agaaaacaga gaactgaag gcaaagtact    1860 atcgggagcc tcggaaagga atacaggctg aagaagttct gcagaaatat ttaaagtcca    1920
aggagtctgt gagtcatgca atattacaga ctgaccaggc tctcacagag acggaaaaaa    1980
agaagaaaga ggcacaagtg aaagcagaag ctgaaaaggc tgaagcgcaa aggttggcgg    2040
cgattcaaag gcagaacgag caaatgatgc aggagaggga gagactccat caggaacaag    2100
tgagacaaat ggagatagcc aaacaaaatt ggctggcaga gcaacagaaa atgcaggaac    2160
aacagatgca ggaacaggct gcacagctca gcacaacatt ccaagctcaa aatagaagcc    2220
ttctcagtga gctccagcac gcccagagga ctgttaataa cgatgatcca tgtgttttac    2280
tctaaagtgc taaatatggg agtttccttt ttttactctt tgtcactgat gacacaacag    2340
aaaagaaact gtagaccttg ggacaatcaa catttaaata                         2380
```

<210> SEQ ID NO 40
<211> LENGTH: 586
<212> TYPE: PRT
<213> ORGANISM: Homo sapiens

<400> SEQUENCE: 40

```
Met Ala Leu Glu Ile His Met Ser Asp Pro Met Cys Leu Ile Glu Asn
1               5                   10                  15

Phe Asn Glu Gln Leu Lys Val Asn Gln Glu Ala Leu Glu Ile Leu Ser
            20                  25                  30

Ala Ile Thr Gln Pro Val Val Val Ala Ile Val Gly Leu Tyr Arg
        35                  40                  45
```

```
Thr Gly Lys Ser Tyr Leu Met Asn Lys Leu Ala Gly Lys Asn Lys Gly
 50                  55                  60

Phe Ser Val Ala Ser Thr Val Gln Ser His Thr Lys Gly Ile Trp Ile
 65                  70                  75                  80

Trp Cys Val Pro His Pro Asn Trp Pro Asn His Thr Leu Val Leu Leu
                     85                  90                  95

Asp Thr Glu Gly Leu Gly Asp Val Glu Lys Ala Asp Asn Lys Asn Asp
                    100                 105                 110

Ile Gln Ile Phe Ala Leu Ala Leu Leu Ser Ser Thr Phe Val Tyr
                115                 120                 125

Asn Thr Val Asn Lys Ile Asp Gln Gly Ala Ile Asp Leu Leu His Asn
            130                 135                 140

Val Thr Glu Leu Thr Asp Leu Leu Lys Ala Arg Asn Ser Pro Asp Leu
145                 150                 155                 160

Asp Arg Val Glu Asp Pro Ala Asp Ser Ala Ser Phe Phe Pro Asp Leu
                165                 170                 175

Val Trp Thr Leu Arg Asp Phe Cys Leu Gly Leu Glu Ile Asp Gly Gln
                180                 185                 190

Leu Val Thr Pro Asp Glu Tyr Leu Glu Asn Ser Leu Arg Pro Lys Gln
            195                 200                 205

Gly Ser Asp Gln Arg Val Gln Asn Phe Asn Leu Pro Arg Leu Cys Ile
210                 215                 220

Gln Lys Phe Phe Pro Lys Lys Cys Phe Ile Phe Asp Leu Pro Ala
225                 230                 235                 240

His Gln Lys Lys Leu Ala Gln Leu Glu Thr Leu Pro Asp Asp Glu Leu
                245                 250                 255

Glu Pro Glu Phe Val Gln Gln Val Thr Glu Phe Cys Ser Tyr Ile Phe
                260                 265                 270

Ser His Ser Met Thr Lys Thr Leu Pro Gly Gly Ile Met Val Asn Gly
            275                 280                 285

Ser Arg Leu Lys Asn Leu Val Leu Thr Tyr Val Asn Ala Ile Ser Ser
290                 295                 300

Gly Asp Leu Pro Cys Ile Glu Asn Ala Val Leu Ala Leu Ala Gln Arg
305                 310                 315                 320

Glu Asn Ser Ala Ala Val Gln Lys Ala Ile Ala His Tyr Asp Gln Gln
                325                 330                 335

Met Gly Gln Lys Val Gln Leu Pro Met Glu Thr Leu Gln Glu Leu Leu
            340                 345                 350

Asp Leu His Arg Thr Ser Glu Arg Glu Ala Ile Glu Val Phe Met Lys
                355                 360                 365

Asn Ser Phe Lys Asp Val Asp Gln Ser Phe Gln Lys Glu Leu Glu Thr
            370                 375                 380

Leu Leu Asp Ala Lys Gln Asn Asp Ile Cys Lys Arg Asn Leu Glu Ala
385                 390                 395                 400

Ser Ser Asp Tyr Cys Ser Ala Leu Leu Lys Asp Ile Phe Gly Pro Leu
                405                 410                 415

Glu Glu Ala Val Lys Gln Gly Ile Tyr Ser Lys Pro Gly His Asn
                420                 425                 430

Leu Phe Ile Gln Lys Thr Glu Glu Leu Lys Ala Lys Tyr Tyr Arg Glu
            435                 440                 445

Pro Arg Lys Gly Ile Gln Ala Glu Glu Val Leu Gln Lys Tyr Leu Lys
450                 455                 460
```

Ser Lys Glu Ser Val Ser His Ala Ile Leu Gln Thr Asp Gln Ala Leu
465                 470                 475                 480

Thr Glu Thr Glu Lys Lys Lys Glu Ala Gln Val Lys Ala Glu Ala
            485                 490                 495

Glu Lys Ala Glu Ala Gln Arg Leu Ala Ala Ile Gln Arg Gln Asn Glu
            500                 505                 510

Gln Met Met Gln Glu Arg Glu Arg Leu His Gln Glu Gln Val Arg Gln
        515                 520                 525

Met Glu Ile Ala Lys Gln Asn Trp Leu Ala Glu Gln Gln Lys Met Gln
    530                 535                 540

Glu Gln Gln Met Gln Glu Gln Ala Ala Gln Leu Ser Thr Thr Phe Gln
545                 550                 555                 560

Ala Gln Asn Arg Ser Leu Leu Ser Glu Leu Gln His Ala Gln Arg Thr
                565                 570                 575

Val Asn Asn Asp Asp Pro Cys Val Leu Leu
                580                 585

<210> SEQ ID NO 41
<211> LENGTH: 1051
<212> TYPE: DNA
<213> ORGANISM: Homo sapiens

<400> SEQUENCE: 41
ggaccgccgc ctggttaaag gcgcttattt cccaggcagc cgctgcagtc gccacacctt      60
tgcccctgct gcgatgaccc tgtcgccact tctgctgttc ctgccaccgc tgctgctgct     120
gctggacgtc cccacggcgg cggtgcaggc gtcccctctg caagcgttag acttctttgg     180
gaatgggcca ccagttaact acaagacagg caatctatac ctgcggggc ccctgaagaa     240
gtccaatgca ccgcttgtca atgtgaccct ctactatgaa gcactgtgcg gtggctgccg     300
agccttcctg atccgggagc tcttcccaac atggctgttg gtcatggaga tcctcaatgt     360
cacgctggtg ccctacggaa acgcacagga acaaaatgtc agtggcaggt gggagttcaa     420
gtgccagcat ggagaagagg agtgcaaatt caacaaggtg gaggcctgcg tgttggatga     480
acttgacatg gagctagcct tcctgaccat tgtctgcatg gaaagtttg aggacatgga     540
gagaagtctg ccactatgcc tgcagctcta cgccccaggg ctgtcgccag acactatcat     600
ggagtgtgca atgggggacc gcggcatgca gctcatgcac gccaacgccc agcggacaga     660
tgctctccag ccaccacacg agtatgtgcc ctgggtcacc gtcaatggga aacccttgga     720
agatcagacc cagctcctta cccttgtctg ccagttgtac cagggcaaga gccggatgt     780
ctgcccttcc tcaaccagct ccctcaggag tgtttgcttc aagtgatggc cggtgagctg     840
cggagagctc atggaaggcg agtgggaacc cggctgcctg ccttttttc tgatccagac     900
cctcggcacc tgctacttac caactggaaa attttatgca tcccatgaag cccagataca     960
caaaattcca ccccatgatc aagaatcctg ctccactaag aatggtgcta agtaaaact    1020
agtttaataa gcaaaaaaaa aaaaaaaaaa a                                   1051

<210> SEQ ID NO 42
<211> LENGTH: 250
<212> TYPE: PRT
<213> ORGANISM: Homo sapiens

<400> SEQUENCE: 42

Met Thr Leu Ser Pro Leu Leu Leu Phe Leu Pro Pro Leu Leu Leu Leu
1               5                   10                  15

```
Leu Asp Val Pro Thr Ala Ala Val Gln Ala Ser Pro Leu Gln Ala Leu
             20                  25                  30

Asp Phe Phe Gly Asn Gly Pro Pro Val Asn Tyr Lys Thr Gly Asn Leu
         35                  40                  45

Tyr Leu Arg Gly Pro Leu Lys Lys Ser Asn Ala Pro Leu Val Asn Val
 50                  55                  60

Thr Leu Tyr Tyr Glu Ala Leu Cys Gly Gly Cys Arg Ala Phe Leu Ile
 65                  70                  75                  80

Arg Glu Leu Phe Pro Thr Trp Leu Leu Val Met Glu Ile Leu Asn Val
                 85                  90                  95

Thr Leu Val Pro Tyr Gly Asn Ala Gln Glu Gln Asn Val Ser Gly Arg
            100                 105                 110

Trp Glu Phe Lys Cys Gln His Gly Glu Glu Cys Lys Phe Asn Lys
            115                 120                 125

Val Glu Ala Cys Val Leu Asp Glu Leu Asp Met Glu Leu Ala Phe Leu
            130                 135                 140

Thr Ile Val Cys Met Glu Glu Phe Glu Asp Met Glu Arg Ser Leu Pro
145                 150                 155                 160

Leu Cys Leu Gln Leu Tyr Ala Pro Gly Leu Ser Pro Asp Thr Ile Met
                165                 170                 175

Glu Cys Ala Met Gly Asp Arg Gly Met Gln Leu Met His Ala Asn Ala
            180                 185                 190

Gln Arg Thr Asp Ala Leu Gln Pro His Glu Tyr Val Pro Trp Val
            195                 200                 205

Thr Val Asn Gly Lys Pro Leu Glu Asp Gln Thr Gln Leu Leu Thr Leu
210                 215                 220

Val Cys Gln Leu Tyr Gln Gly Lys Lys Pro Asp Val Cys Pro Ser Ser
225                 230                 235                 240

Thr Ser Ser Leu Arg Ser Val Cys Phe Lys
                245                 250

<210> SEQ ID NO 43
<211> LENGTH: 17
<212> TYPE: DNA
<213> ORGANISM: Artificial Sequence
<220> FEATURE:
<223> OTHER INFORMATION: Description of artificial sequence:
      Oligonucleotide

<400> SEQUENCE: 43
ctacaagaca ggcaatc                                                17

<210> SEQ ID NO 44
<211> LENGTH: 17
<212> TYPE: DNA
<213> ORGANISM: Artificial Sequence
<220> FEATURE:
<223> OTHER INFORMATION: Description of artificial sequence:
      Oligonucleotide

<400> SEQUENCE: 44
ttcatccaac acgcagg                                                17

<210> SEQ ID NO 45
<211> LENGTH: 875
<212> TYPE: DNA
<213> ORGANISM: Homo sapiens

<400> SEQUENCE: 45
```

-continued

```
ggttgctaag gagtgggtgc ctcagaatca ggctgcaatg ggcattgtct gtgcacaatg      60
ttcctttatt ctgctgctgt ccataataag ggctcgtcca cctcccttcc tcttctgccc     120
attgagcagt caaagaactg aaagtcctta taagcctgtg cacctgggcc tgggccctac     180
agataaggta gctgctattg ctatggcccg catcattgac ctggtgccct gggacgatgg     240
ctccacacat gtgtatgcct ccccggccat cctgcttccc atggagcggc agcgcaacca     300
gctggcgggc gtgaagcagc agctctacca cccagccctg cccacccgc gccacatgga      360 cagggacacc gtcaaggcct gccttcctga tgagcactgc cagtccacca cctactgccg     420
caaagatgaa tttgacaacg cccatttac actccttggg gtccccaaca aaccctgca      480 gtgtttggac atcaccgcca caggccagaa gcttcgcaac aggtaccacg agggaaagct     540
ggcgcccatc gcgccaggca tcaaccgagt ggactggccc tgcttcacgc gcgccatcga     600
ggactggtcc cacttcgtgt cctcggccgg ggagttcaag ctgccttgcc tgaggaagcg     660
agcggagggt ctcagcggct acgcggtgcg gtacttgaag cccgacgtga cccagacctg     720
gcggtactgc ctcaaccaga accccagcct ggaccgctac ggacagaagc ccctgccttt     780
cgactccctg aacactttcc gaagcttcgg ctccagctac agtcgtgtca actacctgac     840
cccctggcat taatctctgg aaaggaggct gactc                                 875
```

<210> SEQ ID NO 46
<211> LENGTH: 271
<212> TYPE: PRT
<213> ORGANISM: Homo sapiens

<400> SEQUENCE: 46

```
Met Gly Ile Val Cys Ala Gln Cys Ser Phe Ile Leu Leu Ser Ile
1               5                   10                  15

Ile Arg Ala Arg Pro Pro Pro Phe Leu Phe Cys Pro Leu Ser Ser Gln
            20                  25                  30

Arg Thr Glu Ser Pro Tyr Lys Pro Val His Leu Gly Leu Gly Pro Thr
        35                  40                  45

Asp Lys Val Ala Ala Ile Ala Met Ala Arg Ile Ile Asp Leu Val Pro
    50                  55                  60

Trp Asp Asp Gly Ser Thr His Val Tyr Ala Ser Pro Ala Ile Leu Leu
65                  70                  75                  80

Pro Met Glu Arg Gln Arg Asn Gln Leu Ala Gly Val Lys Gln Gln Leu
                85                  90                  95

Tyr His Pro Ala Leu Pro Thr Leu Arg His Met Asp Arg Asp Thr Val
            100                 105                 110

Lys Ala Cys Leu Pro Asp Glu His Cys Gln Ser Thr Thr Tyr Cys Arg
        115                 120                 125

Lys Asp Glu Phe Asp Asn Ala His Phe Thr Leu Leu Gly Val Pro Asn
    130                 135                 140

Lys Pro Leu Gln Cys Leu Asp Ile Thr Ala Thr Gly Gln Lys Leu Arg
145                 150                 155                 160

Asn Arg Tyr His Glu Gly Lys Leu Ala Pro Ile Ala Pro Gly Ile Asn
                165                 170                 175

Arg Val Asp Trp Pro Cys Phe Thr Arg Ala Ile Glu Asp Trp Ser His
            180                 185                 190

Phe Val Ser Ser Ala Gly Glu Phe Lys Leu Pro Cys Leu Arg Lys Arg
        195                 200                 205

Ala Glu Gly Leu Ser Gly Tyr Ala Val Arg Tyr Leu Lys Pro Asp Val
    210                 215                 220
```

Thr Gln Thr Trp Arg Tyr Cys Leu Asn Gln Asn Pro Ser Leu Asp Arg
225                 230                 235                 240

Tyr Gly Gln Lys Pro Leu Pro Phe Asp Ser Leu Asn Thr Phe Arg Ser
            245                 250                 255

Phe Gly Ser Ser Tyr Ser Arg Val Asn Tyr Leu Thr Pro Trp His
        260                 265                 270

<210> SEQ ID NO 47
<211> LENGTH: 22
<212> TYPE: DNA
<213> ORGANISM: Artificial Sequence
<220> FEATURE:
<223> OTHER INFORMATION: Description of artificial sequence:
      Oligonucleotide

<400> SEQUENCE: 47
tccaccacct actgccgcaa ag                                          22

<210> SEQ ID NO 48
<211> LENGTH: 20
<212> TYPE: DNA
<213> ORGANISM: Artificial Sequence
<220> FEATURE:
<223> OTHER INFORMATION: Description of artificial sequence:
      Oligonucleotide

<400> SEQUENCE: 48
accctccgct cgcttcctca                                             20

<210> SEQ ID NO 49
<211> LENGTH: 956
<212> TYPE: DNA
<213> ORGANISM: Homo sapiens

<400> SEQUENCE: 49
ggttgctaag gagtgggtgc ctcagaatca ggctgcaatg gcattgtct gtgcacaatg    60
ttcctttatt ctgctgctgt ccataataag ggctcgtcca cctcccttcc tcttctgccc  120
attgagcagt caaagaactg aaagtcctta taagcctgtg cacctgggcc tgggccctac  180
agataaggta gctgctattg ctatggcccg catcattgac ctggtgccct gggacgatgg  240
ctccacacat gtgtatgcct ccccggccat cctgcttccc atggagcggc agcgcaacca  300
gctggcgggc gtgaagcagc agctctacca cccagccctg cccaccctgc gccacatgga  360
cagggacacc gtcaaggcct gccttcctga tgagcactgc cagtccacca cctactgccg  420
caaagatgaa tttgacaacg cccatttta c actccttggg gtccccaaca accctgca    480
gtgtttggac atcaccgcca caggccagaa gcttcgcaac aggtaccacg agggaaagct  540
ggcgcccatc gcgccaggca tcaaccgagt ggactggccc tgcttcacgc gcgccatcga  600
ggactggtcc cacttcgtgt cctcggccgg ggagttcaag ctgccttgcc tgaggaagcg  660
agcggagggt ctcagcggct acgcggtgcg gtacttgaag cccgacgtga cccagacctg  720
gcggcaggaa gccctgtgtg gggcgtgggc agggcgtccg tgctccccccg actcaccgcg  780
ccctatccc tgctgcccgc ctcagtactg cctcaaccag aacccagcc tggaccgcta  840
cggacagaag cccctgcctt tcgactccct gaacactttc cgaagcttcg gctccagcta  900
cagtcgtgtc aactacctga ccccctggca ttaatctctg gaaaggaggc tgactc       956

<210> SEQ ID NO 50
<211> LENGTH: 298

<212> TYPE: PRT
<213> ORGANISM: Homo sapiens

<400> SEQUENCE: 50

Met Gly Ile Val Cys Ala Gln Cys Ser Phe Ile Leu Leu Ser Ile
1               5                   10                  15

Ile Arg Ala Arg Pro Pro Phe Leu Phe Cys Pro Leu Ser Ser Gln
            20                  25                  30

Arg Thr Glu Ser Pro Tyr Lys Pro Val His Leu Gly Leu Gly Pro Thr
        35                  40                  45

Asp Lys Val Ala Ala Ile Ala Met Ala Arg Ile Ile Asp Leu Val Pro
    50                  55                  60

Trp Asp Asp Gly Ser Thr His Val Tyr Ala Ser Pro Ala Ile Leu Leu
65                  70                  75                  80

Pro Met Glu Arg Gln Arg Asn Gln Leu Ala Gly Val Lys Gln Gln Leu
                85                  90                  95

Tyr His Pro Ala Leu Pro Thr Leu Arg His Met Asp Arg Asp Thr Val
            100                 105                 110

Lys Ala Cys Leu Pro Asp Glu His Cys Gln Ser Thr Thr Tyr Cys Arg
        115                 120                 125

Lys Asp Glu Phe Asp Asn Ala His Phe Thr Leu Leu Gly Val Pro Asn
    130                 135                 140

Lys Pro Leu Gln Cys Leu Asp Ile Thr Ala Thr Gly Gln Lys Leu Arg
145                 150                 155                 160

Asn Arg Tyr His Glu Gly Lys Leu Ala Pro Ile Ala Pro Gly Ile Asn
                165                 170                 175

Arg Val Asp Trp Pro Cys Phe Thr Arg Ala Ile Glu Asp Trp Ser His
            180                 185                 190

Phe Val Ser Ser Ala Gly Glu Phe Lys Leu Pro Cys Leu Arg Lys Arg
        195                 200                 205

Ala Glu Gly Leu Ser Gly Tyr Ala Val Arg Tyr Leu Lys Pro Asp Val
    210                 215                 220

Thr Gln Thr Trp Arg Gln Glu Ala Leu Cys Gly Ala Trp Ala Gly Arg
225                 230                 235                 240

Pro Cys Ser Pro Asp Ser Pro Arg Pro Tyr Pro Cys Cys Pro Pro Gln
                245                 250                 255

Tyr Cys Leu Asn Gln Asn Pro Ser Leu Asp Arg Tyr Gly Gln Lys Pro
            260                 265                 270

Leu Pro Phe Asp Ser Leu Asn Thr Phe Arg Ser Phe Gly Ser Ser Tyr
        275                 280                 285

Ser Arg Val Asn Tyr Leu Thr Pro Trp His
    290                 295

<210> SEQ ID NO 51
<211> LENGTH: 16
<212> TYPE: PRT
<213> ORGANISM: Homo sapiens

<400> SEQUENCE: 51

Cys Ser Lys Asp Ser Arg Gly Ile Ala Asp Pro Asn Gln Ser Ala Lys
1               5                   10                  15

<210> SEQ ID NO 52
<211> LENGTH: 13
<212> TYPE: PRT
<213> ORGANISM: Homo sapiens

```
<400> SEQUENCE: 52

Cys Glu Glu Asp Ser Lys Ile Lys Gly Ile His Asp Glu
1               5                   10

<210> SEQ ID NO 53
<211> LENGTH: 12
<212> TYPE: PRT
<213> ORGANISM: Homo sapiens

<400> SEQUENCE: 53

Cys Lys Leu Arg Asn Arg Ile Trp Gly Met Val Asn
1               5                   10

<210> SEQ ID NO 54
<211> LENGTH: 64
<212> TYPE: PRT
<213> ORGANISM: Homo sapiens

<400> SEQUENCE: 54

Arg Tyr Arg Lys Cys Ile Lys Leu Lys Gln Val Gln Ser Pro Pro Thr
1               5                   10                  15

Glu Thr Leu Gly Val Glu Asn Lys Gly Tyr Phe Gly Asp Glu Gln Gln
            20                  25                  30

Ile Arg Thr Glu Pro Ile Leu Pro Glu Ile His Phe Leu Asn Lys Pro
        35                  40                  45

Ala Ser Lys Asp Ser Arg Gly Ile Ala Asp Pro Asn Gln Ser Ala Lys
    50                  55                  60

<210> SEQ ID NO 55
<211> LENGTH: 667
<212> TYPE: PRT
<213> ORGANISM: Homo sapiens

<400> SEQUENCE: 55

Met Leu Pro Gly Cys Ile Phe Leu Met Ile Leu Leu Ile Pro Gln Val
1               5                   10                  15

Lys Glu Lys Phe Ile Leu Gly Val Glu Gly Gln Gln Leu Val Arg Pro
            20                  25                  30

Lys Lys Leu Pro Leu Ile Gln Lys Arg Asp Thr Gly His Thr His Asp
        35                  40                  45

Asp Asp Ile Leu Lys Thr Tyr Glu Glu Leu Leu Tyr Glu Ile Lys
    50                  55                  60

Leu Asn Arg Lys Thr Leu Val Leu His Leu Leu Arg Ser Arg Glu Phe
65                  70                  75                  80

Leu Gly Ser Asn Tyr Ser Glu Thr Phe Tyr Ser Met Lys Gly Glu Ala
                85                  90                  95

Phe Thr Arg His Pro Gln Ile Met Asp His Cys Phe Tyr Gln Gly Ser
            100                 105                 110

Ile Val His Glu Tyr Asp Ser Ala Ala Ser Ile Ser Thr Cys Asn Gly
        115                 120                 125

Leu Arg Gly Phe Phe Arg Ile Asn Asp Gln Arg Tyr Leu Ile Glu Pro
    130                 135                 140

Val Lys Tyr Ser Asp Glu Gly Glu His Leu Val Phe Tyr Asn Leu
145                 150                 155                 160

Arg Val Pro Tyr Gly Ala Asn Tyr Ser Cys Thr Glu Leu Asn Phe Thr
                165                 170                 175

Arg Lys Thr Val Pro Gly Asp Asn Glu Ser Glu Asp Ser Lys Ile
            180                 185                 190
```

```
Lys Gly Ile His Asp Glu Lys Tyr Val Glu Leu Phe Ile Val Ala Asp
        195                 200                 205

Asp Thr Val Tyr Arg Arg Asn Gly His Pro His Asn Lys Leu Arg Asn
    210                 215                 220

Arg Ile Trp Gly Met Val Asn Phe Val Asn Met Ile Tyr Lys Thr Leu
225                 230                 235                 240

Asn Ile His Val Thr Leu Val Gly Ile Glu Ile Trp Thr His Glu Asp
                245                 250                 255

Lys Ile Glu Leu Tyr Ser Asn Ile Glu Thr Thr Leu Leu Arg Phe Ser
                260                 265                 270

Phe Trp Gln Glu Lys Ile Leu Lys Thr Arg Lys Asp Phe Asp His Val
            275                 280                 285

Val Leu Leu Ser Gly Lys Trp Leu Tyr Ser His Val Gln Gly Ile Ser
        290                 295                 300

Tyr Pro Gly Gly Met Cys Leu Pro Tyr Ser Thr Ser Ile Ile Lys
305                 310                 315                 320

Asp Leu Leu Pro Asp Thr Asn Ile Ile Ala Asn Arg Met Ala His Gln
                325                 330                 335

Leu Gly His Asn Leu Gly Met Gln His Asp Glu Phe Pro Cys Thr Cys
                340                 345                 350

Pro Ser Gly Lys Cys Val Met Asp Ser Asp Gly Ser Ile Pro Ala Leu
            355                 360                 365

Lys Phe Ser Lys Cys Ser Gln Asn Gln Tyr His Gln Tyr Leu Lys Asp
        370                 375                 380

Tyr Lys Pro Thr Cys Met Leu Asn Ile Pro Phe Pro Tyr Asn Phe His
385                 390                 395                 400

Asp Phe Gln Phe Cys Gly Asn Lys Lys Leu Asp Glu Gly Glu Glu Cys
                405                 410                 415

Asp Cys Gly Pro Ala Gln Glu Cys Thr Asn Pro Cys Cys Asp Ala His
                420                 425                 430

Thr Cys Val Leu Lys Pro Gly Phe Thr Cys Ala Glu Gly Glu Cys Cys
        435                 440                 445

Glu Ser Cys Gln Ile Lys Lys Ala Gly Ser Ile Cys Arg Pro Ala Lys
        450                 455                 460

Asp Glu Cys Asp Phe Pro Glu Met Cys Thr Gly His Ser Pro Ala Cys
465                 470                 475                 480

Pro Lys Asp Gln Phe Arg Val Asn Gly Phe Pro Cys Lys Asn Ser Glu
                485                 490                 495

Gly Tyr Cys Phe Met Gly Lys Cys Pro Thr Arg Glu Asp Gln Cys Ser
            500                 505                 510

Glu Leu Phe Asp Asp Ala Ile Glu Ser His Asp Ile Cys Tyr Lys
                515                 520                 525

Met Asn Thr Lys Gly Asn Lys Phe Gly Tyr Cys Lys Asn Lys Glu Asn
        530                 535                 540

Arg Phe Leu Pro Cys Glu Lys Asp Val Arg Cys Gly Lys Ile Tyr
545                 550                 555                 560

Cys Thr Gly Gly Glu Leu Ser Ser Leu Leu Gly Glu Asp Lys Thr Tyr
                565                 570                 575

His Leu Lys Asp Pro Gln Lys Asn Ala Thr Val Lys Cys Lys Thr Ile
                580                 585                 590

Phe Leu Tyr His Asp Ser Thr Asp Ile Gly Leu Val Ala Ser Gly Thr
                595                 600                 605
```

```
Lys Cys Gly Glu Gly Met Val Cys Asn Asn Gly Glu Cys Leu Asn Met
610                 615                 620

Glu Lys Val Tyr Ile Ser Thr Asn Cys Pro Ser Gln Cys Asn Glu Asn
625                 630                 635                 640

Pro Val Asp Gly His Gly Leu Gln Cys His Cys Glu Glu Gly Gln Ala
                645                 650                 655

Pro Val Ala Cys Glu Glu Thr Leu His Val Thr
        660                 665
```

<210> SEQ ID NO 56
<211> LENGTH: 39
<212> TYPE: PRT
<213> ORGANISM: Homo sapiens

<400> SEQUENCE: 56

```
Ile Ser Thr Asn Cys Pro Ser Gln Cys Asn Glu Asn Pro Val Asp Gly
1               5                   10                  15

His Gly Leu Gln Cys His Cys Glu Glu Gly Gln Ala Pro Val Ala Cys
            20                  25                  30

Glu Glu Thr Leu His Val Thr
        35
```

<210> SEQ ID NO 57
<211> LENGTH: 62
<212> TYPE: PRT
<213> ORGANISM: Homo sapiens

<400> SEQUENCE: 57

```
Ile Ser Thr Asn Cys Pro Ser Gln Cys Asn Glu Asn Pro Val Asp Gly
1               5                   10                  15

His Gly Leu Gln Cys His Cys Glu Glu Gly Gln Ala Pro Val Ala Cys
            20                  25                  30

Glu Glu Thr Leu His Val Thr Asn Ile Thr Ile Leu Val Val Val Leu
            35                  40                  45

Val Leu Val Ile Val Gly Ile Gly Val Leu Ile Leu Leu Val
        50                  55                  60
```

<210> SEQ ID NO 58
<211> LENGTH: 12
<212> TYPE: PRT
<213> ORGANISM: Homo sapiens

<400> SEQUENCE: 58

```
Ala Pro Gln Lys Ser Pro Trp Leu Thr Lys Pro Cys
1               5                   10
```

<210> SEQ ID NO 59
<211> LENGTH: 14
<212> TYPE: PRT
<213> ORGANISM: Homo sapiens

<400> SEQUENCE: 59

```
Cys Pro Leu Gln Pro Ser His Phe Leu Asp Ile Ser Glu Asp
1               5                   10
```

<210> SEQ ID NO 60
<211> LENGTH: 12
<212> TYPE: PRT
<213> ORGANISM: Homo sapiens

<400> SEQUENCE: 60

Cys Ile Tyr Ser Thr Glu Ile His Tyr Ser Ser Lys
1               5                   10

<210> SEQ ID NO 61
<211> LENGTH: 500
<212> TYPE: DNA
<213> ORGANISM: Homo sapiens

<400> SEQUENCE: 61

| | | | | | |
|---|---|---|---|---|---|
| gcagcctcac | tgtcctgtct | tgaacatcct | ccaccaaagt | gtgaacacag | gtggcatggg | 60 |
| cttcgtaacg | aataagagcg | ccttcaaagc | aggagattcc | ctgtacctgc | gaagggcctt | 120 |
| cgtgaacaac | cttggagagg | aaaggagaac | caggattcag | atccaaagca | tccagaaggc | 180 |
| tttagacatc | cagatcaggg | agattgatag | agaaaaagca | gccctgaaga | gattttggt | 240 |
| aaagcttcac | aagacaactg | gctatttcc | tcaaaagcca | ttgtggtgac | tgatgctgtg | 300 |
| ccaccatagg | ggacgagttc | atctgaaaca | tccaatacag | acagaacaca | cctgggtctc | 360 |
| cttctgtatc | tctctgtgac | ccaagaaagc | agtagaagtg | gctactggga | caagccaaaa | 420 |
| aagaaaaaaa | aggactagat | aattgaggac | acaaatggac | tgcctctaaa | ataataaaca | 480 |
| aaacctccta | caaaagagag | | | | | 500 |

<210> SEQ ID NO 62
<211> LENGTH: 2256
<212> TYPE: DNA
<213> ORGANISM: Homo sapiens

<400> SEQUENCE: 62

| | | | | | |
|---|---|---|---|---|---|
| atgcggctga | tgggccccct | gagcctgaga | gtagggatga | ccctggaagc | ggcgctagtg | 60 |
| ctgatccgca | ggtccccgcg | ctcccgccag | agccgcgacc | cggcttgtgc | cacccagctt | 120 |
| cggggcctgc | agggagcgct | gcttcttctg | agcctgagtc | tgggaccctc | tttgcagtgt | 180 |
| ggctgtgggg | gcgctggtcc | catcacggcc | tttttcataa | agcacatggt | gccaactgtt | 240 |
| agtggatcta | ccatcctgga | ggatgatagc | cctcttctaa | cagctccact | aggcagtgcc | 300 |
| ccagtaggga | ctctgtgtag | gcgccctcac | cccacatttc | ccttccacac | tgccctagca | 360 |
| gaggttctcc | atgagggcgc | tgcccctgca | gcaaacttct | gcctggacat | ccaggaaccg | 420 |
| ccccagtggt | cagctgccgc | gctgttgcta | ggcaacagcg | tgcgagctca | gatcagcgtg | 480 |
| gggtggagga | gaagtggagt | ttggaagttc | aggggcacag | gggcacaggc | ccacgactgc | 540 |
| agcgggatgg | accagtactg | catcctgggc | cgcatcgggg | agggcgccca | cggcatcgtc | 600 |
| ttcaaggcca | agcacgtgga | gccgagggtg | ggctggcagt | gtctgccttc | tatcctgcag | 660 |
| actggcgaga | tagttgccct | caagaaggtg | gccctaaggc | ggttggagga | cggcttccct | 720 |
| aaccaggccc | tgcgggagat | taaggctctg | caggagatgg | aggacaatca | gtatgtggta | 780 |
| caactgaagg | ctgtgttccc | acacggtgga | ggctttgtgc | tggcctttga | gttcatgctg | 840 |
| tcggatctgg | ccgaggtggt | gcgccatgcc | cagaggccac | tagcccaggc | acaggtcaag | 900 |
| agctacctgc | agatgctgct | caagggtgtc | gccttctgcc | atgccaacaa | cattgtacat | 960 |
| cgggacctga | aacctgccaa | cctgctcatc | agcgcctcag | gccagctcaa | gatagcggac | 1020 |
| tttggcctgg | ctcgagtctt | tcccccagac | ggcagccgcc | tctacacaca | ccaggtggcc | 1080 |
| accaggtggt | accgagcccc | cgagctcctg | tatggtgccc | gccagtatga | ccagggcgtc | 1140 |
| gatctgtggt | ctgtgggctg | catcatgggg | gagctgttga | atgggtcccc | cctttttccg | 1200 |
| ggcaagaacg | atattgaaca | gctttgctat | gtgcttcgca | tcttgggcac | cccaaaccct | 1260 |

```
caagtctggc cggagctcac tgagctgccg gactacaaca agatctcctt taaggagcag    1320
gtgcccatgc ccctggagga ggtgctgcct gacgtctctc cccaggcatt ggatctgctg    1380
ggtcaattcc ttctctaccc tcctcaccag cgcatcgcag cttccaagct gtgggagccc    1440
caggagagag gcaaggccga ctttggggtc aagcaaagct tcctggtgga gggcaggttt    1500
aagcatgaga tgtttgagga ggtgttcgct gaagagagaa atgctcccct gcctgcccat    1560
ccatctgagc tgccgattcc tcagcgtcta gggggacctg cccccaaggc ccatccaggg    1620
cccccccaca tccatgactt ccacgtggac cggcctcttg aggagtcgct gttgaaccca    1680
gagctgattc ggcccttcat cctggagggc ccttgcgagg gttggtctcg aggcagaggt    1740
catgttccca gccaagagta tgagaacatc cagtcgagca gaggagattc atggcctgtg    1800 ctcgttttcac tgacctgcat gttctggaag gagccaggac agcagcctac ccgcaagct    1860 gcccagaagc cccggatggc ccctcagcca gctgaaacca ccgtccactg ggaagatggc    1920
tacttggagg cctctggagg ggaggggtt gttcacgaag cccttcgca ggtacaggga    1980 atctcctgct ttgaaggcgc tcttattcgt tacgaagccc atgccacctg tgttcacact    2040
ttggtggagg atgttcaaga caggacacat ctactggccc ctcctaaagc ctttgcctgg    2100
ctgctcctgc aagagcatgc acaaagcaca gcctccactg ccttgcctgg gaacactttg    2160
gctcccccag cacagccaat gctcaactca acaggacaaa gctgcaggcc cagtcccaaa    2220
ccgccagggt gtgagaatat agctcaggag tattga                             2256
```

<210> SEQ ID NO 63
<211> LENGTH: 751
<212> TYPE: PRT
<213> ORGANISM: Homo sapiens

<400> SEQUENCE: 63

```
Met Arg Leu Met Gly Pro Leu Ser Leu Arg Val Gly Met Thr Leu Glu
1               5                  10                  15

Ala Ala Leu Val Leu Ile Arg Arg Ser Pro Arg Ser Arg Gln Ser Arg
            20                  25                  30

Asp Pro Ala Cys Ala Thr Gln Leu Arg Gly Leu Gln Gly Ala Leu Leu
        35                  40                  45

Leu Leu Ser Leu Ser Leu Gly Pro Ser Leu Gln Cys Gly Cys Gly Gly
    50                  55                  60

Ala Gly Pro Ile Thr Ala Phe Phe Ile Lys His Met Val Pro Thr Val
65                  70                  75                  80

Ser Gly Ser Thr Ile Leu Glu Asp Asp Ser Pro Leu Leu Thr Ala Pro
                85                  90                  95

Leu Gly Ser Ala Pro Val Gly Thr Leu Cys Arg Arg Pro His Pro Thr
            100                 105                 110

Phe Pro Phe His Thr Ala Leu Ala Glu Val Leu His Glu Gly Ala Ala
        115                 120                 125

Pro Ala Ala Asn Phe Cys Leu Asp Ile Gln Glu Pro Pro Gln Trp Ser
    130                 135                 140

Ala Ala Ala Leu Leu Leu Gly Asn Ser Val Arg Ala Gln Ile Ser Val
145                 150                 155                 160

Gly Trp Arg Arg Ser Gly Val Trp Lys Phe Arg Gly Thr Gly Ala Gln
                165                 170                 175

Ala His Asp Cys Ser Gly Met Asp Gln Tyr Cys Ile Leu Gly Arg Ile
            180                 185                 190

Gly Glu Gly Ala His Gly Ile Val Phe Lys Ala Lys His Val Glu Pro
```

```
            195                 200                 205
Arg Val Gly Trp Gln Cys Leu Pro Ser Ile Leu Gln Thr Gly Glu Ile
210                 215                 220

Val Ala Leu Lys Lys Val Ala Leu Arg Arg Leu Glu Asp Gly Phe Pro
225                 230                 235                 240

Asn Gln Ala Leu Arg Glu Ile Lys Ala Leu Gln Glu Met Glu Asp Asn
                245                 250                 255

Gln Tyr Val Val Gln Leu Lys Ala Val Phe Pro His Gly Gly Gly Phe
                260                 265                 270

Val Leu Ala Phe Glu Phe Met Leu Ser Asp Leu Ala Glu Val Val Arg
        275                 280                 285

His Ala Gln Arg Pro Leu Ala Gln Ala Gln Val Lys Ser Tyr Leu Gln
        290                 295                 300

Met Leu Leu Lys Gly Val Ala Phe Cys His Ala Asn Asn Ile Val His
305                 310                 315                 320

Arg Asp Leu Lys Pro Ala Asn Leu Leu Ile Ser Ala Ser Gly Gln Leu
                325                 330                 335

Lys Ile Ala Asp Phe Gly Leu Ala Arg Val Phe Ser Pro Asp Gly Ser
                340                 345                 350

Arg Leu Tyr Thr His Gln Val Ala Thr Arg Trp Tyr Arg Ala Pro Glu
        355                 360                 365

Leu Leu Tyr Gly Ala Arg Gln Tyr Asp Gln Gly Val Asp Leu Trp Ser
370                 375                 380

Val Gly Cys Ile Met Gly Glu Leu Leu Asn Gly Ser Pro Leu Phe Pro
385                 390                 395                 400

Gly Lys Asn Asp Ile Glu Gln Leu Cys Tyr Val Leu Arg Ile Leu Gly
                405                 410                 415

Thr Pro Asn Pro Gln Val Trp Pro Glu Leu Thr Glu Leu Pro Asp Tyr
                420                 425                 430

Asn Lys Ile Ser Phe Lys Glu Gln Val Pro Met Pro Leu Glu Glu Val
        435                 440                 445

Leu Pro Asp Val Ser Pro Gln Ala Leu Asp Leu Leu Gly Gln Phe Leu
450                 455                 460

Leu Tyr Pro Pro His Gln Arg Ile Ala Ala Ser Lys Leu Trp Glu Pro
465                 470                 475                 480

Gln Glu Arg Gly Lys Ala Asp Phe Gly Val Lys Gln Ser Phe Leu Val
                485                 490                 495

Glu Gly Arg Phe Lys His Glu Met Phe Glu Glu Val Phe Ala Glu Glu
                500                 505                 510

Arg Asn Ala Pro Leu Pro Ala His Pro Ser Glu Leu Pro Ile Pro Gln
        515                 520                 525

Arg Leu Gly Gly Pro Ala Pro Lys Ala His Pro Gly Pro Pro His Ile
        530                 535                 540

His Asp Phe His Val Asp Arg Pro Leu Glu Glu Ser Leu Leu Asn Pro
545                 550                 555                 560

Glu Leu Ile Arg Pro Phe Ile Leu Glu Gly Pro Cys Glu Gly Trp Ser
                565                 570                 575

Arg Gly Arg Gly His Val Pro Ser Gln Glu Tyr Glu Asn Ile Gln Ser
                580                 585                 590

Ser Arg Gly Asp Ser Trp Pro Val Leu Val Ser Leu Thr Cys Met Phe
        595                 600                 605

Trp Lys Glu Pro Gly Gln Gln Pro Thr Pro Gln Ala Ala Gln Lys Pro
610                 615                 620
```

```
Arg Met Ala Pro Gln Pro Ala Glu Thr Thr Val His Trp Glu Asp Gly
625                 630                 635                 640

Tyr Leu Glu Ala Ser Gly Gly Gly Val His Glu Gly Pro Ser
            645                 650                 655

Gln Val Gln Gly Ile Ser Cys Phe Glu Gly Ala Leu Ile Arg Tyr Glu
                660                 665                 670

Ala His Ala Thr Cys Val His Thr Leu Val Glu Asp Val Gln Asp Arg
            675                 680                 685

Thr His Leu Leu Ala Pro Pro Lys Ala Phe Ala Trp Leu Leu Leu Gln
690                 695                 700

Glu His Ala Gln Ser Thr Ala Ser Thr Ala Leu Pro Gly Asn Thr Leu
705                 710                 715                 720

Ala Pro Pro Ala Gln Pro Met Leu Asn Ser Thr Gly Gln Ser Cys Arg
                725                 730                 735

Pro Ser Pro Lys Pro Pro Gly Cys Glu Asn Ile Ala Gln Glu Tyr
            740                 745                 750

<210> SEQ ID NO 64
<211> LENGTH: 455
<212> TYPE: DNA
<213> ORGANISM: Homo sapiens

<400> SEQUENCE: 64
tcagaccgac agtcaggcag aagcagggcc cccggtctgt ctaggcttca ggatgcctaa      60
gaagctctcg gtgggcagcc agtgctccag aaccaggggg ttgttgtggg caggtctctg     120
gggaggcctg aggggccaca cggtgtcctg ggtgtggggt ctgcatctac atacgactca     180
taggcacctg ccattggggc gatttgtgat ggtttaggga acagggtct gcccttggat      240 gggctggcct acagtcaggg gccttccttg tctgtcttac tttccccgct ctgccagagt    300
gaacccaagg atgccgccag cctcacccca gtggtggca gttacgccgg catgaactc      360 agactcaccg gcacgcatga cttccaaccg tccacacatc tttgcaccca cagtatctgc    420
ttcagagaat gtattctaaa taataaaaat cataa                                455

<210> SEQ ID NO 65
<211> LENGTH: 746
<212> TYPE: DNA
<213> ORGANISM: Homo sapiens

<400> SEQUENCE: 65
cccactttgc tggatgaagc tctgtgaact cttcctggtt cttagtactg cctaattcat      60
gaatccttct ttgctcaaat gaactcaaag ttaatttaaa gttttattc taacatgaga     120 ctctttctcc catgagactt tgcatgaggg agaacagtcg ctaattaaca gccagttctt    180
gaaatcacgc agtcctgaaa tccagctgat gctgctcagc agagaagcag atgtttggag    240
gttaaaacaa agtcacaagt ctgacccaca ctcaaaggga gaagattatg caagagcaaa    300
agcacgagat ggaaaccatg gggccatctt atagtctgtc tgccggagaa agatgaacac    360
aaatcctcgt gcagaaaagt gtgacactaa aagaaccaac ctgatactac tatccttaga    420
aaagcctgca tacaaggttg gctgtcatct gggaatgtag gtgatcaaga gttctctcca    480
ctgacataaa ctttgtttaa ataataagga tgactcattg tgactagact atgcaaataa    540
tgggatgtgt gttaaacatc tcctttcctt ctgggagtct ggaattttgg tgtatgctaa    600
acagtgggtg cctgcaagac cagcctcaaa taaaaaccct gggcactgag tctctaaaaa    660
```

```
gactcccagt aggcaatatt tcacacgtgt tctcacaaac ttactgctgg aggaattatg      720
cacgccttgc atgactctat tggaaa                                          746

<210> SEQ ID NO 66
<211> LENGTH: 782
<212> TYPE: DNA
<213> ORGANISM: Homo sapiens

<400> SEQUENCE: 66
gcacgagaga tgttataata attttcaaaa gaaggtaaaa tcatgactca tatggatata       60
aaaatgaaca ccttgttatg gattgaactg tgtgccccta aaagatatgt tgaagcctga      120
actcccagta cctgagaatg tgaccatgtt tggaaatagt gtctttgcag gtttaatcaa      180
gttaagatga ggtcattaga tgggacctaa tttaatatgg ctgatgccct tataagaaga      240
gggaattttg gacacagaca tacaaggagg acgccatgtg aagacacagt tggaaaagca      300
gggaagagat ggccttgtgt ataaggaggc agagactgga gttatgctgc cacaagccaa      360
ggaacaactg gggctacctg agctggaaga ggcgaggaag gattctcccc tagagggttc      420
tgagggagcg tggacctgcc aacaacttgg tttcagattt ctagtctcca gaactatgca      480
gtaataaatt tctgttgttt taagccaccc agtttgtggc actttgttac gtcagccctg      540
tgaaacaaac aaacaaacaa acaaaaaaca agttaaatat tttatttaac tcataatatg      600
gaaataggtg aggtgttaca accaattcaa aaaagaagtg aaaaataagc ccaaatgtat      660
atagagtaaa ggaatgttga aatgaatgtg caaatggaag caaaactaga ttctcctaca      720
atgggacaga aaagtcaatt gaacctctac tggacagaac ataatttgca tgtgtataga      780
aa                                                                    782

<210> SEQ ID NO 67
<211> LENGTH: 525
<212> TYPE: DNA
<213> ORGANISM: Homo sapiens

<400> SEQUENCE: 67
gcaccaggtt tctggtaagg ggcaattttg tgtttgcctg ttctttggga atatcacctg       60
gagatagatg gattcccaga cccaccaaat ctaggtttta gaccaaaaaa gaatgtttta      120
ttattagaat tgagtatatc tcaggtcctc tttcattact acaacacaaa ataaatctgg      180
gggccaggaa cggtggctca cacctgtaat cccagagtgc taggattaca agcaacaagc      240
atgagctacc acgctcggcc tatgcatctc agtcttaaat tttcttctag gtggatttag      300
gggtttgtgc tcgtggccct aaaaatgaac atgagaaagg cagggagtac ctgcttagtt      360
gcaataggcc ttgtttaggc taaaaataag ctcgatacct gtattttata tactgtaaag      420
agcattaacc ataacctgcc tgcaacagcc tctgtaggta gaaacaatta tggaggtgtc      480
aagtaagaat aaagagctga taacatcaaa aaaaaaaaa aaaaa                      525

<210> SEQ ID NO 68
<211> LENGTH: 11
<212> TYPE: PRT
<213> ORGANISM: Homo sapiens

<400> SEQUENCE: 68

Ala Pro Gln Lys Ser Pro Trp Leu Thr Lys Pro
1               5                   10

<210> SEQ ID NO 69
```

-continued

```
<211> LENGTH: 13
<212> TYPE: PRT
<213> ORGANISM: Homo sapiens

<400> SEQUENCE: 69

Pro Leu Gln Pro Ser His Phe Leu Asp Ile Ser Glu Asp
1               5                   10

<210> SEQ ID NO 70
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 70
ccaugagagu agccagcaat t                                              21

<210> SEQ ID NO 71
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 71
uugcuggcua cucucaugga g                                              21

<210> SEQ ID NO 72
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 72
gguucaggac aaaguccaat t                                              21

<210> SEQ ID NO 73
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 73
uuggacuuug uccugaaccg g                                              21
```

IDENTIFICATION OF TUMOR-ASSOCIATED ANTIGENS FOR DIAGNOSIS AND THERAPY

This application is a divisional of U.S. application Ser. No. 13/086,176 filed Apr. 13, 2011, that has been patented as U.S. Pat. No. 8,975,375, which is a continuation application of U.S. application Ser. No. 12/066,399 filed Jul. 7, 2008, that has been abandoned, which is a U.S. National-Stage Application under 35 USC 371 of PCT/EP2006/008695 filed Sep. 6, 2006, which claims priority to European Patent Office (EPO) Application No. 05019786.2 filed on Sep. 12, 2005, the contents of which are incorporated herein by reference in their entireties.

Despite interdisciplinary approaches and exhaustive use of classical therapeutic procedures, cancers are still among the leading causes of death. More recent therapeutic concepts aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced. Tumor cells biologically differ substantially from their non-malignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens. The specific recognition of tumor-associated antigens involves cellular and humoral mechanisms which are two functionally interconnected units: $CD4^+$ and $CD8^+$ T lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, *Nat. Med.* 4:525-31, 1998). Accordingly, a central aim of tumor immunology is to molecularly define these structures. The molecular nature of these antigens has been enigmatic for a long time. Only after development of appropriate cloning techniques has it been possible to screen cDNA expression libraries of tumors systematically for tumor-associated antigens by analyzing the target structures of cytotoxic T lymphocytes (CTL) (van der Bruggen et al., *Science* 254:1643-7, 1991) or by using circulating autoantibodies (Sahin et al., *Curr. Opin. Immunol.* 9:709-16, 1997) as probes. To this end, cDNA expression libraries were prepared from fresh tumor tissue and recombinantly expressed as proteins in suitable systems. Immunoeffectors isolated from patients, namely CTL clones with tumor-specific lysis patterns, or circulating autoantibodies were utilized for cloning the respective antigens.

In recent years a multiplicity of antigens have been defined in various neoplasias by these approaches.

However, the probes utilized for antigen identification in the classical methods are immunoeffectors (circulating autoantibodies or CTL clones) from patients usually having already advanced cancer. A number of data indicate that tumors can lead, for example, to tolerization and anergization of T cells and that, during the course of the disease, especially those specificities which could cause effective immune recognition are lost from the immunoeffector repertoire. Current patient studies have not yet produced any solid evidence of a real action of the previously found and utilized tumor-associated antigens. Accordingly, it cannot be ruled out that proteins evoking spontaneous immune responses are the wrong target structures.

It was the object of the present invention to provide target structures for a diagnosis and therapy of cancers.

This object is achieved by the subject matter of the claims.

According to the invention, genes are identified which are selectively or aberrantly expressed in tumor cells and thus, provide tumor-associated antigens. These genes and/or their genetic products and/or the derivatives and/or fragments thereof are useful as target structures for therapeutic and diagnostic approaches.

The tumor-associated antigens identified according to the invention have an amino acid sequence encoded by a nucleic acid which is selected from the group consisting of (a) a nucleic acid which comprises a nucleic acid sequence selected from the group consisting of SEQ ID NOs: 1, 5, 9, 13, 17, 21, 25, 28, 30, 35, 39, 41, 45, 49, 61, 62, and 64-67 of the sequence listing, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, a tumor-associated antigen identified according to the invention has an amino acid sequence encoded by a nucleic acid which is selected from the group consisting of SEQ ID NOs: 1, 5, 9, 13, 17, 21, 25, 28, 30, 35, 39, 41, 45, 49, 61, 62, and 64-67 of the sequence listing. In a further preferred embodiment, a tumor-associated antigen identified according to the invention comprises an amino acid sequence selected from the group consisting of SEQ ID NOs: 2, 6, 10, 14, 18, 22, 26, 29, 31, 36, 40, 42, 46, 50-60, 63, 68, and 69 of the sequence listing, a part or derivative thereof.

The present invention generally relates to the use of tumor-associated antigens identified according to the invention or of parts or derivatives thereof, of nucleic acids coding for the tumor-associated antigens identified according to the invention or of parts or derivatives thereof or of nucleic acids directed against said coding nucleic acids, of antibodies or T cells directed against the tumor-associated antigens identified according to the invention or parts or derivatives thereof and/or of host cells expressing the tumor-associated antigens identified according to the invention or parts or derivatives thereof for therapy, prophylaxis, diagnosis and/or monitoring of neoplastic diseases. This may also involve the use of a combination of two or more of these antigens, nucleic acids, antibodies, T cells and/or host cells, in one embodiment also in combination with tumor-associated antigens other than those identified according to the invention, nucleic acids coding therefor or nucleic acids directed against said coding nucleic acids, antibodies or T cells directed against said tumor-associated antigens and/or host cells expressing said tumor associated antigens.

In those embodiments of the invention relating to the use of antibodies directed against the tumor-associated antigens identified according to the invention or parts or derivatives thereof also T cell receptors directed against the tumor-associated antigens identified according to the invention or parts or derivatives thereof, optionally in a complex with MHC molecules, may be used.

Especially suitable for therapy, prophylaxis, diagnosis and/or monitoring is a part of the tumor-associated antigens identified according to the invention which corresponds to the non-transmembrane portion, in particular the extracellular portion of the tumor-associated antigens or is comprised thereof. Therefore, according to the invention, a part of the tumor-associated antigens identified according to the invention which corresponds to the non-transmembrane portion, in particular the extracellular portion of the tumor-associated antigens or is comprised thereof, or a corresponding part of the nucleic acids coding for the tumor-associated antigens identified according to the invention is preferred for therapy, prophylaxis, diagnosis and/or monitoring. Similarly the use of antibodies is preferred which are directed against a part of the tumor-associated antigens identified according to the invention which corresponds to the non-transmembrane portion, in particular the extracellular portion of the tumor-associated antigens or is comprised thereof.

Preferred diseases for a therapy, prophylaxis and/or diagnosis are those in which one or more of the tumor-associated antigens identified according to the invention are selectively expressed or abnormally expressed.

Furthermore, the invention relates to nucleic acids and proteins or peptides, which result from altered splicing (splice variants) of known genes or altered translation using alternative open reading frames. In this aspect the invention relates to nucleic acids which comprise a nucleic acid sequence selected from the group consisting of SEQ ID NOs: 28 and 49 of the sequence listing. Moreover, in this aspect, the invention relates to proteins or peptides which comprise an amino acid sequence selected from the group consisting of SEQ ID NOs: 29 and 50 of the sequence listing.

Altered splicing of a gene results in an altered transcript sequence (splice variant). Translation of a splice variant in the region of its altered sequence results in an altered protein which may be distinctly different in the structure and function from the original protein. Tumor-associated splice variants may produce tumor-associated transcripts and tumor-associated proteins/antigens. These may be utilized as molecular markers both for detecting tumor cells and for therapeutic targeting of tumors. Detection of tumor cells in a sample from a patient may be carried out according to the invention, for example, after extraction of nucleic acids by PCR amplification with splice variant-specific oligonucleotides.

According to the invention, all sequence-dependent detection systems are suitable for detection. These are, apart from PCR, for example gene chip/microarray systems, Northern blot, RNAse protection assays (RDA) and others. All detection systems have in common that detection is based on a specific hybridization with at least one splice variant-specific nucleic acid sequence. However, tumor cells may also be detected according to the invention by antibodies which recognize a specific epitope encoded by the splice variant. Said antibodies may be prepared by using for immunization peptides which are specific for said splice variant. Suitable for immunization are particularly the amino acid sequences which are distinctly different from the variant(s) of the genetic product, which is (are) preferably produced in healthy cells. Detection of the tumor cells with antibodies may be carried out here on a sample isolated from the patient or as imaging with intravenously administered antibodies.

In addition to diagnostic usability, splice variants having new or altered epitopes are attractive targets for immunotherapy as these epitopes may be utilized for targeting antibodies or T lymphocytes as described herein. In passive immunotherapy, antibodies or T lymphocytes which recognize splice variant-specific epitopes are adoptively transferred here. As in the case of other antigens, antibodies may be generated also by using standard technologies with utilization of polypeptides which include these epitopes. Alternatively, it is possible to utilize for immunization nucleic acids coding for peptides which contain said epitopes. Various techniques for in vitro or in vivo generation of epitope-specific T lymphocytes are known and have been described in detail (for example Kessler J H, et al. 2001, Sahin et al., 1997) and are likewise based on utilizing peptides which contain the splice variant-specific epitopes or nucleic acids coding for said peptides. Peptides which contain the splice variant-specific epitopes or nucleic acids coding for said peptides may also be used as pharmaceutically active substances in active immunotherapy (e.g. vaccination, vaccine therapy).

In one aspect, the invention relates to a pharmaceutical composition comprising an agent which recognizes a tumor-associated antigen identified according to the invention or a nucleic acid coding for the tumor-associated antigen and which is preferably selective for cells which have expression or abnormal expression of a tumor-associated antigen identified according to the invention. In a further aspect, the invention relates to a pharmaceutical composition comprising an agent which (I) inhibits expression or activity of a tumor-associated antigen identified according to the invention, and/or (II) has tumor-inhibiting or tumor-destroying activity and is selective for cells expressing or abnormally expressing a tumor-associated antigen identified according to the invention, and/or (III) when administered, selectively increases the amount of complexes between an MHC molecule and a tumor-associated antigen identified according to the invention or a part thereof, such as a peptide epitope. In particular embodiments, said agent may cause induction of cell death, reduction in cell growth, damage to the cell membrane or secretion of cytokines and preferably have a tumor-inhibiting activity. In one embodiment, the agent is an antisense nucleic acid which hybridizes selectively with the nucleic acid coding for the tumor-associated antigen. In a further embodiment, the agent is a siRNA preferably comprising a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in a nucleic acid coding for the tumor-associated antigen, preferably mRNA coding for the tumor-associated antigen. In a further embodiment, the agent is an antibody which binds selectively to the tumor-associated antigen, in particular a complement-activated or toxin conjugated antibody which binds selectively to the tumor-associated antigen. In a preferred embodiment, the antibody which binds selectively to the tumor-associated antigen is coupled to a therapeutically useful substance and/or recruits natural or artificial effector mechanisms to said cell expressing or abnormally expressing said tumor-associated antigen. In a further embodiment, the agent is a cytotoxic T lymphocyte which recognizes the tumor-associated antigen or a part thereof bound by an MHC molecule on a cell and lyses the cells labeled in this way. In a further embodiment, the agent is a T helper lymphocyte which enhances effector functions of other cells specifically recognizing said tumor-associated antigen or a part thereof.

In a further embodiment, the agent comprises two or more agents which each recognize different tumor-associated antigens and/or inhibit expression or activity of different tumor-associated antigens, and/or have tumor-inhibiting or tumor-destroying activity and are selective for cells expressing or abnormally expressing different tumor-associated antigens, and/or when administered, selectively increase the amount of complexes between MHC molecules and different tumor-associated antigens or parts thereof, wherein at least one of said different tumor-associated antigens is a tumor-associated antigen identified according to the invention. Preferably, a tumor-associated antigen selectively limited to tumors serves as a label for recruiting effector mechanisms to this specific location. The invention includes embodiments wherein the agent itself does not have an ability to inhibit activity of a tumor-associated antigen or a tumor-inhibiting or tumor-destroying activity but mediates such effect, in particular by recruiting effector mechanisms, in particular those having cell damaging potential, to a specific location, in particular a tumor or tumor cells.

The activity of a tumor-associated antigen identified according to the invention can be any activity of a protein or a peptide. In one embodiment this activity is an enzymatic activity.

According to the invention the phrase "inhibit expression or activity" includes a complete or essentially complete inhibition of expression or activity and a reduction in expression or activity.

The agent which, when administered, selectively increases the amount of complexes between an MHC molecule and a tumor-associated antigen identified according to the invention or a part thereof comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule.

The invention furthermore relates to a pharmaceutical composition which comprises one or more components selected from the group consisting of (i) a tumor-associated antigen identified according to the invention or a part thereof, (ii) a nucleic acid which codes for a tumor-associated antigen identified according to the invention or a part thereof, (iii) an antibody which binds to a tumor-associated antigen identified according to the invention or to a part thereof, (iv) an antisense nucleic acid which hybridizes specifically with a nucleic acid coding for a tumor-associated antigen identified according to the invention, (v) an siRNA directed against a nucleic acid coding for a tumor-associated antigen identified according to the invention, (vi) a host cell which expresses a tumor-associated antigen identified according to the invention or a part thereof, and (vii) isolated complexes between a tumor-associated antigen identified according to the invention or a part thereof and an MHC molecule.

In one embodiment, a nucleic acid coding for a tumor-associated antigen identified according to the invention or a part thereof is present in the pharmaceutical composition in an expression vector and functionally linked to a promoter. In a further embodiment, a nucleic acid coding for a tumor-associated antigen identified according to the invention or a part thereof is present in the pharmaceutical composition in a virus as further described below.

In a further embodiment, a host cell present in a pharmaceutical composition of the invention secretes the tumor-associated antigen or the part thereof, expresses it on the surface and preferably additionally express an MHC molecule which binds to said tumor-associated antigen or said part thereof. In one embodiment, the host cell expresses the MHC molecule endogenously. In a further embodiment, the host cell expresses the MHC molecule and/or the tumor-associated antigen or the part thereof in a recombinant manner. The host cell is preferably nonproliferative. In a preferred embodiment, the host cell is an antigen-presenting cell, in particular a dendritic cell, a monocyte or a macrophage.

In a further embodiment, an antibody present in a pharmaceutical composition of the invention is a monoclonal antibody. In further embodiments, the antibody is a chimeric or humanized antibody, a fragment of a natural antibody or a synthetic antibody. The antibody may be coupled to a therapeutically or diagnostically useful agent also termed therapeutic or diagnostic agent herein.

An antisense nucleic acid present in a pharmaceutical composition of the invention may comprise a sequence of 6-50, in particular 10-30, 15-30 and 20-30, contiguous nucleotides of the nucleic acid coding for the tumor-associated antigen identified according to the invention.

In further embodiments, a tumor-associated antigen or a part thereof, provided by a pharmaceutical composition of the invention either directly or via expression of a nucleic acid, binds to MHC molecules on the surface of cells, said binding preferably causing a cytolytic response and/or inducing cytokine release.

In particular embodiments of the siRNA targeting the nucleic acid according to SEQ ID NO: 1 the sense RNA strand has the sequence of SEQ ID NO: 70 and the antisense RNA strand has the sequence of SEQ ID NO: 71, or the sense RNA strand has the sequence of SEQ ID NO: 72 and the antisense RNA strand has the sequence of SEQ ID NO: 73.

A pharmaceutical composition of the invention may comprise a pharmaceutically compatible carrier and/or an adjuvant.

A pharmaceutical composition of the invention is preferably used for the treatment or prevention of a disease characterized by selective expression or abnormal expression of a tumor-associated antigen. In a preferred embodiment, the disease is a neoplastic disease, preferably cancer.

In a preferred embodiment, the pharmaceutical composition of the invention is in the form of a vaccine which may be used therapeutically or prophylactically. Such vaccine preferably comprises a tumor-associated antigen identified according to the invention or a part thereof, and/or a nucleic acid which codes for a tumor-associated antigen identified according to the invention or a part thereof. In particular embodiments, the nucleic acid is present in a virus or host cell.

The invention furthermore relates to methods of treating, preventing, diagnosing or monitoring, i.e. determining the regression, progression, course and/or onset of, a disease characterized by expression or abnormal expression of one of more tumor-associated antigens identified according to the invention, preferably a neoplastic disease, in particular cancer. In one embodiment, the treatment or prevention comprises administering a pharmaceutical composition of the invention.

Said methods of diagnosing and/or methods of monitoring according to the invention generally concern the detection of and/or determination of the quantity of one or more parameters selected from the group consisting of (i) a nucleic acid, which codes for a tumor-associated antigen identified according to the invention, or a part thereof, (ii) a tumor-associated antigen identified according to the invention, or a part thereof (iii) an antibody against a tumor-associated antigen identified according to the invention or a part thereof, and (iv) T lymphocytes, preferably cytotoxic or T helper lymphocytes, which are specific for a tumor-associated antigen identified according to the invention or a part thereof and/or a complex between the tumor-associated antigen or a part thereof and an MHC molecule, in a biological sample isolated from a patient, preferably from a patient having said disease, being suspected of having or falling ill with said disease or having a potential for said disease. Means for accomplishing said detection and/or determination of the quantity are described herein and will be apparent to the skilled person.

Preferably, the presence of said nucleic acid, said tumor-associated antigen or said part thereof, said antibody and/or said T lymphocytes and/or a quantity of said nucleic acid, said tumor-associated antigen or said part thereof, said antibody and/or said T lymphocytes which is increased compared to a patient without said disease is indicative for the presence of said disease or a potential for a development of said disease.

The methods of diagnosing and/or monitoring of the invention also include embodiments wherein by detection or determination of the quantity of said nucleic acid, said tumor-associated antigen or said part thereof, said antibody and/or said T lymphocytes it is possible to assess and/or prognose the metastatic behavior of said disease, wherein, preferably, the presence of said nucleic acid, said tumor-associated antigen or said part thereof, said antibody and/or said T lymphocytes and/or a quantity of said nucleic acid, said tumor-associated antigen or said part thereof, said antibody and/or said T lymphocytes which is increased compared to a patient without said disease or without a metastasis of said disease is indicative for a metastatic behavior of said disease or a potential for a metastatic behavior of said disease.

In particular embodiments, said detection or determination of the quantity comprises (i) contacting a biological sample with an agent which binds specifically to said nucleic acid coding for the tumor-associated antigen or said part thereof, to said tumor-associated antigen or said part thereof, to said antibody or said part thereof or to said T lymphocytes, and (ii) detecting the formation of or determining the amount of a complex between the agent and the nucleic acid or the part thereof, the tumor-associated antigen or the part thereof, the antibody or the part thereof, or the T lymphocytes. In one embodiment, the disease is characterized by expression or abnormal expression of two or more different tumor-associated antigens and a detection or determination of the amount comprises a detection or determination of the amount of two or more nucleic acids coding for said two or more different tumor-associated antigens or of parts thereof, of two or more different tumor-associated antigens or of parts thereof, of two or more antibodies binding to said two or more different tumor-associated antigens or to parts thereof and/or of two or more T lymphocytes specific for said two or more different tumor-associated antigens or parts thereof, or complexes thereof with MHC molecules. In a further embodiment, the biological sample isolated from the patient is compared to a comparable normal biological sample.

The methods of monitoring according to the invention preferably comprise a detection of and/or determination of the quantity of one or more of the parameters mentioned above in a first sample at a first point in time and in a further sample at a second point in time, wherein the course of the disease is determined by comparing the two samples.

According to the invention, detection of a nucleic acid or of a part thereof or determining the quantity of a nucleic acid or of a part thereof may be carried out using a oligo- or polynucleotide probe which hybridizes specifically to said nucleic acid or said part thereof or may be carried out by selective amplification of said nucleic acid or said part thereof, e.g. by means of PCR amplification. In one embodiment, the oligo- or polynucleotide probe comprises a sequence of 6-50, in particular 10-30, 15-30 and 20-30, contiguous nucleotides of said nucleic acid.

In particular embodiments, the tumor-associated antigen or the part thereof which is to be detected or the amount of which is to be determined in the methods of the present invention is present intracellularly, on the cell surface or in a complex with an MHC molecule. According to the invention, detection of a tumor-associated antigen or of a part thereof or determining the quantity of a tumor-associated antigen or of a part thereof may be carried out using an antibody binding specifically to said tumor-associated antigen or said part thereof.

According to the invention, detection of an antibody or determining the quantity of an antibody may be carried out using a protein or peptide binding specifically to said antibody.

According to the invention, detection of or determining the quantity of T lymphocytes which are specific for a tumor-associated antigen or a part thereof and/or a complex thereof with an MHC molecule may be carried out using a cell presenting the complex between said tumor-associated antigen or said part thereof and an MHC molecule. T lymphocytes may additionally be detected by detecting their proliferation, their cytokine production, and their cytotoxic activity triggered by specific stimulation with a complex of an MHC molecule and a tumor-associated antigen or a part thereof. T lymphocytes may also be detected with aid of a recombinant MHC molecule or a complex of two or more MHC molecules loaded with immunogenic fragments of one or more tumor-associated antigens.

An agent which is used for detection or determining the quantity in the methods of the invention such as a oligo- or polynucleotide probe, an antibody, a protein or peptide or a cell is preferably labeled in a detectable manner, in particular by a detectable marker such as a radioactive marker or an enzymic marker.

In a particular aspect, the invention relates to a method of treating, preventing, diagnosing or monitoring a disease characterized by expression or abnormal expression of a tumor-associated antigen identified according to the invention, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of a natural antibody.

In certain embodiments, the methods of the invention of diagnosing or monitoring a disease characterized by expression or abnormal expression of a tumor-associated antigen identified according to the invention are performed with a biological sample containing or suspected of containing disseminating tumor cells or metastatic tumor cells. Such biological samples include, for example, blood, serum, bone marrow, sputum, bronchial aspirate, and/or bronchial lavage.

In one particular aspect, the invention relates to a method of treating a patient having a disease characterized by expression or abnormal expression of a tumor-associated antigen identified according to the invention, which method comprises (i) providing a sample containing immunoreactive cells, either obtained from said patient or from another individual of the same species, in particular a healthy individual, or an individual of a different species, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. In one embodiment, the method includes cloning of the T cell receptor of cytolytic T cells obtained and transferring the nucleic acid coding for the T cell receptor to T cells, either obtained from said patient or from another individual of the same species, in particular a healthy individual, or an individual of a different species, which T cells thus receive the desired specificity and, as under (iii), may be introduced into the patient.

In one embodiment, the host cell endogenously expresses an MHC molecule. In a further embodiment, the host cell recombinantly expresses an MHC molecule and/or the tumor-associated antigen or the part thereof. Preferably, the host cell presents the tumor-associated antigen or the part thereof by MHC molecules on its surface. The host cell is preferably nonproliferative. In a preferred embodiment, the host cell is an antigen-presenting cell, in particular a dendritic cell, a monocyte or a macrophage.

The invention also relates to a method of treating a disease characterized by expression or abnormal expression of a tumor-associated antigen identified according to the invention, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

The present invention furthermore relates to a nucleic acid selected from the group consisting of (a) a nucleic acid which comprises a nucleic acid sequence selected from the group consisting of SEQ ID NOs: 1, 5, 9, 13, 17, 21, 25, 28, 30, 35, 39, 41, 45, 49, 61, 62, and 64-67, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The invention furthermore relates to a nucleic acid, which codes for a protein or polypeptide comprising an amino acid sequence selected from the group consisting of SEQ ID NOs: 2, 6, 10, 14, 18, 22, 26, 29, 31, 36, 40, 42, 46, 50-60, 63, 68, and 69, a part or derivative thereof.

In a further aspect, the invention relates to a recombinant nucleic acid molecule, in particular DNA or RNA molecule, which comprises a nucleic acid of the invention.

The invention also relates to host cells which contain a nucleic acid or recombinant nucleic acid molecule of the invention.

The host cell may also comprise a nucleic acid coding for a MHC molecule. In one embodiment, the host cell endogenously expresses the MHC molecule. In a further embodiment, the host cell recombinantly expresses the MHC molecule and/or the nucleic acid or recombinant nucleic acid molecule of the invention or a part thereof. Preferably, the host cell is nonproliferative. In a preferred embodiment, the host cell is an antigen-presenting cell, in particular a dendritic cell, a monocyte or a macrophage.

In a further embodiment, the invention relates to oligonucleotides which hybridize with a nucleic acid identified according to the invention and which may be used as genetic probes or as "antisense" molecules. Nucleic acid molecules in the form of oligonucleotide primers or competent probes, which hybridize with a nucleic acid identified according to the invention or parts thereof, may be used for finding nucleic acids which are homologous to said nucleic acid identified according to the invention, e.g. by PCR amplification, Southern and Northern hybridization. Hybridization may be carried out under low stringency, more preferably under medium stringency and most preferably under high stringency conditions.

In a further aspect, the invention relates to a protein or peptide which is encoded by a nucleic acid selected from the group consisting of (a) a nucleic acid which comprises a nucleic acid sequence selected from the group consisting of SEQ ID NOs: 1, 5, 9, 13, 17, 21, 25, 28, 30, 35, 39, 41, 45, 49, 61, 62, and 64-67, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the invention relates to a protein or peptide which comprises an amino acid sequence selected from the group consisting of SEQ ID NOs: 2, 6, 10, 14, 18, 22, 26, 29, 31, 36, 40, 42, 46, 50-60, 63, 68, and 69, a part or derivative thereof.

In a further aspect, the invention relates to an immunogenic fragment of a tumor-associated antigen identified according to the invention. Said fragment preferably binds to a MHC molecule or an antibody, preferably to a human HLA receptor or a human antibody. According to the invention, a fragment preferably comprises a sequence of at least 6, in particular at least 8, at least 10, at least 12, at least 15, at least 20, at least 30 or at least 50, amino acids.

In this aspect the invention relates, in particular, to a peptide which has or comprises a sequence selected from the group consisting of SEQ ID NOs: 51-60, 68 and of the sequence listing, a part or derivative thereof.

In a further aspect, the invention relates to an agent which binds to a tumor-associated antigen identified according to the invention or to a part thereof. In a preferred embodiment, the agent is a protein or peptide, in particular an antibody, a T cell receptor or an MHC molecule. In further embodiments, the antibody is a monoclonal, chimeric, or humanized antibody, an antibody produced by combinatory techniques, or a fragment of an antibody. In one preferred embodiment, the invention relates to an antibody which binds selectively to a complex of (i) a tumor-associated antigen identified according to the invention or a part thereof and (ii) an MHC molecule to which said tumor-associated antigen identified according to the invention or said part thereof binds, with said antibody not binding to (i) or (ii) alone.

In particular, the invention relates to such an agent, in particular an antibody, which specifically binds to a peptide which has or comprises a sequence selected from the group consisting of SEQ ID NOs: 51-60, 68, and of the sequence listing, a part or derivative thereof.

According to the invention, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the agent does not bind specifically.

Such specific antibodies may, for example, be obtained by immunization using the aforementioned peptides.

The invention furthermore relates to a conjugate between an agent of the invention which binds to a tumor-associated antigen identified according to the invention or to a part thereof or an antibody of the invention and a therapeutic or diagnostic agent. In one embodiment, the therapeutic or diagnostic agent is a toxin.

In a further aspect, the invention relates to a kit for detecting expression or abnormal expression of a tumor-associated antigen identified according to the invention, which kit comprises agents for detection or determining the quantity (i) of the nucleic acid which codes for the tumor-associated antigen or of a part thereof, (ii) of the tumor-associated antigen or of a part thereof, (iii) of antibodies which bind to the tumor-associated antigen or to a part thereof, and/or (iv) of T cells which are specific for the tumor-associated antigen or a part thereof or a complex thereof with an MHC molecule. In one embodiment, the agents for detection of the nucleic acid or the part thereof are nucleic acid molecules for selective amplification of said nucleic acid, which comprise, in particular, a sequence of 6-50, in particular 10-30, 15-30 and 20-30, contiguous nucleotides of said nucleic acid.

DETAILED DESCRIPTION OF THE INVENTION

According to the invention, a "reference" such as a reference sample or reference organism may be used to correlate and compare the results obtained in the methods of the invention from a test sample or test organism, i.e. a patient. Typically the reference organism is a healthy organism, in particular an organism which does not suffer from cancer.

A "reference value" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

"Derivative" of a nucleic acid means according to the invention that single or multiple such as at least 2, at least 4, or at least 6 and preferably up to 3, up to 4, up to 5, up to 6, up to 10, up to 15, or up to 20 nucleotide substitutions, deletions and/or additions are present in said nucleic acid. Furthermore, the term "derivative" also comprises chemical derivatization of a nucleic acid on a nucleotide base, on the sugar or on the phosphate. The term "derivative" also comprises nucleic acids which contain nucleotides and nucleotide analogs not occurring naturally.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1× SDS at temperatures of up to 68° C.

According to the invention, complementary nucleic acids have at least 40%, in particular at least 50%, at least 60%, at least 70%, at least 80%, at least 90% and preferably at least 95%, at least 98% or at least 99%, identical nucleotides.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Nucleic acids coding for tumor-associated antigens may, according to the invention, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

According to the invention, a nucleic acid may furthermore be present in combination with another nucleic acid which codes for a peptide controlling secretion of the protein or peptide encoded by said nucleic acid from a host cell. According to the invention, a nucleic acid may also be present in combination with another nucleic acid which codes for a peptide causing the encoded protein or peptide to be anchored on the cell membrane of the host cell or compartmentalized into particular organelles of said cell. Similarly, a combination with a nucleic acid is possible which represents a reporter gene or any "tag".

In a preferred embodiment, a recombinant nucleic acid molecule is according to the invention a vector, where appropriate with a promoter, which controls expression of a nucleic acid, for example a nucleic acid coding for a tumor-associated antigen identified according to the invention. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids coding for a tumor-associated antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

According to the invention, the term "host cell" relates to any cell which can be transformed or transfected with an exogenous nucleic acid. The term "host cells" comprises according to the invention prokaryotic (e.g. E. coli) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the invention, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selectable marker such as a gene imparting resistance to G418 (and thus enabling stably transfected cell lines to be selected) and the enhancer-promoter sequences of cytomegalovirus (CMV).

In those cases of the invention in which a MHC molecule presents a tumor-associated antigen or a part thereof, an expression vector may also comprise a nucleic acid sequence coding for said MHC molecule. The nucleic acid sequence coding for the MHC molecule may be present on the same expression vector as the nucleic acid coding for the tumor-associated antigen or the part thereof, or both nucleic acids may be present on different expression vectors. In the latter case, the two expression vectors may be cotransfected into a cell. If a host cell expresses neither the tumor-associated antigen or the part thereof nor the MHC molecule, both nucleic acids coding therefor may be transfected into the cell either on the same expression vector or on different expression vectors. If the cell already expresses the MHC molecule, only the nucleic acid sequence coding for the tumor-associated antigen or the part thereof can be transfected into the cell.

The invention also comprises kits for amplification of a nucleic acid coding for a tumor-associated antigen. Such kits comprise, for example, a pair of amplification primers which hybridize to the nucleic acid coding for the tumor-associated antigen. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid coding for the tumor-associated antigen, and the other primer will hybridize to the complementary strand in an arrangement which allows amplification of the nucleic acid coding for the tumor-associated antigen.

"Antisense molecules" or "antisense nucleic acids" may be used for regulating, in particular reducing, expression of a nucleic acid. The term "antisense molecule" or "antisense nucleic acid" refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, an "antisense molecule" also comprises a construct which contains a nucleic acid or a part thereof in reverse orientation with respect to its natural promoter. An antisense transcript of a nucleic acid or of a part thereof may form a duplex with the naturally occurring mRNA specifying the enzyme and thus prevent accumulation of or translation of the mRNA into the active enzyme. Another possibility is the use of ribozymes for inactivating a nucleic acid. Antisense oligonucleotides preferred according to the invention have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a "modified" oligonucleotide. Here, the oligonucleotide may be modified in very different ways, without impairing its ability to bind its target, in order to increase, for example, its stability or therapeutic efficacy. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

It is to be understood that all embodiments described above with respect to oligonucleotides may also apply to polynucleotides.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

siRNA according to the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages.

One or both strands of the siRNA can also comprise a 3'-overhang. As used herein, a "3'-overhang" refers to at least one unpaired nucleotide extending from the 3'-end of an RNA strand. Thus in one embodiment, the siRNA comprises at least one 3'-overhang of from 1 to about 6 nucleotides (which includes ribonucleotides or deoxynucleotides) in length, preferably from 1 to about nucleotides in length, more preferably from 1 to about 4 nucleotides in length, and particularly preferably from about 2 to about 4 nucleotides in length. In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the invention can comprise 3'-overhangs of dideoxythymidylic acid ("TT") or diuridylic acid ("uu").

In order to enhance the stability of the siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation.

siRNA can be expressed from pol III expression vectors without a change in targeting site, as expression of RNAs from pol III promoters is only believed to be efficient when the first transcribed nucleotide is a purine.

siRNA according to the invention can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

siRNA can be obtained using a number of techniques known to those of skill in the art. For example, siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, siRNA is chemically synthesized using appropriately protected ribonucleoside phosphoramidites and a conventional DNA/RNA synthesizer. siRNA can be synthesized as two separate, complementary RNA molecules, or as a single RNA molecule with two complementary regions.

Alternatively, siRNA can also be expressed from recombinant circular or linear DNA plasmids using any suitable promoter. Such embodiments are included according to the present invention when reference is made herein to the administration of siRNA or the incorporation of siRNA into pharmaceutical compositions. Suitable promoters for expressing siRNA of the invention from a plasmid include, for example, the U6 or H1 RNA pol III promoter sequences and the cytomegalovirus promoter.

Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA to cells in vivo is discussed in more detail below. siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art.

siRNA can also be expressed from recombinant viral vectors intracellularly in vivo. The recombinant viral vectors comprise sequences encoding the siRNA and any suitable promoter for expressing the siRNA sequences. The recombinant viral vectors can also comprise inducible or regulatable promoters for expression of the siRNA in a particular tissue or in a particular intracellular environment. siRNA can be expressed from a recombinant viral vector either as two separate, complementary RNA molecules, or as a single RNA molecule with two complementary regions.

The term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

Such proteins and peptides may be used, for example, in producing antibodies and in an immunological or diagnostic assay or as therapeutics. Proteins and peptides described according to the invention may be isolated from biological samples such as tissue or cell homogenates and may also be expressed recombinantly in a multiplicity of pro- or eukaryotic expression systems.

For the purposes of the present invention, "derivatives" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid deletion variants are characterized by the removal of one or more amino acids from the sequence. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:

1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys 4. large aliphatic, nonpolar residues: Met, Leu, Ile, Val (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

The amino acid variants described above may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, "derivatives" of proteins and peptides also comprise single or multiple substitutions, deletions and/or additions of any molecules associated with the protein or peptide, such as carbohydrates, lipids and/or proteins or peptides.

The term "derivative" also extends to all functional chemical equivalents of said proteins and peptides.

According to the invention, a part or fragment of a tumor-associated antigen preferably has a functional property of the protein or peptide from which it has been derived. Such functional properties comprise the interaction with antibodies, the interaction with other peptides or proteins, the selective binding of nucleic acids and an enzymatic activity. A particular property is the ability to form a complex with MHC molecules and, where appropriate, generate an immune response, preferably by stimulating cytotoxic or T helper cells. A part or fragment of a tumor-associated antigen of the invention preferably comprises a sequence of at least 6, in particular at least 8, at least 10, at least 12, at least 15, at least 20, at least 30 or at least 50, consecutive amino acids of the tumor-associated antigen. A part or fragment of a tumor-associated antigen of the invention preferably comprises a sequence of up to 8, in particular up to 10, up to 12, up to 15, up to 20, up to 30 or up to 55, consecutive amino acids of the tumor-associated antigen. A part or fragment of a tumor-associated antigen is preferably a part of the tumor-associated antigen which corresponds to the non-transmembrane portion, in particular the extracellular portion of the antigen, or is comprised thereof.

Preferred parts or fragments of a tumor-associated antigen according to the invention are in particular suitable for the stimulation of cytotoxic T-lymphocytes in vivo but also for the production of expanded and stimulated T-lymphocytes for the therapeutic adoptive transfer ex vivo.

A part or a fragment of a nucleic acid coding for a tumor-associated antigen relates according to the invention to the part of the nucleic acid, which codes at least for the tumor-associated antigen and/or for a part or a fragment of said tumor-associated antigen, as defined above. A part or fragment of a nucleic acid coding for a tumor-associated antigen is preferably that part of the nucleic acid corresponding to the open reading frame.

According to the invention, particular embodiments ought to involve providing "dominant negative" proteins or peptides derived from tumor-associated antigens. A dominant negative protein or peptide is an inactive protein or peptide variant which, by way of interacting with the cellular machinery, displaces an active protein or peptide from its interaction with the cellular machinery or which competes with the active protein or peptide, thereby reducing the effect of said active protein.

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual: Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol. Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology*, 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as F(ab')$_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

According to the invention, the term "antibody" also includes F(ab')$_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric F(ab')$_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

The invention also comprises proteins and peptides which bind specifically to tumor-associated antigens. Binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Antibodies may also be coupled to specific diagnostic substances for displaying cells and tissues expressing tumor-associated antigens. They may also be coupled to therapeutically useful substances.

Diagnostic substances include any label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

According to the invention, the term "therapeutically useful substance" means any molecule which may exert a therapeutic effect. According to the invention, a therapeutically useful substance is preferably selectively guided to a cell which expresses one or more tumor-associated antigens and includes anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "major histocompatibility complex" or "MHC" relates to a complex of genes present in all vertebrates. MHC proteins or molecules are involved in signaling between lymphocytes and antigen presenting cells in normal immune reactions by binding peptides and presenting them for recognition by T cell receptors (TCR). MHC molecules bind peptides within an intracellular processing compartment and present these peptides on the surface of antigen presenting cells for recognition by T cells. The human MHC region also termed HLA is located on chromosome 6 and includes the class I and class II region. In one preferred embodiment of all aspects of the invention an MHC molecule is an HLA molecule.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

"Abnormal expression" means according to the invention that expression is altered, preferably increased, compared to the state in a healthy individual.

According to the invention the term "increased" or "increased amount" preferably refers to an increase by at least 10%, in particular at least 20%, at least 50% or at least 100%. The amount of a substance is also increased in a test sample such as a biological sample compared to a reference sample if it is detectable in the test sample but absent or not detectable in the reference sample.

According to the invention, the term "disease" refers to any pathological state in which tumor-associated antigens are expressed or abnormally expressed. "Abnormal expression" means according to the invention that expression is altered, preferably increased, compared to the state in a healthy individual. An increase in expression refers to an increase by at least 10%, in particular at least 20%, at least 50% or at least 100%. In one embodiment, the tumor-associated antigen is expressed only in tissue of a diseased individual, while expression in a healthy individual is repressed. One example of such a disease is cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the matastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

According to the invention, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the invention, the term "biological sample" also includes fractions of biological samples.

According to the invention, the term "immunoreactive cell" means a cell which can mature into an immune cell (such as B cell, T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

The terms "T cell" and "T lymphocyte" are used interchangeably herein and include T helper cells and cytotoxic T cells which comprise cytolytic T cells.

Some therapeutic methods are based on a reaction of the immune system of a patient, which results in a lysis of antigen-presenting cells such as cancer cells which present one or more tumor-associated antigens. In this connection, for example autologous cytotoxic lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for obtaining specific clones of cytotoxic T lymphocytes (Altman et al., Science 274:94-96, 1996; Dunbar et al., Curr. Biol. 8:413-416, 1998).

The present invention also includes therapeutic methods referred to as adoptive transfer (Greenberg, J. Immunol. 136(5):1917, 1986; Riddel et al., Science 257:238, 1992; Lynch et al., Eur. J. Immunol. 21:1403-1410, 1991; Kast et al., Cell 59:603-614, 1989), wherein cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al., Nat Immunol. 2:962-70, 2001; Kessels et al., Nat Immunol. 2:957-61, 2001).

Adoptive transfer is not the only form of therapy which can be applied according to the invention. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen-presenting cells in vivo possible. The tumor-associated antigen or a fragment thereof may be represented as protein, as DNA (e.g. within a vector) or as RNA. The tumor-associated antigen is processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor-associated antigen to a patient by intradermal injection, for example. However, injection may also be carried out intranodally into a lymph node (Maloy et al., *Proc Natl Acad Sci USA* 98:3299-303, 2001).

The pharmaceutical compositions and methods of treatment described according to the invention may also be used for immunization or vaccination to therapeutically treat or prevent a disease described herein. According to the invention, the terms "immunization" or "vaccination" preferably relate to an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization or a vaccination, preferably one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and/or stimulating particular lymphocytes. Adjuvants are known and comprise in a nonlimiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., Mol. Cells 7:178-186, 1997), incomplete Freund's adjuvant, complete Freund's adjuvant, vitamin E, montanide, alum, CpG oligonucleotides (cf. Kreig et al., Nature 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 µg to about 100 µg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids such as B7-1 and B7-2 (CD80 and CD86, respectively).

The invention also provides for administration of nucleic acids, proteins or peptides. Proteins and peptides may be administered in a manner known per se. In one embodiment, nucleic acids are administered by ex vivo methods, i.e. by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The invention also provides for administering nucleic acids in vivo by using vectors such as viruses and target-controlled liposomes. If according to the invention reference is made to the administration or incorporation into pharmaceutical compositions of nucleic acids this includes embodiments wherein the nucleic acid is present in such vectors.

In a preferred embodiment, a virus or viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of a particular condition characterized by expression of one or more tumor-associated antigens, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. According to the invention, a diagnosis or treatment of cancer may also include the diagnosis or treatment of cancer metastases which have already formed or will form. According to the invention, the term "treatment" comprises therapeutic and prophylactic treatment, i.e. prevention.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 µg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1. ISC-468 mRNA expression
  A. RT-PCR investigations with ISC-468-specific primers showed no significant expression within all tested normal tissues except placenta.
  B. ISC-468 mRNA expression in head and neck, liver, kidney and colon carcinomas.
  C. ISC-468 mRNA expression in breast, ovarian and stomach carcinomas.

Figure 2:
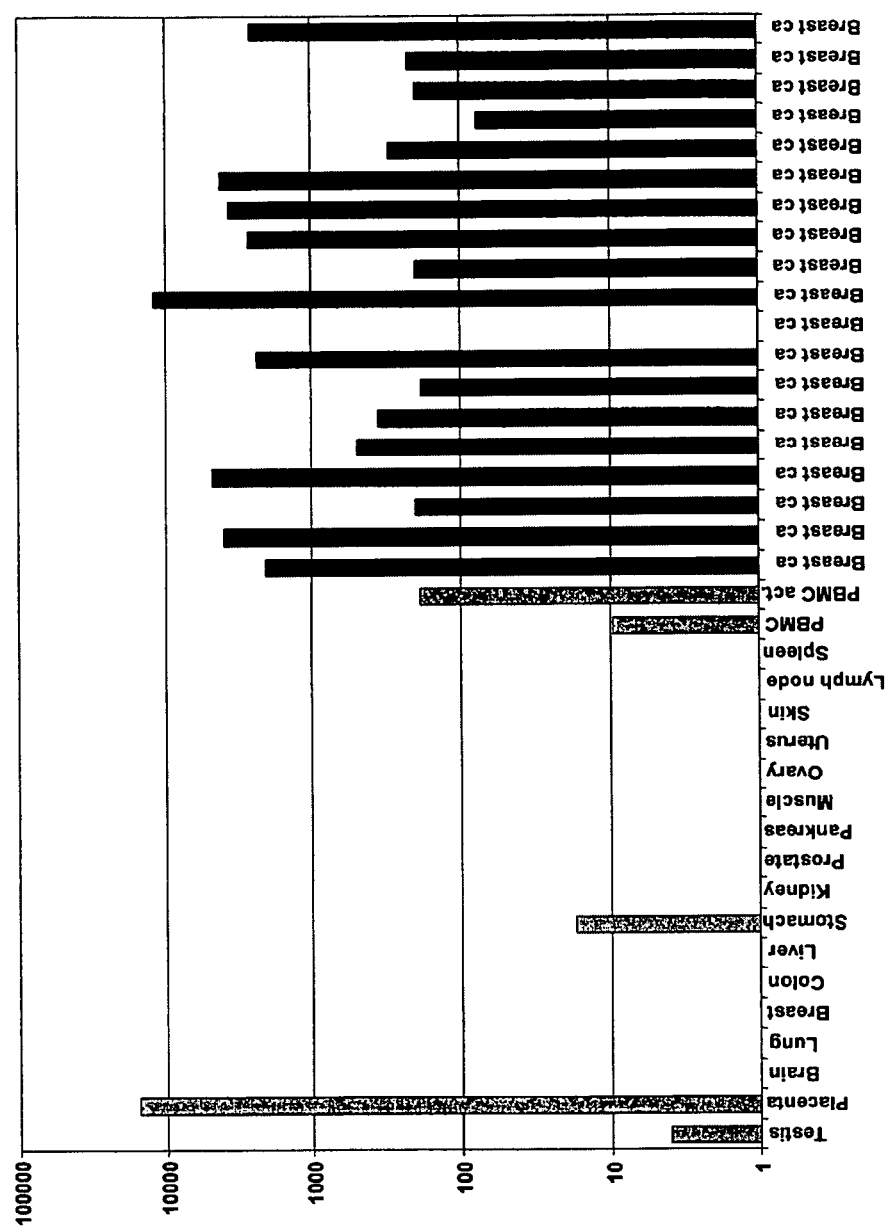

FIG. 2. Quantitative PCR analysis of ISC-468 mRNA expression in normal control tissues and breast cancers
Real-time PCR investigation with ISC-468-specific primers showed selective mRNA expression in normal testis, placenta, stomach and PBMC, and in all breast carcinoma biopsies.

FIG. 3. Specific ISC-507 expression in normal testis and prostate carcinoma
RT-PCR analysis with gene-specific ISC-507 primers shows cDNA amplification exclusively in normal testis (A) and in prostate carcinoma biopsies (B).

Figure 4:
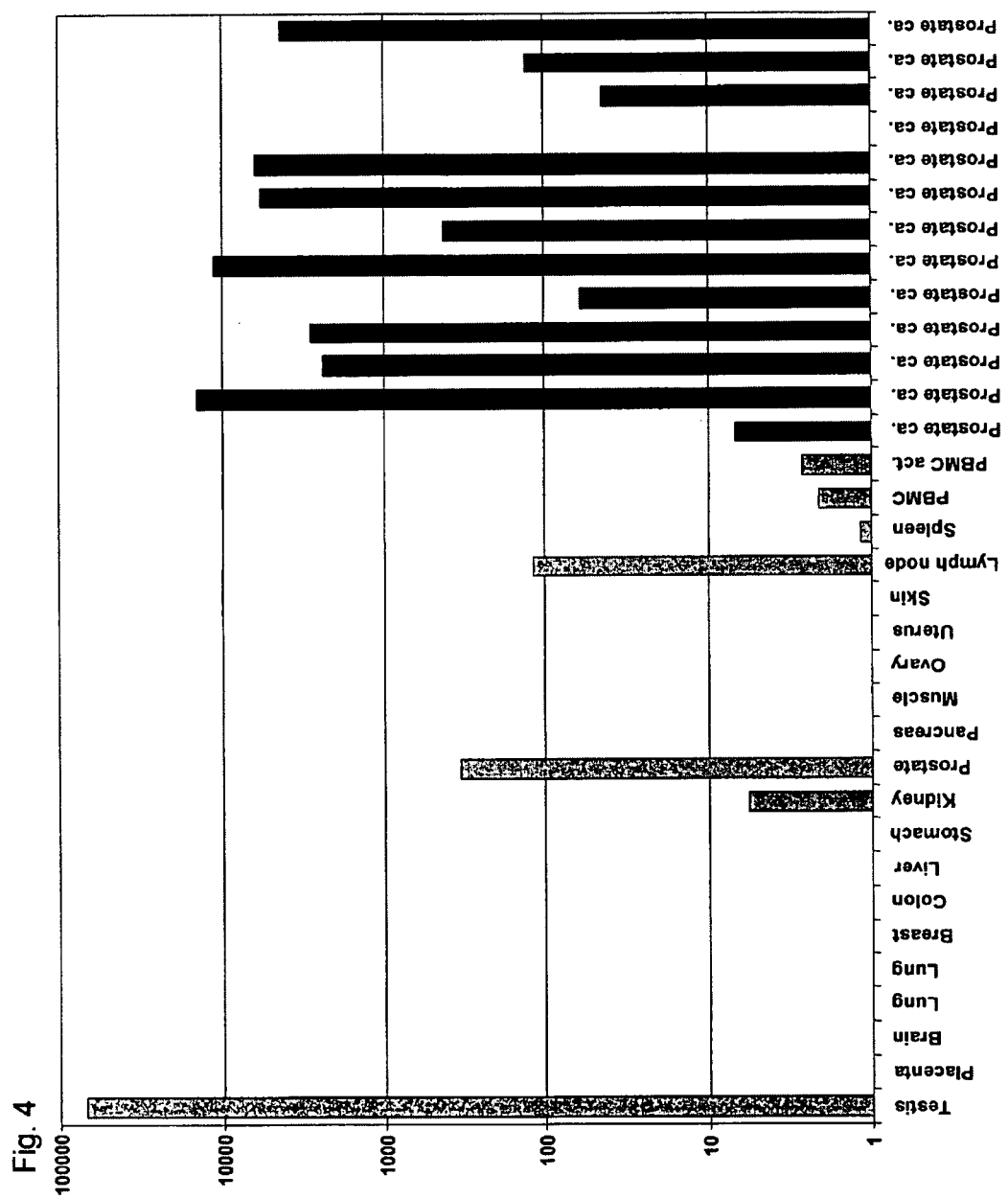

FIG. 4. Quantitative expression of ISC-507
Quantitative RT-PCR with ISC-507-specific primers showed selective expression in testis, lymph node and prostate samples and prostate cancer samples.

Figure 5:
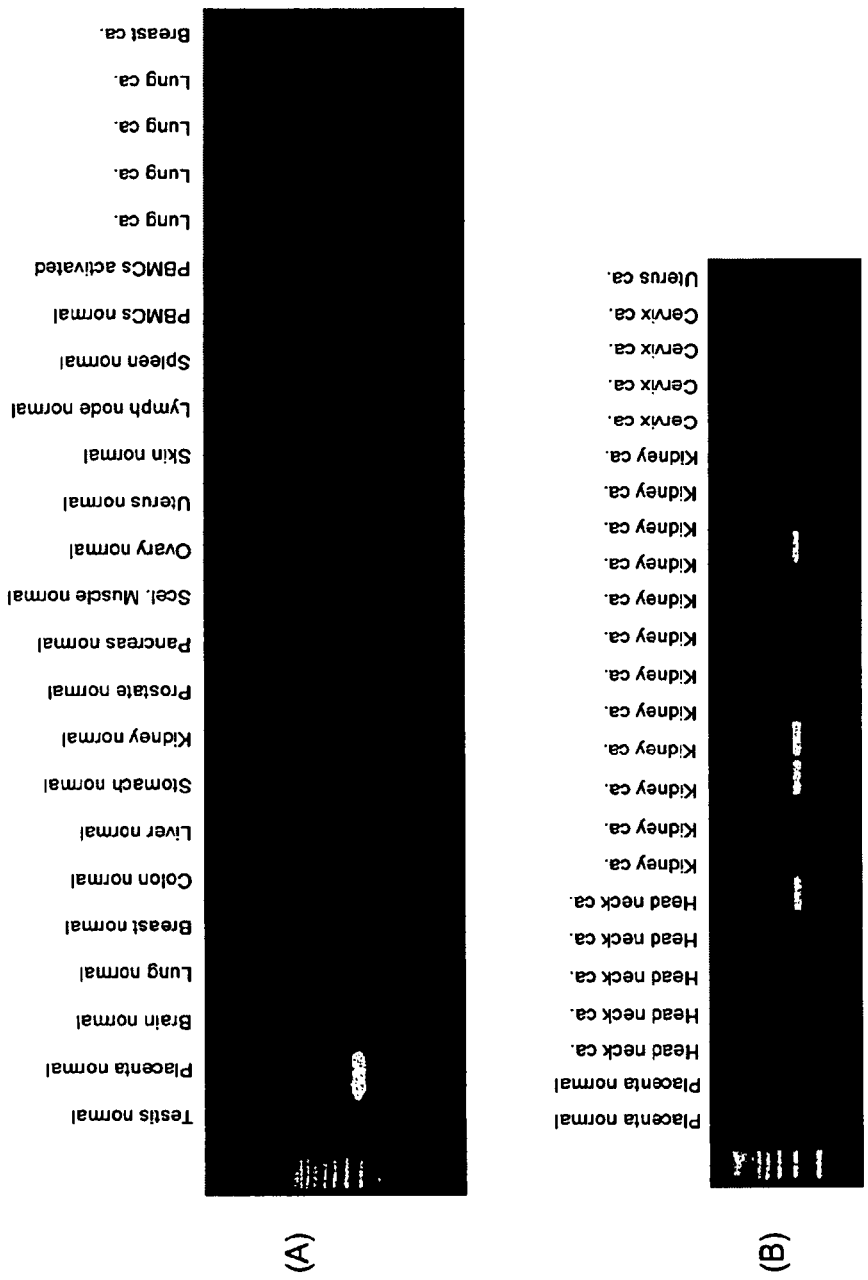
Figure 5:
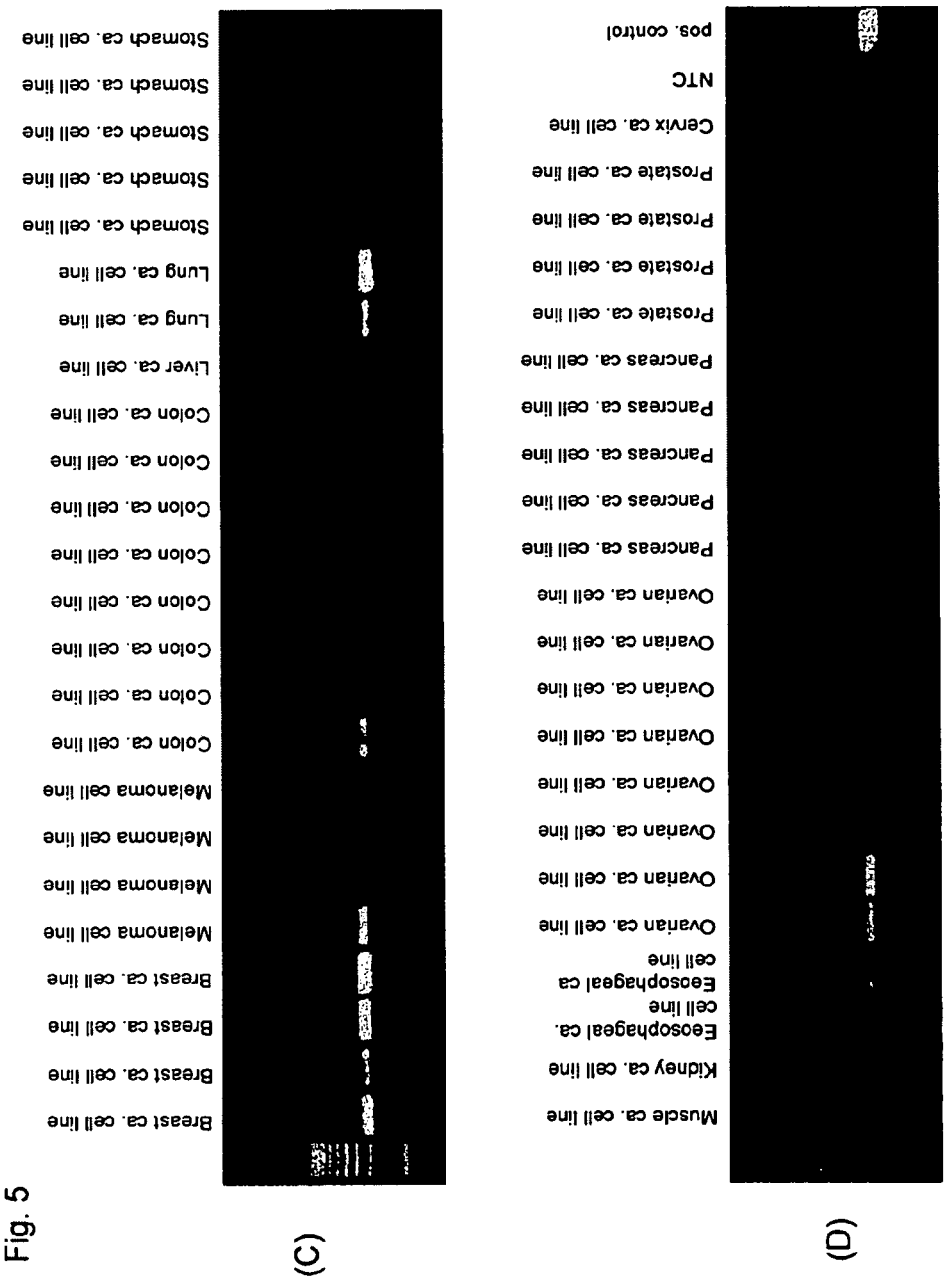

FIG. 5. ISC-466 expression in normal testis and various tumor samples

RT-PCR analysis with ISC-466-specific primers showed no expression within normal tissues except placenta (A), but expression in head and neck carcinoma biopsies and in kidney carcinoma biopsies (B). Distinct expression was also detected in breast and lung carcinoma cell lines, as well as in ovarian carcinoma cell lines (C and D).

Figure 6:
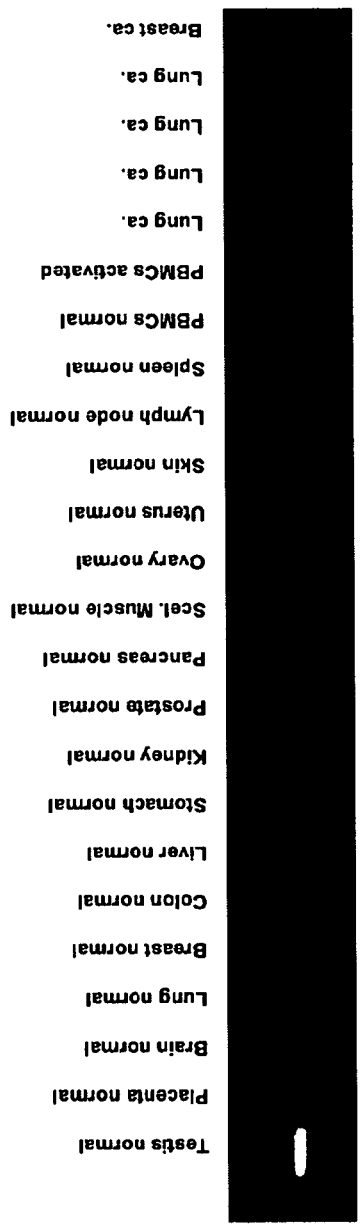

FIG. 6. ISC-518 mRNA expression

RT-PCR analysis with ISC-518-specific primers showed no expression within normal tissues except testis.

Figure 7:
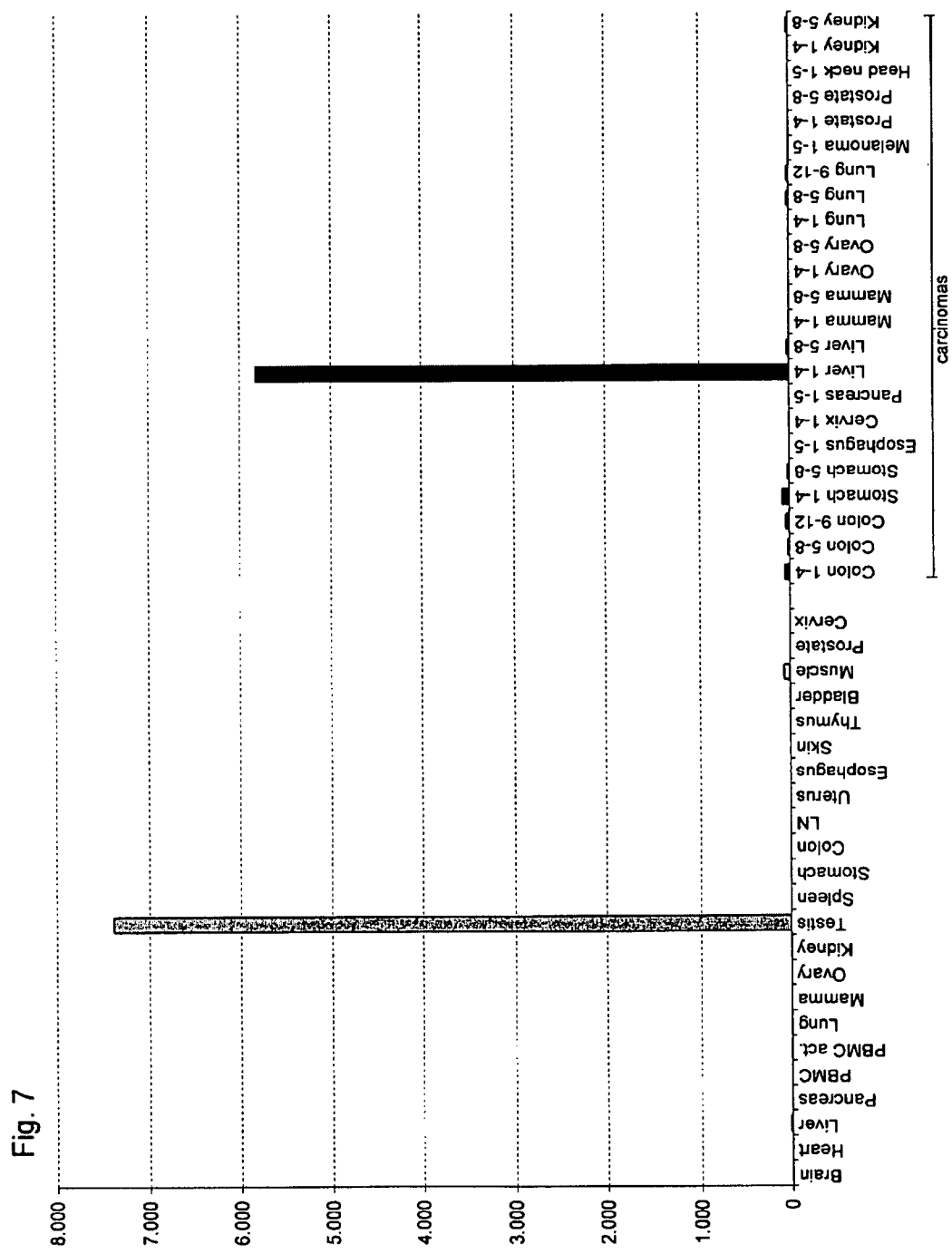

FIG. 7. Quantitative expression of ISC-518

Quantitative RT-PCR showed high and selective expression in normal testis and in one liver carcinoma-pool.

Figure 8:
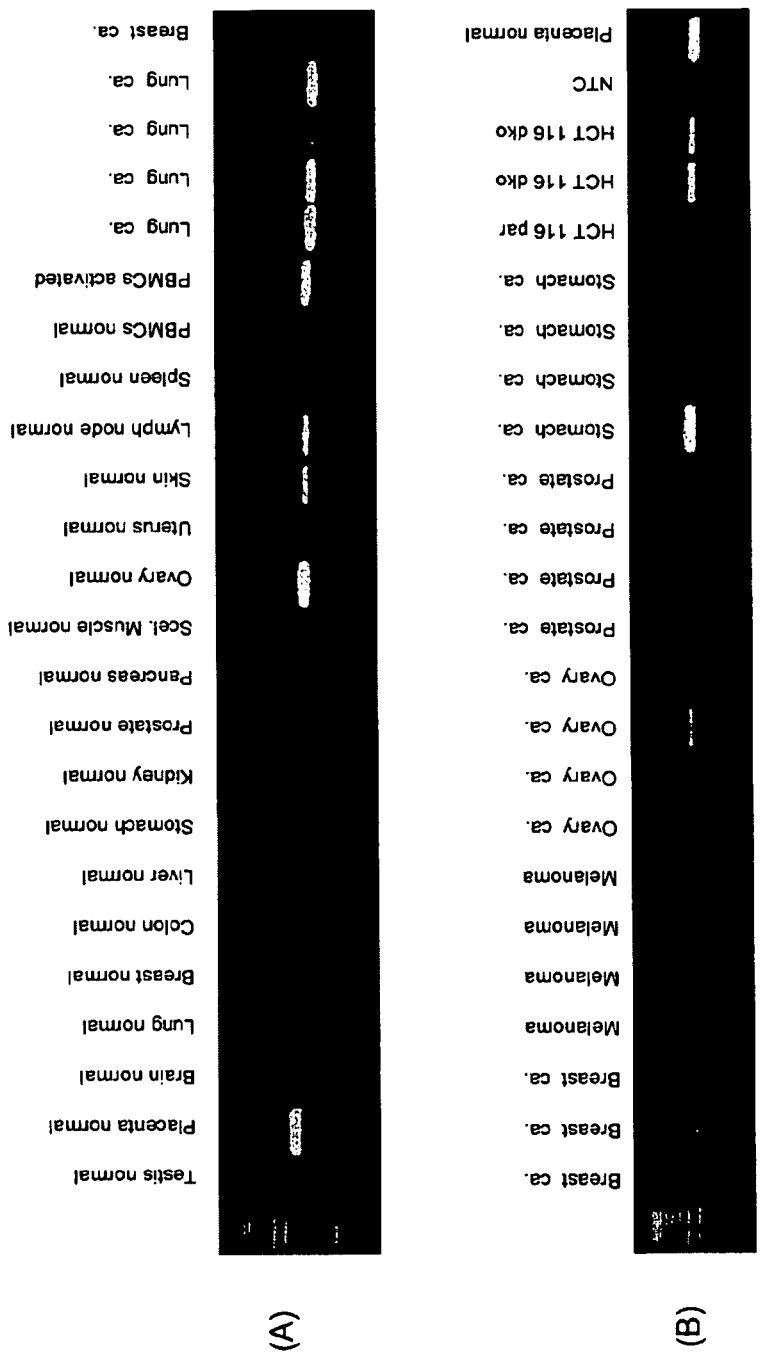
Figure 8:
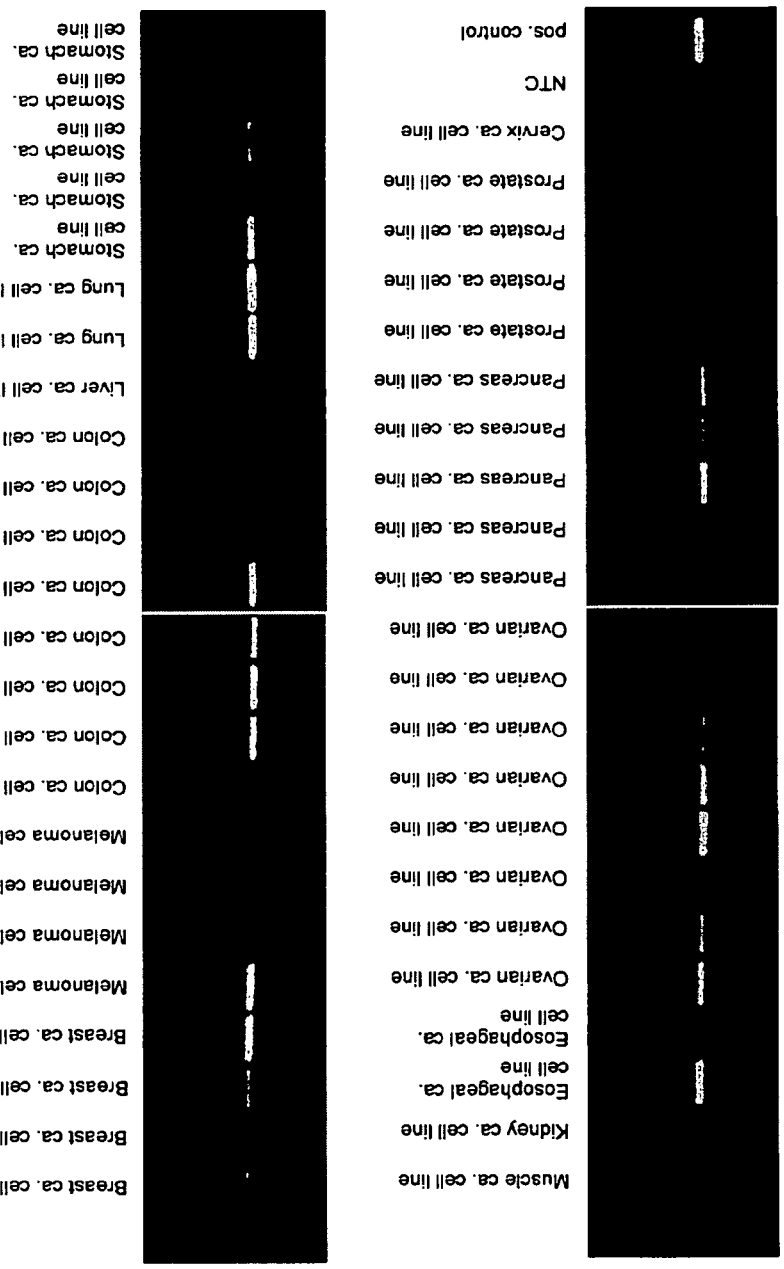

FIG. 8. ISC-477 expression in normal and tumor tissues

RT-PCR investigations with ISC-477-specific primers showed selective expression in placenta and ovary normal tissue (A) and high expression in investigated stomach carcinomas (B), breast, colon and lung carcinomas (C), as well as in ovarian and pancreas carcinoma samples (D).

Figure 9:
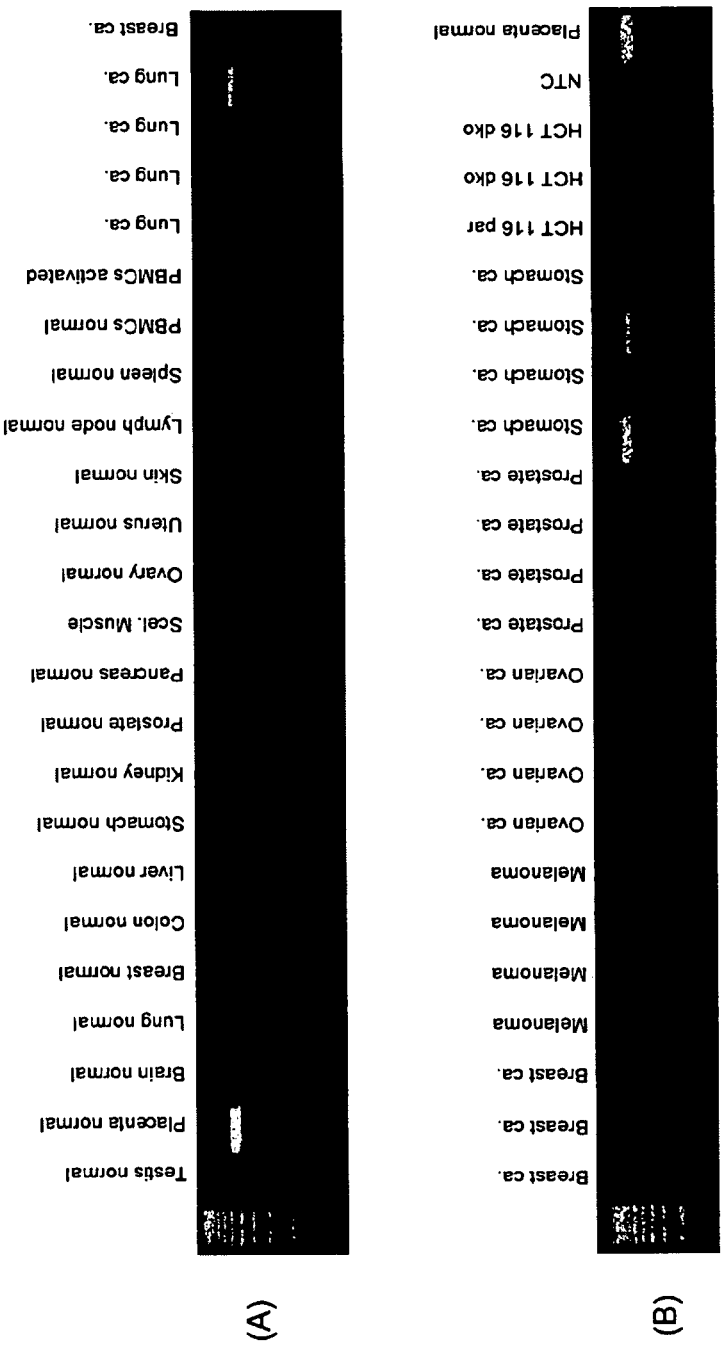
Figure 9:
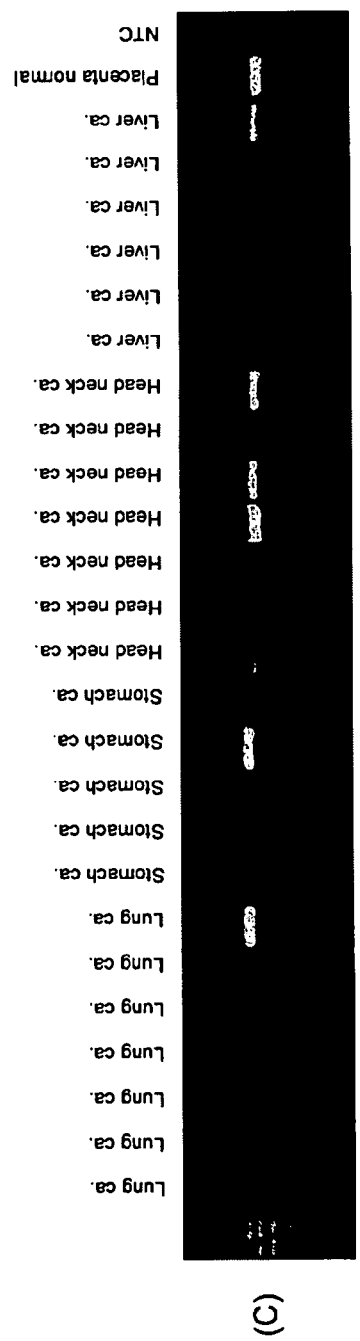

FIG. 9. ISC-489 mRNA expression

RT-PCR investigations with ISC-489-specific primers showed selective expression in placenta control tissue and additionally various levels of expression in lung carcinoma samples (A, C), stomach carcinomas (B, C), head and neck tumors (C) and liver carcinoma samples (C).

Figure 10:
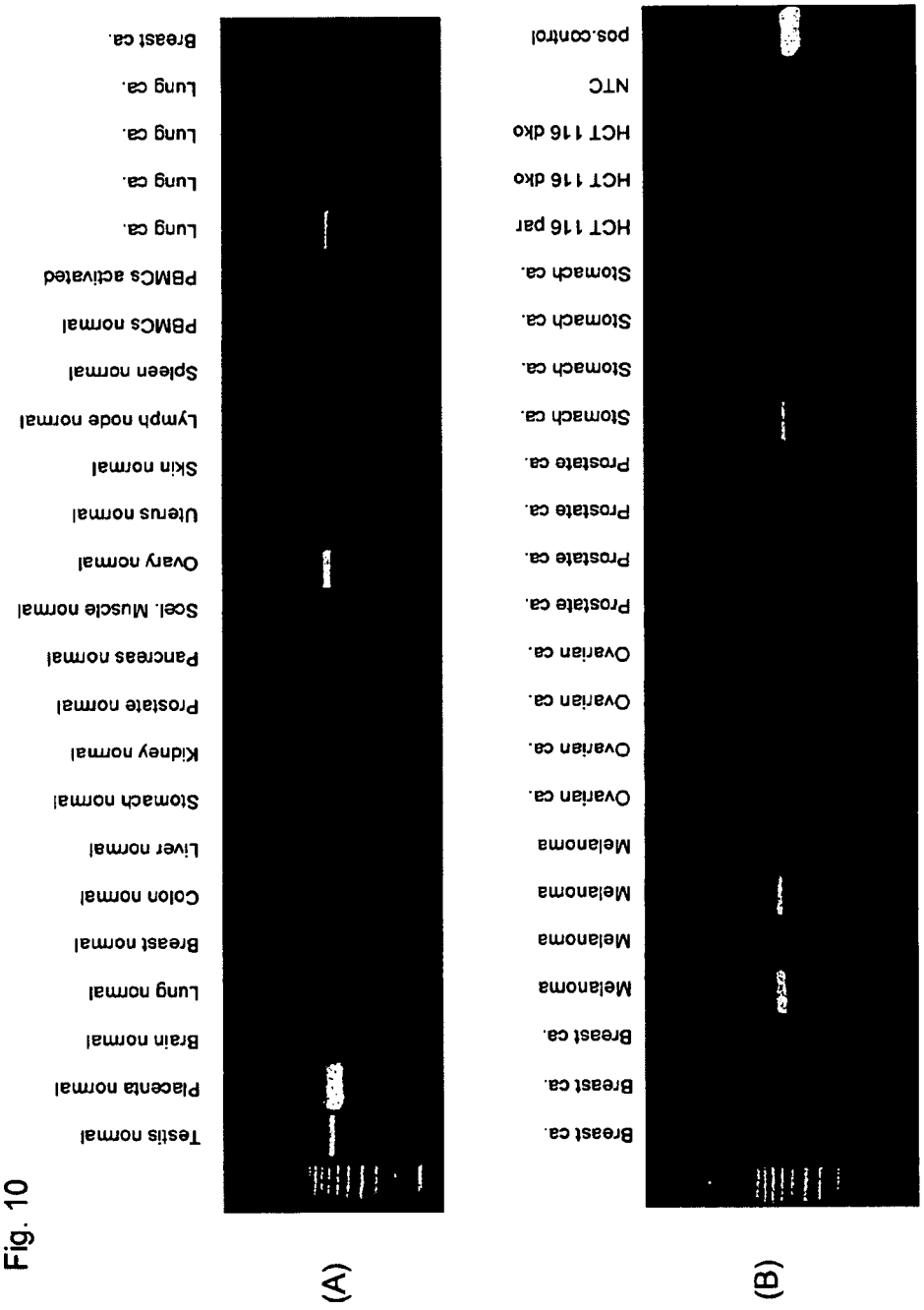
Figure 10:
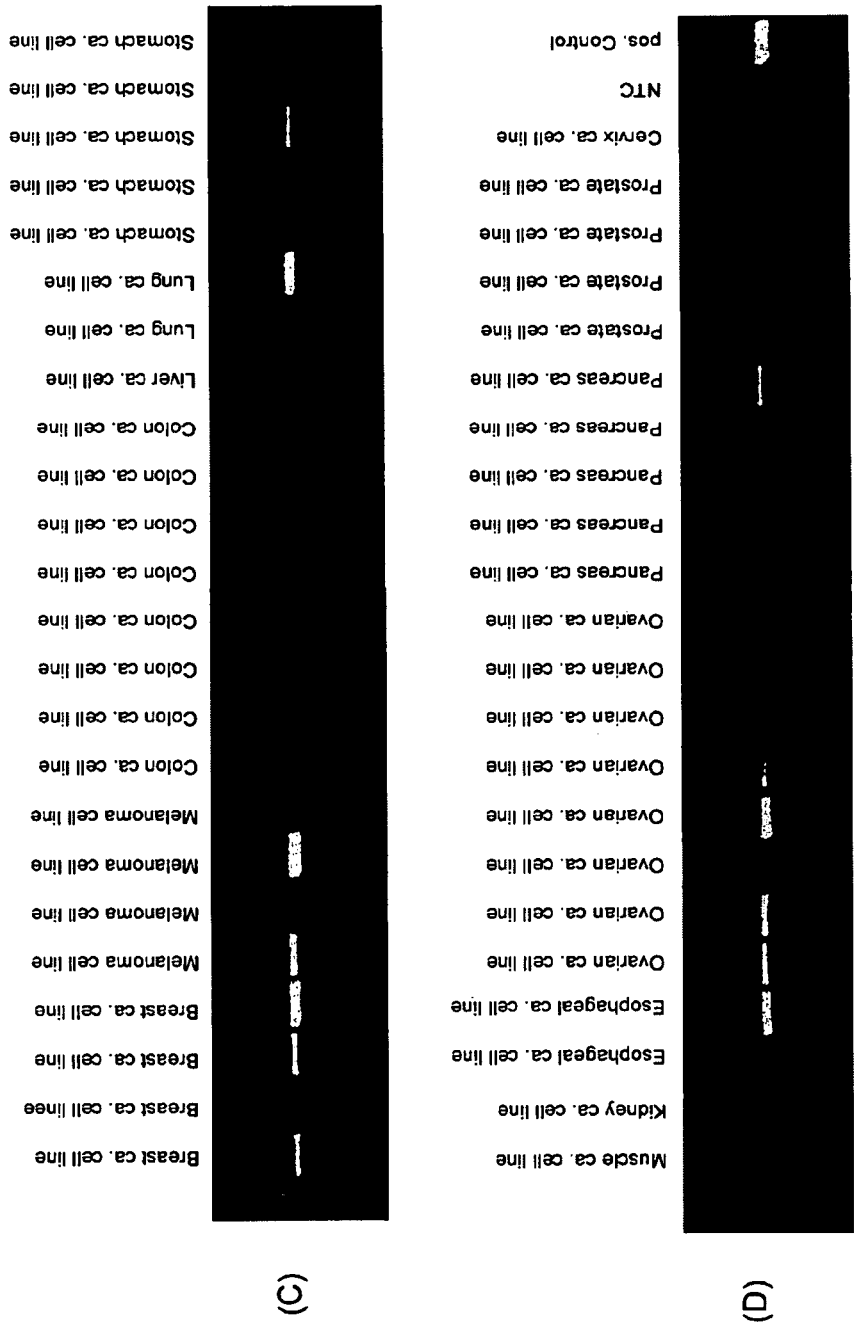

FIG. 10. ISC-461 expression in normal testis and various tumor samples

RT-PCR investigations with ISC-461-specific primers showed selective expression in placenta control tissue and additionally various levels of expression in breast carcinomas and melanomas (B), as well as in breast carcinoma, lung carcinoma and melanoma cell lines (C) and ovarian carcinoma cell lines (D).

Figure 11:
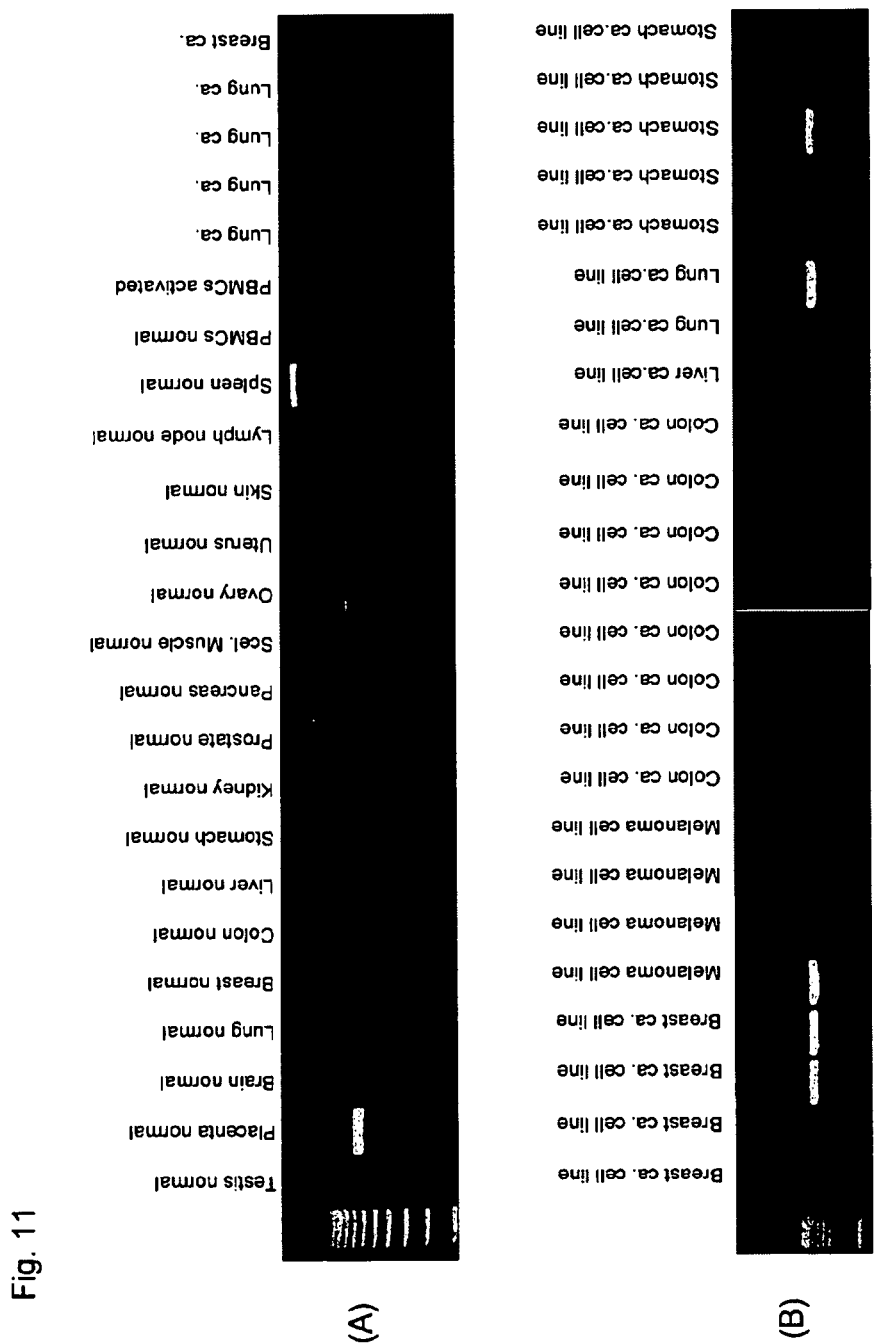

FIG. 11. ISC-465 mRNA expression in placenta and cancer derived samples

RT-PCR investigations with ISC-465-specific primers showed selective expression in placenta (A) and in some cell lines derived from breast cancer, melanoma, lung cancer or stomach cancer (B).

Figure 12:
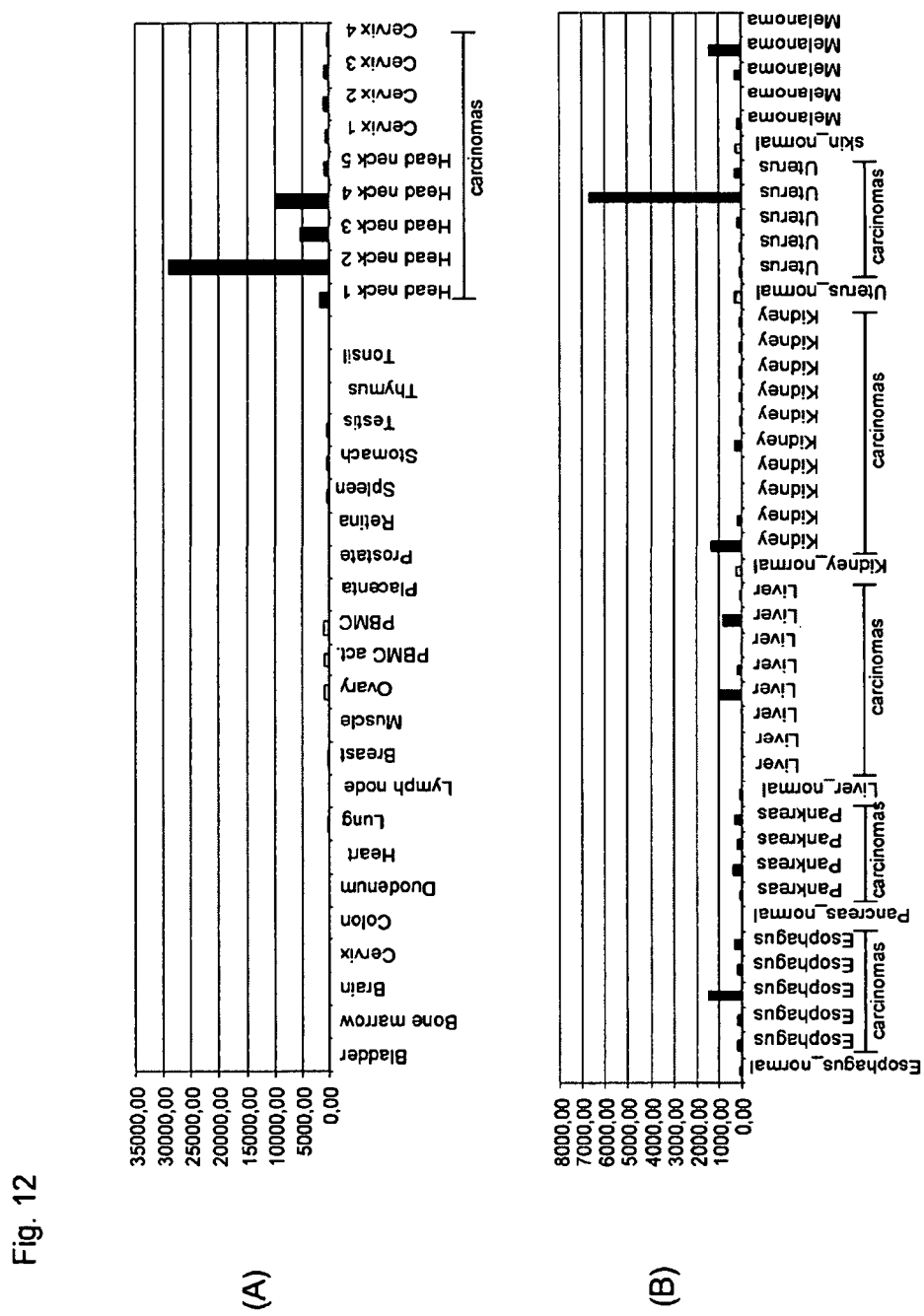

FIG. 12. Quantitative expression of Mem-030

A. Quantitative RT-PCR with Mem-030-specific primers showed a significant overexpression in all investigated head and neck carcinoma samples. The following normal tissues were analyzed: bladder, brain, bone marrow, cervix, colon, duodenum, heart, lung, lymph node, breast, muscle, ovary, PBMC, PBMC-activated, placenta, prostate, retina, spleen, stomach, testis, thymus and tonsil.

B. Prevalence of Mem-030 in esophageal, liver, uterus carcinomas and melanoma derived tissues.

Figure 13:
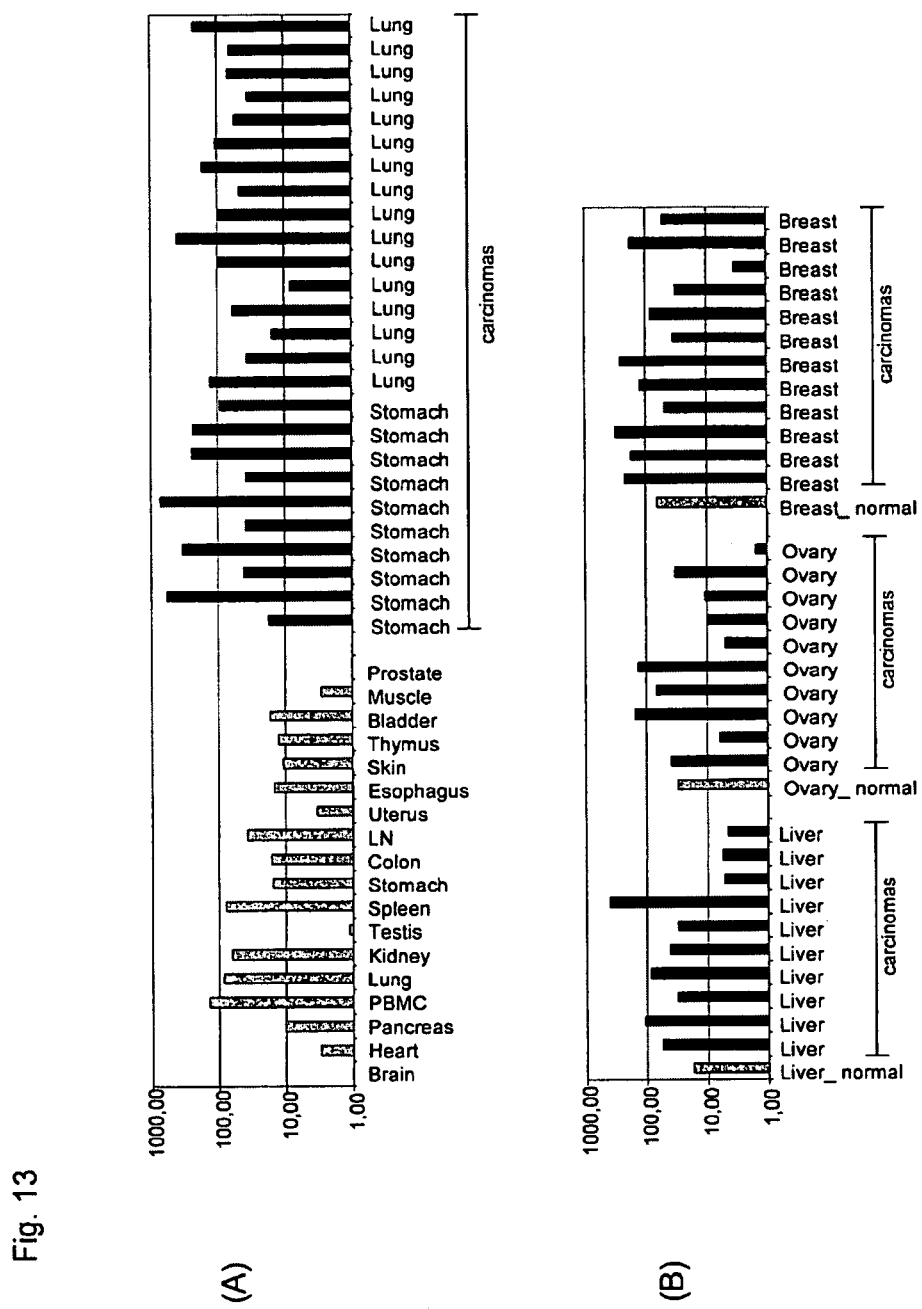

FIG. 13. Quantitative expression of Mem-055

Quantitative RT-PCR with Mem-055-specific primers show high and selective expression in normal control tissues and a significant overexpression in stomach and lung cancer derived tissues (A). Mem-055 is also overexpressed in liver carcinomas, ovarian carcinomas and breast cancer samples (B).

Figure 14:
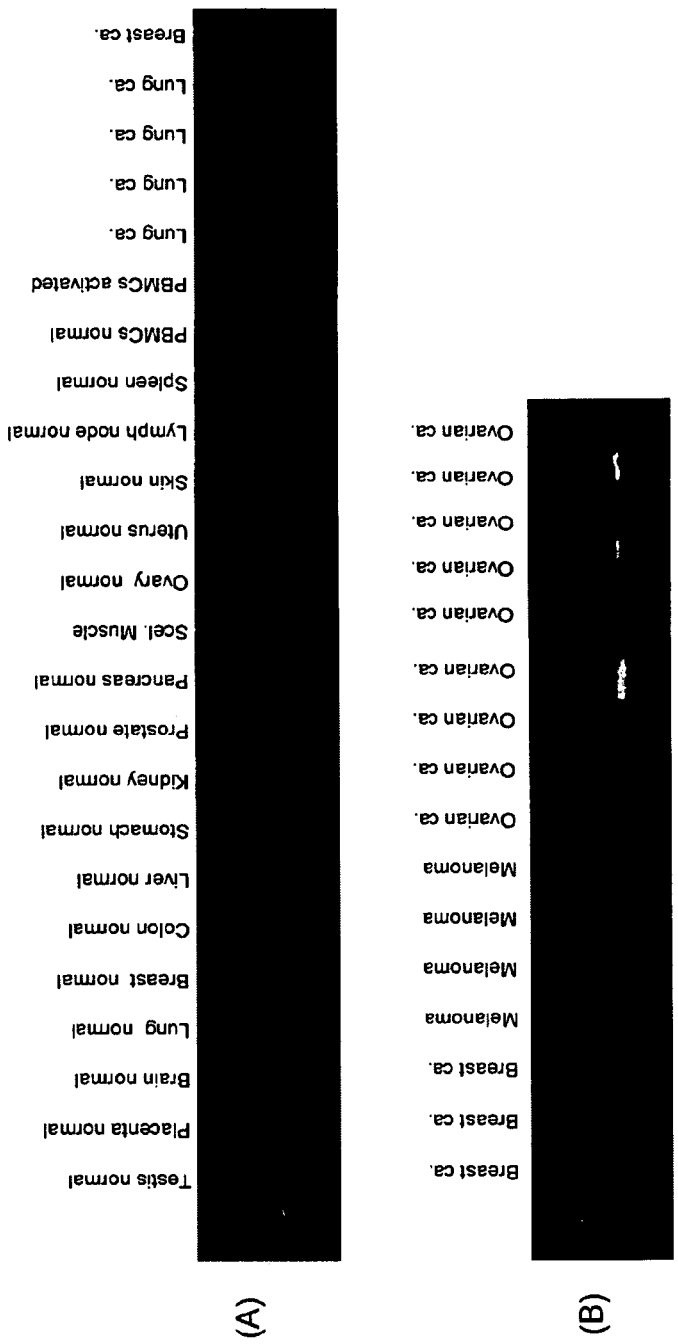

FIG. 14. Mem-062 mRNA expression

RT-PCR analysis with Mem-064-specific primers showed selective expression in testis and weak expression in lung cancer derived tissues (A). Strong, significant expression levels of Mem-064 transcripts were detectable in various ovarian tumors (B).

Figure 15:
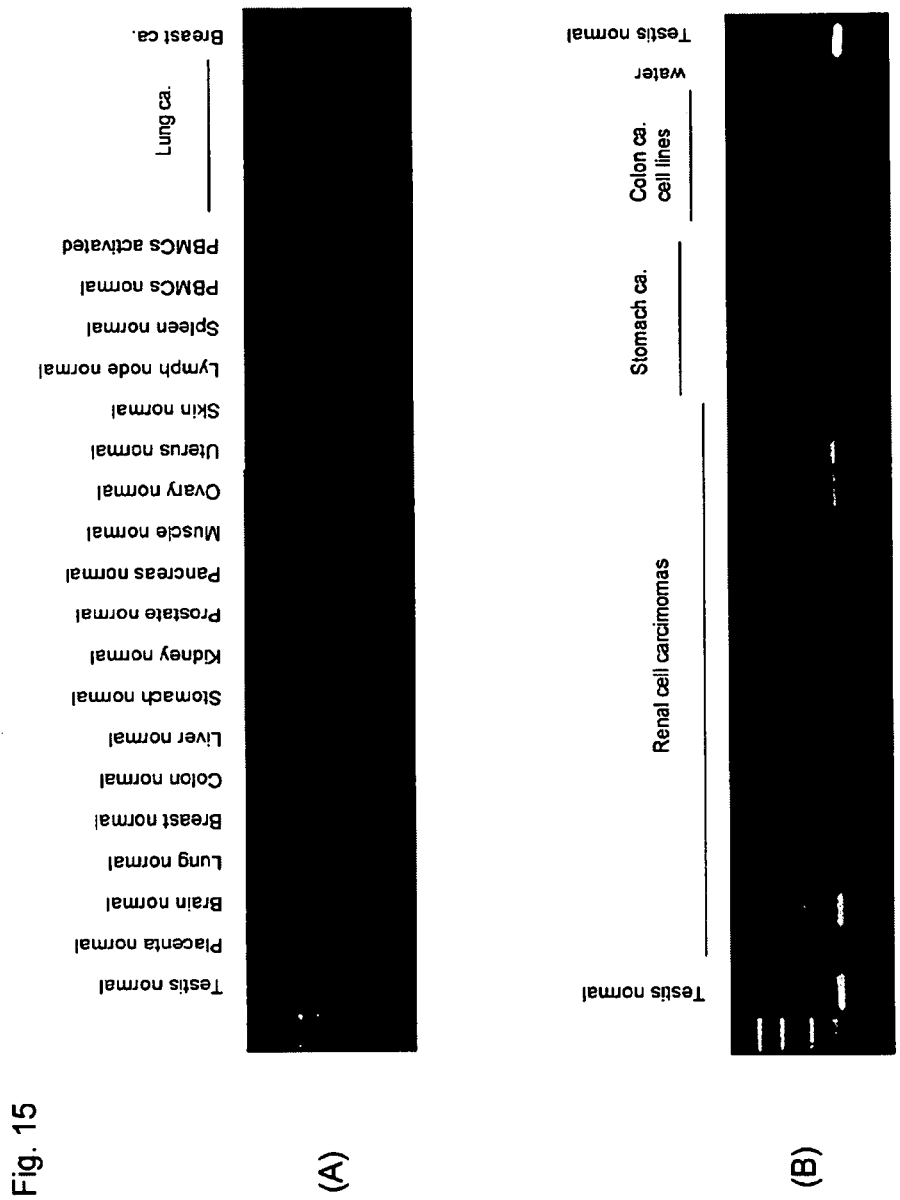

FIG. 15. Specific Mem-068 expression in normal testis and renal cell carcinomas

RT-PCR analysis with gene-specific Mem-068 primers shows cDNA amplification in normal testis, weak in placenta (A), in renal cell carcinomas and in stomach cancers (B).

Figure 16:
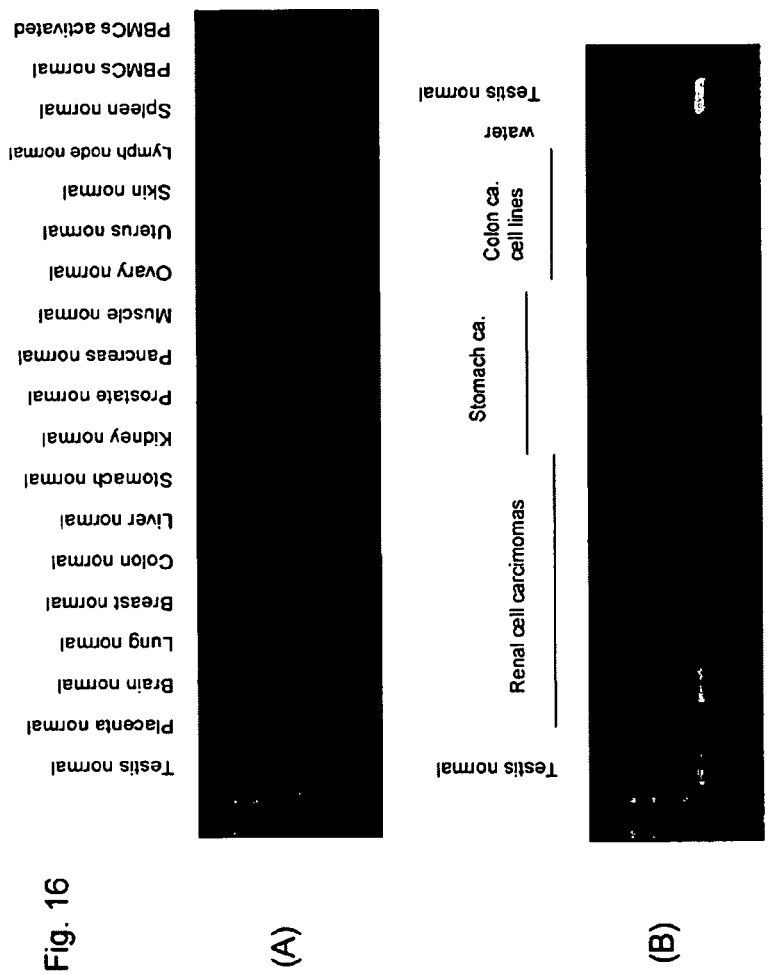

FIG. 16. Mem-071 expression in normal testis and various tumor samples

RT-PCR analysis with Mem-071-specific primers showed no expression within normal tissues except testis (A). Distinct expression was also detected in renal cell carcinoma samples and in stomach cancers (B).

Figure 17:
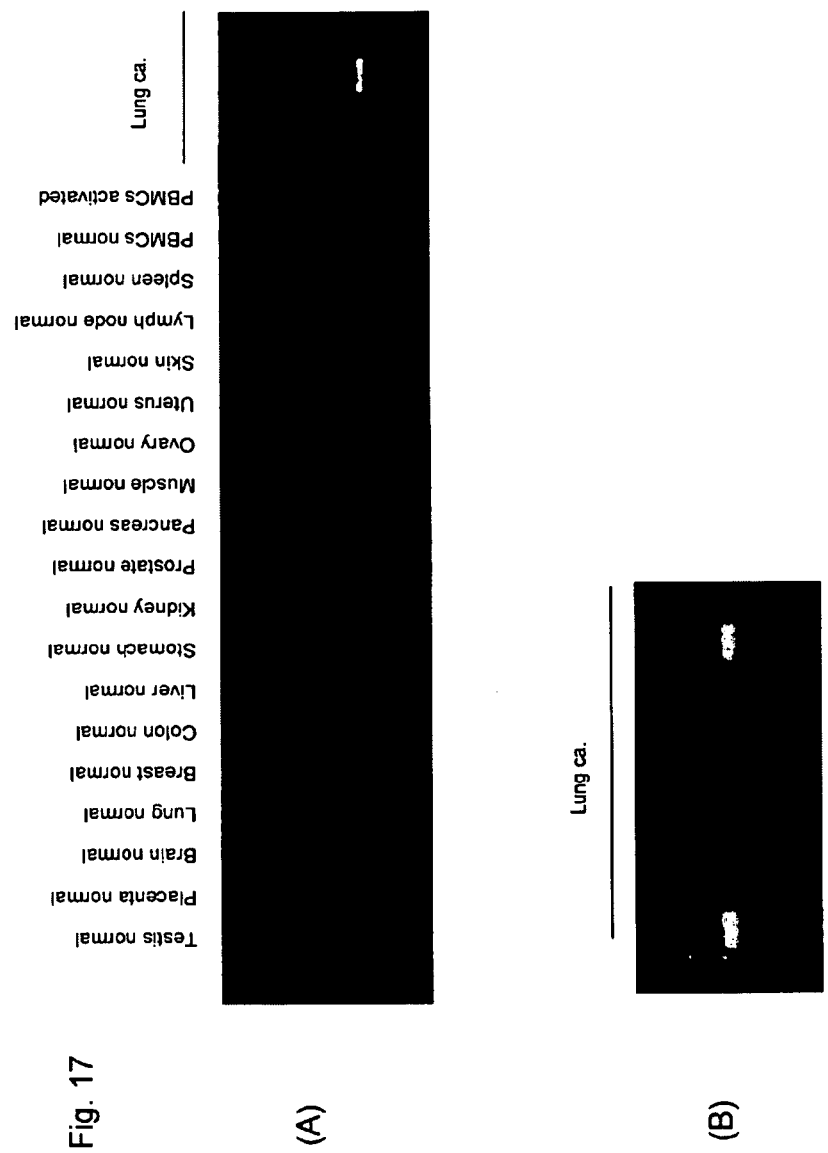

FIG. 17. Mem-072 mRNA expression

RT-PCR analysis with Mem-072-specific primers showed no expression within normal tissues (A) and significant expression in various lung cancer samples (A+B).

Figure 18:
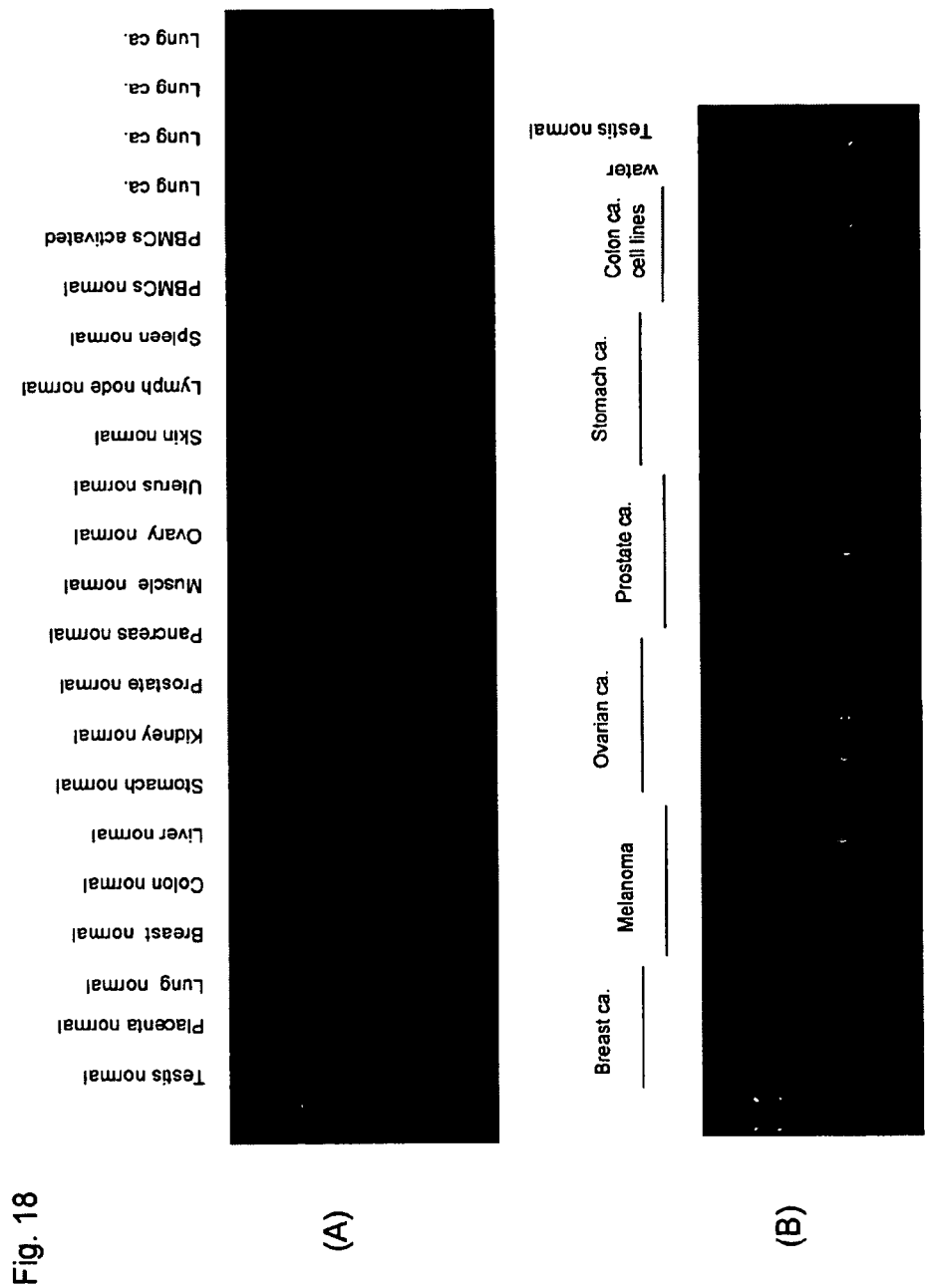

FIG. 18. Mem-106 expression in normal and tumor tissues

RT-PCR investigations with Mem-106-specific primers showed no expression within normal tissues except in testis (A) and high expression were investigated in ovarian- and prostate carcinomas, as well as in melanomas and colon cancer cell lines (B).

Figure 19:
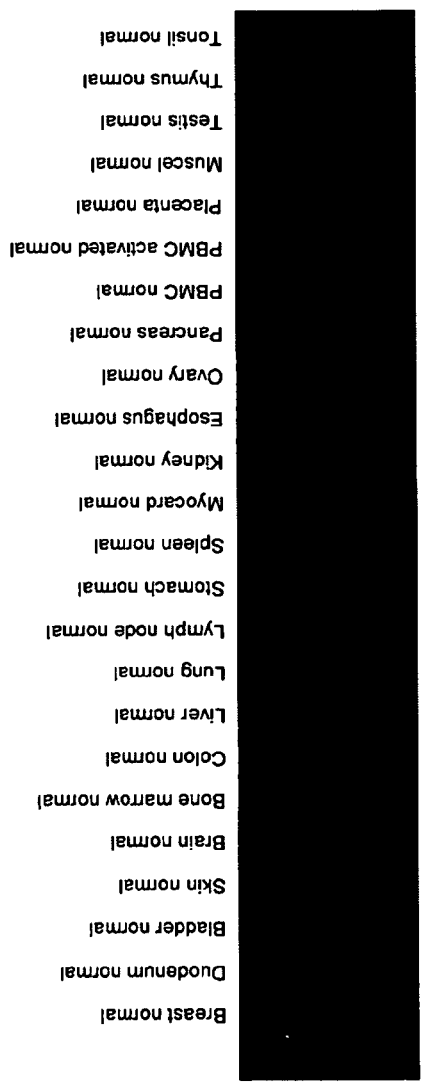
Figure 19:
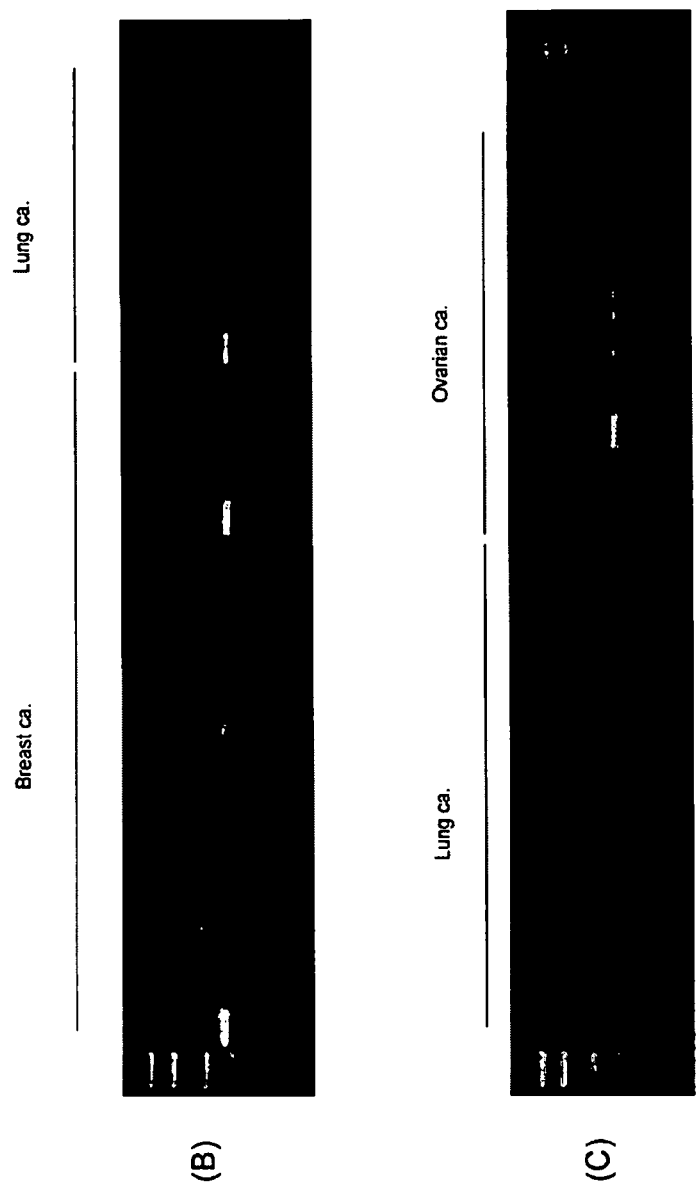

FIG. 19. Mem-131 mRNA expression

RT-PCR investigations with Mem-131-specific primers showed no significant expression within all tested normal tissues except activated PBMC.Mem-131 mRNA expression in breast- and lung-carcinomas.Mem-131 mRNA expression in lung- and ovarian carcinomas.

Figure 20:
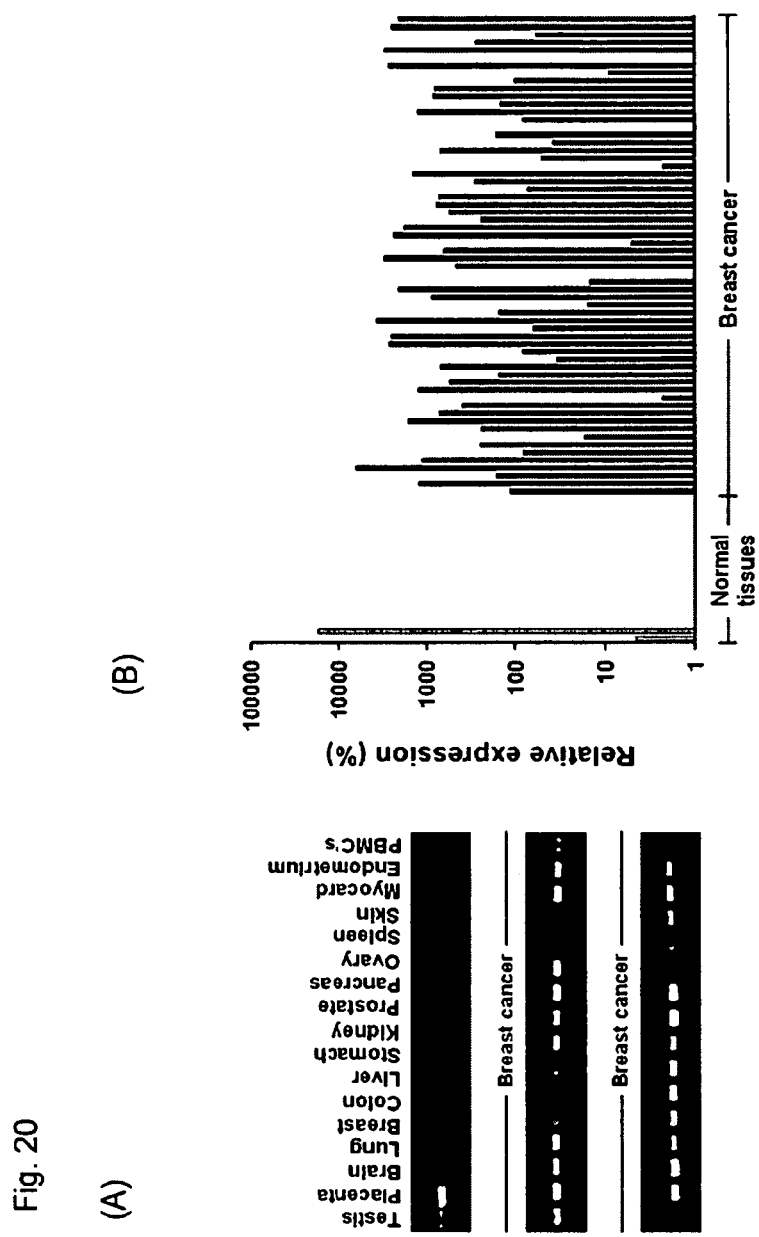

FIG. 20. ISC-468 mRNA expression (A) RT-PCR and B) Real-time PCR (investigation with ISC-468-specific primers showed selective mRNA expression in normal testis, placenta, and in 80% of breast carcinoma biopsies.

Figure 21:
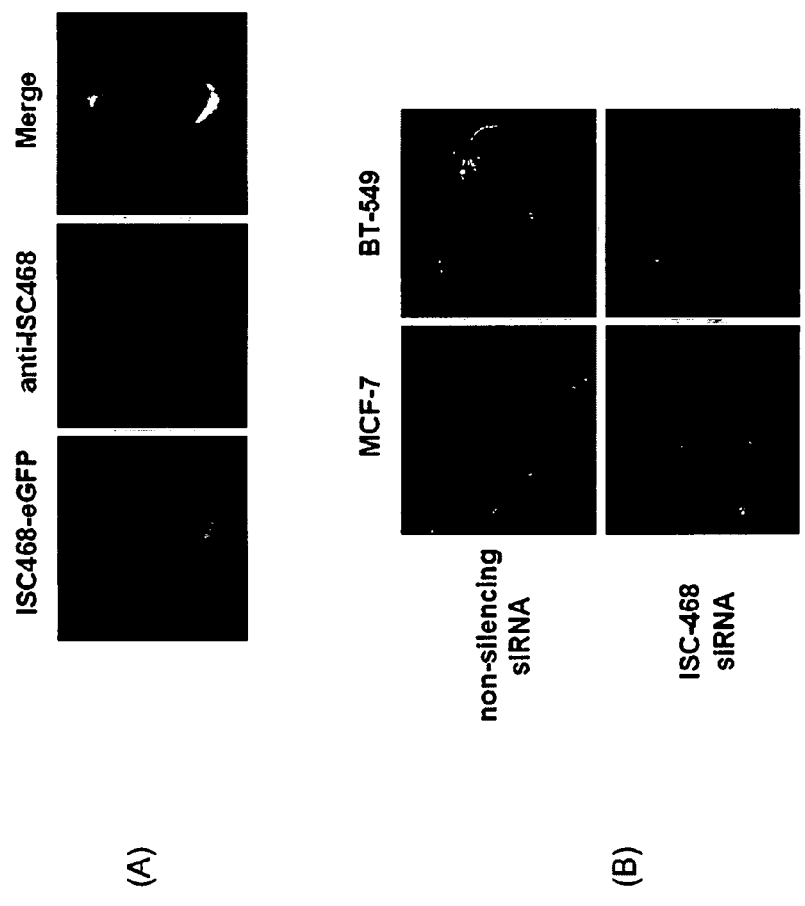
Figure 21:
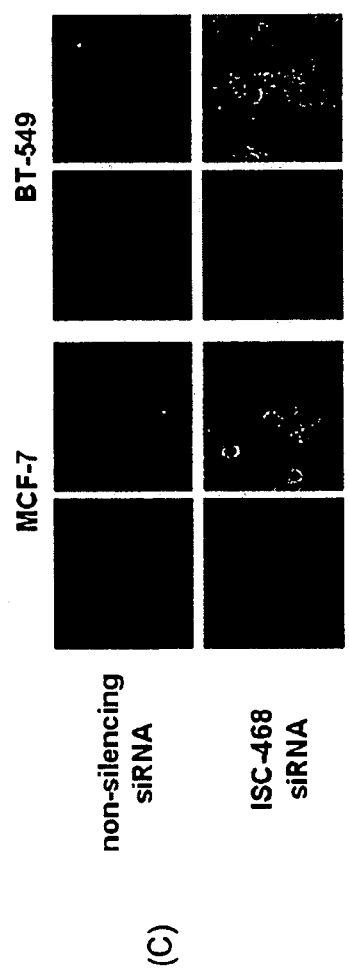

FIG. 21. Immunofluorescence analysis of ISC-468 expression (A) Specificity of anti-ISC-468 antibodies were confirmed by staining of ISC-468-eGFP transfected cells. (B) Staining of MeOH-fixed cells either transfected with ISC-468-specific RNAi duplexes, or non-silencing control duplexes. (C) Staining of non-fixed cells either transfected with ISC-468-specific RNAi duplexes, or non-silencing control duplexes.

Figure 22:
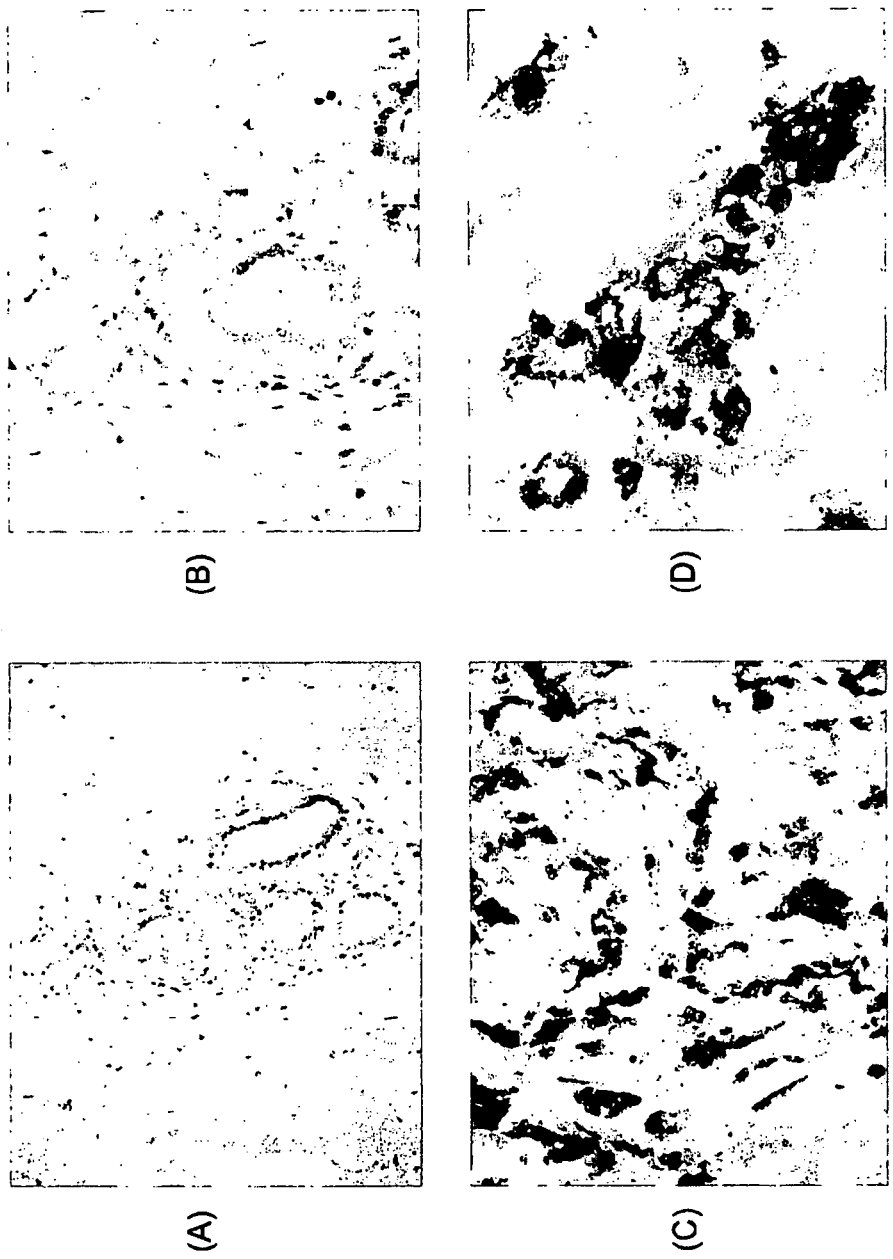

FIG. 22. Immunochistochmical analysis of ISC-468 expression

No expression was detectable in normal breast tissue (A) 100×, (B) 200×. In contrast, strong and homogeneous membrane-staining was observed in breast carcinoma specimens (C) 100×, (D) 200×.

Figure 23:
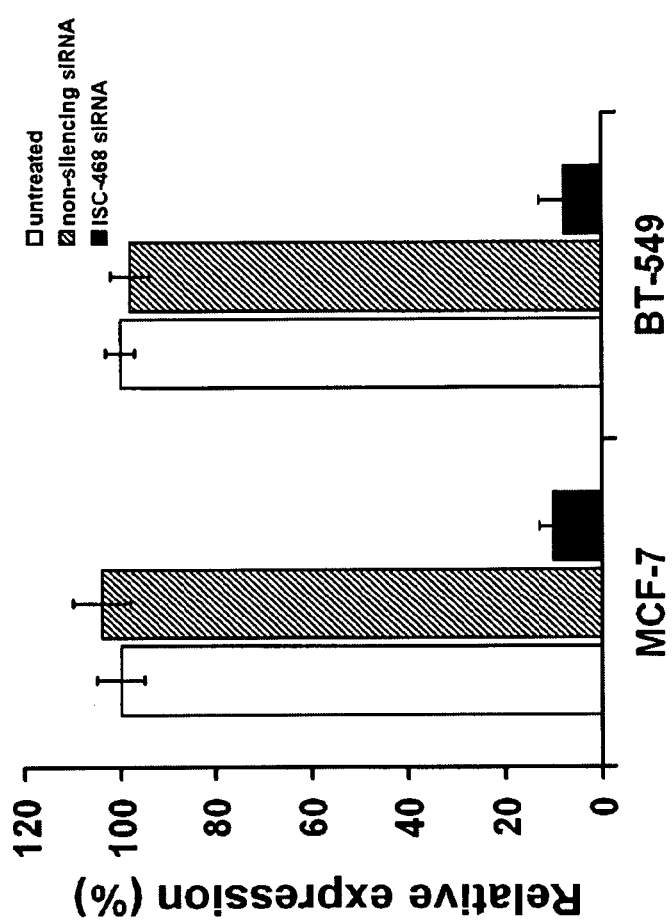

FIG. 23. RNAi-induced knock-down of ISC-468 mRNA expression

Transfection of cells with ISC-468-specific siRNA duplexes resulted in distinct knock-down of ISC-468 mRNA expression compared to control cells.

Figure 24:
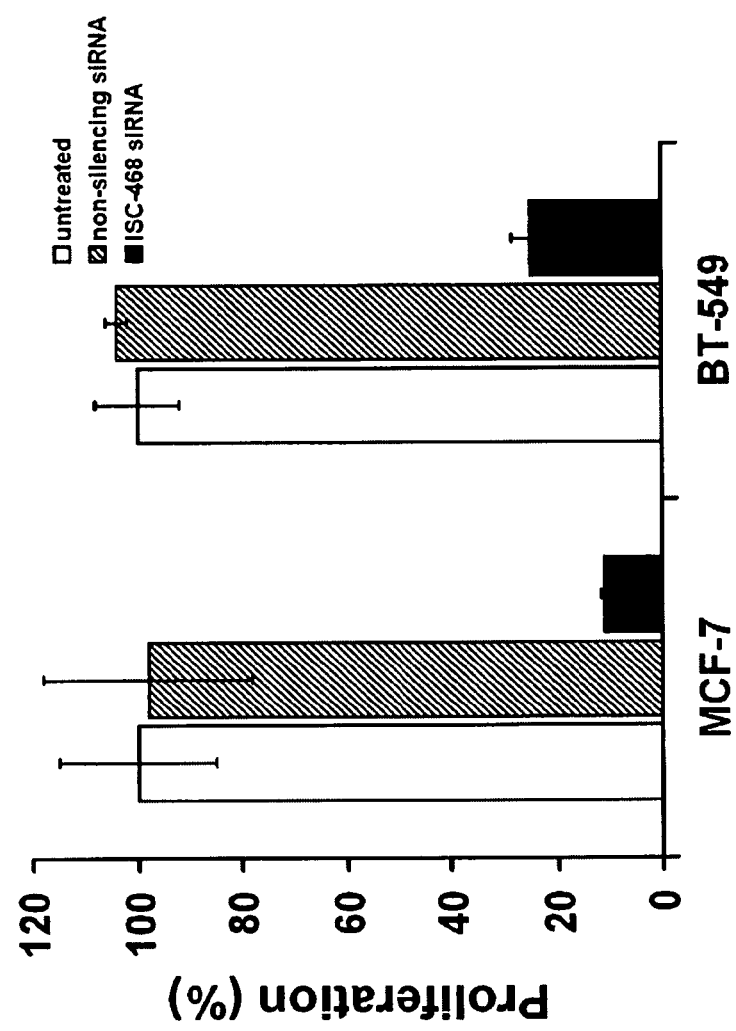

FIG. 24. Cell proliferation analysis

Transfection of cells with ISC-468-specific siRNA duplexes resulted in distinct impairment of cell proliferation compared to control cells.

Figure 25:
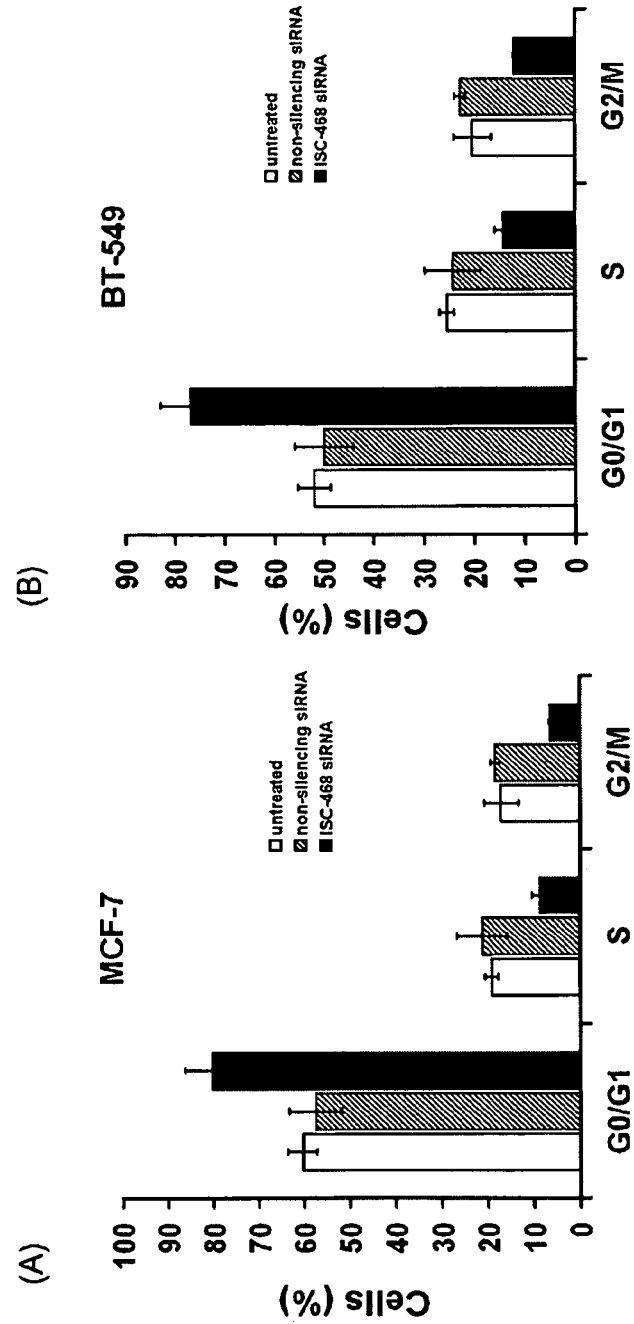

FIG. 25. Cell cycle analysis

Transfection of cells with ISC-468-specific siRNA duplexes resulted in G1/S arrest in (A) MCF-7 and (B) BT-549 breast carcinoma cells compared to control cells.

Figure 26:

FIG. 26. AKT phosphorylierung

Transfection of cells with ISC-468-specific siRNA duplexes resulted in distinct impairment of AKT phosphorylation compared to control cells.

Figure 27:
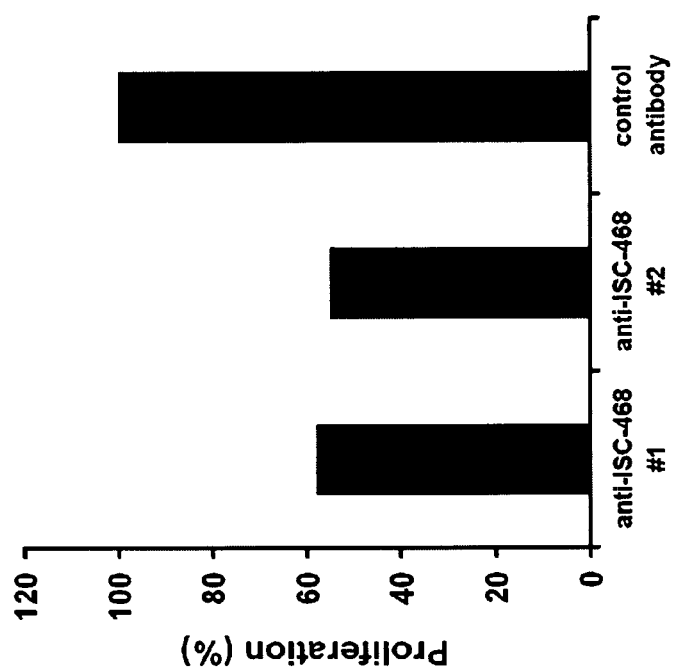

FIG. 27. Antibody-mediated proliferation inhibition

Incubation of MCF-7 breast carcinoma cells with ISC-468 specific antibodies resulted in reduced proliferation compared to cells incubated with an irrelevant control antibody.

Figure 28:
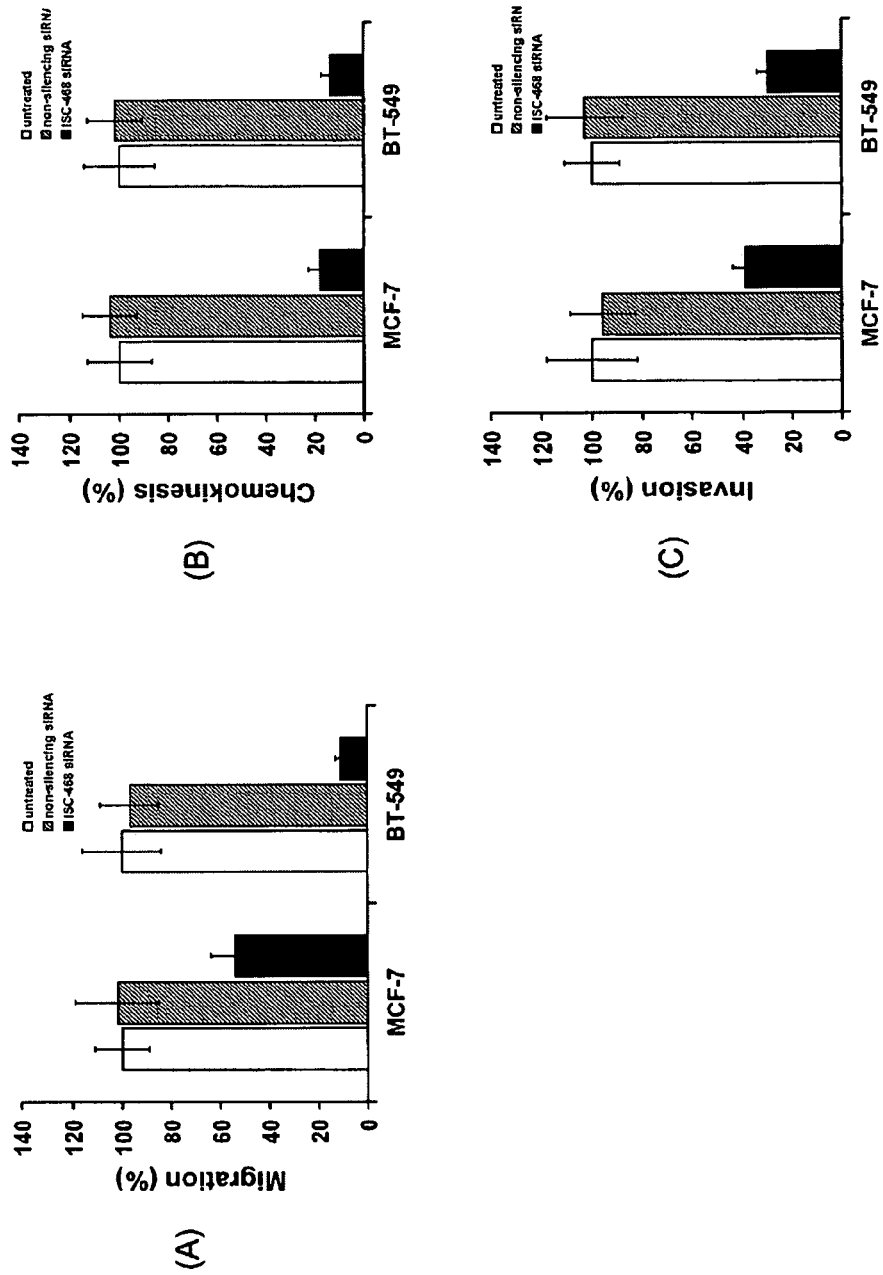

FIG. 28. Cell proliferation analysis

Transfection of cells with ISC-468-specific siRNA duplexes resulted in distinct impairement of (A) chemotaxis, (B) chemokinesis, and (C) invasion compared to control cells.

Figure 29:
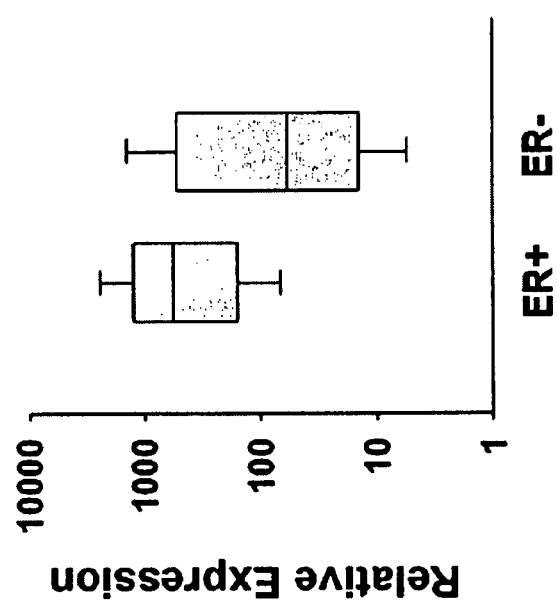

FIG. 29. Estrogen receptor correlation

Expression levels of ISC-468 mRNA in breast carcinoma samples correlates with the estrogen receptor state. Shown are the median, $10^{th}$, and $90^{th}$ percentiles with error bars.

Figure 30:
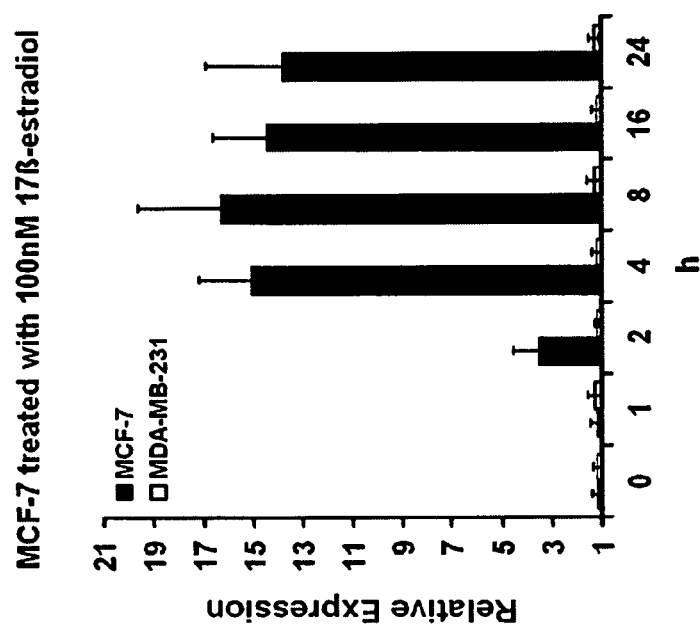

FIG. 30. 17β-estradiol treatment

ISC-468 mRNA expression was induced by treatment of estrogen receptor positive breast carcinoma cell line MCF-7 with 100 nM 17β-estradiol. No induction was seen in estrogen receptor negative cell line MDA-MB-231.

FIG. 31. Sequences

The sequences to which reference is made herein are shown in FIGS. 31A-31J.

EXAMPLES

Material and Methods

The techniques and methods mentioned herein are carried out in a manner known per se and are described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information.

RNA Extraction, Preparation of poly-d(T) Primed cDNA and Conventional RT-PCR Analysis Total RNA was extracted from native tissue material by using guanidinium isothiocyanate as chaotropic agent (Chomczynski & Sacchi, Anal. Biochem. 162:156-9, 1987). After extraction with acidic phenol and precipitation with isopropanol, said RNA was dissolved in DEPC-treated water.

First strand cDNA synthesis from 4 µg of total RNA was carried out in a 20 µl reaction mixture by means of Superscript II (Invitrogen), according to the manufacturer's information. The primer used was a dT(18) oligonucleotide. Integrity and quality of the cDNA were checked by amplification of p53 in a 30 cycle PCR ((SEQ ID NO:33,34)), hybridization temperature 67° C.).

An archive of first strand cDNA was prepared from a number of normal tissues and tumor entities. For expression studies, 0.5 µl of these cDNAs was amplified in a 30 µl reaction mixture, using GOI-specific primers (see below) and 1 U of HotStarTaq DNA polymerase (Qiagen). Each reaction mixture contained 150 µM dNTPs, 0.3 µM of each primer and 3 µl of 10× reaction buffer. The primers were selected so as to be located in two different exons, and elimination of the interference by contaminating genomic DNA as the reason for false-positive results was confirmed by testing nonreverse-transcribed DNA as template. After 15 minutes at 95° C. to activate the HotStarTaq DNA polymerase, 35 cycles of PCR were carried out (0.5 min at 94° C., 0.5 min at the particular hybridization temperature, 0.5 min at 72° C. and final elongation at 72° C. for 6 min). 20 µl of this reaction were fractionated and analyzed on an ethidium bromide-stained agarose gel.

Preparation of Random Hexamer-Primed cDNA and Quantitative Real-Time PCR

The expression of several genes was quantified by real-time PCR. The PCR products were detected using SYBR Green as intercalating reporter dye. The reporter fluorescence of SYBR Green is suppressed in solution and the dye is active only after binding to double-stranded DNA fragments. The increase in the SYBR Green fluorescence as a result of the specific amplification using GOI-specific primers after each PCR cycle is utilized for quantification. Expression of the target gene is quantified absolutely or relative to the expression of a control gene with constant expression in the tissues to be investigated. Expression was measured after standardization of the samples against 18s RNA as so-called housekeeping gene using the $\Delta\Delta\text{-}C_t$ method (PE Biosystems, USA). The reactions were carried out in duplicates and determined in triplicates. The QuantiTect SYBR Green PCR kit (Qiagen, Hilden) was used in accordance with the manufacturer's instructions. The cDNA was synthesized with random primers (Invitrogen) using the protocol described above. Each 5 µl portions of the diluted cDNA were employed in a total volume of 30 µl for the PCR: sense primer 300 nM, antisense primer 300 nM; initial denaturation 95° C. for 15 min; 95° C. for 30 sec; annealing for 30 sec; 72° C. for 30 sec; 40 cycles. The sequences of the primers used are indicated in the respective examples.

Cloning and Sequence Analysis

Cloning of full-lengths and gene fragments took place by conventional methods. To ascertain the sequence, corresponding antigenes were amplified using the proofreading polymerase pfu (Stratagene). After completion of the PCR, adenosine was ligated by means of HotStarTaq DNA polymerase to the ends of the amplicon in order to clone the fragments in accordance with the manufacturer's instructions into the TOPO-TA vector. The sequencing was carried out by a commercial service. The sequences were analysed using conventional prediction programs and algorithms.

Cell Proliferation Analysis 24 h after transfection with siRNA duplexes $1\times10^4$ cells were cultured in medium supplemented with varying concentrations of FCS for 48 h. Proliferation was analyzed by measuring the incorporation of BrdU into newly synthesized DNA strands using the DELFIA cell proliferation Kit (Perkin Elmer) according to the manufacturer's instructions on a Wallac Victor2 multi-label counter (Perkin Elmer).

Cell Cycle Analysis and Apoptosis

Cells were cultured in medium supplemented with FCS in varying concentrations, harvested after 48 h and stained with propidiumiodide prior to flowcytometric DNA content analysis. Apoptotic cells and cells in S/G2/M phases of the cell cycle were quantified using CellQuest-Software (Becton Dickinson).

Cell Migration

Cell migration assays were conducted in transwell chambers with 8.0 µm pore membranes (BD Biosciences) with cells cultured in serum-free medium for 12 h prior to the experiments. For siRNA experiments cells were transferred to serum-free conditions 24 h after transfection with siRNA duplexes as described above. $4\times10^4$ cells in 400 µl serum-free culture medium were added to the upper chamber. The bottom chambers contained 800 µl culture medium supplemented with either FCS, PDGF-BB (Sigma-Aldrich) or SDF-1α/CXCL12 (R&D Systems) as chemoattractants. After 24 hours cells that had migrated to the bottom side of the membrane were fixed in ice-cold methanol; membranes were excised, placed on microscope slides and mounted with Hoechst (Dako) for fluorescence microscopy. Cells in five random visual fields (100× magnification) were counted for each membrane. All experiments were done in triplicates. Effects on chemokinesis of cells was analyzed using the same experimental setup with (i) no chemoattractant added to the upper and lower chamber and (ii) with chemoattractant added to both the upper and lower chamber.

In Vitro Invasion Assay

In vivo invasion assays were conducted in transwell chambers with 8.0 µm pore membranes (BD Biosciences) with cells cultured in serum-free medium for 12 h prior to the experiments. Upper chambers were prepared with 100 µl of Matrigel (BD Biosciences) diluted to 1 mg/ml in serum free medium. Chambers were incubated at 37° C. for 5 h for gelling. For siRNA experiments cells were transferred to serum-free conditions 24 h after transfection with siRNA duplexes as described above. $1 \times 10^5$ cells in 400 µl serum-free culture medium were added to the upper chamber. The bottom chambers contained 800 µl culture medium supplemented with FCS as chemoattractant. After 24 hours invaded cells at the bottom side of the membrane were fixed in ice-cold methanol; membranes were excised, placed on microscope slides and mounted with Hoechst (Dako) for fluorescence microscopy. Cells in five random visual fields (100× magnification) were counted for each membrane. All experiments were done in triplicates.

Example 1: Identification of ISC-468 as Therapeutic and Diagnostic Cancer Target ISC-468 (SEQ ID NO:1) encodes a protein of 212 amino acids (SEQ ID NO:2) and with a molecular weight of 23.6 kDa.

It has been previously described as placenta-specific protein expressed during pregnancy (Fant et al., *Mol Reprod Dev.* 63:430-6, 2002)

The protein is predicted to have a cleavable signal peptide from aa 1-23, followed by a short putative transmembrane domain (aa 25-47) as analysed by bioinformatics tools (TMpred, SOUSI). The remaining protein is predicted to be extracellular and can therefore be used according to the invention as target structure for monoclonal antibodies.

According to the invention, a gene-specific primer pair (SEQ ID NO:3, 4) for ISC-468 was used in RT-PCR analyses to amplify cDNA derived from a comprehensive panel of normal and tumor tissues. As expected, placenta was confirmed as the only healthy tissue expressing this gene (FIG. 1). No significant expression, whatsoever, was detected in any other normal organ tissue. Most surprisingly, when cancer specimen were investigated, we found high and significant levels of expression in a number of different tumor types, including colon, pancreatic, esophageal, stomach, lung, breast, ovrian, head&neck, kidney, prostate and liver carcinomas (FIGS. 1 and 2 as well as tab. 1). Quantitative real-time RT-PCR analysis of ISC-468 expression in 60 breast carcinoma samples revealed that 80% of all samples expressed significant levels of ISC-468 (FIG. 20A, B).

TABLE 1

ISC-468 expression in normal and tumor tissues

| Normal tissues | Expression | Tumor type | Expression |
| --- | --- | --- | --- |
| Brain | − | Colon carcinoma | + |
| Myocardium | − | Pancreatic carcinoma | + |
| Skeletal muscle | − | Esophageal carcinoma | + |
| Myocardium | − | Stomach carcinoma | + |
| Stomach | − | Lung cancer | + |
| Colon | − | Breast cancer | +++ |
| Pancreas | − | Ovarian carcinoma | + |
| Kidney | − | Head & Neck Cancer | + |
| Liver | − | Kidney cancer | + |
| Testis | − | Prostate carcinoma | + |
| Thymus | − | Liver carcinoma | ++ |
| Breast | − | | |
| Ovary | − | | |
| Uterus | − | | |
| Skin | − | | |
| Lung | − | | |
| Placenta | +++ | | |
| Lymph nodes | − | | |
| Spleen | − | | |
| PBMC | − | | |
| Prostate | − | | |

The selective and high expression of ISC-468 transcripts in tumors was not previously known and can be utilized according to the invention for molecular diagnostic methods such as RT-PCR for detecting disseminating tumor cells in the serum and bone marrow and for detecting metastases in other tissues. This molecule can be further used as specific target for therapeutic approaches.

The following peptides, inter alia, were selected for producing ISC-468 specific antibodies according to the invention: SEQ ID NO:58, 59, 60, 68, 69, 2. Specificity of the antibodies was confirmed by immunofluorescence analysis of ISC-468-eGFP transfected cells (FIG. 21A).

The subcellular localization of ISC-468 in endogenously expressing breast carcinoma cell lines MCF-7 and BT-549 was analyzed by immunofluorescence analyses. Staining of either MeOH-fixed (FIG. 21B) or non-fixed (FIG. 21C) cells revealed that ISC-468 is localized at the plasma membranes of the expressing cells. Specificity of the staining was confirmed by RNAi-induced knock-down of ISC-468 expression, resulting in the loss of plasma membrane staining.

Furthermore, ISC-468 specific antibodies were used for immunohistochemical analysis of ISC-468 expression in clinical samples of normal breast and breast carcinomas. Expression of ISC-468 was not detectable in normal breast specimens (FIG. 22A,B). In contrast, breast carcinoma specimens showed strong and homogeneous expression of ISC-468 (FIG. 22C,D). Signals were accentuated at the plasma membrane of the expressing cancer cells, confirming that ISC-468 is a membrane protein selectively expressed in cancer cells.

The extracellular domains of ISC-468 can be used according to the invention as target structure for immunodiagnosis and therapy by means of monoclonal antibodies. In addition, ISC-468 can be employed according to the invention as vaccine (RNA, DNA, protein, peptides) for inducing tumor-specific immune responses (T and B cell-mediated immune responses).

RNAi-induced knock-down of ISC-468 expression was achieved by transfection of cells with siRNA duplexes specifically targeting ISC-468 mRNA (SEQ ID NOs: 70-73). Transfection of endogenously expressing breast carcinoma cell lines MCF-7 and BT-549 resulted in stable and specific reduction of ISC-468 mRNA expression (FIG. 23).

To gain insight into the physiological role of ISC-468 expression several RNAi-based in vitro cell assays were performed. Transfection of breast carcinoma cell lines MCF-7 and BT-549 with siRNA duplexes resulted in a distinct reduction of cell proliferation compared to the respective controls, as analyzed in a BrdU-based proliferation assay (FIG. 24). FACS-based cell cycle analysis showed that the abrogation of cell proliferation resulted from a G1/S arrest (FIG. 25A,B). Additionally, it could be shown that RNAi-induced knock-down of ISC-468 profoundly affects the AKT signaling pathway in endogenously expressing cancer cells by inhibition of AKT phosphorylation (FIG. 26). Furthermore, proliferation of MCF-7 cells was attenuated when cells were incubated with ISC-468 specific antibodies generated against ISC-468 specific peptides (SEQ ID NO:68,69) compared to an irrelevant control antibody (FIG. 27). These results indicate that ISC-468 is a critical factor for the proliferation of cancer cells presumably by mediating growth factor-induced activation of the AKT signaling pathway and others. ISC-468 itself might represent a receptor, co-receptor or membrane-bound chaperone for growth-factors, chemokines or other substances.

Furthermore, the impact of ISC-468 expression on the migratory ability of cancer cells was analyzed. RNAi-induced knock-down of ISC-468 expression in breast carcinoma cell lines MCF-7 and BT-549 resulted in distinct impairment of chemotaxis, chemokinesis and invasion of the cells, as assessed in transwell migration assays (FIG. 28A, B,C). Chemotaxis, chemokinesis and invasion are critical factors for the metastasis of cancer cells to other organs. Therefore, expression of ISC-468 in cancer cells might be a positive factor for cancer cell metastasis.

In breast carcinomas, it could be shown that expression of ISC-468 is correlated with the estrogen-receptor state of the tumor. Quantitative real-time RT-PCR analysis of ISC-468 expression in 60 breast carcinoma samples revealed that estrogen-receptor positive breast carcinomas showed significantly higher levels of ISC-468 expression than receptor-negative tumors (FIG. 29).

Accordingly, expression of ISC-468 could be induced in estrogen-receptor positive breast carcinoma cell line MCF-7 by treatment with 17β-estradiol (FIG. 30).

Example 2: Identification of ISC-507 as Therapeutic and Diagnostic Cancer Target ISC-507 (SEQ ID NO:5) encodes a 754 aa protein (SEQ ID NO:6) with a molecular weight of 85.6 kDa.

ISC-507 is member of a family of zinc-binding proteins with disintegrin and metalloprotease activities that can function as adhesion proteins and/or endopeptidases. Members of this family have been described as involved in a number of biologic processes, including fertilization, neurogenesis, muscle development, and immune response (Seals et al., Genes Dev. 17(1):7-30, 2003)

ISC-507 has one transmembrane domain (aa 671-687), a large N-terminal extracellular and a shorter C-terminal cytoplasmatic region.

ISC-507 expression has been reported to be specifically restricted to mammalian epididymis, the small gland adjacent to the testicle, which is critically involved in maturation of sperm. According to literature, ISC-507 is transferred from the epididymis to the sperm surface and redistributed in the sperm head during acrosome reaction (Adachi et al., Mol Reprod Dev. 64:414-21, 2003).

RT-PCR investigations with ISC-507 specific primers (SEQ ID NO:7, 8) confirmed selective expression in the testis and absence of ISC-507 from any other normal tissue (tab. 2, FIG. 3), except weak expression in prostate and lymph node derived tissues (tab. 2, FIG. 4).

However and most surprisingly, we observed expression of ISC-507 in a significant number of prostate cancers (FIG. 3,4). This protein had not been reported before to be involved in cancer.

TABLE 2

ISC-507 expression in normal and tumor tissues

| Normal tissues | Expression | Tumor type | Expression |
|---|---|---|---|
| Brain | − | Colon carcinoma | − |
| Cerebellum | − | Pancreatic carcinoma | − |
| Myocardium | − | | |
| Skeletal muscle | − | Esophageal carcinoma | − |
| Myocardium | − | | |
| Stomach | − | Stomach carcinoma | − |
| Colon | − | Lung cancer | − |
| Pancreas | − | Breast cancer | − |
| Kidney | − | Ovarian carcinoma | − |
| Liver | − | Uterus carcinoma | − |
| Testis | +++ | Head & Neck Cancer | − |
| Thymus | − | Kidney cancer | − |
| Breast | − | Prostate carcinoma | +++ |
| Ovary | − | Liver carcinoma | − |
| Uterus | − | | |
| Skin | − | | |
| Lung | − | | |
| Placenta | − | | |
| Lymph nodes | + | | |
| Spleen | − | | |
| PBMC | − | | |
| Prostate | + | | |

The absence from toxicity relevant normal tissues and the frequent and significant expression of ISC-507 in prostate cancers make this protein according to the invention a valuable diagnostic and therapeutic marker. This includes according to the invention the detection of disseminated tumor cells in serum, bone marrow, urine, and the detection of metastases in other organs by means of RT-PCR. In addition, the extracellular domains of ISC-507 can be used according to the invention as target structure for immunodiagnosis and therapy by means of monoclonal antibodies. In addition, ISC-507 can be employed according to the invention as vaccine (RNA, DNA, protein, peptides) for inducing tumor-specific immune responses (T and B cell-mediated immune responses).

Antibodies for detecting ISC-507 could be produced with following peptides and proteins: SEQ ID NO:51, 52, 53, 54, 55, 6, 56 and 57.

According to the invention an antibody which binds to ISC-507 might be useful for therapeutic or diagnostic purposes.

Example 3: Identification of ISC-466 as Therapeutic and Diagnostic Cancer Target ISC-466 (SEQ ID NO:9) encodes a 426 aa protein (SEQ ID NO:10) with a molecular weight of 48.2 kDA.

It belongs to the family of pregnancy-specific glycoproteins. The human pregnancy-specific glycoproteins (PSGs) are a group of molecules that are mainly produced by the placental syncytiotrophoblasts during pregnancy and are part of the immunoglobulin superfamily (Beauchemin et al., Exp Cell Res. 252(2):243-9, 1999)

As other PSGs, ISC-466 as well has been reported to be restricted to placenta.

According to the invention, a gene-specific primer pair (SEQ ID NO:11, 12) for ISC-466 was used in RT-PCR analyses to amplify cDNA derived from a comprehensive panel of normal and tumor tissues. The RT-PCR analysis reveals expression of ISC-466 transcripts in normal placenta, and weak expression in thymus and ovary (tab. 3, FIG. 5A). No significant expression was detected in any other normal organ tissue. Most surprisingly, when cancer cell lines were investigated, we found high and significant levels of expression in a number of tumor types, including breast cancer (FIG. 5C), lung cancer (FIG. 5C), ovarian carcinoma (FIG. 5D) and head and neck- and kidney carcinomas (FIG. 5B).

TABLE 3

ISC-466 expression in normal and tumor tissues

| Normal tissues | Expression | Tumor type | Expression |
| --- | --- | --- | --- |
| Brain | − | Colon carcinoma | + |
| Thymus | + | Pancreatic carcinoma | + |
| Myocardium | − | | |
| Skeletal muscle | − | Esophageal carcinoma | + |
| Myocardium | | | |
| Stomach | − | Stomach carcinoma | − |
| Colon | − | Lung cancer | ++ |
| Pancreas | − | Breast cancer | +++ |
| Kidney | − | Ovarian carcinoma | ++ |
| Liver | − | Cervix carcinoma | − |
| Testis | +++ | Head & Neck Cancer | +++ |
| Thymus | − | Kidney cancer | ++ |
| Breast | − | Prostate carcinoma | + |
| Ovary | + | Liver carcinoma | − |
| Uterus | − | Melanoma | + |
| Skin | − | | |
| Lung | − | | |
| Placenta | − | | |
| Lymph nodes | − | | |
| Spleen | − | | |
| PBMC | − | | |
| Prostate | − | | |

In contrast to the observation, that ISC-466 is involved by colorectal carcinomas (Salahshor et al., BMC Cancer. 5:66, 2005), our investigations reveal ISC-466 according to the invention as diagnostic and therapeutic marker for head & neck, breast, ovarian, prostate cancer and melanoma.

Example 4: Identification of ISC-518 as Therapeutic and Diagnostic Cancer Target ISC-518 (SEQ ID NO:13) encodes a 237 aa translation product (SEQ ID NO:14). However, no data with regard to tissue distribution and no connection to cancer is available so far.

ISC-518 is a hypothetical, bioinformaticly predicted gene/protein. Sequence analyses revealed that the protein has a transmembrane domain (aa 102-118). The extracellular C-terminus features a functional domain, which occurs in cell-surface glycoproteins.

According to the invention, a gene-specific primer pair (SEQ ID NO:15, 16) for ISC-518 was used in RT-PCR analyses to amplify cDNA derived from a comprehensive panel of normal and tumor tissues. The only normal tissue we found to express this gene was testis, whereas no significant expression of ISC-518 was detectable in any other normal organ (FIG. 6). Most surprisingly, when cancer specimen were investigated, we found high and significant levels of expression in hepatocarcinomas (FIG. 7)

TABLE 4

ISC-518 expression in normal and tumor tissues

| Normal tissues | Expression | Tumor type | Expression |
| --- | --- | --- | --- |
| Brain | − | Colon carcinoma | − |
| Cerebellum | − | Pancreatic carcinoma | − |
| Myocardium | − | | |
| Skeletal muscle | − | Esophageal carcinoma | − |
| Myocardium | − | | |
| Stomach | − | Stomach carcinoma | + |
| Colon | − | Lung cancer | + |
| Pancreas | − | Breast cancer | + |
| Kidney | − | Ovarian carcinoma | + |
| Liver | − | Uterus carcinoma | − |
| Testis | +++ | Head & Neck Cancer | − |
| Thymus | − | Kidney cancer | − |
| Breast | − | Prostate carcinoma | + |
| Ovary | − | Liver carcinoma | ++ |
| Uterus | − | | |
| Skin | − | | |
| Lung | − | | |
| Placenta | − | | |
| Lymph nodes | − | | |
| Spleen | − | | |
| PBMC | − | | |
| Prostate | − | | |

Bioinformatic investigations showed that the protein encoded by ISC-518 represents a cell surface molecule. The previous unknown selective expression of this surface molecule makes it a target for therapeutic purposes and for developing diagnostic methods for the detection of tumor cells and therapeutic methods for the elimination of tumor cells.

Example 5: Identification of ISC-477 as Therapeutic and Diagnostic Cancer Target ISC-477 (SEQ ID NO:17) encodes a 130 aa translation product (SEQ ID NO:18). ISC-477 is a hypothetical protein. No data with regard to tissue distribution and no connection to cancer was publicly available. Structural analysis reveals a hydrophobic region, which might be a transmembrane region or signal peptide.

According to the invention, a gene-specific primer pair (SEQ ID NO: 19, 20) for ISC-477 was used in RT-PCR analyses to amplify cDNA derived from a comprehensive panel of normal and tumor tissues. The only normal tissues we found to express this gene were placenta and ovary. In contrast, no significant expression of ISC-477 was detectable in any other normal organ (FIG. 8A). Most surprisingly, when cancer specimens were investigated, we found high and significant levels of expression in lung, ovarian, colon and stomach cancer (FIG. 8A-D). Expression levels are clearly higher than expression in normal ovary.

TABLE 5

ISC-477 expression in normal and tumor tissues

| Normal tissues | Expression | Tumor type | Expression |
| --- | --- | --- | --- |
| Brain | − | Colon carcinoma | ++ |
| Cerebellum | − | Pancreatic carcinoma | + |
| Myocardium | − | | |
| Skeletal muscle | − | Esophageal carcinoma | − |
| Myocardium | − | | |
| Stomach | − | Stomach carcinoma | ++ |
| Colon | − | Lung cancer | +++ |
| Pancreas | − | Breast cancer | ++ |
| Kidney | − | Ovarian carcinoma | ++ |
| Liver | − | Kidney cancer | − |

TABLE 5-continued

ISC-477 expression in normal and tumor tissues

| Normal tissues | Expression | Tumor type | Expression |
|---|---|---|---|
| Testis | − | Prostate carcinoma | − |
| Thymus | − | Liver carcinoma | − |
| Breast | − | | |
| Ovary | ++ | | |
| Uterus | − | | |
| Skin | − | | |
| Lung | − | | |
| Placenta | +++ | | |
| Lymph nodes | − | | |
| Spleen | − | | |
| PBMC | − | | |
| Prostate | − | | |

Example 6: Identification of ISC-489 as Therapeutic and Diagnostic Cancer Target ISC-489 (SEQ ID NO:21) encodes a 363 aa translation product (SEQ ID NO:22). The protein is a newly described member of the family of G-protein coupled receptors. However, no data with regard to tissue distribution and no connection to cancer was publically available.

According to the invention, a gene-specific primer pair (SEQ ID NO:23,24) for ISC-489 was used in RT-PCR analyses to amplify cDNA derived from a comprehensive panel of normal and tumor tissues. The only normal tissues we found to express this gene were placenta and esophagus (weak expression). In contrast, no significant expression of ISC-489 was detectable in any other normal organ (FIG. 9A). Most surprisingly, when cancer specimens were investigated, we found high and significant levels of expression in head and neck, and stomach cancers (FIG. 9B, 9C).

As member of the G-protein coupled receptor family, ISC-489 is an integral membrane protein with 7 transmembrane domains and several extracellular loops, which can be targeted on the cell surface.

TABLE 6

ISC-489 expression in normal and tumor tissues

| Normal tissues | Expression | Tumor type | Expression |
|---|---|---|---|
| Brain | − | Colon carcinoma | + |
| Esophagus | + | Stomach carcinoma | ++ |
| Myocardium | − | Lung cancer | + |
| Skeletal muscle | − | Breast cancer | − |
| Myocardium | | Ovarian carcinoma | − |
| Stomach | − | Head & Neck Cancer | +++ |
| Colon | − | Kidney cancer | + |
| Pancreas | − | Prostate carcinoma | − |
| Kidney | − | Liver carcinoma | + |
| Liver | − | | |
| Testis | − | | |
| Thymus | − | | |
| Breast | − | | |
| Ovary | − | | |
| Uterus | − | | |
| Skin | − | | |
| Lung | − | | |
| Placenta | +++ | | |
| Lymph nodes | − | | |
| Spleen | − | | |
| PBMC | − | | |
| Prostate | − | | |

The pronounced expression and unexpected high incidence of ISC-489 in head and neck carcinomas make this protein according to the invention a highly interesting diagnostic and therapeutic marker.

Example 7: Identification of ISC-461 as Therapeutic and Diagnostic Cancer Target ISC-461 (SEQ ID NO:25) encodes a 419 aa protein (SEQ ID NO:26) with a molecular weight of 47.1 kDA. It belongs to the family of pregnancy-specific glycoproteins. The human pregnancy-specific glycoproteins (PSGs) are a group of molecules that are mainly produced by the placental syncytiotrophoblasts during pregnancy and are part of the immunoglobulin superfamily (Beauchemin et al., *Exp Cell Res.* 252(2):243-9, 1999).

As other PSGs, ISC-461 as well has been reported to be restricted to placenta.

According to the invention, a gene-specific primer pair (SEQ ID NO:11, 27) for ISC-461 was used in RT-PCR analyses to amplify cDNA derived from a comprehensive panel of normal and tumor tissues. As expected, placenta was confirmed as expressing this gene, besides weak expression in testis and ovary (FIGS. 10A and 10B). No significant expression, whatsoever, was detected in any other normal organ tissue. Most surprisingly, when cancer derived tissues and cancer cell lines were investigated, we found high and significant levels of expression in a number of tumor types, including breast cancer (FIG. 10C), ovarian carcinoma (FIG. 10D) and melanoma (FIG. 10B, 10C).

TABLE 7

ISC-461 expression in normal and tumor tissues

| Normal tissues | Expression | Tumor type | Expression |
|---|---|---|---|
| Brain | − | Colon carcinoma | − |
| Cerebellum | − | Pancreatic carcinoma | + |
| Myocardium | − | | |
| Skeletal muscle | − | Esophageal carcinoma | + |
| Myocardium | − | | |
| Stomach | − | Stomach carcinoma | + |
| Colon | − | Lung cancer | + |
| Pancreas | − | Breast cancer | ++ |
| Kidney | − | Ovarian carcinoma | ++ |
| Liver | − | Kidney cancer | − |
| Testis | + | Prostate carcinoma | − |
| Thymus | − | Liver carcinoma | − |
| Breast | − | Melanoma | ++ |
| Ovary | + | | |
| Uterus | − | | |
| Skin | − | | |
| Lung | − | | |
| Placenta | +++ | | |
| Lymph nodes | − | | |
| Spleen | − | | |
| PBMC | − | | |
| Prostate | − | | |

A further aim according to the invention was to identify splice variants for ISC-461 which can be utilized both for diagnosis and for therapy.

On investigation of splice variants we could identify a splice form (SEQ ID NO:28) and the protein encoded thereby (SEQ ID NO:29).

Example 8: Identification of ISC-465 as Therapeutic and Diagnostic Cancer Target ISC-465 (SEQ ID NO:30) encodes a 419 aa protein (SEQ ID NO:31) with a molecular weight of 47.0 kDA.

It belongs to the family of pregnancy-specific glycoproteins. The human pregnancy-specific glycoproteins (PSGs)

are a group of molecules that are mainly produced by the placental syncytiotrophoblasts during pregnancy and are part of the immunoglobulin superfamily (Beauchemin et al., *Exp Cell Res.* 252(2):243-9, 1999).

As other PSGs, ISC-465 as well has been reported to be restricted to placenta.

According to the invention, a gene-specific primer pair (SEQ ID NO:11, 32) for ISC-465 was used in RT-PCR analyses to amplify cDNA derived from a comprehensive panel of normal and tumor tissues. As expected, placenta was confirmed as expressing this gene, besides weak expression in normal ovary (FIG. 11A). No significant expression, whatsoever, was detected in any other normal organ tissue. Most surprisingly, when cancer derived tissues and cancer cell lines were investigated, we found high and significant levels of expression in a number of tumor types (FIG. 11A, 11B), especially breast cancer (FIG. 11B).

TABLE 8

ISC-461 expression in normal and tumor tissues

| Normal tissues | Expression | Tumor type | Expression |
|---|---|---|---|
| Brain | − | Colon carcinoma | − |
| Cerebellum | − | Pancreatic carcinoma | + |
| Myocardium | − | | |
| Skeletal muscle | − | Esophageal carcinoma | + |
| Myocardium | | | |
| Stomach | − | Stomach carcinoma | + |
| Colon | − | Lung cancer | + |
| Pancreas | − | Breast cancer | ++ |
| Kidney | − | Ovarian carcinoma | ++ |
| Liver | − | Kidney cancer | − |
| Testis | + | Prostate carcinoma | − |
| Thymus | − | Liver carcinoma | − |
| Breast | − | Melanoma | + |
| Ovary | + | | |
| Uterus | − | | |
| Skin | − | | |
| Lung | − | | |
| Placenta | +++ | | |
| Lymph nodes | − | | |
| Spleen | − | | |
| PBMC | − | | |
| Prostate | − | | |

The selective and high expression of ISC-465 transcripts in tumors was not previously known and can be utilized according to the invention for molecular diagnostic methods such as RT-PCR for detecting disseminating tumor cells in the serum and bone marrow and for detecting metastases in other tissues. This molecule can be further used as specific target for therapeutic approaches.

Example 9: Identification of Mem-030 as Therapeutic and Diagnostic Cancer Target Mem-030 (SEQ ID NO:35) encodes a 592 aa protein (SEQ ID NO:36) with a molecular weight of 67.9 kDA.

Mem-030 belongs to the GBP-proteins, which are large GTPases being able to bind GTP, GDP, and GMP and to catalyze the hydrolysis of GTP to GDP, as well as GMP (Cheng et al., *J Biol. Chem.* 260:15834-9, 1985). GTPases play an important role in cell proliferation, differentiation, signal transduction, and intracellular protein transportation and are interferon inducible (Boehm et al., *J Immunol.* 161(12):6715-23, 1998).

Also, Mem-030 counteracts the proliferative effect of inflammatory cytokines like IFN-g, interleukin 1-b (IL-1b), and tumor necrosis factor-a (TNF-a) 1 on endothelial cells (Guenzi et al., *EMBO J.* 20(20):5568-77, 2001).

According to the invention, a gene-specific primer pair (SEQ ID NO:37, 38) for Mem-030 was used in real time RT-PCR analyses to amplify cDNA derived from a comprehensive panel of normal and tumor tissues. Mem-030 show an ubiquitous expression pattern (FIG. 12A, tab. 9).

Most surprisingly, when cancer derived tissues and cancer cell lines were investigated, we found high and significant levels of overexpression in a number of tumor types (FIG. 12A, 12B), especially head and neck carcinomas.

TABLE 9

Mem-030 expression in normal and tumor tissues

| Normal tissues | Expression | Tumor type | Expression |
|---|---|---|---|
| Brain | + | Colon carcinoma | + |
| Myocardium | + | Pancreatic carcinoma | + |
| Skeletal muscle | + | | |
| Myocardium | + | Esophageal carcinoma | ++ |
| Stomach | + | | |
| Colon | + | Stomach carcinoma | + |
| Pancreas | + | Lung cancer | + |
| Kidney | + | Breast cancer | + |
| Liver | + | Ovarian carcinoma | + |
| Testis | + | Uterus carcinoma | ++ |
| Thymus | + | Head & Neck Cancer | +++ |
| Breast | + | Kidney cancer | + |
| Ovary | + | Prostate carcinoma | + |
| Uterus | + | Liver carcinoma | ++ |
| Skin | + | Melanoma | ++ |
| Lung | + | | |
| Placenta | + | | |
| Lymph nodes | + | | |
| Spleen | + | | |
| PBMC | + | | |
| Prostate | + | | |

Due to bioinformatics and literature analysis, a homologous gene of Mem-030 might be also an attractive therapeutic target (SEQ ID NO:39) and encodes a 586 aa protein (SEQ ID NO:40) with a molecular weight of 66.6 kDA.

Bioinformatic investigations showed that both proteins represent cell surface molecules. The previously unknown selective overexpression of this surface molecule makes it a target for therapeutic purposes and for developing diagnostic methods for the detection of tumor cells and therapeutic methods for the elimination of tumor cells.

Example 10: Identification of Mem-055 as Therapeutic and Diagnostic Cancer Target Mem-055 (SEQ ID NO:41) encodes a 250 aa protein (SEQ ID NO:42) with a molecular weight of 27.9 kDA.

The protein encoded by this gene is a lysosomal thiol reductase that at low pH can reduce protein disulfide bonds. The enzyme is expressed constitutively in antigen-presenting cells and induced by gamma-interferon in other cell types. This enzyme has an important role in MHC class II-restricted antigen processing (Arunachalam et al. *Proc Natl Acad Sci USA.* 97(2):745-50, 2000).

The localization of Mem-055 and the protein topology was predicted by analysis of the putative signal sequences and transmembrane domains with bioinformatic tools (TM-PRED, SOUSI). Mem-055 might have an extracellular C-terminus.

According to the invention, a gene-specific primer pair (SEQ ID NO:43, 44) for Mem-055 was used in real time RT-PCR analyses to amplify cDNA derived from a comprehensive panel of normal and tumor tissues. Mem-055 show an ubiquitous expression pattern (FIG. 13A, tab. 10).

Most surprisingly, when Mem-055 expression within cancer derived tissues was investigated, we found high and significant levels of overexpression in a number of tumor types (FIG. 13A, 13B), especially stomach cancers.

TABLE 10

Mem-055 expression in normal and tumor tissues

| Normal tissues | Expression | Tumor type | Expression |
|---|---|---|---|
| Brain | + | Colon carcinoma | + |
| Myocardium | + | Pancreatic carcinoma | + |
| Skeletal muscle | + | | |
| Myocardium | + | Esophageal carcinoma | + |
| Stomach | + | | |
| Colon | + | Stomach carcinoma | +++ |
| Pancreas | + | Lung cancer | ++ |
| Kidney | + | Breast cancer | ++ |
| Liver | + | Ovarian carcinoma | ++ |
| Testis | + | Uterus carcinoma | + |
| Thymus | + | Head & Neck Cancer | + |
| Breast | + | Kidney cancer | + |
| Ovary | + | Prostate carcinoma | + |
| Uterus | + | Liver carcinoma | ++ |
| Skin | + | Melanoma | + |
| Lung | + | | |
| Placenta | + | | |
| Lymph nodes | + | | |
| Spleen | + | | |
| PBMC | + | | |
| Prostate | + | | |

Mem-055 is a target structure for therapeutic and diagnostic purposes, because of the putative extracellular domain and the unexpected overexpression in different carcinoma types.

Example 11: Identification of Mem-062 as Therapeutic and Diagnostic Cancer Target Mem-062 (SEQ ID NO:45) encodes a 271 aa protein (SEQ ID NO:46) with a molecular weight of 30.7 kDA.

By a computer-based screening method Mem-062 could previously be identified and was described as testis, prostate and placenta specifically expressed (Bera et al., *Biochem Biophys Res Commun.* 312(4):1209-15, 2003)

According to the invention, a gene-specific primer pair (SEQ ID NO:47, 48) for Mem-062 was used in RT-PCR analyses. Mem-062 surprisingly showed a cancer-testis specific expression pattern (FIG. 14A, tab. 11). No expression was detected in any other normal organ tissue. Most surprisingly, when cancer derived tissues were investigated, we found significant levels of Mem-62 expression (FIG. 14B), especially in ovarian carcinomas.

TABLE 11

Mem-062 expression in normal and tumor tissues

| Normal tissues | Expression | Tumor type | Expression |
|---|---|---|---|
| Brain | − | Colon carcinoma | + |
| Myocardium | − | Pancreatic carcinoma | − |
| Skeletal muscle | − | | |
| Myocardium | − | Esophageal carcinoma | − |
| Stomach | − | | |
| Colon | − | Stomach carcinoma | − |
| Pancreas | − | Lung cancer | − |
| Kidney | − | Breast cancer | − |
| Liver | − | Ovarian carcinoma | ++ |
| Testis | − | Uterus carcinoma | − |
| Thymus | − | Head & Neck Cancer | − |
| Breast | − | Kidney cancer | − |

TABLE 11-continued

Mem-062 expression in normal and tumor tissues

| Normal tissues | Expression | Tumor type | Expression |
|---|---|---|---|
| Ovary | − | Prostate carcinoma | − |
| Uterus | − | Liver carcinoma | − |
| Skin | − | Melanoma | − |
| Lung | − | | |
| Placenta | − | | |
| Lymph nodes | − | | |
| Spleen | − | | |
| PBMC | − | | |
| Prostate | − | | |

Alternative splicing results in an alternative transcript (SEQ ID NO:49) and its corresponding translation product (SEQ ID NO:50).

Example 12: Identification of Mem-068 as Therapeutic and Diagnostic Cancer Target Mem-068 (SEQ ID NO:61) is a newly identified cDNA clone.

By a bioinformatic prediction approach (Genscan) Mem-068 could be described as multiple exon gene on chromosome 9 (SEQ ID NO:62). The deduced protein sequence (SEQ ID NO:63) has 751 aa and forms a protein with a molecular weight of 82.4 kDA.

According to the invention, a gene-specific primer pair for Mem-068 was used in RT-PCR analyses. Mem-068 show surprisingly a cancer-testis specific expression pattern (FIG. 15A, tab. 12). No expression was detected in any other normal organ tissue except placenta (weak expression). Most surprisingly, when cancer derived tissues were investigated, we found significant levels of Mem-068 expressed (FIG. 15B), especially in renal cell carcinomas and in stomach cancers.

TABLE 12

Mem-068 expression in normal and tumor tissues

| Normal tissues | Expression | Tumor type | Expression |
|---|---|---|---|
| Brain | − | Colon carcinoma | + |
| Breast | | Renal cell carcinoma | ++ |
| Colon | − | Stomach carcinoma | + |
| Kidney | − | Lung cancer | + |
| Liver | − | Breast cancer | − |
| Lung | | Ovarian carcinoma | − |
| Lymph nodes | − | Melanoma | − |
| Ovary | − | Prostate carcinoma | − |
| Pancreas | − | | |
| Placenta | + | | |
| PBMC | − | | |
| PBMC activated | − | | |
| Prostate | − | | |
| Skeletal muscle | − | | |
| Skin | − | | |
| Stomach | − | | |
| Spleen | − | | |
| Testis | + | | |
| Uterus | − | | |

According to the transmembrane prediction programme TMpred Mem-068 might be expressed at the cell surface, which makes it an interesting target for therapeutic or diagnostic purposes.

Example 13: Identification of Mem-071 as Therapeutic and Diagnostic Cancer Target Mem-071 (SEQ ID NO:64) is a new cDNA clone, which is encoded in 2 exons on chromosome 1.

According to the invention, a gene-specific primer pair for Mem-071 was used in RT-PCR analyses to amplify cDNA derived from a comprehensive panel of normal and tumor tissues. The only normal tissues we found to express this gene was testis (FIG. 16A). In contrast, when cancer specimen were investigated, we found high and significant levels of expression in renal cell carcinomas and stomach cancers (FIG. 16B).

TABLE 13

Mem-071 expression in normal and tumor tissues

| Normal tissues | Expression | Tumor type | Expression |
|---|---|---|---|
| Brain | − | Colon carcinoma | − |
| Breast | − | Renal cell carcinoma | ++ |
| Colon | − | Stomach carcinoma | + |
| Kidney | − | Lung cancer | − |
| Liver | − | Breast cancer | − |
| Lung | − | Ovarian carcinoma | − |
| Lymph nodes | − | Melanoma | − |
| Ovary | − | Prostate carcinoma | − |
| Pancreas | − | | |
| Placenta | − | | |
| PBMC | − | | |
| PBMC activated | − | | |
| Prostate | − | | |
| Skeletal muscle | − | | |
| Skin | − | | |
| Stomach | − | | |
| Spleen | − | | |
| Testis | + | | |
| Uterus | − | | |

The unexpected high incidence of Mem-071 in renal cell carcinomas make this protein according to the invention a highly interesting diagnostic and therapeutic marker.

Example 14: Identification of Mem-072 as Therapeutic and Diagnostic Cancer Target Mem-072 (SEQ ID NO:65) is a newly identified gene, which is encoded in 3 exons on chromosome 16.

According to the invention, a gene-specific primer pair for Mem-072 was used in RT-PCR analyses to amplify cDNA derived from a comprehensive panel of normal and tumor tissues. No expression within all tested normal tissues could be found (FIG. 17A, tab. 14). When cancer derived tissues and cancer cell lines were investigated, we found high and significant levels of expression in lung cancer samples (FIG. 17B).

TABLE 14

Mem-072 expression in normal and tumor tissues

| Normal tissues | Expression | Tumor type | Expression |
|---|---|---|---|
| Brain | − | Colon carcinoma | − |
| Breast | − | Renal cell carcinoma | − |
| Colon | − | Stomach carcinoma | − |
| Kidney | − | Lung cancer | ++ |
| Liver | − | Breast cancer | − |
| Lung | − | Ovarian carcinoma | − |
| Lymph nodes | − | Melanoma | − |
| Ovary | − | Prostate carcinoma | − |
| Pancreas | − | | |
| Placenta | − | | |
| PBMC | − | | |
| PBMC activated | − | | |
| Prostate | − | | |
| Skeletal muscle | − | | |
| Skin | − | | |

TABLE 14-continued

Mem-072 expression in normal and tumor tissues

| Normal tissues | Expression | Tumor type | Expression |
|---|---|---|---|
| Stomach | − | | |
| Spleen | − | | |
| Testis | − | | |
| Uterus | − | | |

The selective and high expression of Mem-072 in lung tumors was not previously known and can be utilized according to the invention for molecular diagnostic methods such as RT-PCR for detecting disseminating tumor cells in the serum and bone marrow and for detecting metastases in other tissues. This molecule can be further used as specific target for therapeutic approaches.

Example 15: Identification of Mem-106 as Therapeutic and Diagnostic Cancer Target Mem-106 (SEQ ID NO:66) is a newly identified cDNA, which is intronless encoded on chromosome 2.

According to the invention, a gene-specific primer pair for Mem-106 was used in RT-PCR analyses. Mem-106 surprisingly showed a cancer-testis specific expression pattern (FIG. 18A, tab. 15). No expression was detected in any other normal organ tissue. Most surprisingly, when cancer derived tissues were investigated, we found significant levels of Mem-106 expression (FIG. 18B), especially in ovarian carcinomas.

TABLE 15

Mem-106 expression in normal and tumor tissues

| Normal tissues | Expression | Tumor type | Expression |
|---|---|---|---|
| Breast | − | Colon carcinoma | + |
| Colon | − | Renal cell carcinoma | − |
| Kidney | − | Stomach carcinoma | − |
| Liver | − | Lung cancer | − |
| Lung | − | Breast cancer | − |
| Lymph nodes | − | Ovarian carcinoma | ++ |
| Ovary | − | Melanoma | ++ |
| Pancreas | − | Prostate carcinoma | − |
| Placenta | − | | |
| PBMC | − | | |
| PBMC activated | − | | |
| Prostate | − | | |
| Skeletal muscle | − | | |
| Skin | − | | |
| Stomach | − | | |
| Spleen | − | | |
| Testis | ++ | | |
| Uterus | − | | |

Mem-106 is a target structure for therapeutic and diagnostic purposes, because of the unexpected overexpression in different carcinoma types.

Example 16: Identification of Mem-131 as Therapeutic and Diagnostic Cancer Target Mem-131 (SEQ ID NO:67) is a newly identified cDNA clone. Mem-131 is a 2 exone gene on chromosome 15.

According to the invention, a gene-specific primer pair for Mem-131 was used in RT-PCR analyses to amplify cDNA derived from a comprehensive panel of normal and tumor tissues. The RT-PCR analysis reveals expression of Mem-131 transcripts only in normal activated PBMCs (tab. 16, FIG. 19A). No significant expression was detected in any other normal organ tissue. Most surprisingly, when cancer samples were investigated, we found high and significant levels of expression in a number of tumor types, including breast cancer (FIG. 19B), lung cancer (FIG. 19B+C) and ovarian carcinoma (FIG. 19C).

TABLE 16

Mem-131 expression in normal and tumor tissues

| Normal tissues | Expression | Tumor type | Expression |
| --- | --- | --- | --- |
| Breast | − | Lung cancer | ++ |
| Duodenum | − | Breast cancer | ++ |
| Bladder | − | Ovarian carcinoma | ++ |
| Skin | − | | |
| Brain | − | | |
| Bone marrow | − | | |
| Colon | − | | |
| Liver | − | | |
| Lung | − | | |
| Lymph node | − | | |

TABLE 16-continued

Mem-131 expression in normal and tumor tissues

| Normal tissues | Expression | Tumor type | Expression |
| --- | --- | --- | --- |
| Stomach | − | | |
| Spleen | − | | |
| Myocard | − | | |
| Kidney | − | | |
| Esophagus | − | | |
| Ovary | − | | |
| Pancreas | − | | |
| PBMC | − | | |
| PBMC activated | ++ | | |
| Placenta | − | | |
| Muscle | − | | |
| Testis | − | | |
| Thymus | − | | |

Our investigations reveals Mem-131 according to the invention as diagnostic and therapeutic marker for lung, breast and ovarian cancers.

The invention claimed is:

1. An isolated antibody that binds specifically to a protein or polypeptide or to a part thereof, the protein or polypeptide being encoded by a nucleic acid that is:
   (a) the nucleic acid of SEQ ID NO. 1, or
   (b) a nucleic acid that has at least 95% sequence identity with the nucleic acid of (a), wherein
   the antibody is a monoclonal antibody, or is an antigen binding fragment of the monoclonal antibody; and
   wherein the antibody binds to an epitope comprised in a sequence selected from the group consisting of SEQ. ID. NOs. 59 and 69.

2. The isolated antibody as claimed in claim 1, wherein the protein or polypeptide comprises the amino acid sequence of SEQ ID NO. 2.

3. A conjugate comprising the isolated antibody as claimed in claim 1, further comprising a therapeutic or diagnostic agent.

4. The conjugate as claimed in claim 3, wherein the therapeutic or diagnostic agent is a toxin.

5. A conjugate comprising the isolated antibody as claimed in claim 2, further comprising a therapeutic or diagnostic agent.

6. The conjugate as claimed in claim 5, wherein the therapeutic or diagnostic agent is a toxin.

7. The isolated antibody of claim 1, wherein the antibody binds to an epitope comprised in SEQ. ID. NO. 59.

8. The isolated antibody of claim 1, wherein the antibody binds to an epitope comprised in SEQ. ID. NO. 69.

9. A pharmaceutical composition, comprising a monoclonal antibody selective for cells expressing or abnormally expressing a tumor-associated antigen, the tumor-associated antigen having a sequence encoded by a nucleic acid that is:
   (a) a nucleic acid which comprises the nucleic acid sequence of SEQ ID NO. 1, or
   (b) a nucleic acid that has at least 95% sequence identity with the nucleic acid of (a), and
   wherein the antibody binds to an epitope comprised in a sequence selected from the group consisting of SEQ. ID. NOs. 59 and 69.

10. The pharmaceutical composition as claimed in claim 9, wherein the antibody binds selectively to the tumor-associated antigen.

11. The pharmaceutical composition as claimed in claim 9 wherein the antibody is coupled to a therapeutic agent or a diagnostic agent.

12. The conjugate as claimed in claim 11, wherein the therapeutic or diagnostic agent is a toxin.

13. The pharmaceutical composition as claimed in claim 9, wherein the tumor-associated antigen comprises the amino acid sequence of SEQ ID NO. 2.

14. The pharmaceutical composition of claim 9, wherein the antibody binds to an epitope comprised in SEQ. ID. NO. 59.

15. The pharmaceutical composition of claim 9, wherein the antibody binds to an epitope comprised in SEQ. ID. NO. 69.

16. A pharmaceutical composition, comprising a monoclonal antibody which binds to a tumor-associated antigen or a part thereof, the tumor-associated antigen having a sequence encoded by a nucleic acid which is selected from the group consisting of:
   (a) a nucleic acid which comprises the nucleic acid sequence of SEQ ID NO. 1, and
   (b) a nucleic acid that has at least 95% sequence identity with the nucleic acid of (a), and
   wherein the antibody binds to an epitope comprised in a sequence selected from the group consisting of SEQ. ID. NOs. 59 and 69.

17. The pharmaceutical composition as claimed in claim 16 wherein the antibody is coupled to a therapeutic agent or a diagnostic agent.

18. The conjugate as claimed in claim 17, wherein the therapeutic or diagnostic agent is a toxin.

19. The pharmaceutical composition as claimed in claim 16, wherein the tumor-associated antigen comprises the amino acid sequence of SEQ ID NO. 2.

20. The pharmaceutical composition of claim 16, wherein the antibody binds to an epitope comprised in SEQ. ID. NO. 59.

21. The pharmaceutical composition of claim 16, wherein the antibody binds to an epitope comprised in SEQ. ID. NO. 69.

* * * * *